US006596482B1

(12) United States Patent
Jones

(10) Patent No.: US 6,596,482 B1
(45) Date of Patent: Jul. 22, 2003

(54) NUCLEIC ACIDS ENCODING BAZ1α TRANSCRIPTIONAL REGULATOR AND METHODS OF USE

(75) Inventor: Michael H. Jones, Ibaraki (JP)

(73) Assignee: Chugai Seiyaku Kabushiki Kaisha, Tokyo (JP)

(*) Notice: Subject to any disclaimer, the term of this patent is extended or adjusted under 35 U.S.C. 154(b) by 0 days.

(21) Appl. No.: 09/418,710

(22) Filed: Oct. 15, 1999

Related U.S. Application Data

(63) Continuation-in-part of application No. PCT/JP98/01783, filed on Apr. 17, 1998.

(30) Foreign Application Priority Data

Apr. 18, 1997 (JP) .............................................. 9-116570
Oct. 24, 1997 (JP) .............................................. 9-310027

(51) Int. Cl.[7] ........................... C12Q 1/68; C12P 21/06; G01N 33/53; C07H 17/00; C07K 14/00
(52) U.S. Cl. ........................... 435/6; 435/7.1; 435/69.1; 435/320.1; 435/325; 435/252.3; 536/23.1; 530/350
(58) Field of Search ...................... 536/23.1; 435/320.1, 435/252.3, 325, 69.1, 6, 7.1; 530/350

(56) References Cited

PUBLICATIONS

Robertson et al. 1994; Genomics 23:42–50.*
Dhalluin et al., "Structure and ligand a histone acetyltransferase bromodomain," Nature, vol. 399, pp. 491–496, Jun. 3, 1999.
Haynes et al., "The bromodomain: a conserved sequence found in human, Drosophila and yeast proteins," Nucleic Acids Research, vol. 20, p. 2603, Apr. 2, 1992.
Ito et al., "ACF consist of two subunits, Acf1 and ISWI, that function cooperatively in the ATP–dependent catalysis of chromatin assembly," Genes & Development, vol. 13, pp. 1529–1539, 1999.
Jones, M.H., "The bromodomain revisited," Letters, pp. 151–153, 1997.
Lu et al., "A Novel Human Gene, WSTF, Is Deleted in Williams Syndrome," Genemics vol. 54, pp. 241–249, 1998.
Tamkun et al., "brhma: A Regulator of Drosophila Homeotic Genes Structurally Related to the Yeast Transcriptional Activator SNF2/SWI2," Cell, vol. 68, pp. 561–572, Feb. 7, 1992.
Beck et al., "A homologue of the Drosophila female sterile hemeotic (fsh) gene in the class region of the human MHC," DNA Seq 1992;2(4):203–10 (abstract).
Haynes et al., "The Drosophila fsh locus, a maternal effect homeotic gene, encodes apparent membrane proteins," Dev Biol Jul. 1989 ;134(1):246–57 (abstract).
GenBank Accession No. M23221, D. melanogaster fsh membrane protein, 7.6 kb mRNA, complete cds., Apr. 26, 1993.
GenBank Accession No. M23222, D. melanogaster fsh membrane protein, 5.9 kb mRNA, complete cds. Apr. 26, 1993.
GenBank Accession No. M85049, D. melanogaster brahma protein mRNA, complete cds., Jul. 13, 1994.
GenBank Accession No. M87651, D. cerevisiae bromodomain of SPT7 gene, partial cds., Apr. 27, 1993.
GenBank Accession No. M61703 M55906, S. cerevisiae SNF2 protein gene, complete cds., Apr. 27, 1993.
GenBank Accession No. X07024, H. sapiens mRNA for CCG1 protein, Jul. 17, 2001.
GenBank Accession No. M80613, human homolog of Drosophila female sterile homeotic mRNA, complete cds., Jun. 22, 1995.
Hillier et al., "Generation and analysis of 280,000 human expressed sequence tags", DATABASE EMBL Online!, Database Assession No. H70181, XP002198410, Oct. 25, 1995.
Hilier et al., "The WashU–Merck EST Project", DATABASE EMBL Online!, Database Assession No. R66814, XP002198411, Jun. 4, 1995.
Hillier et al., "Generation and analysis of 280,000 human expressed sequence tags", DATABASE EMBL Online!, Database Assession No. AA112166, XP002193345, Nov. 9,1996.
Hillier et al., "Generation and analysis of 280,000 human expressed sequence tags", DATABASE EMBL Online!, Database Assession No. AA102574, XP002193346, Oct. 30, 1996.
Jones et al., "A Novel Family of Bromodomains Genes", Genomics, 63, pp. 40–45, 2000.
Nicolas et al., "Molecular cloning of polybromo, a nuclear protein containing multiple domains including five bromodomains, a truncated HMG–box, and two repeats of a novel domain", Gene 175 pp. 233–240, 1996.
Nielson et al., "Cloning and sequencing of a human cDNA encoding a putative trancription factor containing a bromodomain", Biochimica et Biophysica Acta, 1306 pp. 14–16, 1996.
EP Search Report, Jul. 11, 2002.

* cited by examiner

Primary Examiner—Karen Cochrane Carlson
(74) Attorney, Agent, or Firm—Fish & Richardson PC

(57) ABSTRACT

Genes each encoding a novel transcriptional regulator having a bromodomain have been successfully isolated from a human testis cDNA library using primers prepared based on an EST sequence found using the bromodomain sequence of the transcriptional regulator. These genes are structurally analogous to each other.

66 Claims, 20 Drawing Sheets

```
BAZ      SWPFLKLVSKIQ--VPDYYDIIKKPIALNIIREKVNKCEYKLASEFIDDIELMFSNCFEYN
TFIID    SWPFLKPVNKKQ---VKDYYTVIKRPMDLETIGKNIEAHRYHSRAEYLADIELIATNCEQYN
CCG1     TYPFHTPVNAKV--VKDYYKIITRPMDLQTLRENVRKRLYPSREEFREHLELIVKNSATYN
PCAF     AWPFMEPVKRTE--APGYYEVIRSPMDLKTMSERLKNRYYVSKKLFMADLQRVFTNCKEYN
CBP      SLPFRQPVDPQLLGIPDYFDIVKNPMDLSTIKRKLDTGQYQEPWQYVDDVWLMFNNAWLYN

FIG. 1A

*                                                   *       *
BAZ      CKIC-----------------------RKKGDAEN---MVLCDGCDRGHHTYCV--RPKLKTVPEGD-WFCPEC
U13646   CQIC-----------------------KSMDGDE----MLVCDGCESGCHMECF--RPRMTKVPEGD-WFCQRC
RBBP2    CMFCG----------------------RGNNEDK----LLLCDGCDDSYHTFCL--IPPLPDVPKGD-WRCPKC
MOZ.1    CSFCLG---------------------TKEQNREKKPEELISCADCGNSGHPSCLKFSPELTVRVKALRWQCIEC
MOZ.2    CSSCRD---------------------QGKNADN----MLFCDSCDRGFHMECC--DPPLTRMPKGM-WICQIC
p300     CEKCFNEIQGESVSLGDDPSQPQTTINKEQFSKRKNDTLDPELFVECTECGRKMHQICV--LHHEIIWPAG--FVCDGC
CBP      CEKCFTEIQGENVTLGDDPSQPQTTISKDQFEKKKNDTLDPEPFVDCKECGKECGRKMHQICV--LHYDIIWPSG--FVCDNC

FIG. 1B
```

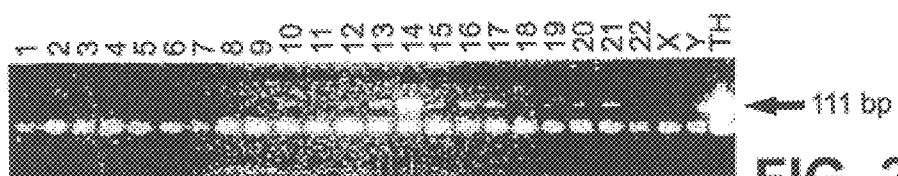
FIG. 2A
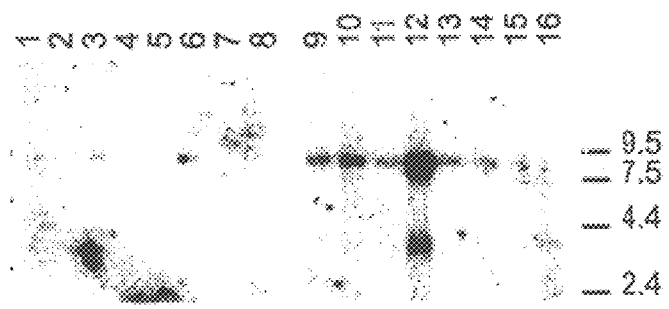
FIG. 3
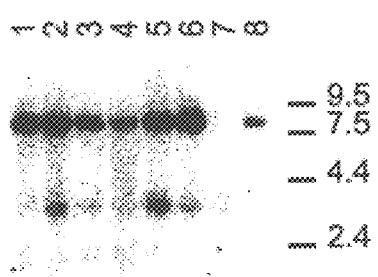
FIG. 4A
FIG. 4B

FIG. 6A bromodomains

```
BAZ     SWPFLKLVSKIQV--PDYDIIKKPIALNIIREK------------------------------VNKCEYKLASEFIDDIELMFSNCFEYN
CCG     SWPFHHPVNKKFV--PDYYKVIVNPMDLETIRKN------------------------------ISKHKYQSRESFLDDVNLILANSVKYN
BAZ2    AWPFLEPVNPRLV--SGYRRIIKNPMDFSTMRER------------------------------LLRGGYTSSEEFAADALLVFDNCQTFN
PCAF    AWPFMEPVKRTEA--PGYYEVIRSPMDLKTMSER------------------------------LKNRYYVSKKLFMADLQRVFTNCKEYN
U13646  ALPFLEPVNPKLV--PGYKMIISKPMDLKTIRQKNEKLIVSETYQFCFFAIFDLKLKMKITQYETPEDFAEDIELMFANCRQFN
CBP     SLPFRQPVDPQLLGIPDYFDIVKNPMDLSTIKRK------------------------------LDTGQYQEPWQYVDDVWLMFNNAWLYN
         *    *                                                                        *
```

FIG. 6B

C4HC3 Zn finger

```
BAZ     CKIC-------------------RKKGDAEN----MVLCDGCDRGHHTYCV--RPKLKTVPEGD-WFCPEC
U13646  CQIC-------------------KSMDGDE-----MLVCDGCESGCHMECF--RPRMTKVPEGD-WFCQRC
RBBP2   CMFCG------------------RGNNEDK-----LLLCDGCDDSYHTFCL--IPPLPDVPKGD-WRCPKC
MOZ.1   CSFCLG-----------------TKEQNREKKPEE-LISCADCGNSGHPSCLKFSPELTVRVKALRWQCIEC
MOZ.2   CSSCRD-----------------QGKNADN-----MLFCDSCDRGFHMECC--DPPLTRMPKGM-WICQIC
p300    CEKCFNEIQGESVSLGDDPSQPQTTINKEQFSKRKNDTLDPELFVECTECGRKMHQICVL--HHEIIWPAG--FVCDGC
BAZ2    CLVC-------------------RKGDNDE-----FLLLCDGCDRGCHIYCH--RPKMEAVPEGD-WFCTVC
         *   *                                 *    *   *    *       *             *
```

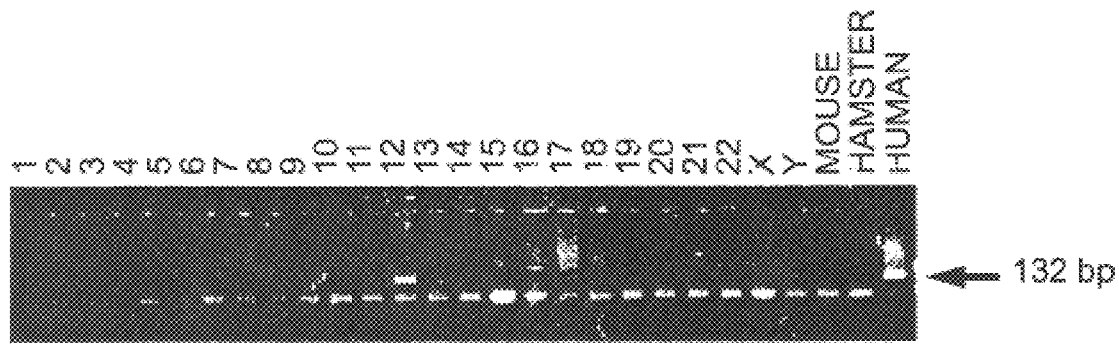
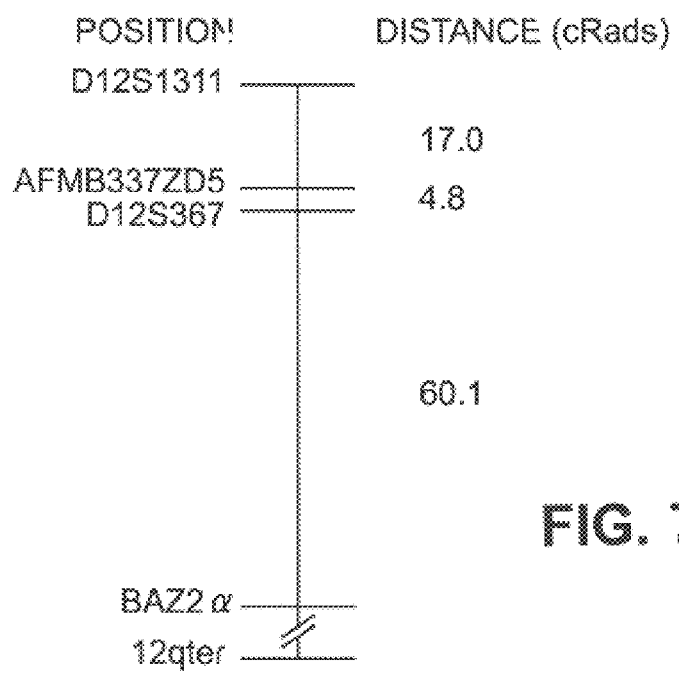
FIG. 7

```
baz1α    1   REEKRKYVEYLKQWSKPREDMEC..........................DDLKELPEPTPVKTR.LPPEIFG
u13646   1   LNDEFTEELVHSQIMSNGVDE.CKIREREADDLLVNINDVRHLPDFSRIGNQCLSSQGFA
baz2α    1   LEERQKQQMILEEMKKPTEDM.C...........................LTDHQPLPDFSRVPGLTLPSGAFS
baz2β    1   LEQRRLELEMAKELKKPNEDM.C...........................LADQKPLPELPRIPGLVLSGSTFS baz1α   46   DALMVLEFLNAFGEL..FDLQDEFPDGVTLEVLEEALVGN.DSEGI LCELL FFFLTAIFQ
u13646  60   DALMVHEFVQNFGHVLGIDLEI.APK...LESLCAGLDGDANHAEQTLQLTRQLLRLALE
baz2α   47   DCLTIVEFLHSFGKVLGFDPAKDVPS...LGVLQEGLLCQGDSLGEVQDI LVRLL KAALH
baz2β   47   DCLMVVQFLRNFGKVLGFDVNIDVPN...LSVLQEGLLNIGDSMGEVQDI LVRLL SAAVC baz1α  103   AIAEEEEEVAKEQLTDADTKGCSLKSLDLDSCTLSEIIRLHILASGADVTSANAKYRYQK
u13646 116   FPGM....GNEKRF.......GQGGGEMGLDRENFSEVMRLFLIDKGKR..........
baz2α  104   DPGFPSYCQSLKIL.........GEKVSEIPLTRDNVSEILRCFLMAYGVE........
baz2β  104   DPGLITGYKARTAL.........GEHLLNVGVNRDNVSEILQIFMEAHCGQ........

baz1α  163   RGGFDATDDACMELRLSNPSLVKKLSSTSVYDLTPGEKMKILHALCGKL
u13646 154   ..................GEELSQPLLTCNFLSISPEQKASILAFLCDEL
baz2α  146   ..................PAICDRLRTQPFQAQPPQQKAAVLAFPVHEL
baz2β  146   ..................TELTESLKTKAFQAHTPAQKASVLAFLINEL
```

FIG. 10

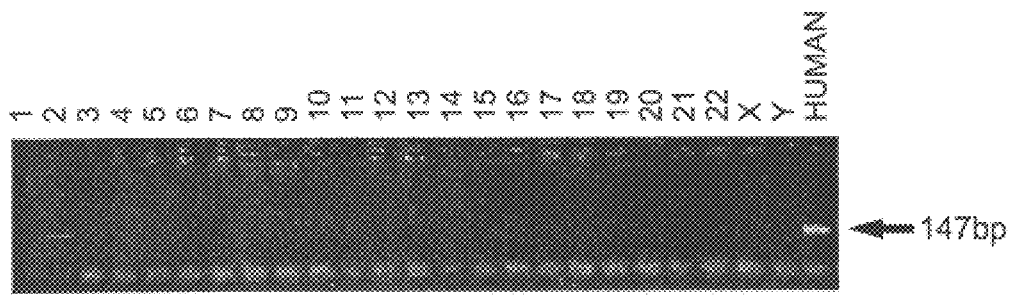
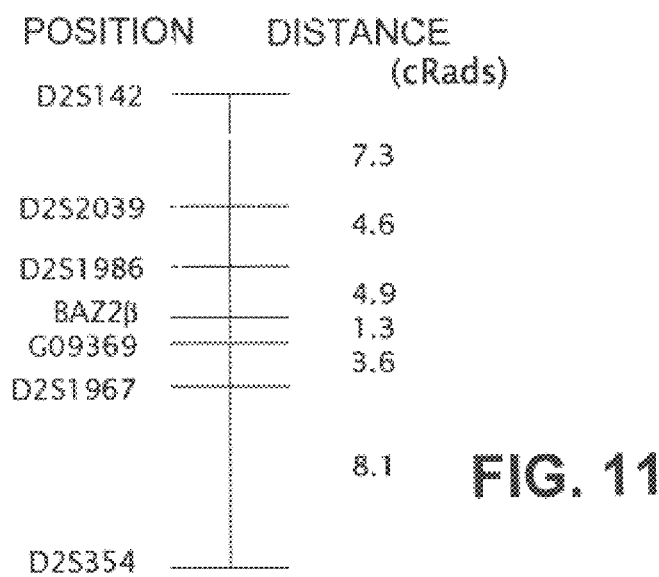
FIG. 11
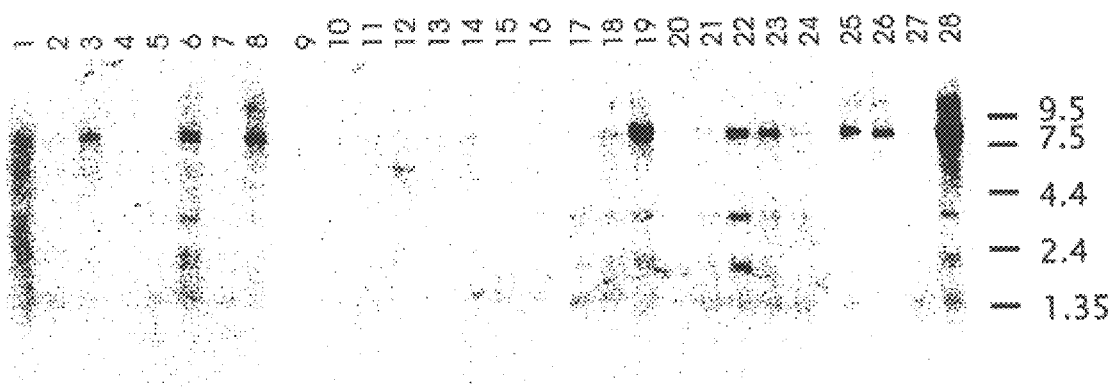
FIG. 12

```
              639            649              659            669            679         689
BA21βS  YPITAVSLMEALSADKGGFLYLNRVLVIL----LQTLLQDEIAEDYGELGMKLSEIPLTHSVSE
        ::::::::::::::::::::::::::::    ::::::::::::::::::::::::::::::::
BA21βL  YPITAVSLMEALSADKGGFLYLNRVLVILLQTLLQTLLQDEIAEDYGELGMKLSEIPLTHSVSE
              630            640              650            660            670            680            690
```

FIG. 13

```
BAZ1Bs    1  ................................................
BAZ1A     1  ................................................
BAZ2A     1  ............................MEMEANEANDHFNFTGL
BAZ2B     1  ................................................

BAZ1Bs    1  ................................................
BAZ1A     1  ................................................
BAZ2A    18  PPAPAASGLKPSPSSGEG.....LYTNGSPMNF.........PQQGKSLNGDVNVNGLS
BAZ2B     1  ......MGQTKSTSSGGGNRKCNQEQSKNQPLDARVDKIKDKKPRK.KAMESSSNSDSDS

BAZ1Bs    1  ................................................
BAZ1A     1  ................................................
BAZ2A    63  .TVSHTTTSGILNSAPHSSSTSHLHHPSVAYDCLWNYSQYPSANPGSNLKDPPLLSQFSG
BAZ2B    54  GTSSDTSSEGI.....SSSDSDDLEEDEEEEDQSIEESEDDDSDSESEAQHK......SN

BAZ1Bs    1  ................................................
BAZ1A     1  ................................................
BAZ2A   122  GQYPLNGILGGSRQPSSPSHNTNLRAGSQKFWANGTHSPMGLNFDSQELYDSFPDQNFE.
BAZ2B   103  NQVLLHGI....SDPKADGQKATEKAQEKRI.....HQPLPLAFESQT..HSFQSQQKQP

BAZ1Bs    1  ................................................
BAZ1A     1  MEDASESSRGVAPLINNVVLPGSPLSLPVSVTGCKSHRVANKKVEARSEKLLPTALPPSE
BAZ2A   181  EVCSGIHP........DEAAEKEMTSVVAENGTGLVCSLE....LEEEQPELKMCGYNGS
BAZ2B   152  QVLSQQLPFIFQSSQAKEESVNKHTSVI..QSTGLVSNVKPLSLVNQAKKETYM......

BAZ1Bs    1  ................................................
BAZ1A    61  PKVDQKLPRSSERRGSGGGTQFPARSRAVAAGEAAARGAAGPERGSPLGRRVSPRCLCSG
BAZ2A   229  VPSVESLHQEVSVLVPDPTVSCLDDPSHLPDQLEDTPILSED...SLEPFNSLAPEPVSG
BAZ2B   204  ..........KLIVPSPDVLKAGNK....NTSEESSLLTSELRSKREQYKQAFP.....

BAZ1Bs    1  ....................MAPLLGRKPFPLVNPLPGEEPF...FTIPHT
BAZ1A   121  EGGQVAVGVIAGKRGRRGRDGSRRAPGGREMPLLHRKPFVRQKPPADLRPDEEVFYCKVT
BAZ2A   286  GLYGIDDTELMGAEDKLPLEDSPVISALDCPSLNNATAFSLLADDSQTSTSIFASP.TSP
BAZ2B   244  .......SQLKKQESSKSLK..KVIAALSNPKATSSSP....AHPKQTLENNHPNPFLTN

BAZ1Bs   29  QEAFRTREEYEARLERYSERIWTCKSTGSSQLTHKEAWEEEQEVAELLKEEFPAWYEKLV
BAZ1A   181  NEIFRHYDDFFERTILCNSLVWSCAVTGRPGLTYQEALESEKKARQNLQS.FP...EPLI
BAZ2A   345  PVLG........ESVLQDNSFDLNNGSDAEQEEMETQSSDFPPSLTQPAPDQSSTIQLHP
BAZ2B   291  ALLGNHQPNGVIQSVIQEAPLALTTKTKMQSKINENIAAASSTPFSSPV.NLSTSGRRTP

BAZ1Bs   89  LEMVHHNTAS....LEKLVDTAWLEIMTKYAVGEECDFEVGKEKMLKVKIVKIHPLEKVD
BAZ1A   237  IPVLYLTSLTHRSRLHEICDDIFAYVKDRYFVEETVEVIRNNGARLQCTILEVLP.....
BAZ2A   397  ATSPAVSPTTSPAVSLVVSPAASPEISPEVCPAASTVVSPAVFSVV..............
BAZ2B   350  GNQTPVMPSASPILH...SQGKEKAVSNNVNPVKTQHHSHPAKSLVEQFRGTDSDIPSSK
```

FIG. 14

```
BAZ1Bs  145  EEATEKKSDGACDSPSSDKENSSQIAQDHQKK...ETVVKEDEGRRESINDRARRSPRKL
BAZ1A   292  ...............PS....HQNGFANGHVNSVDGETIIISDSDDSETQS..........
BAZ2A   443  ..............................................................
BAZ2B   407  DSEDSNEDEEEDDEEEDEEDDEDDESDDSQSESDSNSESDTEGSEEEDDDDKDQDESDSD

BAZ1Bs  202  PTSLKKGERKWAPPKFLPHKYDVK.LQNEDKIISNVPADSLIRTERPPNKEIVRYFTRHN
BAZ1A   324  .CSFQNGKKKDAIDPLL.FKYKVQPTKKELHESAIVKATQISRRKHLFSRDKLKLFLKQH
BAZ2A   443  ..........SPASSAVLPAVSLEVPLTASVTSPKASPVTSPAAAFP.TASPANKDVSS
BAZ2B   467  TEGEKTSMKLNKTTSSVKSPSMSLTGHSTPRNLHIAKAPGSAPAALCSESQSPA......

BAZ1Bs  261  ALRAGTGENAPWVVEDELVKKYSLPS......KFSDFLLDPYKYMTLNPSTKRKNTGSPD
BAZ1A   382  C......EPQEGVIK...IKASSLSTYKIAEQDFSYFFPDDPPTFIFSPANRRR..GRPP
BAZ2A   491  FLETTADVEEITGEGLTASG.SGDVMRRRIATPEEVRLPLQHGWRREVRIKKGSHRWQGE
BAZ2B   521  FLGTSSST.......LTSSPHSGTSKRRRVTDERELRIPLEYGWQRETRIRNFGGRLQGE

BAZ1Bs  315  RKPSKKSKTDNSSLSSPLNPKLWCHVHLKKSLSGSPLKVKNSKNSKSPEEHLEEMMKMMS
BAZ1A   431  KRI.HISQEDN..............VANKQTLA........SYRSKATKER.........
BAZ2A   550  TWYYGPCGKRMKQFPEVIKYLSRNLVHSVRREHFSFSPRMPVGDFFEERDTPEGLQWVQL
BAZ2B   574  VAYYAPCGKKLRQYPEVIKYLSRNGIMDISRDNFSFSAKIRVGDFYEARDGPQEMQWCLL

BAZ1Bs  375  PNKLHTNFHIPKKGPPAKKPGKHSDKPLKAKGRSKGILNGQKSTGNSKSPKKGLKTPKTK
BAZ1A   459  ......................DKLLK................QEEMKSLAFEKAK
BAZ2A   610  SAEEIPSRIQAITGKRGRPRNTEKAKTKEVPKVKRGRGRPPKVKITELLNKTDNRPLKKL
BAZ2B   634  KEEDVIPRIRAMEGRRGRPPNPDRQRAREESRMRRRKGRPPNVGNAEFLDNADAKLLRKL

BAZ1Bs  435  MKQMTLLDMAKGTQKMTRAPRNSGGTPRTSSKPHKHLPPAALHLIAYYKENKDREDKRSA
BAZ1A   477  LKR............................EKADALEAKKKEKEDKEKKR..
BAZ2A   670  EAQET...........LNEEDKAKIAKSKKKMR......QKVQRGECLTTIQGQARNKR
BAZ2B   694  QAQEIARQAAQIKLLRKLQKQEQARVAKEAKKQQAIMAAEEKRKQKEQIKIMKQQEKIKR

BAZ1Bs  495  LSCVISKTARLLSSEDRARLPEELRSLVQKRYELLEHKKRWASM................
BAZ1A   500  ..................EELKKIVEEER...........L...............
BAZ2A   712  KQETKSLKHK......EAKKKSKAEKEKGKT..KQEKLKEK.........VKREKKEKVK
BAZ2B   754  IQQIRMEKELRAQQILEAKKKKKEEAANAKLLEAEKRIKEKEMRRQQAVLLKHQERERRR

L           L         L L              L
BAZ1Bs  539  ...........SEEQRKEYLKKKREELKKKLKEKAKERREKEMLERLEKQKR.YEDQEL
BAZ1A   512  ...........KKKEEKERLKVEREKEREKLREE.....KRKYVEYLKQWSKPREDMEC
BAZ2A   755  M..........KEKEEVTKAKPACKADK.TLATQRRLEERQKQQMILEEMKKPTEDMCL
BAZ2B   814  QHMMLMKAMEARKKAEEKERLKQEKRDEK.RLNKERKLEQRRLELEMAKELKKPNEDMCL

L       L L          L       L    LL           L   L    LL
BAZ1Bs  586  TG.KNLPAFRLVDTPEGLPNTLFGDVAMVVEFLSCYSGLLLPDAQYP..ITAVSLMEAL.
BAZ1A   555  DDLKELPEPTPVKT..RLPPEIFGDALMVLEFLNAFGELFDLQDEFPDGVTLEVLEEALV
BAZ2A   803  TDHQPLPDFSRVPGLT.LPSGAFSDCLTIVEFLHSFGKVLGFDPAK.DVPSLGVLQEGLL
BAZ2B   873  ADQKPLPELPRIPGLV.LSGSTFSDCLMVVQFLRNFGKVLGFDVNI.DVPNLSVLQEGLL
```

FIG. 15

```
                  LXXLL     L      LXXLLXXLL
BAZ1Bs  642  S.ADKGG......FLYLNRVLVILLQTLLQDEIAE....DYGELGMKLSEIPLTLHSVSE
BAZ1A   613  G.NDSEGPLCELLFFFLTAIFQAIAEE..EEEVAKEQLTDADTKGCSLKSLDLDSCTLSE
BAZ2A   861  CQGDSLGEVQDL........LVRLLKAALHDPGFPSYCQSLKILGEKVSEIPLTRDNVSE
BAZ2B   931  NIGDSMGEVQDL........LVRLLSAAVCDPGLITGYKAKTALGEHLLNVGVNRDNVSE

L L                                             L L        L
BAZ1Bs  691  LVRLCLRRSDVQEESEGSDTD.......DNKDSAAFEDNEVQDEFLEKLETSEFFELTSE
BAZ1A   670  ILRLHILASGADVTSANAKYRYQKRGGFDATDDACMELRLSNPSLVKKLSSTSVYDLTPG
BAZ2A   913  ILRCFLMAYGVE.............................PALCDRLRTQPFQAQPPQ
BAZ2B   983  ILQIFMEAHCGQ.............................TELTESLKTKAFQAHTPA

L     L    LL
BAZ1Bs  744  EKLQILTALCHRILMTYSVQD......................HMETRQQMSAELWKER
BAZ1A   730  EKMKILHALCGKLLTLVSTRDFIEDYVDILRQAKQEFRELKAEQHRKEREEAAARIRKRK
BAZ2A   943  QKAAVLAFPVHELNGSTLIINEIDKTLESM...........SSYRKNKWIVEGRLRR..
BAZ2B  1013  QKASVLAFLINELACSKSVVSEIDKNIDYM...........SNLRRDKWVVEGKLRK..

BAZ1Bs  781  LAVLKEENDKKRAEKQKRKEMEAKNKENGKVENGLGKTDRKKRIVKFEPQVDTEA....E
BAZ1A   790  EEKLKEQEQKMKEKQEKLKEDEQRNS...TADISIGEEEREDFDTSIESK.DTEQKELDQ
BAZ2A   989  ...LKTVLAKRTGRSE....VEMGRPEECLG.......RRRSSRIM.E.........ETS
BAZ2B  1059  ...LRIIHAKKTGKRDTSGGIDLGEEQHPLGTPTPGRKRRRKGGDS.DYDDDDDDDSDDQ

BAZ1Bs  837  DMI........SAVKSRRLLAIQAK.KEREIQEREMKV..KLERQAEEEERIRKHKAAAEK
BAZ1A   846  DMFTEDEDDPGSHKRGRRGKRGQNGFKEFTRQEQINCVTRELLTADEEEALKQEHQRKEK
BAZ2A  1025  GMEEEEEEESIAAVPGRRGR..RDGE.....VDATASSIPELERQIEKLSKRQLF.....
BAZ2B  1115  GDEDDEDEEDKEDQKGKKTDICEDED.....EGDQAASVEELEKQIEKLSKQQSQ.....

BAZ1Bs  886  AFQEGIAKAKLVMRRTPIGTDRNHNRYWLFSDEVPGLFIEK...GWV.HDSIDYRFNHHC
BAZ1A   906  ELLEKIQSAIACTNIFPLGRDMYRRYWIFPS.IPGLFIEEDYSGLT.EDMLLPRPSSF.
BAZ2A  1073  .FRKKLLHSSQMLRAVSLGQDRYRRRYWVLPY.LAGIFVEGTEGNLVPEEVIKKETDSLK
BAZ2B  1165  .YRRKLFDASHSLRSVMFGPDRYRRRYWILPR.CGGIFVEGMESGEGLEE.IAKEREKLK

LXXLL
BAZ1Bs  942  KDHTVSGDEDYCPRSKKANLGKNASMNTQHGTATE.........................
BAZ1A   963  QNNVQSQDPQVSTKTGEPLMSESTS.NIDQGPRDH.........................
BAZ2A  1131  VAAHASLNPALFSMKMELAGSNTTASSPARARSRP.LKTKPG...FMQ.PRHFKSPVRGQ
BAZ2B  1222  KAESVQIKEEMF....ETSGDSLNCSNTDHCEQKEDLKEKDNTNLFLQKPGSFSKLSKLL

BAZ1Bs  977  .............................................................
BAZ1A   997  .............................................................
BAZ2A  1186  DSEQPQAQLQPEAQLHVPAQPQPQLQLQLQSHKGFLEQEGSPLSLGQSQHDLSQSAFLSW
BAZ2B  1278  EV....AKMPPESEVMTP.KPNAGANGCTLSY.....QNSGKHSLGSVQSTATQSN....

BAZ1Bs  977  .............................................................
BAZ1A   997  .............................................................
BAZ2A  1246  LSQTQSHSSLLSSSVLTPDSSPGKL.DPAPSQPPEEPEPDEAESSPDLQAFWFNISAQMP
BAZ2B  1324  VEKADSNNLFNTGS.....SGPGKFYSPLPNDQLLKTLTEKNRQ.......WFSLLPRTP
```

FIG. 16

```
BAZ1Bs  977  ................................................
BAZ1A   997  ................................................
BAZ2A  1305  CNAAP.......TPPLAVSEDQP.....TPSPQQLASSKPMNRPSAANPC...SPVQFSS.
BAZ2B  1372  CDDTSLTHADMSTASLVTPQSQPPSKSPSPTPAPLGSS..AQNPVGLNPFALSPLQVKGG

BAZ1Bs  977  ................................................
BAZ1A   997  ................................................
BAZ2A  1350  TPLAGLAPKRRAGDPG...........EMPQSPTGLGQPKRRGRPPSKFFKQMEQRYLTQ
BAZ2B  1430  VSMMGL...QFCGWPTGVVTSNIPFTLSVPSLGSGLGLSEGNG...........NSFLTS

LXXLL
BAZ1Bs  977  .............................VAVETTTPKQGQNLWFLCDSQKELDELL
BAZ1A   997  .............................SVQLPKPVHKPNRWCFYSSCEQLDQLI
BAZ2A  1399  LTA..........................QPVPPEMCSGWWWIPDPEMLDAML
BAZ2B  1476  NVASSKSESPVPQNEKATSAQPAAVEVAKPVDFPSPKPIPEEMQFGWWRIIDPEDLKALL

BAZ1Bs 1005  NCLHPQGIRESQLKERLEKRYQDIIHSI........HLARKPNLGLKS............
BAZ1A  1024  EALNSRGHRESALKETLLQEKSRICAQLARFSEEKFHFSDKPQPDSKPTYSRGRSSNAYD
BAZ2A  1426  KALHPRGIREKALHKHLNK.................HRDFLQEVCLRPS......ADPIF
BAZ2B  1536  KVLHLRGIREKALQKQIQK.................HLDYITQACLKNK......DVAII

BAZ1Bs 1045  ....CDGNQELLNFLRSDLIEVATRLQKGGLGYVEETSEFEARVISLEKLKDFGECVIAL
BAZ1A  1084  PSQMCAEKQLELR.LRDFLLDIEDRIYQGTLGAIKVTDRHIWR.................
BAZ2A  1463  EPRQLPAFQ...EGIMSW..SPKEKTYETDLAVLQWVEELEQRVIMSDLQIRGWTCPSPD
BAZ2B  1573  ELNENEENQVTRDIVENW..SVEEQAMEMDLSVLQQVEDLERRVASASLQVKGWMCPEPA

BAZ1Bs 1101  QASVIKKFLQGFMAPKQKRR...KLQSEDSAKTEEVDEEKKMVEEAKV............
BAZ1A  1126  ..SALESGRYELLSEENKENGIIKTVNED.VEEMEIDEQTKVIVKDRLLGIKTETPSTVS
BAZ2A  1518  ST.......REDLAYCEHLSDSQ....EDITWRGPGREGL.APQRKTTNPLDLAVMRLAA
BAZ2B  1631  SE.......REDLVYFEHKSFTKLCKEHDGEFTGEDESSAHALERKSDNPLDIAVTRLAD

BAZ1Bs 1146  ..............................ASALEKWKTAIREAQ
BAZ1A  1183  TNASTPQSVSSVVHYLAMALFQIEQGIERRFLKAPLDASDSGRSYKTVLDRWRESLLSSA
BAZ2A  1566  LEQNVKRRYLREPLWPTHEVVLEKALLSTPNGAPEGTTTEISYEITPRIRIWRQTLQRCR
BAZ2B  1684  LERNIERR.................IEEDIAPGLRVWRRALSEAR

C   C              C    C      H    C
BAZ1Bs 1161  TFSRMHVLLGMLDACIKWDMSAENARCKVCPKKGEDDKLILCDECNKAFHLFCLRPALYE
BAZ1A  1243  SLSQVFLHLSTLDRSVIWSKSILNARCKICRKKGDAENMVLCDGCDRGHHTYCVRPKLKT
BAZ2A  1626  SAAHVCLCLGHLERSIAWEKSVNKVTCLVCRKGDNDEFLLLCDGCDRGCHIYCHRPKMEA
BAZ2B  1712  SAAQVALCIQQLQKSIAWEKSIMKVYCQICRKGDNEELLLLCDGCDKGCHTYCHRPKITT

C   C
BAZ1Bs 1221  VPDGEWQCPACQPAT.ARRNS.RGRNYTE.ESASEDS...EDDESDEEEEEEEEEE..
BAZ1A  1303  VPEGDWFCPECRPKQRCRRLSFRQRPSLESDEDVEDSMGGEDDEVDGDEEEGQSEEEEYE
BAZ2A  1686  VPEGDWFCTVC..............................................
BAZ2B  1772  IPDGWFCPAC................................................
```

FIG. 17

```
BAZ1Bs1273 ........EDYEVAGLRLR........PRKTIRGKHSVIPPAARSGRRPGKKPHSTRRSQP
BAZ1A  1363 VEQDEDDSQEEEEVSLPKRGRPQVRLPVKT.RGKLSSSFSSRGQQQEPGRYPSRSQQSTP
BAZ2A  1697 ................LAQ...........QVEGEFT.............QKPGFPKRGQK
BAZ2B  1783 ...............IAKASGQTLKIKKLHVKG................KKTNESKKGKK

BAZ1Bs1318 K...............APPVDDAEVDELVLQTK........................
BAZ1A  1422 KTTVSSKTGRSLRKINSAPPT...ETKSLRIASRSTRHSHGPLQADVFVELLSPRRKRRG
BAZ2A  1718 ...........RKSGYSLNFSEGDGRR..............................
BAZ2B  1812 VTLTGDTEDEDSASTSSSLKRGNKDLQK..............................

BAZ1Bs1336 ........................................................
BAZ1A  1479 RKSANNTPENSPNFPNFRVIATKSSEQSRSVNIASKLSLQESESKRRCRKRQSPEPSPVT
BAZ2A  1734 ...............RRVLLKGRESPAAGPRYSEERLSPSKRRRLSMRNHHS......
BAZ2B  1840 .................RKM.....EENTSINLSKQESFTSVKKPK...RDDSK......

Bromodomain motif
BAZ1Bs1336 ...RSSRRQS..LELQKCEEILHKIVKYRFSWPFREPVTRDEAEDYYDVITHPMDFQTVQ
BAZ1A  1539 LGRRSSGRQGGVHELSAFEQLVVELVRHDDSWPFLKLVSKIQVPDYYDIIKKPIALNIIR
BAZ2A  1771 ..............DLTFCEIILMEMESHDAAWPFLEPVNPRLVSGYRRIIKNPMDFSTMR
BAZ2B  1869 ..............DLALCSMILTEMETHEDAWPFLLPVNLKLVPGYKKVIKKPMDFSTIR LXXL
BAZ1Bs1391 NKCSCGSYRSVQEFLTDMKQVFTNAEVYNCRGSHVLSCMVKTE............QCLVVL
BAZ1A  1599 EKVNKCEYKLASEFIDDIELMFSNCFEYNPRNTSEAKAGTRLQAFEH......IQAQKLG
BAZ2A  1818 ERLLRGGYTSSEEFAADALLVFDNCQTFNEDDSEVGKAGHIMRRFFESRWEEFYQGKQAN
BAZ2B  1916 EKLSSGQYPNLETFALDVRLVFDNCETFNEDDSDIGRAGHNMRKYFEKKWTDTFKVS...

L
BAZ1Bs1440 LH......KHLPGHPYVRRKRKKFPDRLAEDEGDSEPEAVGQSRDEDRRSREAEIQEWLQ
BAZ1A  1653 LHVTPSNVDQVSTPPAAKKSRI......................................
BAZ2A  1878 L.........................................................
BAZ2B  1973 ..........................................................

BAZ1Bs1494 DTSLYSAKINSKDHNCFMMLVNTQFCMALTDTVT
BAZ1A  1675 ..................................
BAZ2A  1879 ..................................
BAZ2B  1973 ..................................
```

FIG. 18

NUCLEIC ACIDS ENCODING BAZ1α TRANSCRIPTIONAL REGULATOR AND METHODS OF USE

This is a continuation-in-part of PCT/JP98/01783, filed Apr. 17, 1998, and claims priority from Japanese Application Nos. 9/116570, filed Apr. 18, 1997, and 9/310027, filed Oct. 24, 1997.

TECHNICAL FIELD

The present invention relates to a novel transcriptional regulator containing a bromodomain and a gene encoding it.

BACKGROUND ART

The bromodomain is a characteristic motif of proteins found in transcriptional regulators. Proteins having a bromodomain usually contain one or two (Tamkun, J. W. et al., (1992), Nuc. Acids Res., 20:2603), but sometimes as many as five bromodomain motifs (Nicolas, R. H. and Goodwin, G. H. (1996), Gene, 175 (12):233–240). This motif is found in a wide variety of animals. For example, it is identified in yeast (Winston, F. et al., (1987), Genetics, 115:649–656; Laurent, B. C. et al., (1991), Proc. Natl. Acad. Sci. USA, 88:2687–2691), in Drosophila (Digan, M. E. et al., (1986), Dev. Biol., 114:161–169; Tamkun, J. W. et al., (1992), Cell, 68:561–572), and in the genes for transcriptional regulators in mammals (Denis, G. V. and Green, M. R. (1996), Genes and Devel., 10:261–271; Yang, X. J. et al., (1996), Nature, 382:319–324).

All transcriptional regulators containing a bromodomain serve to control signal-dependent transcription in actively proliferating cells (Tamkun, J. W. et al., (1992), Cell, 68:561–572; Haynes, S. R. et al., (1992), Nuc. Acids Res., 20:2603). Due to this feature of these transcriptional regulators, it is suggested that cancer may develop if the gene for the protein containing a bromodomain is not normally controlled. In fact, several studies have shown that human transcriptional regulators with a bromodomain RING3, p300/CBP, and PCAF may be involved in oncogenesis.

RING3 is a transcriptional regulator highly homologous with the fsh protein that regulates development of Drosophila (Haynes, S. R. et al., (1989), Dev. Biol., 134:246–257). RING3 is a nuclear serine/threonine kinase having autophosphorylating activity. This activity of RING3 correlates with a proliferating state in chronic or acute lymphocytic leukemia. For instance, when Denis and Green collected lymphocytes of peripheral blood from 10 patients suffering from leukemia, kinase activity associated with RING3 was identified in all of the 10 patients but not in normal controls (Denis, G. V. and Green, M. R. (1996), Genes and Develop., 10:261–271). Furthermore, this activity was not detected in the blood cells from patients whose leukemia had remitted by virtue of chemotherapy.

p300 and CBP (CREB binding protein) encode highly similar proteins and are thus often called p300/CBP. p300/CBP is a co-activatot for a transcriptional regulator CREB (cAMP responsive element binding protein) (Kwok, RPS et al., (1994), Nature, 370:223–226), and is considered as a key protein for growth regulation. Mutation in p300/CBP has been found in familial or sporadic cancers. Germline mutation of CBP results in Rubinstein-Taybi syndrome, which causes patients to develop various malignant tumors (Petrij, F. et al., (1995), Nature, 376:348–51), while mutation in p300 is found in sporadic colorectal and gastric cancers (Muraoka, M. et al., (1996), Oncogene, 12:1565–1569). Furthermore, CBP is fused with MOZ (Monocytic leukemia Zinc finger protein) in a t (8; 16) (p11; p13) translocation found in a certain kinds of acute myelocytic leukemia. The fusion protein has histone-acetyltransferase domains derived from both genes (Bannister, A. J. and Kouzarides, T. (1996), Nature, 384:641–643; Orgyzco, V. V. et al., (1996), Cell, 87:953–959; Brownwell, J. E. and Allis, C. D. (1996), Curr. Opin. Genet. Devel., 6:176–184). Since acetylated histone is known to be associated with transcriptionally active chromatin, the fusion protein may be involved in leukemogenesis by way of aberrant histone acetylation (Brownwell, J. E. and Allis, C. D. (1996), Curr. Opin. Genet. Devel., 6:176–184).

p300/CBP is also considered to be associated with cancer since it interacts with known oncogene products. For example, p300/CBP binds to E1A protein (Arany, Z. et al., (1995), Nature, 374:81–84), one of the early genes of adenovirus. p300 is also a co-activator for transcription factors, c-Myb (Dai, P. et al., (1996), Genes Dev., 10:528–540) and c-Fos (Bannister, A. J. and Kouzarides, T. (1996), Nature, 384:641–643).

PCAF, is considered to inhibit the interaction of E1A with p300/CBP by competing with E1A for binding to p300/CBP (Yang, X. J. et al., (1996), Nature, 382:319–324). PCAF also has histone-acetyltransferase activity.

Thus, it is thought that transcriptional regulators containing a bromodomain areinvolved in regulation ofcell growth, and that their aberrant regulation may be closely related to various diseases, particularly to cancer. Transcriptional regulators containing a bromodomain have thus recently received much attention as novel targets for specifically treating cancer.

DISCLOSURE OF THE INVENTION

The objective of the present invention is to provide a novel transcriptional regulator containing a bromodomain and a gene encoding it, and a method of screening for a candidate compound as a medicament by using them.

As a result of research to achieve the above objective, the inventors successfully isolated several genes, each of which encodes a novel transcriptional regulator containing a bromodomain. The genes were isolated from a human testis cDNA library using primers designed based on EST sequences which had been identified using known bromodomain sequences as probes. In addition, the inventors have found that the structures of the isolated genes resemble one another, thus they constitute a family. The inventors have also found that the isolated genes or proteins encoded by them can be used to screen the candidate compounds for a medicament that controls the activity of the proteins or other factors interacting therewith.

Thus, the present invention relates to novel transcriptional regulators each having a bromodomain and the genes encoding them, and to a method of screening for a candidate compound as a medicament using said proteins or genes, and more specifically relates to:

(1) a transcriptional regulator having a bromodomain, which comprises the amino acid sequence shown in SEQ ID NO:1, 13, 21, 27, or 29, or said sequence wherein one or more amino acids are substituted, deleted, or added;

(2) a transcriptional regulator having a bromodomain, which is encoded by DNA hybridizing with DNA comprising the nucleotide sequence shown in SEQ ID NO:2, 14, 22, 28 or 30;

(3) DNA coding for the transcriptional regulator according to (1) or (2);

(4) a vector comprising the DNA according to (3);

(5) a transformant expressibly retaining the DNA according to (3);

(6) a method for producing the transcriptional regulator according to (1) or (2), which comprises culturing the transformant according to (5);

(7) an antibody binding to the transcriptional regulator according to (1) or (2);

(8) a method of screening a compound having binding activity to the transcriptional regulator according to (1) or (2), wherein the method comprises contacting a sample with the transcriptional regulator according to (1) or (2) and selecting a compound having binding activity to the transcriptional regulator according to (1) or (2);

(9) a compound having binding activity to the transcriptional regulator according to (1) or (2), which can be isolated according to the method of (8);

(10) the compound according to (9), which is naturally occurring; and

(11) DNA specifically hybridizing with DNA comprising the nucleotide sequence shown in SEQ ID NO:2, 14, 22, 28, or 30 and having at least 15 nucleotides.

Here, the term "transcriptional regulator(s)" means protein(s) that control gene expression, and "bromodomain" means an amino acid motif conserved among the transcriptional regulators associated with signal-dependent transcription, wherein said motif is involved in protein-protein interaction.

The present invention relates to novel transcriptional regulators having a bromodomain (BAZ family). The nucleotide sequences of cDNA isolated by the inventors, which belong to BAZ family, are shown in SEQ ID NO:2 (BAZ (BAZ1α)), SEQ ID NO:14 (BAZ2α), SEQ ID NO:22 (BAZ2β), and SEQ ID NO:28 and 30 (BAZ1β). The amino acid sequences of proteins encoded by the cDNA are also shown in SEQ ID NO:1 (BAZ(BAZ1α)), SEQ ID NO:13 (BAZ2α), SEQ ID NO:21 (BAZ2β), and SEQ ID NO:27 and 29 (BAZ1β).

The bromodomain is characteristic of a structural region that is conserved among a group of transcriptional regulators involved in signal-dependent transcription (Tamkun, J. W. et al., (1992), Cell, 68:561–572; Haynes, S. R. et al., (1992), Nuc. Acids Res., 20:2603), and it has been reported that the six mammalian genes, i.e., RING3, p300/CBP, PCAF, BRG1, HRX/ALL-1, and TIF1, which encode transcriptional regulators having a bromodomain, are associated with cancer. That the transcriptional regulators having a bromodomain are commonly associated with cancer suggests that the genes isolated by the inventors are also associated with cancer. Other than a bromodomain motif, the proteins encoded by the genes isolated by the inventors share the characteristic motifs of (1) C4HC3 zinc-finger, which is found in the proteins expressed in a wide range of organisms from yeast to human and is believed to be involved in a protein-protein interaction or nonspecific binding to DNA; (2) leucine zipper, which is present in many transcriptional regulators and is known to contribute to form a dimer with the protein itself or other proteins (Busch, S. J. and Sassone-Corsi, P (1990), Trends in Genetics, 6:36–40); (3) LXXLL (SEQ ID NO:37) motif, a motif commonly found among many transcriptional co-activators, which is shown to be required for mediation of transcription induced by a nuclear receptor (Torchia, J. et al., (1997), Nature, 387:677–684; Heery, D. M. et al., (1997), Nature, 387:733–736); and (4) nuclear transport signal, which confers the transporting activity into the nucleus on the proteins synthesized in the cytoplasm.

The combination of a bromodomain and C4HC3 zinc finger is known to be associated with several breakpoint genes of leukemia (Tkachuk, D. C. et al., (1992), Cell, 71:691–700; Gu, Y. et al., (1992), Cell, 71:701–798; Miki, T. et al., (1991), Proc. Nat. Acad. Sci., 88:5167–5171; Le Douarin B. et al., (1995), EMBO J., 14:2020–2033; Borrow, J. et al., (1996), Nature Genet., 14:33–41). Accordingly, the genes isolated by the inventors are important candidates for breakpoint genes of cancers.

The transcriptional regulators of the present invention can be prepared as recombinant proteins generated using a recombinant gene technique, or as naturally occurring proteins, according to a method known to one skilled in the art. The recombinant proteins can be prepared using a method such as incorporating DNA encoding a transcriptional regulator of the present invention (e.g., DNA having the nucleotide sequence shown in SEQ ID NO:2, 14, 22, 28, or 30) into a suitable expression vector, which is then introduced into host cells, and purifying the protein obtained from the transformant. The naturally occurring proteins can be prepared using a method such as preparing a column which utilizes an antibody obtained from a small animal immunized with the recombinant protein prepared as above, and subjecting the extract from a tissue or cells in which a transcriptional regulator of the present invention is overexpressed (e.g., testis and cancer cells) to affinity chromatography using said column.

The present invention also relates to transcriptional regulators functionally equivalent to the transcriptional regulators of the present invention having the amino acid sequence shown in SEQ ID NO:1, 13, 21, 27, or 29. A method of introducing mutation into amino acids of a protein to isolate a protein functionally equivalent to a particular protein is well known to one skilled in the art. Thus, it is well within the art of an ordinarily skilled person to isolate a transcriptional regulator functionally equivalent to the transcriptional regulators of the present invention having the amino acid sequence shown in SEQ ID NO:1, 13, 21, 27, or 29 by appropriately modifying, for example, substituting amino acids without affecting the function of the transcriptional regulator. Mutation in an amino acid of a protein can also occur spontaneously. The transcriptional regulators of the present invention include those having a bromodomain and the amino acid sequence of SEQ ID NO:1, 13, 21, 27, or 29 wherein one or more amino acids are substituted, deleted, or added. Examples of known methods for introducing amino acid mutation into the protein are a site-directed mutagenesis system using PCR (GIBCO-BRL, Gaithersburg, Md.) and a site-directed mutagenesis using oligonucleotides (Kramer, W. and Fritz, H. J. (1987), Methods in Enzymol., 154:350–367). The number of mutagenized amino acids is usually 50 amino acids or less, preferably 30 amino acids or less, more preferably 10 amino acids or less, and most preferably three amino acids or less.

As another method of isolating a functionally equivalent protein utilizing a hybridization technique (Sambrook, J. et al., Molecular Cloning 2nd ed. 9.47–9.58, Cold Spring Harbor Lab. press, 1989) is well known to one skilled in the art. Based on the DNA sequence encoding the transcriptional regulator of the present invention shown in SEQ ID NO:2, 14, 22, 28, or 30, or the fragment thereof, a person with ordinary skill in the art can isolate DNA highly homologous to said DNA sequences using a hybridization technique (Sambrook, J. et al., Molecular Cloning 2nd ed. 9.47–9.58, Cold Spring Harbor Lab. press, 1989) to obtain a transcriptional regulator functionally equivalent to the transcriptional regulators. The transcriptional regulators of the present invention include those encoded by DNA that hybridizes with DNA comprising the DNA sequence shown in SEQ ID NO:2, 14, 22, 28, or 30, and which contains a bromodomain. The hybridization and washing conditions for isolating DNA encoding a functionally equivalent protein are defined as low stringency: 42° C., 2×SSC, 0.1% SDS; moderate stringency: 50° C., 2×SSC, 0.1% SDS; and high stringency: 65° C., 2×SSC, 0.1% SDS. The transcriptional regulators obtained by the hybridization technique may have amino acid homology of preferably 40% or more, more preferably 60% or more, still more preferably 80% or more, or most preferably 95% or more, with the transcriptional regulators having the amino acid sequence shown in SEQ ID NO:1, 13, 21, 27, or 29. In particular, high homology in the bromodomain sequence is considered significant for the function associated with cancer. Functionally equivalent transcriptional regulators to be isolated may contain, other than a bromodomain, a sequence involved in interaction with another protein (e.g., leucine-zipper or LXXLL (SEQ ID NO:37) motif), a sequence involved in binding to DNA (e.g. zinc finger), or a nuclear transport signal. The presence of the bromodomain in the protein can be identified by searching the bromodomain motif PROSITE database on DNASIS (HITACHI Software engineering).

The present invention also relates to DNA that codes for a transcriptional regulator of the present invention. The DNA of the present invention includes cDNA, genomic DNA, and chemically synthesized DNA, but is not limited thereto as long as it codes for a transcriptional regulator of the present invention. cDNA can be prepared, for example, by designing a primer based on the nucleic acid sequence shown in SEQ ID NO:2, 14, 22, 28, or 30 and performing plaque PCR (see Affara, N. A. et al., (1994), Genomics, 22:205–210). The genomic DNA can be prepared according to a standard technique using, for example, Qiagen genomic DNA kits (Qiagen, Hilden, Germany). The DNA sequence thus obtained can be determined according to a standard technique using a commercially available dye terminator sequencing kit (Applied Biosystems) and the like. In addition to applying to the production of recombinant proteins as described below, the DNA of the present invention may be applied to gene therapy and the like.

The present invention also relates to a vector into which the DNA of the present invention is inserted. There is no particular limitations to the vector into which the DNA of the present invention is inserted, and various types of vectors, e.g. for expressing the transcriptional regulators of the present invention in vivo and for preparing recombinant proteins, may be used for each purpose. Vectors used for expressing the transcriptional regulators of the present invention in vivo (in particular, for gene therapy) include the adenovirus vector pAdexLcw and the retrovirus vector pZIPneo. A LacSwitch II expression system (Stratagene; La Jolla, Calif.) is advantageous when mammalian cells, such as CHO, COS, and NIH3T3 cells, are used. An expression vector is particularly useful for producing a transcriptional regulator of the present invention. Although there is no particular limitation to the expression vectors, the following vectors are preferred: pREP4 (Qiagen, Hilden, Germany) when E. coli is used; SP-Q01 (Stratagene, La Jolla, Calif.) when yeast is used; and BAC-to-BAC baculovirus expression system (GIBCO-BRL, Gaithersburg, Md.) when insect cells are used. The DNA of the present invention can be inserted into vectors using a standard method.

The present invention also relates to a transformant expressibly retaining the DNA of the present invention. The transformants of the present invention include one harboring the above-described vector into which the DNA of the present invention is inserted and one having the DNA of the present invention integrated into its genome. The DNA of the present invention can be retained in the transformant in any form as long as the transformant expressibly retains the DNA of the present invention.. There is no limitation to host cells into which a vector of the present invention is introduced. If the cells are used to express a transcriptional regulator of the present invention in vivo, desired cells may be used as target cells. Cells such as E. coli, yeast cells, animal cells, and insect cells can be used for producing the transcriptional regulators of the present invention. The vector can be introduced into the cells by methods such as electroporation and heat shock. Recombinant proteins can be isolated and purified from the transformants generated for producing the said proteins according to a standard method.

The present invention also relates to antibodies that bind to the transcriptional regulators of the present invention. The antibodies of the present invention include, but are not limited to, polyclonal and monoclonal antibodies. Also included are antisera obtained by immunizing an animal such as a rabbit with a transcriptional regulator of the present invention, any class of polyclonal or monoclonal antibodies, humanized antibodies generated by gene recombination, and human antibodies. The antibodies of the present invention can be prepared according to the following method. For polyclonal antibodies, antisera can be obtained by immunizing a small animal, such as a rabbit, with a transcriptional regulator of the present invention, then recovering the fractions that only recognize the transcriptional regulator of the present invention through an affinity column coupled with the transcriptional regulator of the present invention. Immunoglobulin G or M can be prepared by purifying the fractions through a Protein A or G column. For monoclonal antibodies, a small animal, such as a mouse, is immunized with a transcriptional regulator of the invention, the spleen is removed from the mouse and homogenized into cells, the cells are fused with myeloma cells from a mouse using a reagent such as polyethylene glycol, and clones that produce antibodies against the transcriptional regulator of the invention are selected from the resulting fused cells (hybridoma). The hybridoma obtained is then transplanted into the abdominal cavity of a mouse, and the ascites are recovered from the mouse. The obtained monoclonal antibodies can then be prepared by purifying, for example, by ammonium sulfate precipitation through a Protein A or G column, by DEAE ion exchanging chromatography, or through an affinity column coupled with the transcriptional regulator of the invention. Besides being used to purify or detect the transcriptional regulators of the present invention, the antiobodies of the present invention can be applied to antibody therapy.

The present invention also relates to a screening method for a compound that binds to transcriptional regulators of the present invention. The screening method of the present invention includes steps of contacting a transcriptional regulator of the present invention with a test sample and selecting a compound that has binding activity for the transcriptional regulator of the present invention. Test samples used for the screening include, but are not limited to, a cell extract, a supernatant of the cell culture, a library of synthetic low molecular weight compounds, a purified protein, an expression product of a gene library, and a library of synthetic peptides. Methods well known to one skilled in the art for isolating a compound binding to a transcriptional regulator of the present invention using the regulator are as follows. A protein that binds to a transcriptional regulator of the present invention can be screened by West-western blotting comprising steps of generating a cDNA library from the cells expected to express the protein that binds to a transcriptional regulator of the present invention (e.g., testis tissue cell and tumor cell lines HL-60, HeLa S3, Raji, and SW480) using a phage vector (λgt11, ZAP, etc.), allowing the cDNA library to express on the LB-agarose plate, fixing the expressed proteins on a filter, reacting them with the transcriptional regulator of the present invention purified as a biotin-labeled protein or a fusion protein with GST protein, and detecting plaques expressing the protein bound to the regulator on the filter with streptavidin or anti-GST antibody (Skolnik, E. Y., Margolis, B., Mohammadi, M., Lowenstein, E., Fisher, R., Drepps, A., Ullrich, A. and Schlessinger, J. (1991), Cloning of PI3 kinase-associated p85 utilizing a novel method for expression/cloning of target proteins for receptor tyrosine kinases, Cell, 65:83–90). Alternatively, the method comprises expressing in yeast cells a transcriptional regulator of the present invention which is fused with SFR or GAL4 binding region, constructing a cDNA library in which proteins are expressed in a fusion protein with the transcription activation site of VP16 or GAL4 from the cells expected to express a protein that binds to the transcriptional regulator of the present invention, introducing the cDNA library into the above-described yeast cells, isolating the cDNA derived from the library from the detected positive clones, and introducing and expressing it in E. coli. (If a protein that binds to the transcriptional regulator of the present invention is expressed, a reporter gene is activated by the binding of the two proteins. The positive clones can then be identified.) This method can be performed using Two-hybrid system (MATCHMAKER Two-Hybrid System, Mammalian MATCHMAKER Two-Hybrid Assay Kit, MATCHMAKER One-Hybrid System (all from Clontech); HybriZAP Two-Hybrid Vector System (Stratagene) or in accordance with Dalton, S. and Treisman R. (1992), Characterization of SAP-1, a protein recruited by serum response factor to the c-fos serum response element, Cell, 68:597–612). Another method is to apply a culture supernatant or a cell extract from the cells suspected to express a protein which binds to the transcriptional regulator of the present invention onto an affinity column coupled with the transcriptional regulator of the present invention, and purify the protein specifically bound to the column.

Also well known to one skilled in the art are a method of screening molecules that bind to a transcriptional regulator of the present invention by reacting the immobilized transcriptional regulator of present invention with a synthetic compound, natural substance bank, or a random phage peptide display library, and a method of screening low molecular weight compounds, proteins (or their genes), or peptides which bind to a transcriptional regulator of the present invention by utilizing the high-throughput technique of combinatorial chemistry (Wrighton, N. C., Farrell, F. X., Chang, R., Kashuyap, A. K., Barbone, F. P., Mulcahy, L. S., Johnson, D. L., Barrett, R. W., Jolliffe, L. K., Dower, W. J., Small peptides as potent mimetics of the protein hormone erythropoietin, Science (UNITED STATES) Jul. 26, 1996, 273:458–464; Verdine, G. L., The combinatorial chemistry of nature, Nature (ENGLAND), Nov. 7, 1996, 384:11–13; Hogan, J. C. Jr., Directed combinatorial chemistry, Nature (ENGLAND), Nov. 7, 1996, 384:17–19). The compounds thus isolated, which bind to a transcriptional regulator of the present invention, may be used to treat cancer or other proliferative diseases. When the compounds isolated by the screening method of the present invention are used as pharmaceuticals, they can be formulated by a known pharmacological process. For example, they can be administered to a patient with pharmaceutically acceptable carriers and vehicles (e.g., physiological saline, vegetable oil, a dispersant, a surfactant, and a stabilizer). The compounds may be percutaneously, intranasally, transbronchially, intramuscularly, intravenously, or orally administered, depending on their properties.

The present invention also relates to DNA specifically hybridizing with DNA coding a protein of the present invention and having at least 15 nucleotides. As used herein, "specifically hybridizing" means that no cross-hybridization occurs between DNA encoding other proteins under conditions of moderate stringency. Such DNA may be used as a probe for detecting and isolating the DNA encoding the protein of the present invention, and as a primer for amplifying the DNA encoding the protein of the present invention.

An "isolated nucleic acid" is a nucleic acid the structure of which is not identical to that of any naturally occurring nucleic acid or to that of any fragment of a naturally occurring genomic nucleic acid spanning more than three separate genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of different (i) DNA molecules, (ii) transfected cells, and (iii) cell clones: e.g., as these occur in a DNA library such as a cDNA or genomic DNA library.

The term "substantially pure" as used herein in reference to a given polypeptide means that the polypeptide is substantially free from other biological compounds, such as those in cellular material, viral material, or culture medium, with which the polypeptide was associated (e.g., in the course of production by recombinant DNA techniques or before purification from a natural biological source). The substantially pure polypeptide is at least 75% (e.g., at least 80, 85, 95, or 99%) pure by dry weight. Purity can be measured by any appropriate standard method, for example, by column chromatography, polyacrylamide gel electrophoresis, or HPLC analysis.

A "conservative amino acid substitution" is one in which an amino acid residue is replaced with another residue having a chemically similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

As used herein, "percent identity" of two amino acid sequences or of two nucleic acids is determined using the algorithm of Karlin and Altschul (Proc. Natl. Acad. Sci. USA 87:2264–2268, 1990), modified as in Karlin and Altschul (Proc. Natl. Acad. Sci. USA 90:5873–5877, 1993). Such an algorithm is incorporated into the NBLAST and XBLAST programs of Altschul et al. (J. Mol. Biol. 215:403–410, 1990). BLAST nucleotide searches are performed with the NBLAST program, score=100, wordlength=12 to obtain nucleotide sequences homologous to a nucleic acid molecules of the invention. BLAST protein searches are performed with the XBLAST program, score=50, wordlength=3 to obtain amino acid sequences homologous to a reference polypeptide. To obtain gapped alignments for comparison purposes, Gapped BLAST is utilized as described in Altschul et al. (Nucleic Acids Res. 25:3389–3402, 1997). When utilizing BLAST and Gapped BLAST programs, the default parameters of the respective programs (e.g., XBLAST and NBLAST) are used. These programs are available at the web site of the National Center for Biotechnology Information.

Unless otherwise defined, all technical and scientific terms used herein have the same meaning as commonly understood by one of ordinary skill in the art to which this invention belongs. In case of conflict, the present application, including definitions, will control. All publications, patent applications, patents, and other references mentioned herein are incorporated by reference. The materials, methods, and examples are illustrative only and not intended to be limiting. Other features and advantages of the invention will be apparent from the detailed description, and from the claims.

BRIEF DESCRIPTION OF THE DRAWINGS

FIG. 1 compares the domain of BAZ (BAZ1α) with those of other proteins. In FIG. 1A, the bromodomain of BAZ (BAZ1α) (SEQ ID NO:39) is compared with that of TFIID from yeast (SEQ ID NO:39) CCG1 from human (SEQ ID NO:40), p300 (SEQ ID NO:41), and CBP (SEQ ID NO:42). In FIG. 1B, C4HC3 Zn finger of BAZ (BAZ1α) (SEQ ID NO:45) is compared with those of U13646 (SEQ ID NO:44), retinoblastoma binding protein RBP2 (SEQ ID NO:45), two species of MOZ (SEQ ID NOs: 47 and 47, respectively), p300 (SEQ ID NO:48), and CBP (SEQ ID NO:49). The conserved amino acids, cysteine and histidine, are indicated by "*." In both FIGS. 1A and B, identical amino acids are represented by bold letters, and similar amino acids are underlined.

FIGS. 2A and 2B show a chromosome map of BAZ (BAZ1α). FIG. 2A shows assignments of chromosome 14 based on the analysis of a monochromosome hybrid cell panel using primers B (SEQ ID NO:6) and M (SEQ ID NO:7). The numbers 1 to Y in the figure refer to chromosome numbers, and TH refers to total human chromosomes. The 111 bp product was specifically amplified in the cell line GM10479, monochromosome1 for a human chromosome14. FIG. 2B depicts the location of BAZ (BAZ1α) on chromosome 14 as determined by Genebridge 4 radiation hybrid panel analysis.

FIG. 3 shows the expression of BAZ (BAZ1α) in normal tissues (Lane 1, heart; Lane 2, brain; Lane 3, placenta; Lane 4, lung; Lane 5, liver; Lane 6, skeletal muscle; Lane 7, kidney; Lane 8, pancreas; Lane 9, spleen; Lane 10, thymus; Lane 11, prostate; Lane 12, testis; Lane 13, ovary; Lane 14, small intestine; Lane 15, colon (mucous lining); and Lane 16, leukocytes in the peripheral blood). The bottom of the figure shows control bands using actin probes.

FIGS. 4A and 4B show the expression of BAZ (BAZ1α) in carcinoma. FIG. 4A depicts the Northern blot analysis in the carcinoma cell lines (Lane 1, promyelocytic leukemia HL-60; Lane 2, HeLa S3 cells; Lane 3, chronic myelocytic leukemia K-562; Lane 4, lymphoblastic leukemia MOLT-4; Lane 5,Burkitt's lymphoma Raji; Lane 6, large intestine adenocarcinoma SW480; Lane 7, lung carcinoma A549; and Lane 8, melanoma G361). FIG. 4B shows the RT-PCR analysis of primary lung carcinoma of Lane 10. The top panel shows the amplified product of 554 bp from BAZ (BAZ1α) gene using primers U and N, and the bottom shows the amplified product of 442 bp from G3PDH gene using primers G3U and G3L. In the figures, L refers to normal human lung; T, to normal human testis; and G, to normal human genomic DNA.

FIGS. 6A and 6B show alignments of the domain of BAZ2α and that of other proteins. In FIG. 6A, the bromodomain of BAZ2α (SEQ ID NO:52) (BAZ2 in the figure) is aligned with BAZ (SEQ ID NO:50) (BAZ1α) human CCG1 (SEQ ID NO:51), PCAF (SEQ ID NO:53), U13646 (SEQ ID NO:54) and CBP (SEQ ID NO:55). In FIG. 6B, C4HC3 Zn finger of BAZ2α (SEQ ID NO:62) is aligned with BAZ (BAZ1α) (SEQ ID NO:56), U13646 (SEQ ID NO:57), retinoblastoma binding protein RBP2 (SEQ ID NO:58), 2 zinc fingers of MOZ (SEQ ID NOs:59 and 60, respectively), and p300 (SEQ ID NO:61). The conserved cysteine and histidine are indicated by "*."

FIG. 7 shows a chromosome map of BAZ2α. FIG. 7A shows assignments of chromosome 12 based on the analysis of a monochromosome hybrid cell panel using primers D (SEQ ID NO:16) and E (SEQ ID NO:17). The numbers 1 to Y in the figure refer to chromosome numbers. The product of 132 bp was specifically amplified in the cell line GM10868a, a monochromosome for human chromosome 12. FIG. 7B depicts the location of BAZ2 (BAZ2α) on chromosome 12 as determined by Genebridge 4 radiation hybrid panel analysis.

FIG. 10 compares the amino acid sequence of LH domain in BAZ2β (SEQ ID NO:66) with those of corresponding domains in other proteins (BAZ1α [SEQ ID NO:63], U13646 [SEQ ID NO:64], and BAZ2α [SEQ ID NO:65]). The positions of conserved leucine residues are indicated by arrows on the sequences. LXXLL (SEQ ID NO:37) motifs are boxed.

FIG. 11 shows a chromosome map of BAZ2β. The product of 147 bp was specifically amplified in the cell line as a monochromosome for human chromosome 2. This product was amplified by PCR using primers nb7n and nb7ee. The numbers 1 to Y in the figure indicate chromosome numbers. The location of BAZ2β on chromosome 2 was determined by Genebridge 4 radiation hybrid panel analysis.

FIG. 12 shows an analysis of the expression of BAZ2β in normal tissues, carcinoma cell lines, and fetal tissues (Lane 1, heart; Lane 2, brain; Lane 3, placenta; Lane 4, lung; Lane 5, liver; Lane 6, skeletal muscle; Lane 7, kidney; Lane 8, pancreas; Lane 9, spleen; Lane 10, thymus; Lane 11, prostate; Lane 12, testis; Lane 13, uterus; Lane 14, small intestine; Lane 15, colon (mucous lining); Lane 16, leukocytes in the peripheral blood; Lane 17, fetal brain; Lane 18, fetal lung; Lane 19, fetal liver; Lane 20, fetal kidney; Lane 21, acute leukemia HL-60; Lane 22, HeLa S3 cells; Lane 23, chronic myelocytic leukemia K-562; Lane 24, lymphoblastic leukemia MOLT-4; Lane 25, Burkitt's lymphoma Raji; Lane 26, large intestine adenocarcinoma SW480; Lane 27, lung carcinoma A549; and Lane 28, melanoma G361). The sizes of the transcripts are indicated on the right side of the figure.

FIG. 13 shows the alignments of variable portions of BAZ1βS (SEQ ID NO:67) and BAZ1βL (SEQ ID NO:68).

FIG. 14 shows the alignments of N terminal amino acid sequences from BAZ1βS (SEQ ID NO:69) and three other members of the BAZ family ("BAZ1A" [SEQ ID NO:70], "BAZ2A" [SEQ ID NO:71], and "BAZ2B" [SEQ ID NO:72]). The residues with 50% or more sequence homology are indicated by bold letters, and those with 50% or more sequence similarity, underlined. Conserved LXXLL (SEQ ID NO:37) motifs and C4HC3 zinc fingers are indicated on the alignments. Conserved leucine residues in the surrounding region of the LXXLL (SEQ ID NO:37) motif are indicated. The location of a bromodomain motif is indicated by a black line on the alignments.

FIG. 15 shows the alignments of the amino acid sequences from BAZ1βS and three other members of the BAZ family (continued from FIG. 14).

FIG. 16 shows the alignments of the amino acid sequences from BAZ1βS and three other members of the BAZ family (continued from FIG. 15.

FIG. 17 shows the alignments of the amino acid sequences from BAZ1βS and three other members of the BAZ family (continued from FIG. 16).

FIG. 18 shows the alignments of the amino acid sequences from BAZ1βS and three other members of the BAZ family (continued from FIG. 17).

FIG. 19A shows mapping of BAZ1β on chromosome seven by monochromosome hybrid cell line panel analysis. A product of 156 bp was observed to be amplified in the cell line GM10791 by PCR using primers nb3S and nb3T. The numbers 1 to Y in the figure indicate chromosome numbers. FIG. 19B shows the location of BAZ1β on chromosome seven as determined by Genebridge 4 radiation hybrid panel analysis. BAZ1β is located between 7q11–21 markers D7S489 and D7S669.

In FIG. 20A, the BAZ1β probe is hybridized with two transcripts in a wide range of tissues (Lane 1, heart; Lane 2, brain; Lane 3, placenta; Lane 4, lung; Lane 5, liver; Lane 6, skeletal muscle; Lane 7, kidney; Lane 8, pancreas; Lane 9, spleen; Lane 10, thymus; Lane 11, prostate; Lane 12, testis; Lane 13, uterus; Lane 14, small intestine; Lane 15, colon (mucous lining); and Lane 16, leukocytes in the peripheral blood). FIG. 20B shows controls using an actin probe. In FIG. 20B, the blot in FIG. 20A was used to rehybridize with the actin probe.

BEST MODE FOR IMPLEMENTING THE INVENTION

Figure 2B:
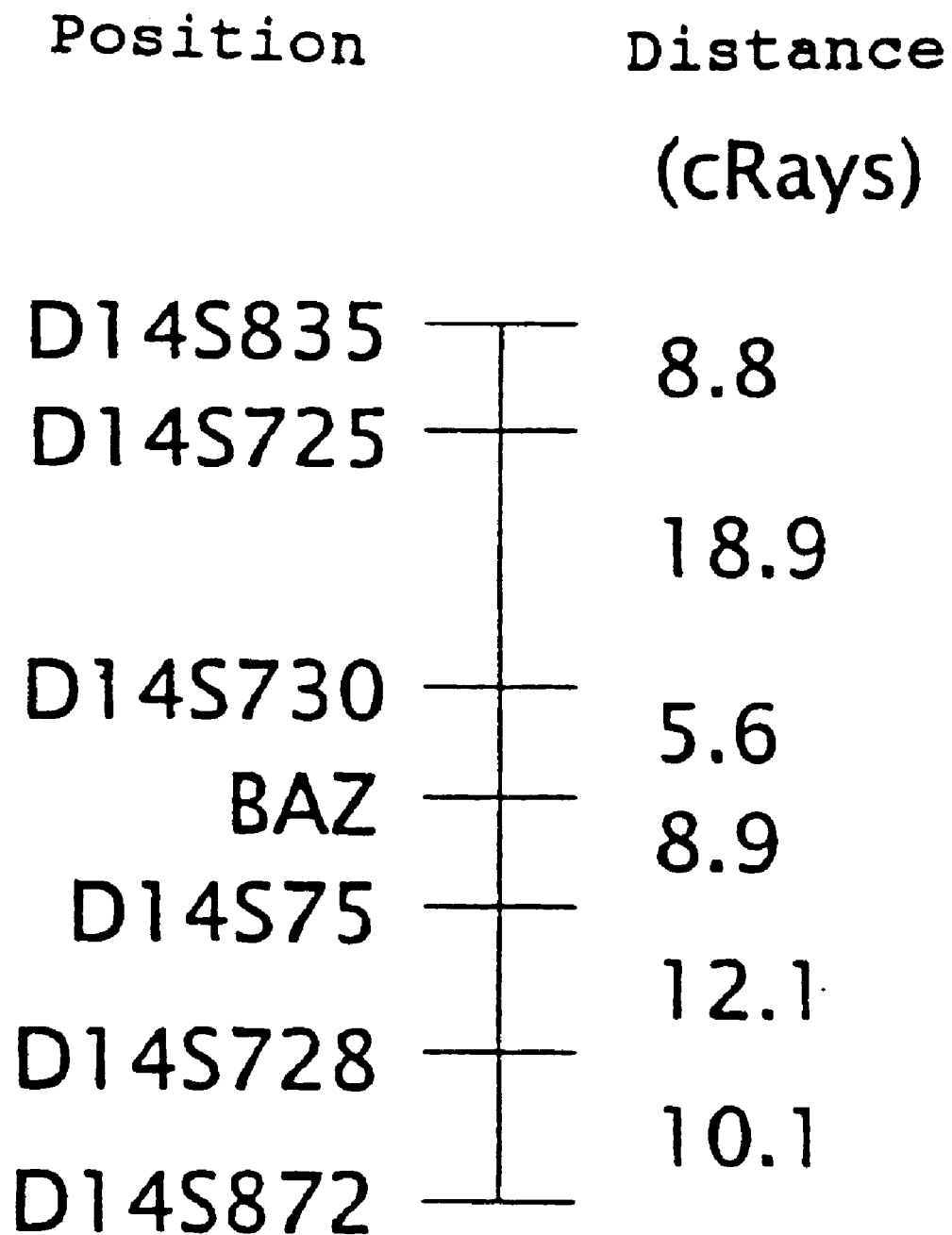

The present invention is further illustrated with reference to the following examples, but is not to be construed to be limited thereto.

EXAMPLE 1

Isolation and Analysis of BAZ Gene (1) Identification of novel genes each containing a bromodomain The EST database was searched by means of BLAST using the DNA sequence that encodes the 5' bromodomain motif of the RING3 gene (SEQ ID NO:3) (Beck, S. et al., (1992), DNA Sequence, 2:203–210), and a number of ESTs identical to the probe sequence were retrieved. The following experiment was then performed for one of those EST, H70181. H70181 has the highest homology to transcription activator GCN5 of yeast (Georgakopoulos, T. and Thireos, G. (1992), EMBO J., 11(11):4145–4152) or human (Candau, R. et al., (1996), Mol. Cell. Biol., 16(2):593–602).

(2) Isolation of a full-length sequence

To clone a full-length sequence of EST H70181, PCR primers were designed; primer U, SEQ ID NO:4/AGAAAAAGACAATCTCCAGAGCA, and primer L, SEQ ID NO:5/GCTGTCATCATGTCGTACCAATTC. The specific product of 129 bp obtained from testis cDNA was amplified by RT-PCR using said primers. The amplified product was directly purified through a QIA Quick (Qiagen) purification column. This PCR product was used as a probe for screening the testis cDNA library (Clontech; HL3023a). The probe was labeled with [α-$^{32}$P]dCTP by random priming, and purified using a Chromaspin 10 Column (Clontech); the cDNA clone obtained was used to re-screen the library. This process was repeated until a series of overlapped clones was obtained, and thus a full-length sequence was obtained. The isolated sequence was 5,934 bp in total. The isolated gene was designated "BAZ" (Bromodomain, Atypical Zinc finger). BAZ has an open reading frame (ORF) (SEQ ID NO:1) coding for 1,674 amino acids from the nucleotide positions 125–5147. The ORF is followed by 787 bp of a 3' untranslated region and terminated with a poly-A tail. The polyadenylation signal (AATAAA) is located at 21 bp upstream from the poly-A tail. The nucleotide sequence together with the deduceded amino acid sequence therefrom is shown in SEQ ID NO:2.

The filter screening of the library was performed in ExpressHyb hybridization solution (Clontech) at 65° C. for 1 hour. The filter was then washed until a final stringency of 1×SSC and 0.1% SDS at 65° C. was attained. All the sequencing was performed on automated sequencing apparatus ABI 377 (Perkin Elmer, Norwalk, Conn.), utilizing ABI dye terminator chemistry.

(3) Identification of the homology and motifs characterizing the transcription factors A protein database search using the amino acid sequence of BAZ revealed that a protein encoded by a continuous 2.2 Mb gene sequence of the chromosome III of C. Eelegans (Wilson, R. et al., (1994), Nature, 368:32–38) is most similar (46% similarity and 23% identity). The same regions having similarity were found in various transcription factors such as the 250 KD subunit of TFIID (Ruppert, S., Wang, E., and Tjian, R. (1993), Nature 362:175–179) and p300/CBP (Eckner, R. et al., (1994), Genes Dev., 8(8):869–884; Chrivia, J. C. et al., (1993), Nature, 365:855–859). A motif search of amino acid sequences in the PROSITE database on DNASIS (HITACHI Software Engineering Co.) identified a single bromodomain (amino acid residues 1569–1627 of SEQ ID NO:1). The sequence of this bromodomain, together with those of other bromodomains, is shown in FIG. 1A. A BLAST search using C4HC3 Zn finger (C4HC3ZF), which is the motif conserved among a great variety of proteins such as U13646, identified retinoblastoma binding protein RBP2 (Fattaey, A. R. et al., (1993), Oncogene, 8:3149–3156), MOZ (Borrow, J. et al., (1996), Nature Genet., 14:33–41), and p300/CBP (Koken, M. H. et al.; (1995), CR Acad. Sci. III, 318:733–739), a motif of 45 amino acids (corresponding to amino acid residues 1269–1313 of SEQ ID NO:l). C4HC3ZFs present in these genes are shown in FIG. 1B. The function of BAZ as a transcriptional regulator is implied by the fact that it is similar to several transcriptional regulators, in particular, a bromodomain motif conserved together with C4HC3ZF and p300/CBP. The similarity of BAZ to p300/CBP is not limited to C4HC3 zinc finger and bromodomain regions; well conserved regions are also found adjacent to the bromodomain. Homology was not found between BAZ and histone-acetyltransferase domain, and between BAZ and other domains in which p300/CBP is present. However, BAZ potentially has HAT activity since the histone-acetyltransferase domain is not well conserved among proteins.

Several sorts of sequence motifs characterized by the nuclear proteins were identified at 11 sites by employing the PSORT program (available at the PSORT WWW Server) utilizing a wide variety of conserved nuclear localization sequences.

(4) Mapping of BAZ

Primers B: SEQ ID NO:6/ AACACAAGTGAAGCAAAAGCTGGA and M: SEQ ID NO:7/GTGGTGTGCTAACTTGGTCCACAT (obtained from the 3' end of the gene) were used to amplify DNA obtained from each of the 24 monochromosomes of human/rodent somatic cell lines available from Coriell Cell Respositories, New Jersey (Dubois, B. L. and Naylor, S. (1993), Genomics, 16:315–319). The expected product of 111 bp was amplified only from GM10479, a monochromosomal cell line for human chromosome 14 (see FIG. 2A). Primers B (SEQ ID NO:6) and M (SEQ ID NO:7) were subsequently used for PCR onto a GeneBridge 4 radiation hybrid panel (Research Genetics, Huntsville, Ala.). The binary codes generated by assessing whether each hybrid is positive or negative for amplification were compared with the analogous codes for the markers constituting a framework map, using the server located at the web site of the Whitehead Institute for Biomedical Research/MIT Center for Genome Research. This step was repeated using primers W: SEQ ID NO:8/ CCCATCGTGAGTCAAGAGTGTCTGT and X: SEQ ID NO:9/CTCGCTTCTACCTTTTTATTGGCT (from the 5' end of the gene). Based on the pattern obtained from this panel by identifying the amplification in the panel, BAZ was proved to be located on the 14q between the two markers D14S730 and D14S75 (see FIG. 2B).

(5) Analysis of BAZ expression in the normal tissues

The probe as synthesized in Example 1(2) by amplifying cDNAs from testis with PCR using the above-described primers U (SEQ ID NO:4) and L (SEQ ID NO:5) was used for Northern blot analysis of 16 panels of normal tissues. The probe hybridized with a single species of mRNA of 7.0 kb, which corresponds to the length of the ORF identified from the sequence of the gene. Though this transcript was expressed in almost all the tissues at very low levels, it was expressed in testis at a relatively high level (see FIG. 3). The transcript was not detectable in brain, lung, liver, kidney, and colon (it was possibly expressed at non-detectable levels). A slightly smaller transcript of 6.5 kb was also detected only in testis at a low level. Since the cells divide more vigorously in the testis than any other tissue examined, the expression pattern is thought to correspond to the role for BAZ during active proliferation. Hybridization for Northern blot analysis was performed in Express Hyb hybridization solution (Clontech) at 65° C. for 1 hour. The filters were washed until the final stringency reached 1×SSC and 0.1% SDS at 65° C. Imaging was performed using a Fuji BAS Image Analyzer (Fuji Photo Film).

(6) Analysis of BAZ expression in tumor

That BAZ is highly expressed in the testis suggests the possibility of its high level expression in vigorously proliferating tumors. Thus, Northern analysis of eight panels of tumor cell lines was carried out, using the same probe as used in Example 1(5). As a result, the transcript of 7.0 kb alone was hybridized with the probe as when the normal tissue was used. Compared with most normal tissues, however, the transcriptional levels are remarkably higher in most of the tumor cell lines (see FIG. 4A). Specifically, the expression was higher in the tumor cell lines HL-60, HeLa S3, Raji, and SW480. In contrast, the expression levels in K-562, MOLT-4, A549, and G361 are almost the same as those in normal tissues.

RT-PCR wasused to examine theexpression of BAZ in the primary lung carcinomas as shown in Table 1.

TABLE 1

| Sample No. | Patients | | Carcinoma |
|---|---|---|---|
| | age | sex | |
| 1 | 49 | male | papillary adenocarcinoma |
| 2 | 63 | male | papillary adenocarcinoma (moderately differentiated) |
| 3 | 60 | male | papillary adenocarcinoma (poorly differentiated) |
| 4 | 70 | male | squamous cell carcinoma (fusiform cell variant) |
| 5 | 76 | male | papillary adenocarcinoma |
| 6 | 65 | male | large lung cell carcinoma (moderately differentiated) |
| 7 | 77 | male | squamous cell carcinoma (poorly differentiated) |

TABLE 1-continued

| Sample No. | Patients | | |
|---|---|---|---|
| | age | sex | Carcinoma |
| 8 | 45 | male | acinic adenocarcinoma |
| 9 | 50 | male | carcinoid tumor |
| 10 | 66 | male | choriocarcinoma |

Each of the 10 samples was amplified using the primers G3U SEQ ID NO:10/ TCATCATCTCTGCCCCCTCTGTCTG and G3L SEQ ID NO:11/GACGCCTGCTTCACCACCTTCTTG, which are the primers for amplifying 442 bp of a house-keeping gene G3PDH, and the primers U, SEQ ID NO:4 and N, SEQ ID NO:12/TCATGTGGTCAATCAATTGTTTGT, which are primers for BAZ (see FIG. 4). G3PDH was used to determine that an equal amount of mRNA was present in each sample.

The primers for BAZ were selected to specifically amplify the cDNA but not genomic DNA. The amplified product was definitely detected in the sample from the testis and the two lung tumors, but not from the other eight samples from the lung tumor or the normal lungs.

RT-PCR was performed according to a standard technique in which total RNA was extracted according to the AGPC method (Chomczynski, P. and Sacchi, N. (1987), Analytical Biochem., 162:156–159), then single-stranded DNA was synthesised with an oligo (dT15) primer and MMLV reverse transcriptase, a part of which was used for the RT-PCR. The RT-PCR was performed using AmpliTaq gold (ABI), with 27 cycles of annealing at 60° C. to amplify G3PDH and 33 cycles of annealing at 55° C. to amplify BAZ. The conditions for hybridization and imaging were the same as in Example 1(5).

EXAMPLE 2

Isolation and Analysis of BAZ2α Gene (1) Identification of a novel gene containing a bromodomain and isolation of its full-length sequence The DNA encoding the bromodomain of BAZ is highly homologous to that of GCN5. The DNA sequence encoding the bromodomain motif of human GCN5 gene (Candau, R. et al., (1996), Mol. Cell. Biol., 16 Q):593–602) was used to search the EST database using BLAST. The Motif search was performed using PROSITE. Proteins were compared using Bestfit in GCG. The nuclear transport signal was identified using PSORT. As a result, a number of ESTs were found to be identical to the probe sequence. Among them, an EST (Accession Number: N76552) obtained from a fetal liver/spleen cDNA library proved to be a novel gene.

To start cloning the full-length sequence of EST N76552, PCR primers were designed to amplify a particular product of 91 bp from the testis cDNA library; primer NB16U (SEQ ID NO:15/TGACTCTGAAGTAGGCAAGGCTGG) and primer NB16L (SEQ ID NO:16/CTTGCCTCACAGATTGGCCTGT). The PCR product was used as a probe to screen the testis cDNA library (Clontech; HL3023a). The amplified product was directly purified through a QIA Quick (Qiagen) purification column. The cDNA clone having sequences corresponding to EST was used to re-screen the library.

This process was repeated until a series of overlapped clones having a full-length sequence of the complete coding region was obtained. All the sequencing was performed with automated sequencing apparatus ABI 377 (Perkin Elmer, Norwalk, Conn.), utilizing ABI dye terminator chemistry. As a result, a continuous sequence consisting of 9,408 bp nucleotides in total size was generated. Theoretical translation of this sequence showed a presence of methionine codon at the nucleotide position of 740. An open reading frame (ORF) coding 1878 amino acids starts from this position and terminates at the nucleotide position 6373. The ORF is followed by a 3' untranslated region consisting of at least a 3 kb nucleotide sequence. The nucleotide sequence of the cDNA obtained is shown in SEQ ID NO:14, and the amino acid sequence deduced from the cDNA is shown in SEQ ID NO:13. The isolated clone was designated BAZ2α.

Figure 5:
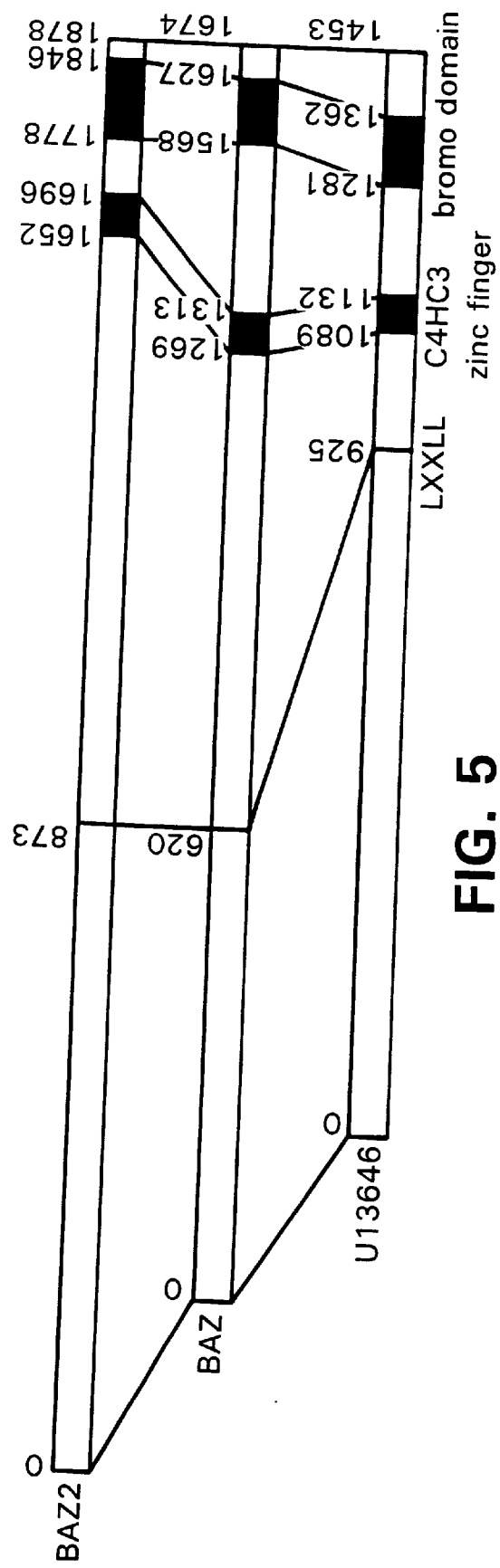
FIG. 5 compares the conserved domains among BAZ (BAZ1α), BAZ2α, and U13646.

(2) Identification of the homology and motifs characteristic of transcription factors Like BAZ, BAZ2α was shown to have the highest homology with the protein encoded by a C. elegans bromodomain gene U13646, the gene forming a part of a continuous 2.2 Mb segment of chromosome III of C. elegans (Wilson, R. et al., (1994), Nature, 368:32–38) by searching the protein databases with the amino acid sequence of BAZ2α. The regions which showed similarity were identified using various transcription factors such as the 250 KD subunit of TFIID (Ruppert, S., Wang, E. and Tjian, R. (1993), Nature 362:175–179) and p300/CBP (Eckner, R. et al., (1994), Genes Dev., 8(8):869–884; Chrivia, J. C. et al., (1993), Nature, 365:855–859). The bromodomain was located between the amino acid residues 1788 and 1846. The alignments of BAZ2α, BAZ, and U13646 are shown in FIG. 5. The alignments of the sequence of the BAZ2α bromodomain and those of other bromodomains are shown in FIG. 6A. Moreover, a single motif consisting of 45 amino acids (amino acid residues 1652–1696) was identified. This motif codes C4HC3 Zinc finger (C4HC3ZF), a motif conserved among a large number of proteins such as BAZ, U13646, retinoblastoma binding protein RBP2 (Fattaey, A. R. et al., (1993), Oncogene, 8:3149–3156), MOZ (Borrow, J. et al., (1996) Nature Genet., 14:33–41), and p300/CBP (Koken, M. H. et al., (1995) CR, 4 cad. Sci. III, 318:733–739) by BLAST searching. The alignments of C4HC3ZF from these genes are shown in FIG. 6B. BAZ2α resembles BAZ, which suggests the possibility that the two proteins closely relate and form a part of a protein family having a similar function. Like BAZ, BAZ2α wholly resembles several transcription factors and has C4HC3ZF and bromodomain motifs conserved among p300/CBP and TIF1, especially indicating that BAZ is likely to function as a transcriptional regulator.

An LXXLL (SEQ ID NO:37) motif, which is believed to be required for mediating transcription induced by nuclear receptors (Torchia, J. et al., (1997), Nature, 387:677–684; Herry, D. M. et al., (1997), Nature 387:733–736), is located at amino acid residue 872. PROSITE motif searching revealed that this motif was located at the 3' end of the leucine zipper (amino acid residues 852–873). The relative locations of LXXLL (SEQ ID NO:37), C4HC3, and bromodomain motifs in BAZ2α are remarkably similar to those of U13646 and BAZ (FIG. 5). Furthermore, in either case, the LXXLL (SEQ ID NO:37) motif is located behind the helix structure characterized by conserved lysine residues existing at regular intervals.

(3) Mapping of BAZ2α

To locate BAZ2α on the chromosome, PCR primers D:(SEQ ID NO:17/TTGCCGTATTTGGCTGGTATC) and E:(SEQ ID NO:18/CATAGAGAAGAGGGCAGGGTTGA), which amplify a fragment of 132 bp, were used to amplify the DNA from each of the 24 monochromosomes of human/rodent somatic cell lines (Dubois, B. L. and Naylor, S. (1993), Genomics, 16:315–319) obtained from Coriell Cell Respositories (New Jersey). The BAZ2α-containing region was identified using 91 GeneBridge 4 radiation hybrid panels (Walter M. A. et al., (1994), Nature Genetics, 7:22–28). These panels were screened by PCR using primers D and E again. The binary codes generated by assessing whether each hybrid is positive or negative for amplification were compared with the analogous codes for the markers constituting a framework map, using the server located at the web site of the Whitehead Institute for Biomedical Research/MIT Center for Genome Research. BAZ2α was thus proved to be located 12q24.3-ter from D12S367 (see FIG. 7B).

(4) Analysis of the BAZ2α expression

Figure 8A:
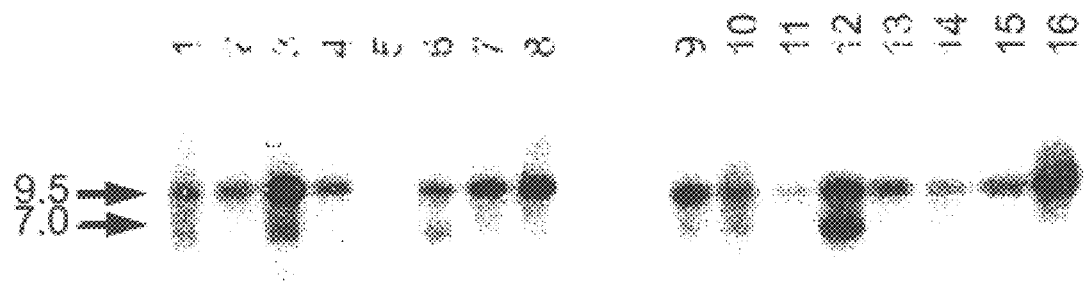
FIG. 8A shows the expression of BAZ2α in normal tissues (A: Lane 1, heart; Lane 2, brain; Lane 3, placenta; Lane 4, lung; Lane 5, liver; Lane 6, skeletal muscle; Lane 7, kidney; Lane 8, pancreas; Lane 9, spleen; Lane 10, thymus; Lane 11, prostate; Lane 12, testis; Lane 13, uterus; Lane 14, small intestine; Lane 15, colon (mucous lining); and Lane 16, leukocytes in the peripheral blood).
Figure 8B:
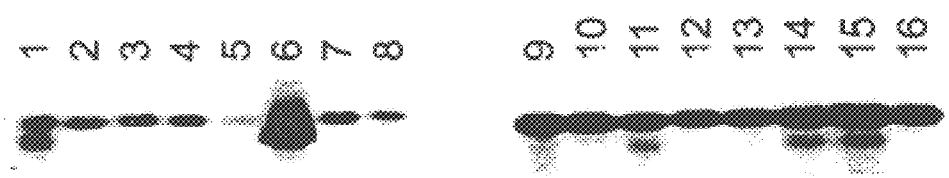
FIG. 8B shows controls using actin probe.

The probe (a 481 bp fragment of BAZ2α gene) prepared by amplifying the DNA from one of the clones obtained from the testis cDNA library (Clontech) in Example 2(1) using primers gt10F (SEQ ID NO:19/CTTTTGAGCAAGTTCAGCCT) and NB16N (SEQ ID NO:20/GTCGGCTTCTTCATTTCCTCCA) was used for Northern analysis of 16 panels of normal tissues (Clontech). The probe was labeled with [α-$^{32}$P]dCTP by random priming and purified using a Chromaspin 10 column (Clontech). Hybridization for Northern analysis and library filter screening were performed in the ExpressHyb hybridization solution (Clontech) at 65° C. for 1 hour. The filters were then washed until the final stringency reached 0.5×SSC and 0.1% SDS. Imaging was performed using a Fuji BAS Image Analyzer. The result showed that this probe was hybridized with a single species of mRNA of 10.5 kb in almost all the tissues; this length corresponds to that of ORF identified from the gene sequence (FIG. 8). The transcript was expressed in almost all the tissues at a low level. Another transcript of 9.0 kb was detected and was primarily expressed in the testis. This band survived the high-stringent wash. The second transcript is thought to be an alternatively spliced form of, or a different gene closely related to, BAZ2α.

EXAMPLE 3

Isolation and Analysis of BAZ2β Gene (1) Identification of a novel gene containing a bromodomain and isolation of its full-length sequence A BLAST search was performed against the EST databases using the various nucleotide sequences containing a known bromodomain motif. Several ESTs which may encode the bromodomain gene were identified based on the result of the search using the nucleotide sequence of the SMAP gene (Nielsen, M. S. et al., (1996), Biochem. Biophys. Acta). Among them, an EST (Genbank Accession Number: AA015589) obtained from a retinal cDNA library was proved to be a novel gene, the protein deduced from which has the highest homology with BAZ2α.

Its full-length nucleotide sequence was isolated. The full-length gene for EST AA015589 was cloned as follows. First, PCR primers NB7U (SEQ ID NO:23/CTGACTGAAATGGAAACTCATGAGG) and NB7L (SEQ ID NO:24/CTAGAGCAAAGGTTTCAAGGTTTGG) were designed to obtain the specific product of 165 bp from the testis cDNA. The amplified product was directly purified with a QIA Quick (Qiagen) purification column. The PCR product was used as a probe to screen the testis cDNA library, and the cDNA clone containing the EST sequence was used to re-screen the library. This process was repeated until the nucleotide sequence covering the whole coding region of the gene was obtained by assembling the clones. As a result, a nucleotide sequence consisting of 7,585 bp in total was obtained. This full-length sequence contains an open reading frame (ORF) consisting of 1972 amino acids (6,282 nucleotides) with ATG at the nucleotide position 367 as the initiation codon, followed by 3' UTR of 1303 bp. SEQ ID NO:22 shows the nucleotide sequence of the cDNA thus obtained, and SEQ ID NO:21 shows the amino acid sequence deduced from the nucleotide sequence. All the sequencing was performed on automated sequencing apparatus ABI 377 (Perkin Elmer, Norwalk, Conn.), utilizing ABI dye terminator chemistry. Hybridization for the library filter screening was performed using ExpressHyb hybridization solution (Clontech) at 65° C. for 1 hour. The filters were washed until the final stringency reached 0.5×SSC and 0.1% SDS. Subsequently, the filters were subjected to autoradiography at −70° C. for 1 to 3 days to intensify their signals.

(2) Homology and the characteristics of the motifs of the transcriptional regulator The motifs of the protein encoded by the gene obtained were searched for in PROSITE. The proteins were compared using Bestfit from GCG. A nuclear transport signal was identified through the PSORT WWW Server.

Figure 9:
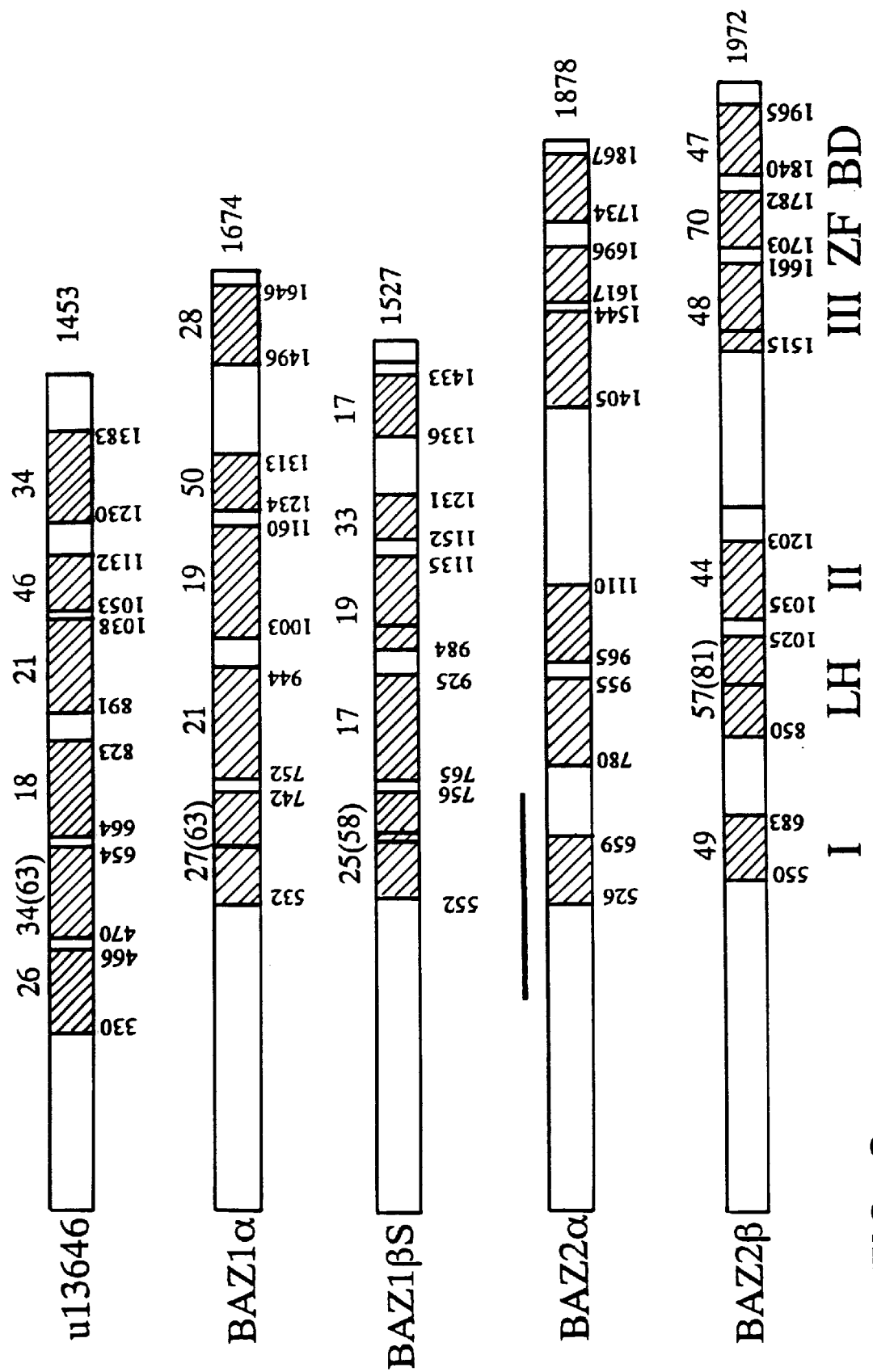
FIG. 9 compares the conserved domains of BAZ2β; BAZ1α, BAZ2α, U13646, and BAZ1βS. Each has at least five domains. BAZ1α lacks domain I. The figures on the bars of BAZ2β, BAZ1α, U13646, and BAZ1βS represent the percentage of the homology with BAZ2α. The values in the LH domain represent the percentage of the homology with leucine residues. Black bands in the LH domain indicate where the LXXLL (SEQ ID NO:37) motif is present in all three BAZ genes. LH, ZF, and BD represent leucine-rich helix domain, C4HC3 zinc finger, and bromodomain, respectively.

As for BAZ and BAZ2α, a database search based on the amino acid sequences predicted from the registered genes showed that this gene has the greatest similarity to the protein encoded by the bromodomain gene U13646 from the nematode (*C. elegans*). This nematode bromodomaingene corresponds to a portion of a 2.2 Mb segment derived from chromosome III of the nematode (*C. elegans*) (Wilson, R. et al., (1994), Nature, 368:32–38). The gene, however, shows homology to BAZ and BAZ2α to a larger extent. Actually, the similarity of the protein encoded by this gene to BAZ and BAZ2α suggests the possibility that these three proteins are closely related to one another, and, moreover, that they are a part of a broader family of proteins with similar functions. This gene was designated BAZ2β (for bromodomain, atypical zinc finger), since it has the greatest association with BAZ2α. BAZ was also renamed BAZ1α. The amino acid sequence of BAZ2β is shown in FIG. 9 together with those of BAZ1α, BAZ2α, U13646, and BAZ1βS described below. At least five regions or domains can be identified from the sequences. The first domain (I) is not present in BAZ1α, but is in the other three proteins. The existence of a leucine-rich helical structure (LH) was predicted from the analysis of the next domain. LXXLL (SEQ ID NO:37) motif is present at the central part of this domain on all BAZs except U13646. This motif potentially confers the interaction with the nuclear receptors on the protein (Torchia, J. et al., (1997), Nature, 387:677–684; Heery, D. M. et al., (1997), Nature, 387:733–736). Both domains II and III are highly conserved, suggesting their functional importance. Each protein has a highly conserved C4HC3 zinc finger (Aasland, R. et al., (1995), Trends Biochem. Sci., 20:56–59; Koken, M. H. et al., (1995), CR Acad. Sci. III, 318:733–739; Saha, V. et al., (1995), Proc. Natl. Acad. Sci., 92:9737–9741) and a bromodomain. In addition, a conserved region is found upstream from the zinc-finger motif, and the region can also be functionally important. Similarly, there are conserved sequences upstream from the bromodomain motif. Such conserved domains are aligned in FIG. 10. Like BAZ1α and BAZ2α, BAZ2β exhibits great similarity to several transcription factors and is thus expected to function as a transcription factor. Consistent with this function, estimation of the protein localization in the cell using the PSORT program revealed that BAZ2β has 19 consensus nuclear localization sequences (Robbins, J. et al., (1991), Cell, 64:615–23) in total.

(3) Chromosomal mapping of BAZ2β

To create a chromosome map of BAZ2β, primers nb7n (SEQ ID NO:25/TGTTGCTGCATCACTTGTGTAGTT) and NB7ee (SEQ ID NO:26/GGCATGACAATAATGTCTGCAAA) were prepared and used toamplify the DNA obtained from each of the 24 human/rodent monochromosomal somatic cell lines (Dubois, B. L. and Naylor, S. (1993), Genomics, 16:315–319). The amplification of the 147 bp fragment as expected PCR product indicated that the gene was likely to be located on human monochromosome 2 (FIG. 11). The locus region of BAZ2β was determined by use of 91 radiation hybrid panels of GeneBridge 4 (Walter, M. A. et al., (1994), Nature Genetics, 7:22–28). The hybrid panels were screened by PCR using primers nb7n and nb7ee again. The binary codes generated by assessing whether each hybrid is positive or negative for the amplification were compared with the analogous codes for the markers constituting a framework map, using the server located at the web site of the Whitehead Institute for Biomedical Research/MIT Center for Genome Research to identify the chromosomal locus of this gene. As a result, BAZ2β was confirmed to be located on chromosome 2q23–24 and between markers D2S 1986 and G09369 (FIG. 11).

(4) Analysis of the BAZ2β expression

The CDNA probe containing the sequence correponding to nucleotide residues 1700–4000 was used for Northern analysis of 16 normal tissues, eight tumor cell lines, and four fetal tissues (FIG. 12). The probe was labeled with [α-$^{32}$P] dCTP by random priming and purified on a Chromaspin 10 column (Clontech). Hybridization for Northern analysis was performed at 65° C. for 1 hour using ExpressHyb hybridization solution (Clontech). Subsequently, the filters were washed at 65° C. until the final stringency reached 0.5×SSC and 0.1% SDS. Autoradiography was then performed at −70° C. for 1 to 3 days to intensify the signals of the filters. This probe detected an mRNA of about 9.5 kb, a transcript whose size agreed with that of the ORF identified from the nucleotide sequence, in almost all the tissues examined. Besides this band, a transcript of about 6.5 kb was predominantly expressed in the testis. Since this band remained unchanged even after the high stringent wash (0.1×SSC, at 65° C.), it was considered to be specifically expressed. The second transcript could be an alternatively spliced product of BAZ2β, but no clone implying this event was found. It was also likely that expression of another gene closely related to BAZ2β was detected. In addition to these transcripts, several mRNAs were detected in most tissues. Such transcripts were considered to be derived from other genes each having an analogous sequence. Another analysis using another probe containing a bromodomain revealed the expression of the transcript of 6.5 kb only in the testis and of a 8.5 kb transcript in a wide range of tissues.

EXAMPLE 4

Isolation and Analysis of BAZ1β (BAZ1βS and BAZ1βgL) Genes (1) Identification of novel genes containing a bromodomain and isolation of their full-length nucleotide sequences A BLAST search was performed against the EST database using the nucleotide sequence of the bromodomain motif from human GCN5 gene (Candau et al., (1996), Mol. Cell. Biol., 16:593–602). Several ESTs possibly coding a number of bromodomain genes were identified. Among them, an EST (Gnbank accession Number: AA01307) derived from a retinal cDNA library was found to be a novel gene.

Its full-length sequence was isolated. The full-length gene for EST AA01307 was cloned as follows. First, PCR primers nb3U (SEQ ID NO:31/TGGATGATGCTGAGGTGGATGA) and nb3L (SEQ ID NO:24/GGGGTGCTGGATGACATCATAG) were designed to obtain a product of 184 bp specific to the primers from a testis cDNA library. The amplified product was directly purified using a QIA Quick (Qiagen) purification column. The PCR product was used as a probe to screen the testis cDNA library (Clontech HL3024a), and the cDNA clone containing the EST sequence was used to re-screen the library. This process was repeated after joining the clones. As a result, two types of nucleotide sequences were obtained and designated BAZ1β. The two sequences were further designated BAZ1βS for the shorter sequence and BAZ1βL for the longer one. The shorter sequence consisted of 5,561 nucleotides and encoded a protein of 1527 amino acids; the longer sequence consisted of 5,573 nucleotides and encoded a protein of 1531 amino acids, containing a tandem repeat of TACAGACCCTCC (SEQ ID NO:73) in one frame. This repeat gave rise to an insertion of four amino acids LLQT at position 658, which interestingly resulted in an additional LXXLL (SEQ ID NO:37) motif. BAZ1βS had four LXXLL (SEQ ID NO:57) motifs initiated at positions 655, 658, 1000, and 1436, while BAZ1βL had five LXXLL (SEQ ID NO:37) motifs initiated at positions 655, 658, 663, 1004, and 1440. FIG. 13 shows an alignment of the portions having multiple LXXLL (SEQ ID NO:37) motifs of BAZ1βS and BAZ1βL.

To determine whether the variability of the LXXLL (SEQ ID NO:37) motif is attributed to alteration of splicing or polymorphism, a pair of primers consisting of NB3KK (SEQ ID NO:33/GAGTGCAGATAAGGGTGGCTTTTT) and NB3LL (SEQ ID NO:34/CCAATTCACCATAGTCTTCGGCTA), which correspond to both sides of the variable region, was prepared and used to amplify genomic DNA and cDNA. As a result, these primers amplified a product of the same size from both of the templates. This implies the sequence variant is generated within an intron. Therefore, the variation of the sequence is probably caused by polymorphism. This may affect the interaction with the nuclear receptors. The nucleotide sequence of BAZ1βS cDNA thus obtained is shown in SEQ ID NO:28, and the deduced amino acid sequence of the protein encoded by the cDNA is shown in SEQ ID NO:27. The nucleotide sequence of BAZ1βL cDNA is also shown in SEQ ID NO:30, and the deduced amino acid sequence of the protein encoded by the cDNA is shown in SEQ ID NO:29. All the nucleotide sequences were determined with automated sequencing apparatus ABI 377, using ABI dye terminator chemistry. Hybridization for the filter screening of the library was performed in ExpressHyb hybridization solution (Clontech) at 65° C. for 1 hour. The filters were washed at 65° C. until the final stringency reached 0.5×SSC and 0.1% SDS. Subsequently, the filters were autoradiographed at −70° C. for 4 days to intensify the signals or autoradiographed for 4 hours with the Fuji BAS system.

(2) Homology and characteristics of the motifs of the transcriptional regulator

The motifs of the proteins encoded by BAZ1βS and BAZ1βL genes were searched in PROSITE. The proteins were compared using a MAP program of a BCM search launcher under the default setting conditions; the output results were edited using a box shade program. A nuclear transport signal was identified through the PSORT WWW Server.

Several motifs characteristic of transcriptional regulators were found in both BAZ1βS and BAZ1βL. They were bromodomain, C4HC3 zinc finger (C4HC3ZF), and LXXLL (SEQ ID NO:37) motifs. LLXXLL (SEQ ID NO:37) motifs were present in the leucine-rich domain conserved among other BAZ family member protein genes and U13646 (FIG. 9). Although the importance of this domain has not been clarified, it can form a leucine zipper responsible for forming a dimer of the protein. It has been reported that such motifs are commonly found in the transcriptional regulators of eukaryotes (Busch and Sassone-Corsi, 1990) and that LXXLL (SEQ ID NO:37) motifs also interact with the nuclear receptors (Torchia et al., (1997), Nature, 387:677–684; Heery et al., (1997), Nature 387:733–736). That the predicted amino acid sequences have extensive similarity to several kinds of transcription regulators indicates the possibility that their genes function as transcriptional regulators. This is further supported by the fact that 13 nuclear localized consensus sequences (Robbins et al., (1991), Cell, 64:615–23) were found in total based on the prediction of the cellular localization of the proteins using the PSORT program. The predicted amino acid sequences exhibited the highest similarity to BAZ1α. They also showed similarity to the proteins encoded by BAZ2α, BAZ2β, and *C. elegans* bromodomain gene U13646. Among the six domains, the first domain existed in BAZ2α, BAZ2β, and U13646, but not in BAZ1βS, BAZ1βL, or BAZ1α. Comparing the whole structures of these gene products, the region between domains II and III is the most similar to that of BAZ1α (FIGS. 14–18). Like other members of BAZ family, these gene products also have motifs that are present in the protein assumed to be encoded by nematode (*C. elegans*) bromodomain gene U13646 (Wilson et al., (1994) Nature, 368:32–38) that is identified by analyzing genome sequences of the genes. Alignment of the sequences of BAZ1βS, other members of the BAZ family, and U13646 reveals that the most highly conserved regions are located between the center and the C terminus of the sequences (FIGS. 14–18). For U13646, this region is not depicted in the figures, and only N terminal region is aligned with that of BAZ1βS and BAZ1α.

(3) Chromosomal mapping of BAZ1β

Figure 19A:
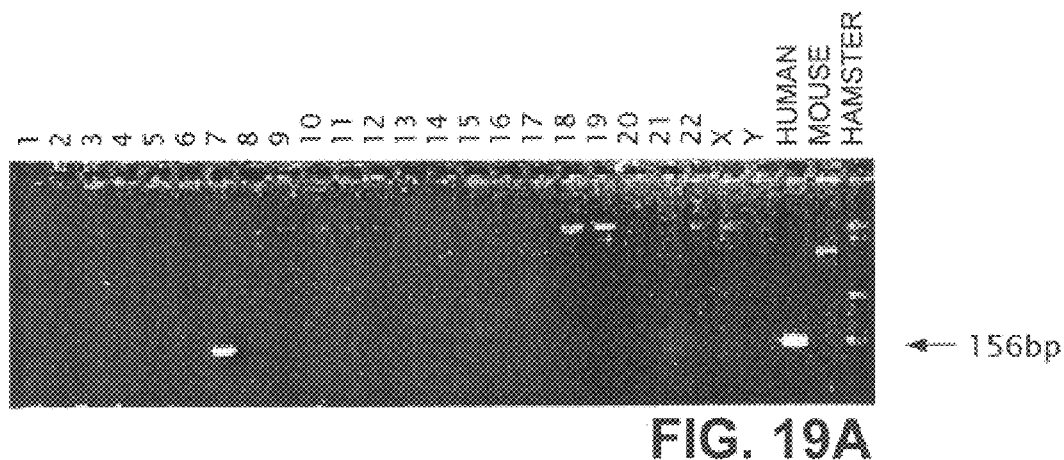
FIGS. 19A and 19B show a chromosome map of BAZ1β.
Figure 19B:
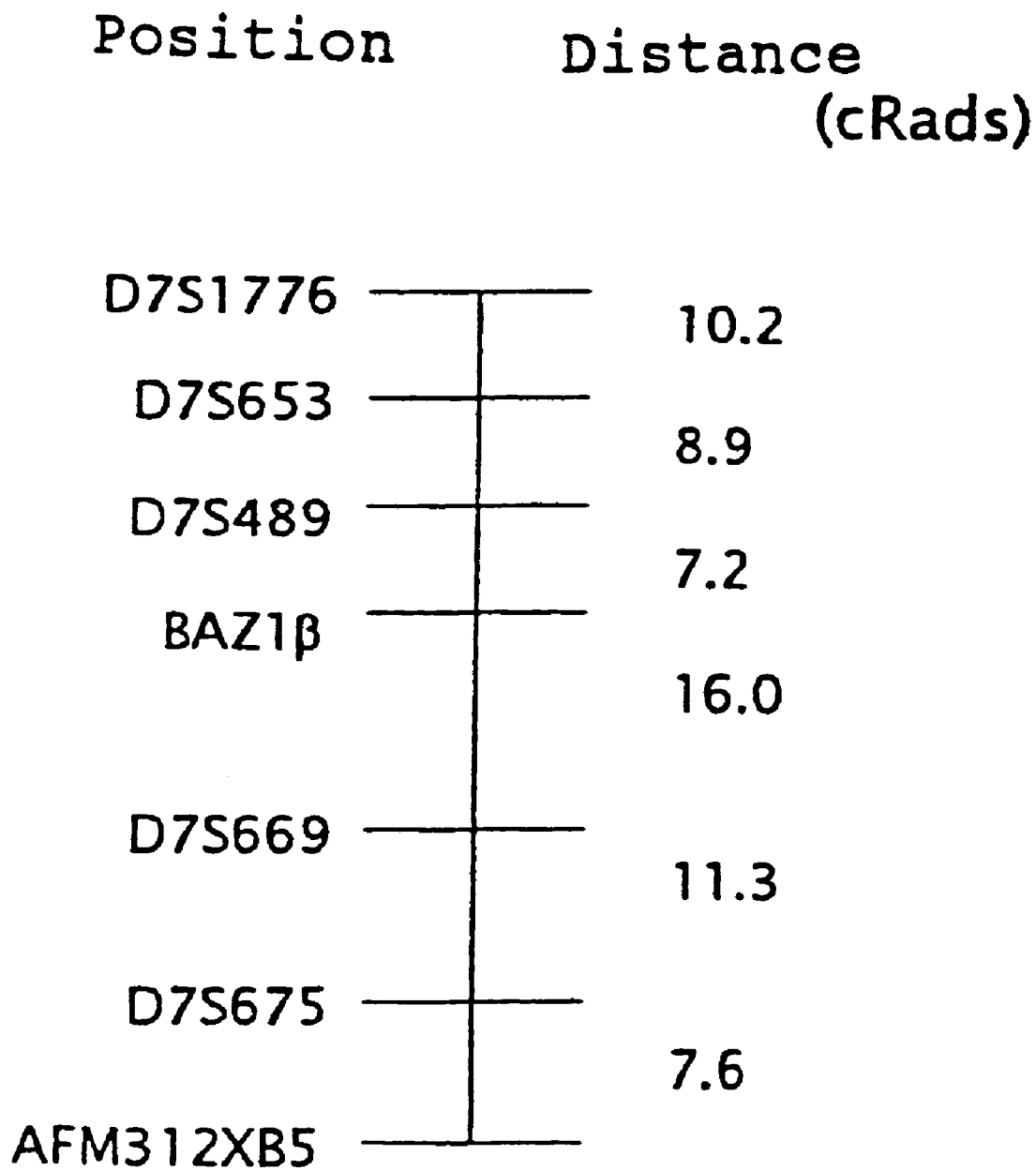

To create a chromosone map of BAZ1β, primers nb3S (SEQ ID NO:35/GAAACGGGAGGAGCTGAAAAAG) and nb3T (SEQ ID NO:36/CCTTCAGGGGTATCCACCAATC) were prepared and used to amplify the DNA obtained from each of the 24 human/rodent monochromosonal somatic cell lines (Dubois, B. L. and Naylor, S. (1993), Genomics, 16:315–319). The expected PCR product of 156 bp was amplified from GM10791 from two distinct cell lines, suggesting that the BAZ1β gene is likely to be located on human chromosone 7 (FIG. 19A). The locus of BAZ1β was determined using 91 radiation hybrid panels of GeneBridge 4 (Walter, M. A. et al., (1994), Nature Genetics, 7:22–28). The hybrid panels were screened by performing PCR with primers nb3S and nb3T again. The locus of this gene was identified by comparing the binary codes generated by assessing each hybrid as positive or negative for the amplification with the analogous codes for the markers constituting a framework map using the server located at the web site of the Whitehead Institute for Biomedical Research/MIT Center for Genome Research. As a result, BAZ1β was confirmed to be mapped on chromosome 7q11–22 and also located between the markers D7S489 and D7S669 (FIG. 19B).

(4) Analysis of the BAZ1β expression

Figure 20A:
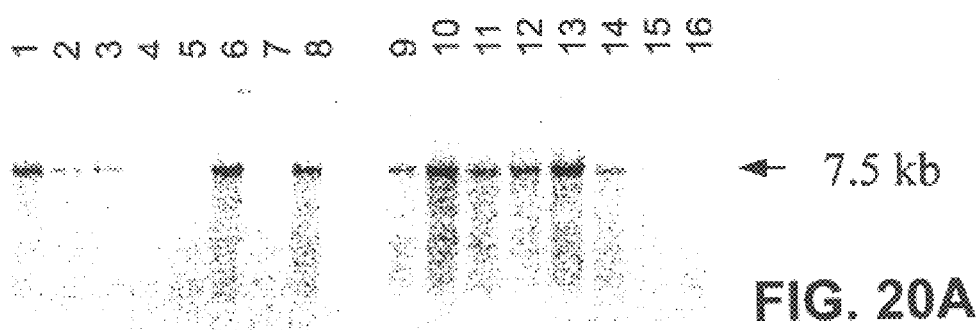
FIGS. 20A and 20B show the expression analysis of BAZ1β in normal tissues.
Figure 20B:
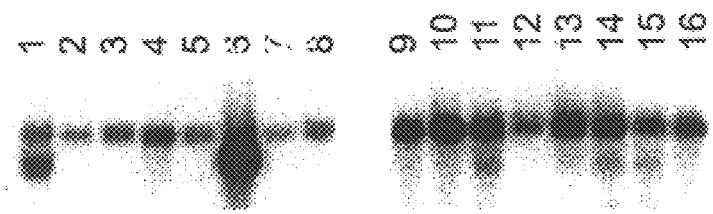

The cDNA probe of 156 bp prepared by PCR for the testis cDNA using primers nb3S and nb3T was used for Northern analysis of 16 panels of normal tissues (FIG. 20). The probe was labeled with [α-$^{32}$P]dCTP by random priming and purified with a Chromaspin 10 column (Clontech). Hybridization for Northern analysis was performed at 65° C. for 1 hour in ExpressHyb hybridization solution (Clontech). The filters were washed at 65° C. until the final stringency reached 0.5×SSC and 0.1% SDS. Subsequently, autoradiography was performed at −70° C. for 4 days to intensify the signals of the filters or for 4 hours with a Fuji BAS system. This probe detected an mRNA of 7.5 kb in almost all the tissues examined. The transcript was analogous to a 7.0 kb transcript of BAZ1α.

EXAMPLE 5

Expression and Purification of BAZ2β Fusion Protein

Figure 21:
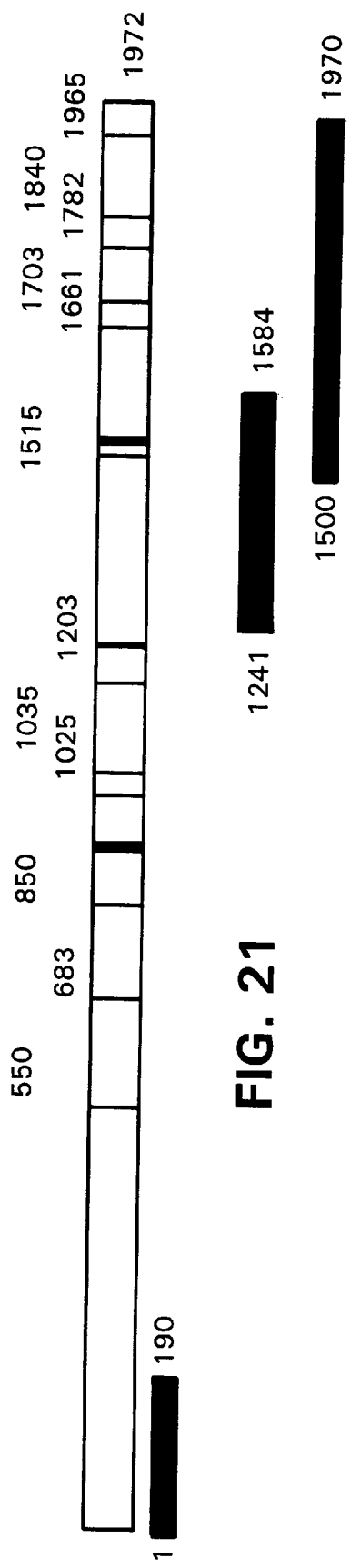
FIG. 21 shows the regions within BAZ2β which are covered by expression clones. Conserved domains (shadowed boxes) and LXXLL (SEQ ID NO:37) motifs (black lines) are indicated. Positions of the first and the last amino acids of each domain are indicated on the bar. Clone 1 covers amino acids 1–190; clone 9, amino acids 1241–1584; and clone 11, amino acids 1500–1970.

Three constructs for BAZ2β were prepared with pGEX vector (Pharmacia) used to express fusion proteins in bacteria. Each of the three constructs contained the sequence corresponding to the amino acid positions 1–190, 1241–1584, or 1500–1970 of BAZ2α (FIG. 21). The expression of the fusion protein was mediated by the IPTG-inducible promoter located upstream from the cloning site. The expressed proteins were purified through an affinity matrix containing glutathione-Sepharose beads since the expressed protein was fused to glutathione-S-transferase (GST). Specifically, the GST fusion proteins were expressed and purified according to the instructions appended to GST purification modules (Pharmacia). The cultured volume was 400 ml, and proteins were induced by 0.1 mM IPTG at 30° C. overnight. Western blotting was performed using BioRad reagents included in an Alkaline Phosphatase Conjugate Substrate kit, according to the manual appended to the kit.

Figure 22:
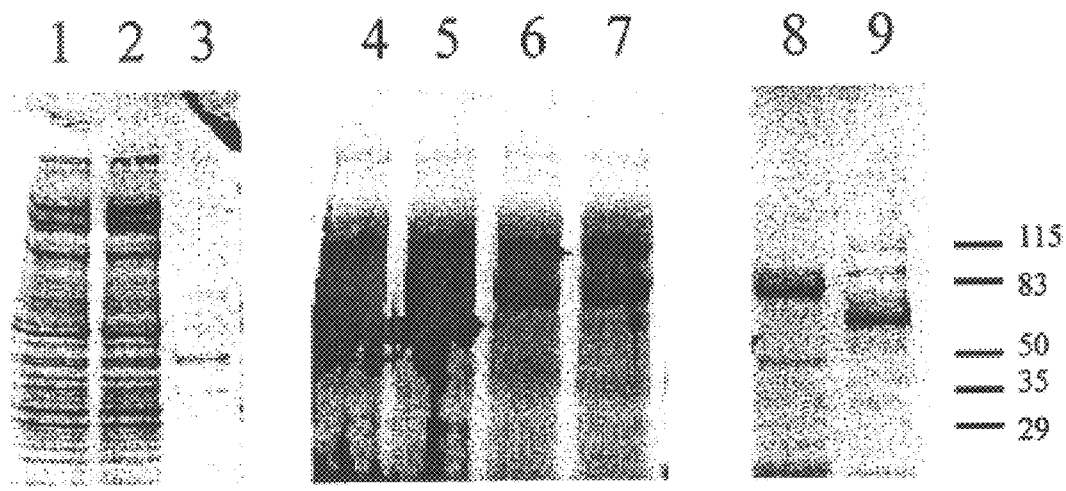
FIG. 22 is a photograph of electrophoretic patterns showing SDS-PAGE analysis of GST protein (Lane 1, cell lysate (BAZ2β.1); Lane 2, flow through fraction (BAZ2β.1); Lane 3, purified fusion protein (BAZ2β.1); Lane 4, cell lysate (BAZ2β.11); Lane 5, cell lysate (BAZ2β.9); Lane 6, flow through fraction (BAZ2β.11); Lane 7, flow through fraction (BAZ2β.9); Lane 8, purified protein (BAZ2β.11); and Lane 9, purified protein (BAZ2β.9). The positions of molecular weight markers are indicated on the right (kDa).
Figure 23:
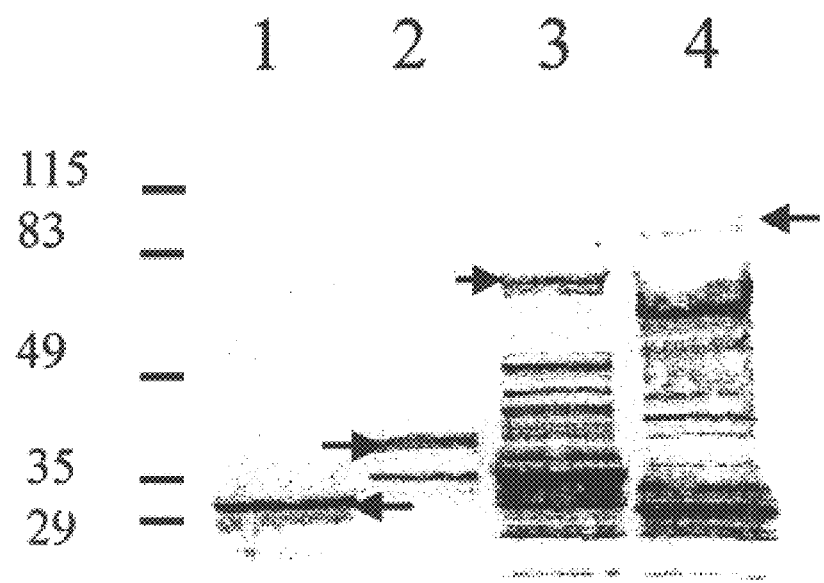
FIG. 23 is a photograph of electrophoresis showing Western analysis of purified GST-fusion protein (Lane 1, GST; Lane 2, GST-BAZ2β.1; Lane 3, GST-BAZ2β.9; and Lane 4, GST-BAZ2β.11).

The results of analyzing the expressed protein on the 4–20% gradient SDS-polyacrylamide gel showed that the induced proteins were not detected in the bacterial cell lysates before purification (FIG. 22, Lanes 1, 4, and 5), indicating that the induction through the promoter was not strong in any construct. In any case, however, distinctive proteins. (Table 2) with molecular weights corresponding to those predicted were detected (FIG. 23, Lanes 3, 8, and 9). To prove that the purified proteins were the desired fusion proteins, western blot was carried out using the anti-GST antibody. As a result, purified protein with the corresponding size predicted for each protein was detected.

TABLE 2

| Construct | Amino acid region | Predicted MWT kDal | Detected MWT kDal |
|---|---|---|---|
| BAZ2β.1 | 1–190 | 51 | 50 |
| BAZ2β.9 | 1241–1584 | 67 | 65 |
| BAZ2β.11 | 1500–1970 | 84 | 85 |

Industrial Applicability

The present invention provides a novel transcriptional regulator having a bromodomain, DNA coding said transcriptional regulator, a vector containing said DNA, a transformant expressively retaining said DNA, an antibody binding to said transcriptional regulator, and the method of screening a compound binding to said transcriptional regulator. A transcriptional regulator and DNA of the present invention are expected to be used as indices to diagnose and treat cancer and proliferative diseases, and to screen a drug with a new action mechanism. A compound binding to a transcriptional regulator of the present invention could also be used as a pharmaceutical to treat the diseases described above.

What is claimed is:

1. An isolated nucleic acid encoding a polypeptide comprising an amino acid sequence at least 60% identical to SEQ ID NO:1, wherein the polypeptide regulates transcription of a gene and comprises a bromodomain.

2. The isolated nucleic acid of claim 1, wherein the amino acid sequence is at least 70% identical to SEQ ID NO:1.

3. The isolated nucleic acid of claim 1, wherein the amino acid sequence is at least 80% identical to SEQ ID NO:1.

4. The isolated nucleic acid of claim 1, wherein the amino acid sequence is at least 90% identical to SEQ ID NO:1.

5. The isolated nucleic acid of claim 1, wherein the amino acid sequence is at least 95% identical to SEQ ID NO:1.

6. An isolated nucleic acid encoding a polypeptide comprising an amino acid sequence as set forth in SEQ ID NO:1.

7. An isolated nucleic acid encoding a polypeptide consisting of SEQ ID NO:1.

8. An isolated nucleic acid comprising the coding sequence of SEQ ID NO:2.

9. An isolated nucleic acid encoding a polypeptide comprising the amino acid sequence set forth in SEQ ID NO:1 with up to 30 conservative amino acid substitutions, wherein the polypeptide regulates transcription of a gene and comprises a bromodomain.

10. An isolated nucleic acid that hybridizes under high stringency conditions to the coding sequence of SEQ ID NO:2, wherein said nucleic acid encodes a polypeptide that regulates transcription of a gene and comprises a bromodomain.

11. The nucleic acid of claim 10, wherein the nucleic acid is at least 15 nucleotides in length.

12. An isolated nucleic acid that hybridizes under high stringency conditions to the coding sequence of SEQ ID NO:2, wherein said nucleic acid encodes a polypeptide that comprises SEQ ID NO:1.

13. A vector comprising the nucleic acid of claim 1.

14. A vector comprising the nucleic acid of claim 6.

15. A vector comprising the nucleic acid of claim 7.

16. A vector comprising the nucleic acid of claim 8.

17. A vector comprising the nucleic acid of claim 9.

18. A vector comprising the nucleic acid of claim 10.

19. A vector comprising the nucleic acid of claim 12.

20. A cultured host cell comprising the nucleic acid of claim 1.

21. A cultured host cell comprising the nucleic acid of claim 6.

22. A host cell comprising the nucleic acid of claim 7.

23. A host cell comprising the nucleic acid of claim 8.

24. A cultured host cell comprising the nucleic acid of claim 9.

25. A cultured host cell comprising the nucleic acid of claim 10.

26. A cultured host cell comprising the nucleic acid of claim 12.

27. A host cell comprising the vector of claim 15.

28. A host cell comprising the vector of claim 16.

29. A method of preparing a polypeptide, the method comprising culturing the host cell of claim 20, wherein the host cell expresses the polypeptide, and isolating the polypeptide from the host cell.

30. A method of preparing a polypeptide, the method comprising culturing the host cell of claim 21, wherein the host cell expresses the polypeptide, and isolating the polypeptide from the host cell.

31. A method of preparing a polypeptide, the method comprising culturing the host cell of claim 22, wherein the host cell expresses the polypeptide, and isolating the polypeptide from the host cell.

32. A method of preparing a polypeptide, the method comprising culturing the host cell of claim 23, wherein the host cell expresses the polypeptide, and isolating the polypeptide from the host cell.

33. A method of preparing a polypeptide, the method comprising culturing the host cell of claim 24, wherein the host cell expresses the polypeptide, and isolating the polypeptide from the host cell.

34. A method of preparing a polypeptide, the method comprising culturing the host cell of claim 25, wherein the host cell expresses the polypeptide, and isolating the polypeptide from the host cell.

35. A method of preparing a polypeptide, the method comprising culturing the host cell of claim 26, wherein the host cell expresses the polypeptide, and isolating the polypeptide from the host cell.

36. A method of screening for a compound that binds to a polypeptide, the method comprising:
   providing the nucleic acid of claim 1;
   introducing the nucleic acid into a cell and allowing the cell to produce the polypeptide encoded by the nucleic acid;
   contacting a test compound with the polypeptide; and
   determining whether the test compound has bound to the polypeptide.

37. The method of claim 36, wherein the polypeptide is isolated from the cell.

38. The method of claim 36, wherein the test compound is contacted with the polypeptide in the cell.

39. The method of claim 36, wherein the nucleic acid encodes a polypeptide comprising an amino acid sequence at least 70% identical to SEQ ID NO:1.

40. The method of claim 36, wherein the nucleic acid encodes a polypeptide comprising an amino acid sequence at least 80% identical to SEQ ID NO:1.

41. The method of claim 36, wherein the nucleic acid encodes a polypeptide comprising an amino acid sequence at least 90% identical to SEQ ID NO:1.

42. The method of claim 41, wherein the polypeptide is isolated from the cell.

43. The method of claim 36, wherein the nucleic acid encodes a polypeptide comprising an amino acid sequence at least 95% identical to SEQ ID NO:1.

44. The method of claim 43, wherein the polypeptide is isolated from the cell.

45. A method of screening for a compound that binds to a polypeptide, the method comprising:
providing a nucleic acid encoding a polypeptide comprising the amino acid sequence of SEQ ID NO:1;
introducing the nucleic acid into a cell and allowing the cell to produce the polypeptide encoded by the nucleic acid;
contacting a test compound with the polypeptide; and
determining whether the test compound has bound to the polypeptide.

46. The method of claim 45, wherein the polypeptide is isolated from the cell.

47. A method of screening for a compound that binds to a polypeptide, the method comprising:
providing the nucleic acid of claim 7;
introducing the nucleic acid into a cell and allowing the cell to produce the polypeptide encoded by the nucleic acid;
contacting a test compound with the polypeptide; and
determining whether the test compound has bound to the polypeptide.

48. A method of screening for a compound that binds to a polypeptide, the method comprising:
providing the nucleic acid of claim 8;
introducing the nucleic acid into a cell and allowing the cell to produce the polypeptide encoded by the nucleic acid;
contacting a test compound with the polypeptide; and
determining whether the test compound has bound to the polypeptide.

49. A method of screening for a compound that binds to a polypeptide, the method comprising:
providing the nucleic acid of claim 9;
introducing the nucleic acid into a cell and allowing the cell to produce the polypeptide encoded by the nucleic acid;
contacting a test compound with the polypeptide; and
determining whether the test compound has bound to the polypeptide.

50. The method of claim 49, wherein the polypeptide is isolated from the cell.

51. The method of claim 49, wherein the test compound is contacted with the polypeptide in the cell.

52. A method of screening for a compound that binds to a polypeptide, the method comprising:
providing the nucleic acid of claim 10;
introducing the nucleic acid into a cell and allowing the cell to produce the polypeptide encoded by the nucleic acid;
contacting a test compound with the polypeptide; and
determining whether the test compound has bound to the polypeptide.

53. The method of claim 52, wherein the polypeptide is isolated from the cell.

54. The method of claim 52, wherein the test compound is contacted with the polypeptide in the cell.

55. A method of screening for a compound that binds to a polypeptide, the method comprising:
providing the vector of claim 13;
introducing the vector into a cell and allowing the cell to produce the polypeptide encoded by the nucleic acid;
contacting a test compound with the polypeptide; and
determining whether the test compound has bound to the polypeptide.

56. The method of claim 55, wherein the polypeptide is isolated from the cell.

57. The method of claim 55, wherein the test compound is contacted with the polypeptide in the cell.

58. A method of screening for a compound that binds to a polypeptide, the method comprising:
providing the vector of claim 14;
introducing the vector into a cell and allowing the cell to produce the polypeptide encoded by the nucleic acid;
contacting a test compound with the polypeptide; and
determining whether the test compound has bound to the polypeptide.

59. A method of screening for a compound that binds to a polypeptide, the method comprising:
providing the vector of claim 17;
introducing the vector into a cell and allowing the cell to produce the polypeptide encoded by the nucleic acid;
contacting a test compound with the polypeptide; and
determining whether the test compound has bound to the polypeptide.

60. A method of screening for a compound that binds to a polypeptide, the method comprising:
providing the vector of claim 18;
introducing the vector into a cell and allowing the cell to produce the polypeptide encoded by the nucleic acid;
contacting a test compound with the polypeptide; and
determining whether the test compound has bound to the polypeptide.

61. A method of screening for a compound that binds to a polypeptide, the method comprising:
providing the cell of claim 20;
allowing the cell to produce the polypeptide encoded by the nucleic acid;
contacting a test compound with the polypeptide; and
determining whether the test compound has bound to the polypeptide.

62. The method of claim 61, wherein the polypeptide is isolated from the cell.

63. The method of claim 61, wherein the test compound is contacted with the polypeptide in the cell.

64. A method of screening for a compound that binds to a polypeptide, the method comprising:
providing the cell of claim 21;
allowing the cell to produce the polypeptide encoded by the nucleic acid;
contacting a test compound with the polypeptide; and
determining whether the test compound has bound to the polypeptide.

65. A method of screening for a compound that binds to a polypeptide, the method comprising:
providing the cell of claim 24;
allowing the cell to produce the polypeptide encoded by the nucleic acid;
contacting a test compound with the polypeptide; and
determining whether the test compound has bound to the polypeptide.

66. A method of screening for a compound that binds to a polypeptide, the method comprising:

provridng the cell of claim 25;

allowing the cell to produce the polypeptide encoded by the nucleic acid;

contacting a test compound with the polypeptide; and determining whether the test compound has bound to the polypeptide.

* * * * *

UNITED STATES PATENT AND TRADEMARK OFFICE
CERTIFICATE OF CORRECTION

PATENT NO. : 6,596,482 B1
DATED : July 22, 2003
INVENTOR(S) : Michael H. Jones

It is certified that error appears in the above-identified patent and that said Letters Patent is hereby corrected as shown below:

<u>Title page,</u>
Item [56], References Cited, OTHER PUBLICATIONS, Lu et al., references "Genemics" should read -- Genomics --.
Beck et al., references, "hemeotic (fsh)" should read -- homeotic (fsh) --.
and "class region" should read -- class II region --.
Hayes et al., reference, "*Dev Biol* Jul. 1989; 134(1):246-57 (abstract)."
should read -- *Dev Biol* 1989 Jul; 134(1):246-57 (abstract). --.
GenBank Accession No. M87651, "D. cerevisiae" should read -- S. cerevisiae --.
Jones et al., reference, "Bromodomains" should read -- Bromodomain --.

<u>Drawings:</u>
Figure 6B, Moz.1line, the second T should not be bolded:
"L̲ISCADCGNSGHPSCL̲KFSPELTVRVKA̲LRWQCIEC"
should read -- L̲ISCADCGNSGHPSCL̲KFSPELTVRVKA̲LRWQCIEC --

Figure 15, BAZ2A 755 line, the V should not be bold:
"M………..KEKEEVTK̲AKPACKAD̲K."
should read -- M………..KEKEEVTK̲AKPACKAD̲K. --.

Figure 16, BAZ2A 989 line, the first L and A should be in bold:
"…LKTV̲LAKR̲TGR̲SE…." should read -- …LAKTV̲LAKR̲TGR̲SE…. --

Figure 17, BAZ2B 1712 line, the M should be underlined:
"SAAQVALCI̲QQLQK̲SIAWEKSIMKVYCQI̲CRKGDN"
should read -- SAAQVALCI̲QQLQK̲SIAWEKSIM̲KVYCQI̲CRKGDN --

UNITED STATES PATENT AND TRADEMARK OFFICE
CERTIFICATE OF CORRECTION

PATENT NO. : 6,596,482 B1
DATED : July 22, 2003
INVENTOR(S) : Michael H. Jones

It is certified that error appears in the above-identified patent and that said Letters Patent is hereby corrected as shown below:

Figure 18, Cont.
should read
-- LGRSSGRQGGVHELSAFEQLVVELVRHDDSW
PFLKLVSKIQVPDYYDIIKKPIALNIIR --.

Signed and Sealed this

Eighth Day of June, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,596,482 B1
DATED : July 22, 2003
INVENTOR(S) : Michael H. Jones

It is certified that error appears in the above-identified patent and that said Letters Patent is hereby corrected as shown below:

<u>Drawings,</u>
Figure 16, BAZ2A 989 line, the first L and A should be in bold:
"...LKT<u>V</u>LAK<u>R</u>TG<u>R</u>SE...." should read -- ...LKT<u>V</u>LAK<u>R</u>TG<u>R</u>SE.... --.

Figure 17, BAZ2B 1712 line, the M should be underlined:
"SAAQVALC<u>I</u>QQL<u>QK</u>SIAWEKSIMKVYCQ<u>I</u>CRKGDN" should read
-- SAAQVALC<u>I</u>QQL<u>QK</u>SIAWEKSI<u>M</u>KVYCQ<u>I</u>CRKGDN --

Figure 18, BAZ1A 1539 line, the fourth I should be underlined:
"LGRRSSGRQGGVHE<u>LS</u>AFEQ<u>LVVEL</u>VRHDDSWPFLKLVS<u>K</u>IQVPDYYD<u>I</u>IKK PIALNIIR" should read
-- LGRRSSGRQGGVHE<u>LS</u>AFEQ<u>LVVEL</u>VRHDDSWPFLKLVS<u>K</u>IQVPDYYD<u>I</u>IK KP<u>I</u>ALNIIR --

Signed and Sealed this

First Day of February, 2005

JON W. DUDAS
*Director of the United States Patent and Trademark Office*

UNITED STATES PATENT AND TRADEMARK OFFICE
CERTIFICATE OF CORRECTION

PATENT NO. : 6,596,482 B1
DATED : July 22, 2003
INVENTOR(S) : Michael H. Jones

It is certified that error appears in the above-identified patent and that said Letters Patent is hereby corrected as shown below:

<u>Drawings</u>,
Figure 16, BAZ2A 989 line, the first L and A should be in bold:
"...LKT<u>V</u>LAK<u>R</u>TG<u>R</u>SE...." should read -- ...LKTVLAKRTGRSE.... --.

Figure 17, BAZ2B 1712 line, the M should be underlined:
"SAAQVALC<u>I</u>QQL<u>QK</u>SIAWEKSIMKVYCQ<u>I</u>CRKGDN" should read
-- SAAQVALC<u>I</u>QQL<u>QK</u>SIAWEKS<u>I</u><u>M</u>KVYCQ<u>I</u>CRKGDN --.

Figure 18, BAZ1A 1539 line, the fourth I should be underlined:
"LGRRSSGRQGGVH<u>EL</u>SAFEQ<u>LVVEL</u>VRHDDSWPFLKLVS<u>K</u>IQVPDYYD<u>I</u>IKK PIALNIIR" should read
-- LGRRSSGRQGGVH<u>EL</u>SAFEQ<u>LVVEL</u>VRHDDSWPFLKLVS<u>K</u>IQVPDYYD<u>I</u>IK KP<u>I</u>ALNIIR --.

This certificate supersedes Certificate of Correction issued February 1, 2005.

Signed and Sealed this

Third Day of January, 2006

JON W. DUDAS
*Director of the United States Patent and Trademark Office*

SEQUENCE LISTING

<160> NUMBER OF SEQ ID NOS: 73

<210> SEQ ID NO 1
<211> LENGTH: 1674
<212> TYPE: PRT
<213> ORGANISM: Homo sapiens

<400> SEQUENCE: 1

```
Met Glu Asp Ala Ser Glu Ser Ser Arg Gly Val Ala Pro Leu Ile Asn
 1               5                  10                  15

Asn Val Val Leu Pro Gly Ser Pro Leu Ser Leu Pro Val Ser Val Thr
                20                  25                  30

Gly Cys Lys Ser His Arg Val Ala Asn Lys Lys Val Glu Ala Arg Ser
            35                  40                  45

Glu Lys Leu Leu Pro Thr Ala Leu Pro Pro Ser Glu Pro Lys Val Asp
        50                  55                  60

Gln Lys Leu Pro Arg Ser Ser Glu Arg Gly Ser Gly Gly Thr
 65                 70                  75                  80

Gln Phe Pro Ala Arg Ser Arg Ala Val Ala Ala Gly Glu Ala Ala Ala
                85                  90                  95

Arg Gly Ala Ala Gly Pro Glu Arg Gly Ser Pro Leu Gly Arg Arg Val
                100                 105                 110

Ser Pro Arg Cys Leu Cys Ser Gly Glu Gly Gly Gln Val Ala Val Gly
            115                 120                 125

Val Ile Ala Gly Lys Arg Gly Arg Arg Gly Arg Asp Gly Ser Arg Arg
        130                 135                 140

Ala Pro Gly Gly Arg Glu Met Pro Leu Leu His Arg Lys Pro Phe Val
145                 150                 155                 160

Arg Gln Lys Pro Pro Ala Asp Leu Arg Pro Asp Glu Val Phe Tyr
                165                 170                 175

Cys Lys Val Thr Asn Glu Ile Phe Arg His Tyr Asp Asp Phe Phe Glu
                180                 185                 190

Arg Thr Ile Leu Cys Asn Ser Leu Val Trp Ser Cys Ala Val Thr Gly
            195                 200                 205

Arg Pro Gly Leu Thr Tyr Gln Glu Ala Leu Glu Ser Glu Lys Lys Ala
        210                 215                 220

Arg Gln Asn Leu Gln Ser Phe Pro Glu Pro Leu Ile Ile Pro Val Leu
225                 230                 235                 240

Tyr Leu Thr Ser Leu Thr His Arg Ser Arg Leu His Glu Ile Cys Asp
                245                 250                 255

Asp Ile Phe Ala Tyr Val Lys Asp Arg Tyr Phe Val Glu Glu Thr Val
                260                 265                 270

Glu Val Ile Arg Asn Asn Gly Ala Arg Leu Gln Cys Thr Ile Leu Glu
            275                 280                 285

Val Leu Pro Pro Ser His Gln Asn Gly Phe Ala Asn Gly His Val Asn
        290                 295                 300

Ser Val Asp Gly Glu Thr Ile Ile Ile Ser Asp Ser Asp Ser Glu
305                 310                 315                 320

Thr Gln Ser Cys Ser Phe Gln Asn Gly Lys Lys Asp Ala Ile Asp
                325                 330                 335

Pro Leu Leu Phe Lys Tyr Lys Val Gln Pro Thr Lys Glu Leu His
                340                 345                 350

Glu Ser Ala Ile Val Lys Ala Thr Gln Ile Ser Arg Arg Lys His Leu
```

-continued

```
                355                 360                 365
Phe Ser Arg Asp Lys Leu Lys Leu Phe Leu Lys Gln His Cys Glu Pro
    370                 375                 380

Gln Glu Gly Val Ile Lys Ile Lys Ala Ser Ser Leu Ser Thr Tyr Lys
385                 390                 395                 400

Ile Ala Glu Gln Asp Phe Ser Tyr Phe Phe Pro Asp Pro Pro Thr
                    405                 410                 415

Phe Ile Phe Ser Pro Ala Asn Arg Arg Gly Arg Pro Pro Lys Arg
                420                 425                 430

Ile His Ile Ser Gln Glu Asp Asn Val Ala Asn Lys Gln Thr Leu Ala
                435                 440                 445

Ser Tyr Arg Ser Lys Ala Thr Lys Glu Arg Asp Lys Leu Leu Lys Gln
    450                 455                 460

Glu Glu Met Lys Ser Leu Ala Phe Glu Lys Ala Lys Leu Lys Arg Glu
465                 470                 475                 480

Lys Ala Asp Ala Leu Glu Ala Lys Lys Lys Glu Lys Glu Asp Lys Glu
                485                 490                 495

Lys Lys Arg Glu Glu Leu Lys Lys Ile Val Glu Glu Arg Leu Lys
                500                 505                 510

Lys Lys Glu Glu Lys Glu Arg Leu Lys Val Glu Arg Glu Lys Glu Arg
            515                 520                 525

Glu Lys Leu Arg Glu Glu Lys Arg Lys Tyr Val Glu Tyr Leu Lys Gln
    530                 535                 540

Trp Ser Lys Pro Arg Glu Asp Met Glu Cys Asp Asp Leu Lys Glu Leu
545                 550                 555                 560

Pro Glu Pro Thr Pro Val Lys Thr Arg Leu Pro Pro Glu Ile Phe Gly
                565                 570                 575

Asp Ala Leu Met Val Leu Glu Phe Leu Asn Ala Phe Gly Glu Leu Phe
                580                 585                 590

Asp Leu Gln Asp Glu Phe Pro Asp Gly Val Thr Leu Glu Val Leu Glu
                595                 600                 605

Glu Ala Leu Val Gly Asn Asp Ser Glu Gly Pro Leu Cys Glu Leu Leu
    610                 615                 620

Phe Phe Phe Leu Thr Ala Ile Phe Gln Ala Ile Ala Glu Glu Glu Glu
625                 630                 635                 640

Glu Val Ala Lys Glu Gln Leu Thr Asp Ala Asp Thr Lys Gly Cys Ser
                645                 650                 655

Leu Lys Ser Leu Asp Leu Asp Ser Cys Thr Leu Ser Glu Ile Leu Arg
                660                 665                 670

Leu His Ile Leu Ala Ser Gly Ala Asp Val Thr Ser Ala Asn Ala Lys
                675                 680                 685

Tyr Arg Tyr Gln Lys Arg Gly Gly Phe Asp Ala Thr Asp Asp Ala Cys
    690                 695                 700

Met Glu Leu Arg Leu Ser Asn Pro Ser Leu Val Lys Lys Leu Ser Ser
705                 710                 715                 720

Thr Ser Val Tyr Asp Leu Thr Pro Gly Glu Lys Met Lys Ile Leu His
                725                 730                 735

Ala Leu Cys Gly Lys Leu Leu Thr Leu Val Ser Thr Arg Asp Phe Ile
                740                 745                 750

Glu Asp Tyr Val Asp Ile Leu Arg Gln Ala Lys Gln Glu Phe Arg Glu
                755                 760                 765

Leu Lys Ala Glu Gln His Arg Lys Glu Arg Glu Glu Ala Ala Ala Arg
    770                 775                 780
```

-continued

```
Ile Arg Lys Arg Lys Glu Glu Lys Leu Lys Glu Gln Glu Gln Lys Met
785                 790                 795                 800

Lys Glu Lys Gln Glu Lys Leu Lys Glu Asp Glu Gln Arg Asn Ser Thr
            805                 810                 815

Ala Asp Ile Ser Ile Gly Glu Glu Arg Glu Asp Phe Asp Thr Ser
        820                 825                 830

Ile Glu Ser Lys Asp Thr Glu Gln Lys Glu Leu Asp Gln Asp Met Phe
        835                 840                 845

Thr Glu Asp Glu Asp Asp Pro Gly Ser His Lys Arg Gly Arg Arg Gly
850                 855                 860

Lys Arg Gly Gln Asn Gly Phe Lys Glu Phe Thr Arg Gln Glu Gln Ile
865                 870                 875                 880

Asn Cys Val Thr Arg Glu Leu Leu Thr Ala Asp Glu Glu Ala Leu
                885                 890                 895

Lys Gln Glu His Gln Arg Lys Glu Lys Glu Leu Leu Glu Lys Ile Gln
                900                 905                 910

Ser Ala Ile Ala Cys Thr Asn Ile Phe Pro Leu Gly Arg Asp Arg Met
            915                 920                 925

Tyr Arg Arg Tyr Trp Ile Phe Pro Ser Ile Pro Gly Leu Phe Ile Glu
930                 935                 940

Glu Asp Tyr Ser Gly Leu Thr Glu Asp Met Leu Leu Pro Arg Pro Ser
945                 950                 955                 960

Ser Phe Gln Asn Asn Val Gln Ser Gln Asp Pro Gln Val Ser Thr Lys
                965                 970                 975

Thr Gly Glu Pro Leu Met Ser Glu Ser Thr Ser Asn Ile Asp Gln Gly
            980                 985                 990

Pro Arg Asp His Ser Val Gln Leu Pro Lys Pro Val His Lys Pro Asn
        995                 1000                1005

Arg Trp Cys Phe Tyr Ser Ser Cys Glu Gln Leu Asp Gln Leu Ile Glu
        1010                1015                1020

Ala Leu Asn Ser Arg Gly His Arg Glu Ser Ala Leu Lys Glu Thr Leu
1025                1030                1035                1040

Leu Gln Glu Lys Ser Arg Ile Cys Ala Gln Leu Ala Arg Phe Ser Glu
            1045                1050                1055

Glu Lys Phe His Phe Ser Asp Lys Pro Gln Pro Asp Ser Lys Pro Thr
            1060                1065                1070

Tyr Ser Arg Gly Arg Ser Ser Asn Ala Tyr Asp Pro Ser Gln Met Cys
            1075                1080                1085

Ala Glu Lys Gln Leu Glu Leu Arg Leu Arg Asp Phe Leu Leu Asp Ile
        1090                1095                1100

Glu Asp Arg Ile Tyr Gln Gly Thr Leu Gly Ala Ile Lys Val Thr Asp
1105                1110                1115                1120

Arg His Ile Trp Arg Ser Ala Leu Glu Ser Gly Arg Tyr Glu Leu Leu
                1125                1130                1135

Ser Glu Glu Asn Lys Glu Asn Gly Ile Ile Lys Thr Val Asn Glu Asp
            1140                1145                1150

Val Glu Glu Met Glu Ile Asp Glu Gln Thr Lys Val Ile Val Lys Asp
            1155                1160                1165

Arg Leu Leu Gly Ile Lys Thr Glu Thr Pro Ser Thr Val Ser Thr Asn
        1170                1175                1180

Ala Ser Thr Pro Gln Ser Val Ser Ser Val Val His Tyr Leu Ala Met
1185                1190                1195                1200
```

```
Ala Leu Phe Gln Ile Glu Gln Gly Ile Glu Arg Arg Phe Leu Lys Ala
                1205                1210                1215

Pro Leu Asp Ala Ser Asp Ser Gly Arg Ser Tyr Lys Thr Val Leu Asp
            1220                1225                1230

Arg Trp Arg Glu Ser Leu Leu Ser Ser Ala Ser Leu Ser Gln Val Phe
        1235                1240                1245

Leu His Leu Ser Thr Leu Asp Arg Ser Val Ile Trp Ser Lys Ser Ile
    1250                1255                1260

Leu Asn Ala Arg Cys Lys Ile Cys Arg Lys Lys Gly Asp Ala Glu Asn
1265                1270                1275                1280

Met Val Leu Cys Asp Gly Cys Asp Arg Gly His His Thr Tyr Cys Val
                1285                1290                1295

Arg Pro Lys Leu Lys Thr Val Pro Glu Gly Asp Trp Phe Cys Pro Glu
            1300                1305                1310

Cys Arg Pro Lys Gln Arg Cys Arg Arg Leu Ser Phe Arg Gln Arg Pro
        1315                1320                1325

Ser Leu Glu Ser Asp Glu Asp Val Glu Asp Ser Met Gly Gly Glu Asp
    1330                1335                1340

Asp Glu Val Asp Gly Asp Glu Glu Gly Gln Ser Glu Glu Glu Glu
1345                1350                1355                1360

Tyr Glu Val Glu Gln Asp Glu Asp Ser Gln Glu Glu Glu Val
            1365                1370                1375

Ser Leu Pro Lys Arg Gly Arg Pro Gln Val Arg Leu Pro Val Lys Thr
        1380                1385                1390

Arg Gly Lys Leu Ser Ser Ser Phe Ser Ser Arg Gly Gln Gln Gln Glu
    1395                1400                1405

Pro Gly Arg Tyr Pro Ser Arg Ser Gln Gln Ser Thr Pro Lys Thr Thr
        1410                1415                1420

Val Ser Ser Lys Thr Gly Arg Ser Leu Arg Lys Ile Asn Ser Ala Pro
1425                1430                1435                1440

Pro Thr Glu Thr Lys Ser Leu Arg Ile Ala Ser Arg Ser Thr Arg His
            1445                1450                1455

Ser His Gly Pro Leu Gln Ala Asp Val Phe Val Glu Leu Leu Ser Pro
        1460                1465                1470

Arg Arg Lys Arg Gly Arg Lys Ser Ala Asn Asn Thr Pro Glu Asn
        1475                1480                1485

Ser Pro Asn Phe Pro Asn Phe Arg Val Ile Ala Thr Lys Ser Ser Glu
    1490                1495                1500

Gln Ser Arg Ser Val Asn Ile Ala Ser Lys Leu Ser Leu Gln Glu Ser
1505                1510                1515                1520

Glu Ser Lys Arg Arg Cys Arg Lys Arg Gln Ser Pro Glu Pro Ser Pro
            1525                1530                1535

Val Thr Leu Gly Arg Arg Ser Ser Gly Arg Gln Gly Gly Val His Glu
        1540                1545                1550

Leu Ser Ala Phe Glu Gln Leu Val Val Glu Leu Val Arg His Asp Asp
    1555                1560                1565

Ser Trp Pro Phe Leu Lys Leu Val Ser Lys Ile Gln Val Pro Asp Tyr
    1570                1575                1580

Tyr Asp Ile Ile Lys Lys Pro Ile Ala Leu Asn Ile Ile Arg Glu Lys
1585                1590                1595                1600

Val Asn Lys Cys Glu Tyr Lys Leu Ala Ser Glu Phe Ile Asp Asp Ile
            1605                1610                1615

Glu Leu Met Phe Ser Asn Cys Phe Glu Tyr Asn Pro Arg Asn Thr Ser
```

-continued

```
                   1620                1625                1630
Glu Ala Lys Ala Gly Thr Arg Leu Gln Ala Phe Phe His Ile Gln Ala
            1635                1640                1645

Gln Lys Leu Gly Leu His Val Thr Pro Ser Asn Val Asp Gln Val Ser
        1650                1655                1660

Thr Pro Pro Ala Ala Lys Lys Ser Arg Ile
1665                1670

<210> SEQ ID NO 2
<211> LENGTH: 5934
<212> TYPE: DNA
<213> ORGANISM: Homo sapiens
<220> FEATURE:
<221> NAME/KEY: CDS
<222> LOCATION: (125)...(5146)
<221> NAME/KEY: misc_feature
<222> LOCATION: (1)...(5934)
<223> OTHER INFORMATION: n = A,T,C or G

<400> SEQUENCE: 2
gaattccggc ttttcccatc gtgtagtcaa gagtctgtgc cagacttgaa ggctttactt      60
tgttagccat gtgtttatga accccagcg ctttccctag atcttttggc tgataatctc     120 aaac atg gag gat gct tct gaa tct tca cga ggg gtt gct cca tta att     169
     Met Glu Asp Ala Ser Glu Ser Ser Arg Gly Val Ala Pro Leu Ile
         1               5                  10                  15 aat aat gta gtt ctc cca ggc tct ccg ctg tct ctt cct gta tca gtg     217
Asn Asn Val Val Leu Pro Gly Ser Pro Leu Ser Leu Pro Val Ser Val
                20                  25                  30 aca ggc tgt aaa agt cat cga gta gcc aat aaa aag gta gaa gcg agg     265
Thr Gly Cys Lys Ser His Arg Val Ala Asn Lys Lys Val Glu Ala Arg
            35                  40                  45 agt gaa aag ctc ctc cca aca gct ctt cct cct tca gag ccg aaa gta     313
Ser Glu Lys Leu Leu Pro Thr Ala Leu Pro Pro Ser Glu Pro Lys Val
        50                  55                  60 gat cag aaa ctt ccc agg agc tcc gag agg cgg gga agt ggc ggt ggg     361
Asp Gln Lys Leu Pro Arg Ser Ser Glu Arg Arg Gly Ser Gly Gly Gly
    65                  70                  75 acg caa ttc ccc gcg cgg agt cgg gca gtg gca gcg gga gaa gcg gca     409
Thr Gln Phe Pro Ala Arg Ser Arg Ala Val Ala Ala Gly Glu Ala Ala
80                  85                  90                  95 gcc agg ggc gcg gcg ggg ccg gag aga ggc agt ccc ctg gga aga cgg     457
Ala Arg Gly Ala Ala Gly Pro Glu Arg Gly Ser Pro Leu Gly Arg Arg
                100                 105                 110 gtc tcc cct cgt tgc ctt tgt agt gga gaa ggt gga caa gtg gca gtc     505
Val Ser Pro Arg Cys Leu Cys Ser Gly Glu Gly Gly Gln Val Ala Val
            115                 120                 125 ggc gtg atc gca ggg aag cgg ggc cgg cgc ggg cgc gac ggg tcc agg     553
Gly Val Ile Ala Gly Lys Arg Gly Arg Arg Gly Arg Asp Gly Ser Arg
        130                 135                 140 cga gcc ccg ggc gga cgg gag atg ccg ctg cta cac cga aag ccg ttt     601
Arg Ala Pro Gly Gly Arg Glu Met Pro Leu Leu His Arg Lys Pro Phe
    145                 150                 155 gtg aga cag aag ccg ccc gcg gac ctg cgg ccc gac gag gaa gtt ttc     649
Val Arg Gln Lys Pro Pro Ala Asp Leu Arg Pro Asp Glu Glu Val Phe
160                 165                 170                 175 tac tgt aaa gtc acc aac gag atc ttc cgc cac tac gat gac ttt ttt     697
Tyr Cys Lys Val Thr Asn Glu Ile Phe Arg His Tyr Asp Asp Phe Phe
                180                 185                 190 gaa cga acc att ctg tgc aac agc ctt gtg tgg agt tgt gct gtg acg     745
Glu Arg Thr Ile Leu Cys Asn Ser Leu Val Trp Ser Cys Ala Val Thr
```

-continued

| | | | | 195 | | | | 200 | | | | 205 | | | |
|---|---|---|---|---|---|---|---|---|---|---|---|---|---|---|---|
| ggt | aga | cct | gga | ctg | acg | tat | cag | gaa | gca | ctt | gag | tca | gaa | aaa | aaa | 793
| Gly | Arg | Pro | Gly | Leu | Thr | Tyr | Gln | Glu | Ala | Leu | Glu | Ser | Glu | Lys | Lys |
| | | 210 | | | | 215 | | | | 220 | | | | | |

```
gca aga cag aat ctt cag agt ttt cca gaa cca cta att att cca gtt    841
Ala Arg Gln Asn Leu Gln Ser Phe Pro Glu Pro Leu Ile Ile Pro Val
    225                 230                 235 tta tac ttg acc agc ctt acc cat cgt tcg cgc tta cat gaa att tgt    889
Leu Tyr Leu Thr Ser Leu Thr His Arg Ser Arg Leu His Glu Ile Cys
240                 245                 250                 255 gat gat atc ttt gca tat gtc aag gat cga tat ttt gtc gaa gaa act    937
Asp Asp Ile Phe Ala Tyr Val Lys Asp Arg Tyr Phe Val Glu Glu Thr
                260                 265                 270 gtg gaa gtc att agg aac aat ggt gca agg ttg cag tgt acg att ttg    985
Val Glu Val Ile Arg Asn Asn Gly Ala Arg Leu Gln Cys Thr Ile Leu
            275                 280                 285 gaa gtc ctc cct cca tca cat caa aat ggt ttt gct aat gga cat gtt   1033
Glu Val Leu Pro Pro Ser His Gln Asn Gly Phe Ala Asn Gly His Val
        290                 295                 300 aac agt gtg gat gga gaa act att atc atc agt gat agt gat gat tca   1081
Asn Ser Val Asp Gly Glu Thr Ile Ile Ile Ser Asp Ser Asp Asp Ser
305                 310                 315 gaa aca caa agc tgt tct ttt caa aat ggg aag aaa aaa gat gca att   1129
Glu Thr Gln Ser Cys Ser Phe Gln Asn Gly Lys Lys Lys Asp Ala Ile
320                 325                 330                 335 gat ccc tta cta ttc aag tat aaa gtg caa ccc act aaa aaa gaa tta   1177
Asp Pro Leu Leu Phe Lys Tyr Lys Val Gln Pro Thr Lys Lys Glu Leu
                340                 345                 350 cat gag tct gct att gtt aaa gca aca caa atc agc cgg aga aaa cac   1225
His Glu Ser Ala Ile Val Lys Ala Thr Gln Ile Ser Arg Arg Lys His
            355                 360                 365 cta ttt tct cgt gat aaa cta aag ctt ttt ctg aag caa cac tgt gaa   1273
Leu Phe Ser Arg Asp Lys Leu Lys Leu Phe Leu Lys Gln His Cys Glu
        370                 375                 380 cca caa gaa gga gtc att aaa ata aag gca tca tct ctt tca acg tat   1321
Pro Gln Glu Gly Val Ile Lys Ile Lys Ala Ser Ser Leu Ser Thr Tyr
385                 390                 395 aaa ata gca gaa caa gat ttt tct tat ttc ttc cct gat gat cca ccc   1369
Lys Ile Ala Glu Gln Asp Phe Ser Tyr Phe Phe Pro Asp Asp Pro Pro
400                 405                 410                 415 aca ttt atc ttc agt cct gct aac aga cga aga ggg aga cct ccc aaa   1417
Thr Phe Ile Phe Ser Pro Ala Asn Arg Arg Arg Gly Arg Pro Pro Lys
                420                 425                 430 cga ata cat att agt caa gag gac aat gtt gct aat aaa cag act ctt   1465
Arg Ile His Ile Ser Gln Glu Asp Asn Val Ala Asn Lys Gln Thr Leu
            435                 440                 445 gca agt tat agg agc aaa gct act aaa gaa aga gat aaa ctt ttg aaa   1513
Ala Ser Tyr Arg Ser Lys Ala Thr Lys Glu Arg Asp Lys Leu Leu Lys
        450                 455                 460 caa gaa gaa atg aag tca ctg gct ttt gaa aag gct aaa tta aaa aga   1561
Gln Glu Glu Met Lys Ser Leu Ala Phe Glu Lys Ala Lys Leu Lys Arg
    465                 470                 475 gaa aaa gca gat gcc cta gaa gcg aag aaa aaa gaa aaa gaa gat aaa   1609
Glu Lys Ala Asp Ala Leu Glu Ala Lys Lys Lys Glu Lys Glu Asp Lys
480                 485                 490                 495 gag aaa aag agg gaa gaa ttg aaa aaa att gtt gaa gaa gag aga cta   1657
Glu Lys Lys Arg Glu Glu Leu Lys Lys Ile Val Glu Glu Glu Arg Leu
                500                 505                 510 aag aaa aaa gaa gaa aaa gag agg ctt aaa gta gaa aga gaa aag gaa   1705
```

-continued

```
                    Lys Lys Lys Glu Glu Lys Glu Arg Leu Lys Val Glu Arg Lys Glu
                                515                 520                 525 aga gag aag tta cgt gaa gaa aag cga aag tat gtg gaa tac tta aaa       1753
Arg Glu Lys Leu Arg Glu Lys Arg Lys Tyr Val Glu Tyr Leu Lys
            530                 535                 540 cag tgg agt aaa cct aga gaa gat atg gaa tgt gat gac ctt aag gaa       1801
Gln Trp Ser Lys Pro Arg Glu Asp Met Glu Cys Asp Asp Leu Lys Glu
545                 550                 555 ctt cca gaa cca aca cca gtg aaa act aga cta cct cct gaa atc ttt       1849
Leu Pro Glu Pro Thr Pro Val Lys Thr Arg Leu Pro Pro Glu Ile Phe
560                 565                 570                 575 ggt gat gct ctg atg gtt ttg gag ttc ctt aat gca ttt ggg gaa ctt       1897
Gly Asp Ala Leu Met Val Leu Glu Phe Leu Asn Ala Phe Gly Glu Leu
                580                 585                 590 ttt gat ctt caa gat gag ttt cct gat gga gta acc cta gaa gta tta       1945
Phe Asp Leu Gln Asp Glu Phe Pro Asp Gly Val Thr Leu Glu Val Leu
            595                 600                 605 gag gaa gct ctt gtt gga aat gac agt gaa ggc cca ctg tgt gaa ttg       1993
Glu Glu Ala Leu Val Gly Asn Asp Ser Glu Gly Pro Leu Cys Glu Leu
                610                 615                 620 ctt ttt ttc ttc ctg act gca atc ttc cag gca ata gct gaa gaa gaa       2041
Leu Phe Phe Phe Leu Thr Ala Ile Phe Gln Ala Ile Ala Glu Glu Glu
625                 630                 635 gag gaa gta gcc aaa gag caa cta act gat gct gac acc aaa ggc tgc       2089
Glu Glu Val Ala Lys Glu Gln Leu Thr Asp Ala Asp Thr Lys Gly Cys
640                 645                 650                 655 agt ttg aaa agt ttg gat ctt gat agc tgc act ctt tca gaa atc ctc       2137
Ser Leu Lys Ser Leu Asp Leu Asp Ser Cys Thr Leu Ser Glu Ile Leu
                660                 665                 670 aga ctg cac atc tta gct tca ggt gct gat gta aca tca gca aat gca       2185
Arg Leu His Ile Leu Ala Ser Gly Ala Asp Val Thr Ser Ala Asn Ala
            675                 680                 685 aag tat aga tat caa aaa cga gga gga ttt gat gct aca gat gat gct       2233
Lys Tyr Arg Tyr Gln Lys Arg Gly Gly Phe Asp Ala Thr Asp Asp Ala
        690                 695                 700 tgt atg gag ctt cgt ttg agc aat ccc agt cta gtg aag aaa ctg tca       2281
Cys Met Glu Leu Arg Leu Ser Asn Pro Ser Leu Val Lys Lys Leu Ser
705                 710                 715 agc acc tca gtg tat gat ttg aca cca gga gaa aaa atg aag ata ctc       2329
Ser Thr Ser Val Tyr Asp Leu Thr Pro Gly Glu Lys Met Lys Ile Leu
720                 725                 730                 735 cat gct ctc tgt gga aag cta ctg acc cta gtt tca act agg gat ttt       2377
His Ala Leu Cys Gly Lys Leu Leu Thr Leu Val Ser Thr Arg Asp Phe
                740                 745                 750 att gaa gat tat gtt gat ata tta cga cag gca aag cag gag ttc cgg       2425
Ile Glu Asp Tyr Val Asp Ile Leu Arg Gln Ala Lys Gln Glu Phe Arg
            755                 760                 765 gaa tta aaa gca gaa caa cat cga aaa gag agg gaa gaa gca gct gcc       2473
Glu Leu Lys Ala Glu Gln His Arg Lys Glu Arg Glu Glu Ala Ala Ala
        770                 775                 780 aga att cgt aaa agg aag gaa gaa aaa ctt aag gag caa gaa caa aaa       2521
Arg Ile Arg Lys Arg Lys Glu Glu Lys Leu Lys Glu Gln Glu Gln Lys
785                 790                 795 atg aaa gag aaa caa gaa aaa ctg aaa gaa gat gag caa aga aat tca       2569
Met Lys Glu Lys Gln Glu Lys Leu Lys Glu Asp Glu Gln Arg Asn Ser
800                 805                 810                 815 acg gca gat ata tct att ggg gag gaa gaa agg gaa gat ttt gat act       2617
Thr Ala Asp Ile Ser Ile Gly Glu Glu Glu Arg Glu Asp Phe Asp Thr
                820                 825                 830
```

-continued

```
agc att gag agc aaa gac aca gag caa aag gaa tta gat caa gat atg      2665
Ser Ile Glu Ser Lys Asp Thr Glu Gln Lys Glu Leu Asp Gln Asp Met
        835                 840                 845 ttc act gaa gat gaa gat gac cca gga tca cat aaa aga ggc aga agg      2713
Phe Thr Glu Asp Glu Asp Asp Pro Gly Ser His Lys Arg Gly Arg Arg
850                 855                 860 ggg aaa aga gga caa aat gga ttt aaa gaa ttt aca agg caa gaa cag      2761
Gly Lys Arg Gly Gln Asn Gly Phe Lys Glu Phe Thr Arg Gln Glu Gln
        865                 870                 875 atc aac tgt gta aca aga gag ctt ctt act gct gat gag gaa gaa gca      2809
Ile Asn Cys Val Thr Arg Glu Leu Leu Thr Ala Asp Glu Glu Glu Ala
880                 885                 890                 895 tta aaa cag gaa cac caa cga aaa gag aaa gag ctc tta gaa aaa atc      2857
Leu Lys Gln Glu His Gln Arg Lys Glu Lys Glu Leu Leu Glu Lys Ile
                900                 905                 910 caa agt gcc ata gcc tgt acc aat atc ttt ccc ttg ggt cgc gac cgc      2905
Gln Ser Ala Ile Ala Cys Thr Asn Ile Phe Pro Leu Gly Arg Asp Arg
            915                 920                 925 atg tat aga cga tac tgg att ttc cct tct att cct gga ctc ttt att      2953
Met Tyr Arg Arg Tyr Trp Ile Phe Pro Ser Ile Pro Gly Leu Phe Ile
        930                 935                 940 gaa gag gat tat tct ggt ctt act gaa gac atg ctg ttg cct aga cct      3001
Glu Glu Asp Tyr Ser Gly Leu Thr Glu Asp Met Leu Leu Pro Arg Pro
945                 950                 955 tca tca ttt cag aat aat gta cag tct caa gat cct cag gta tcc act      3049
Ser Ser Phe Gln Asn Asn Val Gln Ser Gln Asp Pro Gln Val Ser Thr
960                 965                 970                 975 aaa act gga gag cct ttg atg tct gaa tct acc tcc aac att gac caa      3097
Lys Thr Gly Glu Pro Leu Met Ser Glu Ser Thr Ser Asn Ile Asp Gln
                980                 985                 990 ggt cca cgt gac cat tct gtg cag ctg cca aaa cca gtg cat aag cca      3145
Gly Pro Arg Asp His Ser Val Gln Leu Pro Lys Pro Val His Lys Pro
            995                 1000                1005 aat cgg tgg tgc ttt tac agt tct tgt gaa cag cta gac cag ctt att      3193
Asn Arg Trp Cys Phe Tyr Ser Ser Cys Glu Gln Leu Asp Gln Leu Ile
        1010                1015                1020 gaa gct ctt aat tct aga gga cat aga gaa agt gcc tta aaa gaa act      3241
Glu Ala Leu Asn Ser Arg Gly His Arg Glu Ser Ala Leu Lys Glu Thr
    1025                1030                1035 ttg tta caa gag aaa agc aga ata tgt gca cag cta gcc cgt ttt tct      3289
Leu Leu Gln Glu Lys Ser Arg Ile Cys Ala Gln Leu Ala Arg Phe Ser
1040                1045                1050                1055 gaa gag aaa ttt cat ttt tca gac aaa cct cag cct gat agc aaa cca      3337
Glu Glu Lys Phe His Phe Ser Asp Lys Pro Gln Pro Asp Ser Lys Pro
                1060                1065                1070 aca tat agt cgg gga aga tct tcc aat gca tat gat cca tct cag atg      3385
Thr Tyr Ser Arg Gly Arg Ser Ser Asn Ala Tyr Asp Pro Ser Gln Met
            1075                1080                1085 tgt gca gaa aag caa ctt gaa cta agg ctg aga gat ttt ctt tta gat      3433
Cys Ala Glu Lys Gln Leu Glu Leu Arg Leu Arg Asp Phe Leu Leu Asp
        1090                1095                1100 att gaa gat aga atc tac caa gga aca tta gga gcc atc aag gtt aca      3481
Ile Glu Asp Arg Ile Tyr Gln Gly Thr Leu Gly Ala Ile Lys Val Thr
    1105                1110                1115 gat cga cat atc tgg aga tca gca tta gaa agt gga cgg tat gag ctg      3529
Asp Arg His Ile Trp Arg Ser Ala Leu Glu Ser Gly Arg Tyr Glu Leu
1120                1125                1130                1135 tta agt gag gaa aac aag gaa aat ggg ata att aaa act gtg aat gaa      3577
Leu Ser Glu Glu Asn Lys Glu Asn Gly Ile Ile Lys Thr Val Asn Glu
                1140                1145                1150
```

```
gac gta gaa gag atg gaa att gat gaa caa aca aag gtc ata gta aaa    3625
Asp Val Glu Glu Met Glu Ile Asp Glu Gln Thr Lys Val Ile Val Lys
            1155                1160                1165 gac aga ctt ttg ggg ata aaa aca gaa act cca agt act gta tca aca    3673
Asp Arg Leu Leu Gly Ile Lys Thr Glu Thr Pro Ser Thr Val Ser Thr
    1170                1175                1180 aat gca agt aca cca caa tca gtg agc agt gtg gtt cat tat ctg gca    3721
Asn Ala Ser Thr Pro Gln Ser Val Ser Ser Val Val His Tyr Leu Ala
        1185                1190                1195 atg gca ctc ttt caa ata gag cag ggc att gag cgg cgt ttt ctg aaa    3769
Met Ala Leu Phe Gln Ile Glu Gln Gly Ile Glu Arg Arg Phe Leu Lys
1200                1205                1210                1215 gct cca ctt gat gcc agt gac agt ggg cgt tct tat aaa aca gtt ctg    3817
Ala Pro Leu Asp Ala Ser Asp Ser Gly Arg Ser Tyr Lys Thr Val Leu
            1220                1225                1230 gac cgt tgg aga gag tct ctc ctt tct tct gct agt cta tcc caa gtt    3865
Asp Arg Trp Arg Glu Ser Leu Leu Ser Ser Ala Ser Leu Ser Gln Val
    1235                1240                1245 ttt ctt cac cta tcc acc ttg gat cgt agc gtg ata tgg tct aaa tct    3913
Phe Leu His Leu Ser Thr Leu Asp Arg Ser Val Ile Trp Ser Lys Ser
        1250                1255                1260 ata ctg aat gcg cgt tgc aag ata tgt cga aag aaa ggc gat gct gaa    3961
Ile Leu Asn Ala Arg Cys Lys Ile Cys Arg Lys Lys Gly Asp Ala Glu
1265                1270                1275 aac atg gtt ctt tgt gat ggc tgt gat agg ggt cat cat acc tac tgt    4009
Asn Met Val Leu Cys Asp Gly Cys Asp Arg Gly His His Thr Tyr Cys
1280                1285                1290                1295 gtt cga cca aag ctc aag act gtg cct gaa gga gac tgg ttt tgt cca    4057
Val Arg Pro Lys Leu Lys Thr Val Pro Glu Gly Asp Trp Phe Cys Pro
            1300                1305                1310 gaa tgt cga cca aag caa cgt tgt aga aga ctg tcc ttt aga cag aga    4105
Glu Cys Arg Pro Lys Gln Arg Cys Arg Arg Leu Ser Phe Arg Gln Arg
    1315                1320                1325 cca tcc ttg gaa agt gat gaa gat gtg gaa gac agt atg gga ggt gag    4153
Pro Ser Leu Glu Ser Asp Glu Asp Val Glu Asp Ser Met Gly Gly Glu
        1330                1335                1340 gat gat gaa gtt gat ggc gat gaa gaa gaa ggt caa agt gag gag gaa    4201
Asp Asp Glu Val Asp Gly Asp Glu Glu Glu Gly Gln Ser Glu Glu Glu
1345                1350                1355 gag tat gag gta gaa caa gat gaa gat gac tct caa gaa gag gaa gaa    4249
Glu Tyr Glu Val Glu Gln Asp Glu Asp Asp Ser Gln Glu Glu Glu Glu
1360                1365                1370                1375 gtc agc cta ccc aaa cga gga aga cca caa gtt aga ttg cca gtt aaa    4297
Val Ser Leu Pro Lys Arg Gly Arg Pro Gln Val Arg Leu Pro Val Lys
            1380                1385                1390 aca aga ggg aaa ctt agc tct tct ttc tca agt cgt ggc caa caa caa    4345
Thr Arg Gly Lys Leu Ser Ser Ser Phe Ser Ser Arg Gly Gln Gln Gln
    1395                1400                1405 gaa cct gga aga tac cct tcc agg agt cag cag agc aca ccc aaa aca    4393
Glu Pro Gly Arg Tyr Pro Ser Arg Ser Gln Gln Ser Thr Pro Lys Thr
        1410                1415                1420 act gtt tct tct aaa act ggt aga agc cta aga aag ata aac tct gct    4441
Thr Val Ser Ser Lys Thr Gly Arg Ser Leu Arg Lys Ile Asn Ser Ala
1425                1430                1435 cct cct aca gaa aca aaa tct tta aga att gcc agt cgt tct act cgc    4489
Pro Pro Thr Glu Thr Lys Ser Leu Arg Ile Ala Ser Arg Ser Thr Arg
1440                1445                1450                1455 cac agt cat ggc cca ctg caa gca gat gta ttt gtg gaa ttg ctt agt    4537
His Ser His Gly Pro Leu Gln Ala Asp Val Phe Val Glu Leu Leu Ser
```

-continued

| | | | | | | | | | | | | | | | | |
|---|---|---|---|---|---|---|---|---|---|---|---|---|---|---|---|---|
| | | | | 1460 | | | | 1465 | | | | 1470 | | | | |
| cct | cgt | aga | aaa | cgc | aga | ggc | agg | aaa | agt | gct | aat | aat | aca | cca | gaa | 4585 |
| Pro | Arg | Arg | Lys | Arg | Arg | Gly | Arg | Lys | Ser | Ala | Asn | Asn | Thr | Pro | Glu | |
| | | | 1475 | | | | | 1480 | | | | | 1485 | | | |
| aat | agt | ccc | aac | ttc | cct | aac | ttc | aga | gtc | att | gcc | aca | aag | tca | agt | 4633 |
| Asn | Ser | Pro | Asn | Phe | Pro | Asn | Phe | Arg | Val | Ile | Ala | Thr | Lys | Ser | Ser | |
| | | | 1490 | | | | | 1495 | | | | | 1500 | | | |
| gaa | cag | tca | aga | tct | gta | aat | att | gct | tca | aaa | ctt | tct | ctc | caa | gag | 4681 |
| Glu | Gln | Ser | Arg | Ser | Val | Asn | Ile | Ala | Ser | Lys | Leu | Ser | Leu | Gln | Glu | |
| | | 1505 | | | | | 1510 | | | | | 1515 | | | | |
| agt | gaa | tcc | aaa | aga | aga | tgc | aga | aaa | aga | caa | tct | cca | gag | cca | tcg | 4729 |
| Ser | Glu | Ser | Lys | Arg | Arg | Cys | Arg | Lys | Arg | Gln | Ser | Pro | Glu | Pro | Ser | |
| 1520 | | | | | 1525 | | | | | 1530 | | | | | 1535 | |
| cct | gtg | aca | ctg | ggt | cga | agg | agt | tct | ggc | cga | cag | gga | gga | gtt | cat | 4777 |
| Pro | Val | Thr | Leu | Gly | Arg | Arg | Ser | Ser | Gly | Arg | Gln | Gly | Gly | Val | His | |
| | | | | 1540 | | | | | 1545 | | | | | 1550 | | |
| gaa | ttg | tct | gct | ttt | gaa | caa | ctt | gtt | gta | gaa | ttg | gta | cga | cat | gat | 4825 |
| Glu | Leu | Ser | Ala | Phe | Glu | Gln | Leu | Val | Val | Glu | Leu | Val | Arg | His | Asp | |
| | | | 1555 | | | | | 1560 | | | | | 1565 | | | |
| gac | agc | tgg | cct | ttt | ttg | aaa | ctt | gtt | tct | aaa | atc | cag | gtc | cca | gac | 4873 |
| Asp | Ser | Trp | Pro | Phe | Leu | Lys | Leu | Val | Ser | Lys | Ile | Gln | Val | Pro | Asp | |
| | | 1570 | | | | | 1575 | | | | | 1580 | | | | |
| tac | tat | gac | atc | atc | aaa | aag | ccc | att | gcc | tta | aat | ata | att | cgt | gaa | 4921 |
| Tyr | Tyr | Asp | Ile | Ile | Lys | Lys | Pro | Ile | Ala | Leu | Asn | Ile | Ile | Arg | Glu | |
| | | 1585 | | | | | 1590 | | | | | 1595 | | | | |
| aaa | gtg | aat | aag | tgt | gaa | tat | aaa | tta | gca | tct | gag | ttt | att | gat | gac | 4969 |
| Lys | Val | Asn | Lys | Cys | Glu | Tyr | Lys | Leu | Ala | Ser | Glu | Phe | Ile | Asp | Asp | |
| 1600 | | | | | 1605 | | | | | 1610 | | | | | 1615 | |
| att | gag | tta | atg | ttt | tcg | aac | tgc | ttt | gaa | tac | aac | cct | cgt | aac | aca | 5017 |
| Ile | Glu | Leu | Met | Phe | Ser | Asn | Cys | Phe | Glu | Tyr | Asn | Pro | Arg | Asn | Thr | |
| | | | | 1620 | | | | | 1625 | | | | | 1630 | | |
| agt | gaa | gca | aaa | gct | gga | act | agg | ctt | caa | gca | ttt | ttt | cat | att | cag | 5065 |
| Ser | Glu | Ala | Lys | Ala | Gly | Thr | Arg | Leu | Gln | Ala | Phe | Phe | His | Ile | Gln | |
| | | | 1635 | | | | | 1640 | | | | | 1645 | | | |
| gct | caa | aag | ctt | gga | ctc | cac | gtc | aca | ccc | agt | aat | gtg | gac | caa | gtt | 5113 |
| Ala | Gln | Lys | Leu | Gly | Leu | His | Val | Thr | Pro | Ser | Asn | Val | Asp | Gln | Val | |
| | | 1650 | | | | | 1655 | | | | | 1660 | | | | |
| agc | aca | cca | ccg | gct | gcg | aaa | aag | tca | cga | atc | tgactttgtc | | cttctaaagg | | | 5166 |
| Ser | Thr | Pro | Pro | Ala | Ala | Lys | Lys | Ser | Arg | Ile | | | | | | |
| | | 1665 | | | | | 1670 | | | | | | | | | |

| | | |
|---|---|---|
| atatatttga agaaaaacaa attgttcatg aaaatggaac attaaatcat gctgtataaa | | 5226 |
| gcaataacaa acaattgatt gaccacatga aagtgtggcc tgcactatat tctcaatttt | | 5286 |
| aatattaagc actcaggaga atgtaggaaa gatatccttt gctacagttt tgttcagtat | | 5346 |
| ctaataagtt tgatagatgt attggataca gtactggttt acagaggttt ttgtacattt | | 5406 |
| ttganatcat tcatgtgtcc agagatcttg gaaatatttt tttcacccac gatttatttt | | 5466 |
| gttattgatg atttattttt aaagtggtgg tattaaggga gagttatcta catggatgag | | 5526 |
| tcttccgcta tagcacagtt tagaaaaggt gtttatgtct taattaattg tttgagtaca | | 5586 |
| ttctttcaac actacacatg aatgaatcca atcttataac cttgaagtgc tgtaccagtg | | 5646 |
| ctggctgcag gtattaagtc caagtttatt aactagatat ttatttagta ttgagagtaa | | 5706 |
| tttgtgaatt tgttttgtat ttataaaatt tatacctgga aaatgttcct taatgtttta | | 5766 |
| aaccttttac tgtgttttta ttcctctaac ttccttaatg atcaatcaaa aaaagtaaca | | 5826 |
| ccctcccttt ttcctgacag ttctttcagc tttacagaac tgtattataa gttcgatgta | | 5886 |
| taatttaac tgttcaaata aaatacattt ttccaataaa aaaaaaa | | 5934 |

<210> SEQ ID NO 3
<211> LENGTH: 140
<212> TYPE: DNA
<213> ORGANISM: Homo sapiens

<400> SEQUENCE: 3
gactaccacg acatcatcaa gaaaccaatg gatctgggca cagtcaagcg gaaaatggac      60
aatcgcgagt acaagagcgc gccggaattt gccgccgacg tgcgattaat attcaccaac     120
tgctacaagt acaatccgcc                                                 140

<210> SEQ ID NO 4
<211> LENGTH: 23
<212> TYPE: DNA
<213> ORGANISM: Artificial Sequence
<220> FEATURE:
<223> OTHER INFORMATION: Synthetically generated primer

<400> SEQUENCE: 4
agaaaaagac aatctccaga gca                                              23

<210> SEQ ID NO 5
<211> LENGTH: 24
<212> TYPE: DNA
<213> ORGANISM: Artificial Sequence
<220> FEATURE:
<223> OTHER INFORMATION: Synthetically generated primer

<400> SEQUENCE: 5
gctgtcatca tgtcgtacca attc                                             24

<210> SEQ ID NO 6
<211> LENGTH: 24
<212> TYPE: DNA
<213> ORGANISM: Artificial Sequence
<220> FEATURE:
<223> OTHER INFORMATION: Synthetically generated primer

<400> SEQUENCE: 6
aacacaagtg aagcaaaagc tgga                                             24

<210> SEQ ID NO 7
<211> LENGTH: 24
<212> TYPE: DNA
<213> ORGANISM: Artificial Sequence
<220> FEATURE:
<223> OTHER INFORMATION: Synthetically generated primer

<400> SEQUENCE: 7
gtggtgtgct aacttggtcc acat                                             24

<210> SEQ ID NO 8
<211> LENGTH: 25
<212> TYPE: DNA
<213> ORGANISM: Artificial Sequence
<220> FEATURE:
<223> OTHER INFORMATION: Synthetically generated primer

<400> SEQUENCE: 8
cccatcgtga gtcaagagtg tctgt                                            25

<210> SEQ ID NO 9
<211> LENGTH: 24
<212> TYPE: DNA

```
<213> ORGANISM: Artificial Sequence
<220> FEATURE:
<223> OTHER INFORMATION: Synthetically generated primer

<400> SEQUENCE: 9
ctcgcttcta ccttttatt ggct                                              24

<210> SEQ ID NO 10
<211> LENGTH: 25
<212> TYPE: DNA
<213> ORGANISM: Artificial Sequence
<220> FEATURE:
<223> OTHER INFORMATION: Synthetically generated primer

<400> SEQUENCE: 10
tcatcatctc tgccccctct gtctg                                            25

<210> SEQ ID NO 11
<211> LENGTH: 24
<212> TYPE: DNA
<213> ORGANISM: Artificial Sequence
<220> FEATURE:
<223> OTHER INFORMATION: Synthetically generated primer

<400> SEQUENCE: 11
gacgcctgct tcaccacctt cttg                                             24

<210> SEQ ID NO 12
<211> LENGTH: 24
<212> TYPE: DNA
<213> ORGANISM: Artificial Sequence
<220> FEATURE:
<223> OTHER INFORMATION: Synthetically generated primer

<400> SEQUENCE: 12
tcatgtggtc aatcaattgt ttgt                                             24

<210> SEQ ID NO 13
<211> LENGTH: 1878
<212> TYPE: PRT
<213> ORGANISM: Homo sapiens
<220> FEATURE:
<221> NAME/KEY: VARIANT
<222> LOCATION: (1)...(1878)
<223> OTHER INFORMATION: Xaa = Any Amino Acid

<400> SEQUENCE: 13
```

Met Glu Met Glu Ala Asn Glu Ala Asn Asp His Phe Asn Phe Thr Gly
 1               5                  10                  15

Leu Pro Pro Ala Pro Ala Ala Ser Gly Leu Lys Pro Ser Pro Ser Ser
             20                  25                  30

Gly Glu Gly Leu Tyr Thr Asn Gly Ser Pro Met Asn Phe Pro Gln Gln
         35                  40                  45

Gly Lys Ser Leu Asn Gly Asp Val Asn Val Asn Gly Leu Ser Thr Val
     50                  55                  60

Ser His Thr Thr Thr Ser Gly Ile Leu Asn Ser Ala Pro His Ser Ser
 65                  70                  75                  80

Ser Thr Ser His Leu His His Pro Ser Val Ala Tyr Asp Cys Leu Trp
                 85                  90                  95

Asn Tyr Ser Gln Tyr Pro Ser Ala Asn Pro Gly Ser Asn Leu Lys Asp
            100                 105                 110

Pro Pro Leu Leu Ser Gln Phe Ser Gly Gly Gln Tyr Pro Leu Asn Gly
        115                 120                 125

```
Ile Leu Gly Gly Ser Arg Gln Pro Ser Ser Pro Ser His Asn Thr Asn
    130                 135                 140
Leu Arg Ala Gly Ser Gln Lys Phe Trp Ala Asn Gly Thr His Ser Pro
145                 150                 155                 160
Met Gly Leu Asn Phe Asp Ser Gln Glu Leu Tyr Asp Ser Phe Pro Asp
                165                 170                 175
Gln Asn Phe Glu Glu Val Cys Ser Gly Ile His Pro Asp Glu Ala Ala
                180                 185                 190
Glu Lys Glu Met Thr Ser Val Val Ala Glu Asn Gly Thr Gly Leu Val
                195                 200                 205
Cys Ser Leu Glu Leu Glu Glu Xaa Gln Pro Glu Leu Lys Met Cys Gly
    210                 215                 220
Tyr Asn Gly Ser Val Pro Ser Val Glu Ser Leu His Gln Glu Val Ser
225                 230                 235                 240
Val Leu Val Pro Asp Pro Thr Val Ser Cys Leu Asp Asp Pro Ser His
                245                 250                 255
Leu Pro Asp Gln Leu Glu Asp Thr Pro Ile Leu Ser Glu Asp Ser Leu
                260                 265                 270
Glu Pro Phe Asn Ser Leu Ala Pro Glu Pro Val Ser Gly Gly Leu Tyr
                275                 280                 285
Gly Ile Asp Asp Thr Glu Leu Met Gly Ala Glu Asp Lys Leu Pro Leu
    290                 295                 300
Xaa Asp Ser Pro Val Ile Ser Ala Leu Asp Cys Pro Ser Leu Asn Asn
305                 310                 315                 320
Ala Thr Ala Phe Ser Leu Leu Ala Asp Asp Ser Gln Thr Ser Thr Ser
                325                 330                 335
Ile Phe Ala Ser Pro Thr Ser Pro Pro Val Leu Gly Glu Ser Val Leu
                340                 345                 350
Gln Asp Asn Ser Phe Asp Leu Asn Asn Gly Ser Asp Ala Glu Gln Glu
                355                 360                 365
Glu Met Glu Thr Gln Ser Ser Asp Phe Pro Pro Ser Leu Thr Gln Pro
    370                 375                 380
Ala Pro Asp Gln Ser Ser Thr Ile Gln Leu His Pro Ala Thr Ser Pro
385                 390                 395                 400
Ala Val Ser Pro Thr Thr Ser Pro Ala Val Ser Leu Val Val Ser Pro
                405                 410                 415
Ala Ala Ser Pro Glu Ile Ser Pro Glu Val Cys Pro Ala Ala Ser Thr
                420                 425                 430
Val Val Ser Pro Ala Val Phe Ser Val Val Ser Pro Ala Ser Ser Ala
                435                 440                 445
Val Leu Pro Ala Val Ser Leu Glu Val Pro Leu Thr Ala Ser Val Thr
    450                 455                 460
Ser Pro Lys Ala Ser Pro Val Thr Ser Pro Ala Ala Ala Phe Pro Thr
465                 470                 475                 480
Ala Ser Pro Ala Asn Lys Asp Val Ser Ser Phe Leu Glu Thr Thr Ala
                485                 490                 495
Asp Val Glu Glu Ile Thr Gly Glu Gly Leu Thr Ala Ser Gly Ser Gly
                500                 505                 510
Asp Val Met Arg Arg Ile Ala Thr Pro Glu Glu Val Arg Leu Pro
    515                 520                 525
Leu Gln His Gly Trp Arg Arg Glu Val Arg Ile Lys Lys Gly Ser His
    530                 535                 540
```

-continued

```
Arg Trp Gln Gly Glu Thr Trp Tyr Tyr Gly Pro Cys Gly Lys Arg Met
545                 550                 555                 560

Lys Gln Phe Pro Glu Val Ile Lys Tyr Leu Ser Arg Asn Leu Val His
            565                 570                 575

Ser Val Arg Arg Glu His Phe Ser Phe Ser Pro Arg Met Pro Val Gly
        580                 585                 590

Asp Phe Phe Glu Glu Arg Asp Thr Pro Glu Gly Leu Gln Trp Val Gln
    595                 600                 605

Leu Ser Ala Glu Glu Ile Pro Ser Arg Ile Gln Ala Ile Thr Gly Lys
610                 615                 620

Arg Gly Arg Pro Arg Asn Thr Glu Lys Ala Lys Thr Lys Glu Val Pro
625                 630                 635                 640

Lys Val Lys Arg Gly Arg Gly Arg Pro Pro Lys Val Lys Ile Thr Glu
            645                 650                 655

Leu Leu Asn Lys Thr Asp Asn Arg Pro Leu Lys Lys Leu Glu Ala Gln
            660                 665                 670

Glu Thr Leu Asn Glu Glu Asp Lys Ala Lys Ile Ala Lys Ser Lys Lys
        675                 680                 685

Lys Met Arg Gln Lys Val Gln Arg Gly Glu Cys Leu Thr Thr Ile Gln
690                 695                 700

Gly Gln Ala Arg Asn Lys Arg Lys Gln Glu Thr Lys Ser Leu Lys His
705                 710                 715                 720

Lys Glu Ala Lys Lys Ser Xaa Ala Glu Lys Glu Lys Gly Lys Thr
            725                 730                 735

Lys Gln Glu Lys Leu Lys Glu Lys Val Lys Arg Glu Lys Lys Glu Lys
            740                 745                 750

Val Lys Met Lys Glu Lys Glu Val Thr Lys Ala Lys Pro Ala Cys
            755                 760                 765

Lys Ala Asp Lys Thr Leu Ala Thr Gln Arg Arg Leu Glu Glu Arg Gln
770                 775                 780

Lys Gln Gln Met Ile Leu Glu Glu Met Lys Lys Pro Thr Glu Asp Met
785                 790                 795                 800

Cys Leu Thr Asp His Gln Pro Leu Pro Asp Phe Ser Arg Val Pro Gly
            805                 810                 815

Leu Thr Leu Pro Ser Gly Ala Phe Ser Asp Cys Leu Thr Ile Val Glu
        820                 825                 830

Phe Leu His Ser Phe Gly Lys Val Leu Gly Phe Asp Pro Ala Lys Asp
    835                 840                 845

Val Pro Ser Leu Gly Val Leu Gln Glu Gly Leu Leu Cys Gln Gly Asp
850                 855                 860

Ser Leu Gly Glu Val Gln Asp Leu Leu Val Arg Leu Leu Lys Ala Ala
865                 870                 875                 880

Leu His Asp Pro Gly Phe Pro Ser Tyr Cys Gln Ser Leu Lys Ile Leu
            885                 890                 895

Gly Glu Lys Val Ser Glu Ile Pro Leu Thr Arg Asp Asn Val Ser Glu
        900                 905                 910

Ile Leu Arg Cys Phe Leu Met Ala Tyr Gly Val Xaa Pro Ala Leu Cys
    915                 920                 925

Asp Arg Leu Arg Thr Gln Pro Phe Gln Ala Gln Pro Pro Gln Gln Lys
    930                 935                 940

Ala Ala Val Leu Ala Phe Pro Val His Glu Leu Asn Gly Ser Thr Leu
945                 950                 955                 960

Ile Ile Asn Glu Ile Asp Lys Thr Leu Glu Ser Met Ser Ser Tyr Arg
```

-continued

```
                        965                 970                 975
Lys Asn Lys Trp Ile Val Glu Gly Arg Leu Arg Arg Leu Lys Thr Val
                980                 985                 990
Leu Ala Lys Arg Thr Gly Arg Ser Glu Val Glu Met Gly Arg Pro Glu
            995                 1000                1005
Glu Cys Leu Gly Arg Arg Ser Ser Arg Ile Met Glu Glu Thr Ser
    1010                1015                1020
Gly Met Glu Glu Glu Glu Glu Glu Ser Ile Ala Ala Val Pro Gly
1025                1030                1035                1040
Arg Arg Gly Arg Arg Asp Gly Glu Val Asp Ala Thr Ala Ser Ser Ile
                1045                1050                1055
Pro Glu Leu Glu Arg Gln Ile Glu Lys Leu Ser Lys Arg Gln Leu Phe
                1060                1065                1070
Phe Arg Lys Lys Leu Leu His Ser Ser Gln Met Leu Arg Ala Val Ser
            1075                1080                1085
Leu Gly Gln Asp Arg Tyr Arg Arg Arg Tyr Trp Val Leu Pro Tyr Leu
        1090                1095                1100
Ala Gly Ile Phe Val Glu Gly Thr Glu Gly Asn Leu Val Pro Glu Glu
1105                1110                1115                1120
Val Ile Lys Lys Glu Thr Asp Ser Leu Lys Val Ala Ala His Ala Ser
                1125                1130                1135
Leu Asn Pro Ala Leu Phe Ser Met Lys Met Glu Leu Ala Gly Ser Asn
                1140                1145                1150
Thr Thr Ala Ser Ser Pro Ala Arg Ala Arg Ser Arg Pro Leu Lys Thr
            1155                1160                1165
Lys Pro Gly Phe Met Gln Pro Arg His Phe Lys Ser Pro Val Arg Gly
            1170                1175                1180
Gln Asp Ser Glu Gln Pro Gln Ala Gln Leu Gln Pro Glu Ala Gln Leu
1185                1190                1195                1200
His Val Pro Ala Gln Pro Gln Pro Gln Leu Gln Leu Gln Leu Gln Ser
                1205                1210                1215
His Lys Gly Phe Leu Glu Gln Glu Gly Ser Pro Leu Ser Leu Gly Gln
            1220                1225                1230
Ser Gln His Asp Leu Ser Gln Ser Ala Phe Leu Ser Trp Leu Ser Gln
            1235                1240                1245
Thr Gln Ser His Ser Ser Leu Leu Ser Ser Val Leu Thr Pro Asp
            1250                1255                1260
Ser Ser Pro Gly Lys Leu Asp Pro Ala Pro Ser Gln Pro Pro Glu Glu
1265                1270                1275                1280
Pro Glu Pro Asp Glu Ala Glu Ser Pro Asp Leu Gln Ala Phe Trp
            1285                1290                1295
Phe Asn Ile Ser Ala Gln Met Pro Cys Asn Ala Ala Pro Thr Pro Pro
            1300                1305                1310
Leu Ala Val Ser Glu Asp Gln Pro Thr Pro Ser Pro Gln Gln Leu Ala
        1315                1320                1325
Ser Ser Lys Pro Met Asn Arg Pro Ser Ala Ala Asn Pro Cys Ser Pro
        1330                1335                1340
Val Gln Phe Ser Ser Thr Pro Leu Ala Gly Leu Ala Pro Lys Arg Arg
1345                1350                1355                1360
Ala Gly Asp Pro Gly Glu Met Pro Gln Ser Pro Thr Gly Leu Gly Gln
            1365                1370                1375
Pro Lys Arg Arg Gly Arg Pro Pro Ser Lys Phe Phe Lys Gln Met Glu
        1380                1385                1390
```

-continued

```
Gln Arg Tyr Leu Thr Gln Leu Thr Ala Gln Pro Val Pro Pro Glu Met
        1395                1400                1405
Cys Ser Gly Trp Trp Trp Ile Pro Asp Pro Glu Met Leu Asp Ala Met
        1410                1415                1420
Leu Lys Ala Leu His Pro Arg Gly Ile Arg Glu Lys Ala Leu His Lys
1425                1430                1435                1440
His Leu Asn Lys His Arg Asp Phe Leu Gln Glu Val Cys Leu Arg Pro
            1445                1450                1455
Ser Ala Asp Pro Ile Phe Glu Pro Arg Gln Leu Pro Ala Phe Gln Glu
            1460                1465                1470
Gly Ile Met Ser Trp Ser Pro Lys Glu Lys Thr Tyr Glu Thr Asp Leu
        1475                1480                1485
Ala Val Leu Gln Trp Val Glu Leu Glu Gln Arg Val Ile Met Ser
        1490                1495                1500
Asp Leu Gln Ile Arg Gly Trp Thr Cys Pro Ser Pro Asp Ser Thr Arg
1505                1510                1515                1520
Glu Asp Leu Ala Tyr Cys Glu His Leu Ser Asp Ser Gln Glu Asp Ile
            1525                1530                1535
Thr Trp Arg Gly Pro Gly Arg Glu Gly Leu Ala Pro Gln Arg Lys Thr
        1540                1545                1550
Thr Asn Pro Leu Asp Leu Ala Val Met Arg Leu Ala Ala Leu Glu Gln
        1555                1560                1565
Asn Val Lys Arg Arg Tyr Leu Arg Glu Pro Leu Trp Pro Thr His Glu
            1570                1575                1580
Val Val Leu Glu Lys Ala Leu Leu Ser Thr Pro Asn Gly Ala Pro Glu
1585                1590                1595                1600
Gly Thr Thr Thr Glu Ile Ser Tyr Glu Ile Thr Pro Arg Ile Arg Ile
            1605                1610                1615
Trp Arg Gln Thr Leu Gln Arg Cys Arg Ser Ala Ala His Val Cys Leu
        1620                1625                1630
Cys Leu Gly His Leu Glu Arg Ser Ile Ala Trp Glu Lys Ser Val Asn
        1635                1640                1645
Lys Val Thr Cys Leu Val Cys Arg Lys Gly Asp Asn Asp Glu Phe Leu
        1650                1655                1660
Leu Leu Cys Asp Gly Cys Asp Arg Gly Cys His Ile Tyr Cys His Arg
1665                1670                1675                1680
Pro Lys Met Glu Ala Val Pro Glu Gly Asp Trp Phe Cys Thr Val Cys
            1685                1690                1695
Leu Ala Gln Gln Val Glu Gly Glu Phe Thr Gln Lys Pro Gly Phe Pro
        1700                1705                1710
Lys Arg Gly Gln Lys Arg Lys Ser Gly Tyr Ser Leu Asn Phe Ser Glu
        1715                1720                1725
Gly Asp Gly Arg Arg Arg Val Leu Leu Lys Gly Arg Glu Ser Pro
        1730                1735                1740
Ala Ala Gly Pro Arg Tyr Ser Glu Glu Arg Leu Ser Pro Ser Lys Arg
1745                1750                1755                1760
Arg Arg Leu Ser Met Arg Asn His His Ser Asp Leu Thr Phe Cys Glu
            1765                1770                1775
Ile Ile Leu Met Glu Met Glu Ser His Asp Ala Ala Trp Pro Phe Xaa
        1780                1785                1790
Glu Pro Val Asn Pro Arg Leu Val Ser Gly Tyr Arg Arg Ile Ile Lys
        1795                1800                1805
```

-continued

```
Asn Pro Met Asp Phe Ser Thr Met Arg Glu Arg Leu Leu Arg Gly Gly
    1810                1815                1820

Tyr Thr Ser Ser Glu Glu Phe Ala Ala Asp Ala Leu Leu Val Phe Asp
1825                1830                1835                1840

Asn Cys Gln Thr Phe Asn Glu Asp Asp Ser Glu Val Gly Lys Ala Gly
                1845                1850                1855

His Ile Met Arg Arg Phe Phe Glu Ser Arg Trp Glu Glu Phe Tyr Gln
    1860                1865                1870

Gly Lys Gln Ala Asn Leu
        1875

<210> SEQ ID NO 14
<211> LENGTH: 9408
<212> TYPE: DNA
<213> ORGANISM: Homo sapiens
<220> FEATURE:
<221> NAME/KEY: CDS
<222> LOCATION: (740)...(6373)
<221> NAME/KEY: misc_feature
<222> LOCATION: (1)...(9408)
<223> OTHER INFORMATION: n = A,T,C or G

<400> SEQUENCE: 14
gttccactca cagatttctt cttattgccc aggcttgagt gcaatgacct gttctcagct      60
tactcaacct ctgcctcttg ggtttcagtg atttttctgc ctcggcctcc tgagtagcta     120
agggaggagt cttgagatta tcatccacgg agggtgaag aggagagggt ggaaggggaa      180
taagaagaca ttcgggaggt gtcttgaggc tcagggagtt atcagttata gaatgttgtt     240
gagttggagg aagtggctgg cggcccatcc tgttttttaa agtttcacct gtgaagtagg     300
gccagtaggg caatcctgaa gaatgacgat gctccgctgc cgccattctg acctgtaagg    360
ccgaaagaaa gggaatgttt tcacacatat tcatttgatg gacaaaatta ccgccaccaa    420
cacggtctgc accttctgtt gctggtgata aattttgca ccttcccatc ctccaggttt     480
caaaatagca gtatcagtgt cataatatca cccttccact gagtactgcc gacagctggg    540
gagtaaaaaa aagtcattgg gacatcaccc tacagcagtt caggctgtgt ggttcgcaag    600
aagcatacac tggcttttg attcttgcta gttcccagct cacagtttgg gaggatccaa    660
caccaacctt tacgtgaagt ggaggcccaa ggacagtgag gagctgggtg gtcccagcct    720
ggagctgtgc cagcctgac atg gaa atg gag gca aac gag gca aac gac cat    772
                      Met Glu Met Glu Ala Asn Glu Ala Asn Asp His
                       1               5                  10 ttt aac ttt act ggc ctt ccc cct gca cct gct gcc tca gga ctg aaa     820
Phe Asn Phe Thr Gly Leu Pro Pro Ala Pro Ala Ala Ser Gly Leu Lys
           15                  20                  25 ccc tct cct tcc tca ggg gag ggc ctc tac act aac ggg tct ccc atg    868
Pro Ser Pro Ser Ser Gly Glu Gly Leu Tyr Thr Asn Gly Ser Pro Met
       30                  35                  40 aac ttc ccc cag caa ggg aaa agt ttg aat ggg gat gtg aat gtt aat    916
Asn Phe Pro Gln Gln Gly Lys Ser Leu Asn Gly Asp Val Asn Val Asn
   45                  50                  55 ggc tta tct act gta tct cac act act act tca ggg att ttg aac tct    964
Gly Leu Ser Thr Val Ser His Thr Thr Thr Ser Gly Ile Leu Asn Ser
60                  65                  70                  75 gct ccc cac tcc tcc agc acc tca cac ctc cat cac ccc agc gtg gcc   1012
Ala Pro His Ser Ser Ser Thr Ser His Leu His His Pro Ser Val Ala
               80                  85                  90 tac gac tgt ctc tgg aac tac tca cag tac cca tct gcc aat cct ggc   1060
Tyr Asp Cys Leu Trp Asn Tyr Ser Gln Tyr Pro Ser Ala Asn Pro Gly
```

-continued

```
                 95                  100                 105
agc aac ctc aag gac cca ccc ctt ctc tcc cag ttc tcg ggg gga caa    1108
Ser Asn Leu Lys Asp Pro Pro Leu Leu Ser Gln Phe Ser Gly Gly Gln
        110                 115                 120 tac cca ctc aac ggc atc ctt ggg ggc agc cgg caa cct tca tcc cca    1156
Tyr Pro Leu Asn Gly Ile Leu Gly Gly Ser Arg Gln Pro Ser Ser Pro
    125                 130                 135 agt cat aac act aac ctt cgg gct ggg agc caa aag ttc tgg gcc aac    1204
Ser His Asn Thr Asn Leu Arg Ala Gly Ser Gln Lys Phe Trp Ala Asn
140                 145                 150                 155 ggt acc cat agt ccc atg ggg ctt aac ttt gat tca caa gaa ctg tat    1252
Gly Thr His Ser Pro Met Gly Leu Asn Phe Asp Ser Gln Glu Leu Tyr
                160                 165                 170 gat tcc ttt cct gac cag aat ttt gag gag gta tgc agt ggt atc cat    1300
Asp Ser Phe Pro Asp Gln Asn Phe Glu Glu Val Cys Ser Gly Ile His
            175                 180                 185 cct gat gag gca gca gaa aaa gag atg act tcc gtt gtg gca gaa aat    1348
Pro Asp Glu Ala Ala Glu Lys Glu Met Thr Ser Val Val Ala Glu Asn
        190                 195                 200 ggc act ggc ttg gta tgc agc ttg gag ctg gaa gaa naa cag cca gaa    1396
Gly Thr Gly Leu Val Cys Ser Leu Glu Leu Glu Glu Xaa Gln Pro Glu
    205                 210                 215 ctg aag atg tgt ggc tac aat ggc tct gtc cct tct gtg gaa tcg tta    1444
Leu Lys Met Cys Gly Tyr Asn Gly Ser Val Pro Ser Val Glu Ser Leu
220                 225                 230                 235 cac caa gag gtc tca gtc ctg gtc cct gac ccc aca gtg agc tgt tta    1492
His Gln Glu Val Ser Val Leu Val Pro Asp Pro Thr Val Ser Cys Leu
                240                 245                 250 gat gat cct tca cat ctt cct gat caa ctg gaa gac act cca atc ctc    1540
Asp Asp Pro Ser His Leu Pro Asp Gln Leu Glu Asp Thr Pro Ile Leu
            255                 260                 265 agt gaa gac tct ctg gag ccc ttc aac tct ctg gca cca gag cca gtg    1588
Ser Glu Asp Ser Leu Glu Pro Phe Asn Ser Leu Ala Pro Glu Pro Val
        270                 275                 280 agt gga gga cta tat ggt att gat gac acg gag ctg atg ggt gca gaa    1636
Ser Gly Gly Leu Tyr Gly Ile Asp Asp Thr Glu Leu Met Gly Ala Glu
    285                 290                 295 gac aag ctg cct ctt gan gac agc cct gtg att tct gcc ctt gat tgc    1684
Asp Lys Leu Pro Leu Xaa Asp Ser Pro Val Ile Ser Ala Leu Asp Cys
300                 305                 310                 315 cct tcc ctc aat aat gct act gcc ttc agt ctc ctg gca gat gat agt    1732
Pro Ser Leu Asn Asn Ala Thr Ala Phe Ser Leu Leu Ala Asp Asp Ser
                320                 325                 330 caa aca tca act tct atc ttt gcc agt ccc act tct cca cct gtc cta    1780
Gln Thr Ser Thr Ser Ile Phe Ala Ser Pro Thr Ser Pro Pro Val Leu
            335                 340                 345 ggg gag tct gtc ctg caa gat aac agc ttt gac ctg aat aat ggt agt    1828
Gly Glu Ser Val Leu Gln Asp Asn Ser Phe Asp Leu Asn Asn Gly Ser
        350                 355                 360 gac gct gaa cag gaa gaa atg gaa act caa tct tca gac ttc cca cca    1876
Asp Ala Glu Gln Glu Glu Met Glu Thr Gln Ser Ser Asp Phe Pro Pro
    365                 370                 375 tcc ctg acc cag cca gct cct gat cag tca tcc act att cag cta cat    1924
Ser Leu Thr Gln Pro Ala Pro Asp Gln Ser Ser Thr Ile Gln Leu His
380                 385                 390                 395 cca gca acc tca cca gca gtc tcg cca aca acc tcc cca gca gtc tcc    1972
Pro Ala Thr Ser Pro Ala Val Ser Pro Thr Thr Ser Pro Ala Val Ser
                400                 405                 410 cta gtg gtt tct cca gca gcc tcc cca gaa atc tct cca gaa gtt tgt    2020
```

```
                Leu Val Val Ser Pro Ala Ala Ser Pro Glu Ile Ser Pro Glu Val Cys
                            415                 420                 425 ccc gca gct tct aca gtt gtc tct cca gca gtc ttc tca gtg gtc tct         2068
Pro Ala Ala Ser Thr Val Val Ser Pro Ala Val Phe Ser Val Val Ser
430                 435                 440 cca gct tct tca gca gtc ctc cca gca gtc tcc tta gaa gtc ccg ttg         2116
Pro Ala Ser Ser Ala Val Leu Pro Ala Val Ser Leu Glu Val Pro Leu
            445                 450                 455 acg gct tca gtg aca tcc cca aaa gcc tct ccc gta act tcc cca gca         2164
Thr Ala Ser Val Thr Ser Pro Lys Ala Ser Pro Val Thr Ser Pro Ala
460                 465                 470                 475 gct gcc ttt cca aca gcc tcc cca gca aat aag gat gtc agc agc ttt         2212
Ala Ala Phe Pro Thr Ala Ser Pro Ala Asn Lys Asp Val Ser Ser Phe
                480                 485                 490 cta gaa acc act gct gac gtg gaa gag atc act gga gaa gga ctc act         2260
Leu Glu Thr Thr Ala Asp Val Glu Glu Ile Thr Gly Glu Gly Leu Thr
            495                 500                 505 gct tct ggt agt ggt gat gtc atg agg aga cgt att gct acc cca gaa         2308
Ala Ser Gly Ser Gly Asp Val Met Arg Arg Arg Ile Ala Thr Pro Glu
510                 515                 520 gaa gtt cgt ctt ccc ctc caa cat ggg tgg cgg aga gag gtg cgc atc         2356
Glu Val Arg Leu Pro Leu Gln His Gly Trp Arg Arg Glu Val Arg Ile
525                 530                 535 aag aag ggc agc cac cga tgg cag ggg gag acn tgg tat tat ggc ccc         2404
Lys Lys Gly Ser His Arg Trp Gln Gly Glu Thr Trp Tyr Tyr Gly Pro
540                 545                 550                 555 tgt ggg aag agg atg aag caa ttt cca gaa gtg atc aag tac ctg agc         2452
Cys Gly Lys Arg Met Lys Gln Phe Pro Glu Val Ile Lys Tyr Leu Ser
                560                 565                 570 cgc aac ctg gta cac agt gtc cgc cga gag cac ttc agc ttc agt ccc         2500
Arg Asn Leu Val His Ser Val Arg Arg Glu His Phe Ser Phe Ser Pro
            575                 580                 585 cgt atg cct gtt gga gat ttc ttt gaa gaa aga gac acg cca gag ggc         2548
Arg Met Pro Val Gly Asp Phe Phe Glu Glu Arg Asp Thr Pro Glu Gly
                590                 595                 600 ttg cag tgg gtg cag ctc tca gca gag gag atc ccg tcg agg att cag         2596
Leu Gln Trp Val Gln Leu Ser Ala Glu Glu Ile Pro Ser Arg Ile Gln
            605                 610                 615 gca att act ggc aaa cgg ggt cga cct cga aac act gag aag gct aag         2644
Ala Ile Thr Gly Lys Arg Gly Arg Pro Arg Asn Thr Glu Lys Ala Lys
620                 625                 630                 635 act aag gaa gtc ccc aag gtg aaa cgg ggt cga ggt cgg cca cct aag         2692
Thr Lys Glu Val Pro Lys Val Lys Arg Gly Arg Gly Arg Pro Pro Lys
                640                 645                 650 gtc aaa atc act gag cta ttg aac aag aca gac aac cgc ccc cta aag         2740
Val Lys Ile Thr Glu Leu Leu Asn Lys Thr Asp Asn Arg Pro Leu Lys
            655                 660                 665 aaa ctg gag gcc caa gaa aca ttg aat gag gag gat aaa gca aag att         2788
Lys Leu Glu Ala Gln Glu Thr Leu Asn Glu Glu Asp Lys Ala Lys Ile
                670                 675                 680 gct aaa agc aag aag aag atg agg cag aag gtt caa cgg gga gag tgt         2836
Ala Lys Ser Lys Lys Lys Met Arg Gln Lys Val Gln Arg Gly Glu Cys
685                 690                 695 ctn act act atc caa ggg cag gcc aga aat aag cgg aaa caa gag acc         2884
Leu Thr Thr Ile Gln Gly Gln Ala Arg Asn Lys Arg Lys Gln Glu Thr
700                 705                 710                 715 aag agc tta aag cac aag gaa gct aag aag aaa tcc nag gct gag aaa         2932
Lys Ser Leu Lys His Lys Glu Ala Lys Lys Lys Ser Xaa Ala Glu Lys
                720                 725                 730
```

```
gaa aaa gga aag aca aag cag gaa aaa ctg aag gaa aaa gtc aag agg    2980
Glu Lys Gly Lys Thr Lys Gln Glu Lys Leu Lys Glu Lys Val Lys Arg
            735                 740                 745 gaa aag aag gag aag gtt aaa atg aag gaa aag gag gag gtg acc aaa    3028
Glu Lys Lys Glu Lys Val Lys Met Lys Glu Lys Glu Glu Val Thr Lys
        750                 755                 760 gcc aag cca gcc tgt aaa gca gat aag acc ctg gcc aca cag agg cgc    3076
Ala Lys Pro Ala Cys Lys Ala Asp Lys Thr Leu Ala Thr Gln Arg Arg
765                 770                 775 ttg gag gaa cgg cag aag cag cag atg atc ttg gag gaa atg aag aag    3124
Leu Glu Glu Arg Gln Lys Gln Gln Met Ile Leu Glu Glu Met Lys Lys
780                 785                 790                 795 ccg aca gag gat atg tgt ctg act gac cac cag ccc ctg cct gac ttc    3172
Pro Thr Glu Asp Met Cys Leu Thr Asp His Gln Pro Leu Pro Asp Phe
                800                 805                 810 tca cga gtc cct ggt ctg aca ttg ccc agt gga gcc ttc tca gac tgc    3220
Ser Arg Val Pro Gly Leu Thr Leu Pro Ser Gly Ala Phe Ser Asp Cys
            815                 820                 825 ttg acc att gtg gag ttc ctg cat agc ttt ggc aag gtg ctg ggc ttt    3268
Leu Thr Ile Val Glu Phe Leu His Ser Phe Gly Lys Val Leu Gly Phe
        830                 835                 840 gat cct gcc aaa gat gtg cct agc ctg ggg gtc ctg cag gag gga ctc    3316
Asp Pro Ala Lys Asp Val Pro Ser Leu Gly Val Leu Gln Glu Gly Leu
845                 850                 855 ctg tgt caa ggt gac agc ttg ggt gag gtg caa gac ctg ctg gtc agg    3364
Leu Cys Gln Gly Asp Ser Leu Gly Glu Val Gln Asp Leu Leu Val Arg
860                 865                 870                 875 ctg ctg aag gct gca ctc cat gat cct ggc ttt ccc tcc tac tgt cag    3412
Leu Leu Lys Ala Ala Leu His Asp Pro Gly Phe Pro Ser Tyr Cys Gln
                880                 885                 890 tcc cta aag atc ttg ggg gag aag gtg tct gaa atc cca ctg aca aga    3460
Ser Leu Lys Ile Leu Gly Glu Lys Val Ser Glu Ile Pro Leu Thr Arg
            895                 900                 905 gac aat gtg tca gag atc ctg cgc tgc ttc ctt atg gca tat gga gta    3508
Asp Asn Val Ser Glu Ile Leu Arg Cys Phe Leu Met Ala Tyr Gly Val
        910                 915                 920 nag cca gcc ctc tgt gac cgc ctg cgc acc cag cct ttt cag gcc cag    3556
Xaa Pro Ala Leu Cys Asp Arg Leu Arg Thr Gln Pro Phe Gln Ala Gln
925                 930                 935 cca ccc cag cag aag gct gct gtc ctg gcc ttc cct gtg cat gag ctc    3604
Pro Pro Gln Gln Lys Ala Ala Val Leu Ala Phe Pro Val His Glu Leu
940                 945                 950                 955 aat ggc tcc acc ctc atc atc aat gag att gac aag act ctg gag agt    3652
Asn Gly Ser Thr Leu Ile Ile Asn Glu Ile Asp Lys Thr Leu Glu Ser
                960                 965                 970 atg tcc agc tac agg aaa aac aag tgg att gtt gaa ggc cgg ctc cgg    3700
Met Ser Ser Tyr Arg Lys Asn Lys Trp Ile Val Glu Gly Arg Leu Arg
            975                 980                 985 agg ctg aaa act gtt ctg gcc aag cga act ggg cgg tct gaa gta gag    3748
Arg Leu Lys Thr Val Leu Ala Lys Arg Thr Gly Arg Ser Glu Val Glu
        990                 995                 1000 atg gga agg cca gag gaa tgc ctg gga cgg agg cgc agt tct cgg atc    3796
Met Gly Arg Pro Glu Glu Cys Leu Gly Arg Arg Arg Ser Ser Arg Ile
    1005                1010                1015 atg gag gag acc agt ggc atg gaa gaa gag gaa gaa gag gag tct ata    3844
Met Glu Glu Thr Ser Gly Met Glu Glu Glu Glu Glu Glu Glu Ser Ile
1020                1025                1030                1035 gca gct gtc cct ggc cgc agg ggt cga aga gat gga gag gtt gat gcc    3892
Ala Ala Val Pro Gly Arg Arg Gly Arg Arg Asp Gly Glu Val Asp Ala
                1040                1045                1050
```

-continued

```
aca gca tct agc atc cca gag cta gag cgc cag ata gaa aaa ctc agc      3940
Thr Ala Ser Ser Ile Pro Glu Leu Glu Arg Gln Ile Glu Lys Leu Ser
            1055                1060                1065 aag cgt cag ctt ttc ttt cgc aaa aag ctg ctt cac tca tcc cag atg      3988
Lys Arg Gln Leu Phe Phe Arg Lys Lys Leu Leu His Ser Ser Gln Met
        1070                1075                1080 ctt cgg gcg gtc tcc ctg ggt cag gac cgc tac aga cgt cgc tac tgg      4036
Leu Arg Ala Val Ser Leu Gly Gln Asp Arg Tyr Arg Arg Arg Tyr Trp
    1085                1090                1095 gta ttg ccg tat ttg gct ggt atc ttt gta gaa gga aca gag ggg aac      4084
Val Leu Pro Tyr Leu Ala Gly Ile Phe Val Glu Gly Thr Glu Gly Asn
1100                1105                1110                1115 tta gtt cct gag gag gtg ata aag aag gaa act gac tcc tta aaa gtg      4132
Leu Val Pro Glu Glu Val Ile Lys Lys Glu Thr Asp Ser Leu Lys Val
                1120                1125                1130 gca gcc cat gcg tca ctc aac cct gcc ctc ttc tct atg aag atg gag      4180
Ala Ala His Ala Ser Leu Asn Pro Ala Leu Phe Ser Met Lys Met Glu
            1135                1140                1145 tta gct ggc tcc aac acc act gcc agt tct cct gcc cgg gcc cga agc      4228
Leu Ala Gly Ser Asn Thr Thr Ala Ser Ser Pro Ala Arg Ala Arg Ser
        1150                1155                1160 cga cct cta aaa act aag ccc ggg ttt atg caa cct agg cat ttt aag      4276
Arg Pro Leu Lys Thr Lys Pro Gly Phe Met Gln Pro Arg His Phe Lys
    1165                1170                1175 tcc cct gtc agg ggt cag gat tca gaa cag ccc cag gcc cag ctt cag      4324
Ser Pro Val Arg Gly Gln Asp Ser Glu Gln Pro Gln Ala Gln Leu Gln
1180                1185                1190                1195 cct gag gct cag ctt cat gtt cct gcc cag ccc cag cct cag ctt cag      4372
Pro Glu Ala Gln Leu His Val Pro Ala Gln Pro Gln Pro Gln Leu Gln
                1200                1205                1210 ctt cag ctt cag tcc cat aag ggg ttc ctg gag caa gaa ggc tcc cct      4420
Leu Gln Leu Gln Ser His Lys Gly Phe Leu Glu Gln Glu Gly Ser Pro
            1215                1220                1225 ttg tca ctg ggt cag agc cag cat gac ctc agc cag tca gcc ttc ctg      4468
Leu Ser Leu Gly Gln Ser Gln His Asp Leu Ser Gln Ser Ala Phe Leu
        1230                1235                1240 tct tgg ctg agc cag act cag agc cat agc tcc ctg ttg agc agc tca      4516
Ser Trp Leu Ser Gln Thr Gln Ser His Ser Ser Leu Leu Ser Ser Ser
    1245                1250                1255 gtc ctc aca cct gat agc agt ccg gga aaa cta gac cca gct cca tca      4564
Val Leu Thr Pro Asp Ser Ser Pro Gly Lys Leu Asp Pro Ala Pro Ser
1260                1265                1270                1275 caa ccc ccg gag gag cca gag cct gat gag gca gaa tcc agc cct gat      4612
Gln Pro Pro Glu Glu Pro Glu Pro Asp Glu Ala Glu Ser Ser Pro Asp
                1280                1285                1290 ctt caa gca ttc tgg ttt aac atc tca gcc cag atg ccc tgc aat gct      4660
Leu Gln Ala Phe Trp Phe Asn Ile Ser Ala Gln Met Pro Cys Asn Ala
            1295                1300                1305 gcc ccc aca ccg ccc ctt gca gtt tct gag gac caa ccc act ccc tcc      4708
Ala Pro Thr Pro Pro Leu Ala Val Ser Glu Asp Gln Pro Thr Pro Ser
        1310                1315                1320 cct cag cag ctt gcc tcc tcc aag cca atg aat aga cct agt gct gcc      4756
Pro Gln Gln Leu Ala Ser Ser Lys Pro Met Asn Arg Pro Ser Ala Ala
    1325                1330                1335 aac cct tgt tct cca gtg cag ttc tct tcc acg ccc ttg gct ggg ttg      4804
Asn Pro Cys Ser Pro Val Gln Phe Ser Ser Thr Pro Leu Ala Gly Leu
1340                1345                1350                1355 gcc cct aag agg cga gca gga gac cct gga gaa atg cca cag agt ccc      4852
Ala Pro Lys Arg Arg Ala Gly Asp Pro Gly Glu Met Pro Gln Ser Pro
```

-continued

| | | | | |
|---|---|---|---|---|
| | 1360 | 1365 | 1370 | |
| aca ggg ctg gga cag ccc aaa cgg aga ggg aga cct ccc agt aag ttc<br>Thr Gly Leu Gly Gln Pro Lys Arg Arg Gly Arg Pro Pro Ser Lys Phe<br>             1375                          1380                         1385 | | | | 4900 |
| ttc aaa cag atg gaa cag cgt tac cta acc cag ctg aca gcc cag cct<br>Phe Lys Gln Met Glu Gln Arg Tyr Leu Thr Gln Leu Thr Ala Gln Pro<br>             1390                          1395                         1400 | | | | 4948 |
| gtc cca cct gag atg tgc tca ggc tgg tgg tgg ata cca gat cct gag<br>Val Pro Pro Glu Met Cys Ser Gly Trp Trp Trp Ile Pro Asp Pro Glu<br>             1405                          1410                         1415 | | | | 4996 |
| atg ttg gat gcc atg ctc aag gcc cta cac ccc cga ggt atc cgg gag<br>Met Leu Asp Ala Met Leu Lys Ala Leu His Pro Arg Gly Ile Arg Glu<br>1420                       1425                         1430                       1435 | | | | 5044 |
| aag gca ctt cac aaa cac ctt aac aag cac agg gac ttc ttg cag gaa<br>Lys Ala Leu His Lys His Leu Asn Lys His Arg Asp Phe Leu Gln Glu<br>                       1440                          1445                       1450 | | | | 5092 |
| gtc tgc ctg cgg ccc tca gct gac ccc atc ttt gag ccc agg caa cta<br>Val Cys Leu Arg Pro Ser Ala Asp Pro Ile Phe Glu Pro Arg Gln Leu<br>             1455                          1460                         1465 | | | | 5140 |
| cct gcc ttt caa gaa ggg att atg agc tgg tcc ccc aaa gag aag aca<br>Pro Ala Phe Gln Glu Gly Ile Met Ser Trp Ser Pro Lys Glu Lys Thr<br>             1470                          1475                         1480 | | | | 5188 |
| tac gag aca gac cta gca gtg ctt caa tgg gta gag gag ctg gag cag<br>Tyr Glu Thr Asp Leu Ala Val Leu Gln Trp Val Glu Glu Leu Glu Gln<br>             1485                          1490                         1495 | | | | 5236 |
| cgg gtt atc atg tct gat ctg cag att cgg ggc tgg aca tgt cct agc<br>Arg Val Ile Met Ser Asp Leu Gln Ile Arg Gly Trp Thr Cys Pro Ser<br>1500                       1505                         1510                       1515 | | | | 5284 |
| cca gac tct acc cgt gaa gac ttg gcc tac tgt gag cac ctc tcc gac<br>Pro Asp Ser Thr Arg Glu Asp Leu Ala Tyr Cys Glu His Leu Ser Asp<br>                       1520                          1525                       1530 | | | | 5332 |
| tcc cag gag gat atc acc tgg cga ggt ccg ggc agg gag gga ctg gca<br>Ser Gln Glu Asp Ile Thr Trp Arg Gly Pro Gly Arg Glu Gly Leu Ala<br>             1535                          1540                         1545 | | | | 5380 |
| cct caa cgt aaa act acc aac cct ttg gac ctg gct gtg atg cgg ctg<br>Pro Gln Arg Lys Thr Thr Asn Pro Leu Asp Leu Ala Val Met Arg Leu<br>             1550                          1555                         1560 | | | | 5428 |
| gct gcc ctg gaa caa aat gta aaa cgg cgg tac ctg cgg gag ccc ctc<br>Ala Ala Leu Glu Gln Asn Val Lys Arg Arg Tyr Leu Arg Glu Pro Leu<br>             1565                          1570                         1575 | | | | 5476 |
| tgg cca act cat gag gtt gtg ctg gag aaa gcc ctg ctt agc aca cct<br>Trp Pro Thr His Glu Val Val Leu Glu Lys Ala Leu Leu Ser Thr Pro<br>1580                       1585                         1590                       1595 | | | | 5524 |
| aat ggt gcc cct gag ggc acc act aca gag ata tca tat gag atc acc<br>Asn Gly Ala Pro Glu Gly Thr Thr Thr Glu Ile Ser Tyr Glu Ile Thr<br>                       1600                          1605                       1610 | | | | 5572 |
| cct cgc att cgt atc tgg cgc cag acc ctc cag cgg tgc cgg agc gca<br>Pro Arg Ile Arg Ile Trp Arg Gln Thr Leu Gln Arg Cys Arg Ser Ala<br>             1615                          1620                         1625 | | | | 5620 |
| gcc cat gtg tgc ttg tgc ctg ggc cat ctg gag agg tcc att gcc tgg<br>Ala His Val Cys Leu Cys Leu Gly His Leu Glu Arg Ser Ile Ala Trp<br>             1630                          1635                         1640 | | | | 5668 |
| gag aag tct gtc aac aaa gtg aca tgt cta gtc tgc cgg aag ggt gac<br>Glu Lys Ser Val Asn Lys Val Thr Cys Leu Val Cys Arg Lys Gly Asp<br>             1645                          1650                       1655 | | | | 5716 |
| aat gat gag ttt ctt ctg ctt tgt gat ggg tgt gac cgt ggc tgc cac<br>Asn Asp Glu Phe Leu Leu Leu Cys Asp Gly Cys Asp Arg Gly Cys His<br>1660                       1665                         1670                       1675 | | | | 5764 |
| att tac tgc cat cgt ccc aag atg gag gct gtc cca gaa gga gat tgg | | | | 5812 |

-continued

```
Ile Tyr Cys His Arg Pro Lys Met Glu Ala Val Pro Glu Gly Asp Trp
            1680                1685                1690 ttc tgt act gtc tgt ttg gct cag cag gtg gag gga gaa ttc act cag      5860
Phe Cys Thr Val Cys Leu Ala Gln Gln Val Glu Gly Glu Phe Thr Gln
        1695                1700                1705 aag cct ggt ttc cca aag cgt ggc cag aag cgg aaa agt ggt tat tcg      5908
Lys Pro Gly Phe Pro Lys Arg Gly Gln Lys Arg Lys Ser Gly Tyr Ser
    1710                1715                1720 ctg aac ttc tca gaa ggt gat ggc cgc cga cgc cgg gta ctg ttg aag      5956
Leu Asn Phe Ser Glu Gly Asp Gly Arg Arg Arg Arg Val Leu Leu Lys
1725                1730                1735 ggc cga gaa agc cca gca gca ggg cct cgg tac tcg gaa gaa agg ctc      6004
Gly Arg Glu Ser Pro Ala Ala Gly Pro Arg Tyr Ser Glu Glu Arg Leu
1740                1745                1750                1755 tcc ccc tcc aag cgg cgg cga ctc tct atg cgg aac cac cac agt gat      6052
Ser Pro Ser Lys Arg Arg Arg Leu Ser Met Arg Asn His His Ser Asp
                1760                1765                1770 ctc aca ttt tgc gag att atc ctg atg gag atg gaa tcc cat gat gca      6100
Leu Thr Phe Cys Glu Ile Ile Leu Met Glu Met Glu Ser His Asp Ala
            1775                1780                1785 gcc tgg cct ttc nta gag cct gtg aac cca cgt ttg gtg agt ggg tac      6148
Ala Trp Pro Phe Xaa Glu Pro Val Asn Pro Arg Leu Val Ser Gly Tyr
        1790                1795                1800 cgg cgc atc atc aaa aat cct atg gat ttt tcc acc atg cgg gag cgg      6196
Arg Arg Ile Ile Lys Asn Pro Met Asp Phe Ser Thr Met Arg Glu Arg
    1805                1810                1815 ctg ctc agg gga ggg tac acc agc tca gag gag ttt gcg gct gat gcc      6244
Leu Leu Arg Gly Gly Tyr Thr Ser Ser Glu Glu Phe Ala Ala Asp Ala
1820                1825                1830                1835 ctc ctg gta ttt gac aac tgc cag act ttc aac gag gat gac tct gaa      6292
Leu Leu Val Phe Asp Asn Cys Gln Thr Phe Asn Glu Asp Asp Ser Glu
                1840                1845                1850 gta ggc aag gct ggg cac atc atg cgc cgc ttc ttc gag agc cgc tgg      6340
Val Gly Lys Ala Gly His Ile Met Arg Arg Phe Phe Glu Ser Arg Trp
            1855                1860                1865 gag gag ttt tat cag gga aaa cag gcc aat ctg tgaggcaagg gaggtgggga    6393
Glu Glu Phe Tyr Gln Gly Lys Gln Ala Asn Leu
        1870                1875 gtcaccttgt ggcatctccc cccaccttcc aaacaaaaac ctgccatttt cacctgctga    6453
tgctgccctg ggtccagact caagtcagat acaaccctga ttttgacct tgcccttggc     6513
agtgccccac atcctcttat tcctacatcc ctttctccct tccctcctct tgctcctcaa    6573
gtaagaggtg cagagaggag tccttctgga ctaaaagcca aaaaagaaa gaaaaaaata     6633
atttttcttt tctgttttat ttgctaatta aaaatgggga gggggaaagt cgtccctact    6693
tcctcctccg tgcttcctct cctcccctgt acgtgcccca gcattctggg gttatttaac    6753
aatagcaata gttctagtga atgtgtgaaa ccaagaaaca ctctgtactg tgtgcggacc    6813
cgcagtgacg gccagtaaag tggacttaac tcccaagtgt gtcgcggccg acaccgggc     6873
cctggacatg ctgcttccat gttcagtccc ttccctgctt ctcgctgtct ttcttttccc    6933
acctcccacc ccccagtttt cagattttct ctcatccaat aatgtaaaac tatcgtgtac    6993
gggttcctcc ctccttttct cttctcccaa atcttttccc ttcaaaggaa aaaaaatgt     7053
tcagaggtcc ctgtcttctg tccccatctt cctgccgata gctatcccct gtatgatgtt    7113
ggatgctcct cacatgctga gtttccagcc ttttctgaaa ctcattagct ggggagaggg    7173
cagggaggct tcctgggcct tccaacctcc ttccccacct ccttcccaaa ccctcttggg    7233
```

-continued

```
aactcctcag ggacaactac tgctgagttt gggtgcaccc aaagatggag gccaagtagc    7293
aatggggccg gcctcacaga gagcgccgtg tgtgtgtgtg tgtgtgtgtg tgtgtgtgtg    7353
tccgccacac aacgcgctgt gtgtgtgtgt gtgtgtctca cacacacagc gcgcagtgtg    7413
tgtgtgtgtg tgtgtgtgta tgtgtgtgtg tgtgtgaccc tgtattgttt gataggatcc    7473
attcagtttc cccaagtacc tgttttcatt cccattttc ccattgttta aaccatcac     7533 tttttttgtct ttgggaaacc acaggaacaa tttctctgga gacaaggctg tgtctctctc   7593
ctggtcattt ttgttccagc ctcttcagac tgtgcatctt ttcagcagga actccctctc   7653
ttctcggtag ctttgaatct taagcttcta cgggagagtg gtagaactgg atcatttcat   7713
aatcccattt agttgtgctt ttcttcatat acttcatacc ccaggacccc ttccccagca   7773
gcagagaccc tggagcacag gagagtaggg aggaggggtt ctgggtccat cactgcctta   7833
catgtgacta tgtccaagtt aagcccccaa cacgagagga aagctgctga ctcccagcta   7893
tagccatggg cacttggccc cctgcttttc ctgctcagca gagcccctcc cttcagagat   7953
tacgggtact tgcactgggg aagtggctgc tggctggccc aagcagagag ctgaggcatc   8013
caagaaatgt tccattgggg ggtgggggtg ccaggtgagg tggagcattc cttgtattct   8073
ggcagcactg aagagccact gaaggggta gggcagtgt aggtcctggg gcagcccctt    8133 tattcccttta tgccccttct ccctcatagc ctatttctaa agtcgccttt tctgtcagat   8193
aaacctcaaa acttttaatt ttatttgaga ttttttttg cttttaagag gtggattgaa    8253
gaatatttga attgacttta tattatgcat aaatatttat atttatcta aataactgcg    8313 ctgtaacaaa ctttgtgtta gacagttgaa actgttagag ttggggctc tgcttttcc    8373 ccctggcaat tttcccttgg tataagatgt gctagattaa tttcattgtg aggtggatgg    8433
gggagtgaaa ttgtgaggtg gatggggag tgaaatctcc atggttcctg ctttgtgttc    8493
ctctcccagc tccatctctt tccctaggga ccaggcactc atatggcggg gtggggtcct   8553
agcctcagtt tgaagaagtg ggggctggag cggggttggg ggtggtaggg atagggcatg   8613
atcaaagggg ccatttcttg cttttctttc ctcatcttca ctgccccctt gagctaggtg   8673
gattttctct tcatgacaag agtatttggt agggaaagca ggtttaaaat aaaaagacaa    8733
cccaccccct gcccttttgc ttccctccca tcagtctggt tgacaggaag aaaccacacc    8793
atcaacacca acaagttnt gtgttccttt tacagcaaaa gggacttttt atataaccaa     8853
atgtggtgtt ttagtgactt tttgataatg tacagttttt tgtgaattta aatttatttc    8913
tttctatatt tttaggacca atttcatttt taataaggtt aaaaagaaaa aaaagtcta    8973 gcgaaaaaac tcctgttttt gccatgtgat gttccacaag tgcagctgta gaaagtgct     9033 tgtcagttgt tgaataaaaa aaccacattt gatagagatt caaaagactc tgtgtattca    9093
tcttcccttc tacacacctg aggggagac ggcgttggga taggtatgac tggcttaaga    9153
gaccacaggc aagggaacaa caggggctcc tgttccatac cctctgtgtg ggatggaaag    9213
ggtcattagt gctcccgcct aaatgtctgg ctgagttgct ggaagcaaag gggggattca    9273
gtgcatccag gtcctgcctt gtgagatgtg gccccagctt cctaagctgc cacctctgtg    9333
ttcctgtcat agcaaatatg ggaccatcac cagcttacca cttcccactc acggataaga    9393
caccaagacg tagac                                                    9408
```

<210> SEQ ID NO 15
<211> LENGTH: 24
<212> TYPE: DNA
<213> ORGANISM: Artificial Sequence

```
<220> FEATURE:
<223> OTHER INFORMATION: Synthetically generated primer

<400> SEQUENCE: 15
tgactctgaa gtaggcaagg ctgg                                    24

<210> SEQ ID NO 16
<211> LENGTH: 22
<212> TYPE: DNA
<213> ORGANISM: Artificial Sequence
<220> FEATURE:
<223> OTHER INFORMATION: Synthetically generated primer

<400> SEQUENCE: 16
cttgcctcac agattggcct gt                                      22

<210> SEQ ID NO 17
<211> LENGTH: 21
<212> TYPE: DNA
<213> ORGANISM: Artificial Sequence
<220> FEATURE:
<223> OTHER INFORMATION: Synthetically generated primer

<400> SEQUENCE: 17
ttgccgtatt tggctggtat c                                       21

<210> SEQ ID NO 18
<211> LENGTH: 23
<212> TYPE: DNA
<213> ORGANISM: Artificial Sequence
<220> FEATURE:
<223> OTHER INFORMATION: Synthetically generated primer

<400> SEQUENCE: 18
catagagaag agggcagggt tga                                     23

<210> SEQ ID NO 19
<211> LENGTH: 20
<212> TYPE: DNA
<213> ORGANISM: Artificial Sequence
<220> FEATURE:
<223> OTHER INFORMATION: Synthetically generated primer

<400> SEQUENCE: 19
cttttgagca agttcagcct                                         20

<210> SEQ ID NO 20
<211> LENGTH: 22
<212> TYPE: DNA
<213> ORGANISM: Artificial Sequence
<220> FEATURE:
<223> OTHER INFORMATION: Synthetically generated primer

<400> SEQUENCE: 20
gtcggcttct tcatttcctc ca                                      22

<210> SEQ ID NO 21
<211> LENGTH: 1972
<212> TYPE: PRT
<213> ORGANISM: Homo sapiens

<400> SEQUENCE: 21

Met Gly Gln Thr Lys Ser Thr Ser Ser Gly Gly Gly Asn Arg Lys Cys
  1               5                  10                  15

Asn Gln Glu Gln Ser Lys Asn Gln Pro Leu Asp Ala Arg Val Asp Lys
```

-continued

```
                20                  25                  30
Ile Lys Asp Lys Lys Pro Arg Lys Lys Ala Met Glu Ser Ser Ser Asn
             35                  40                  45
Ser Asp Ser Asp Ser Gly Thr Ser Ser Asp Thr Ser Ser Glu Gly Ile
 50                  55                  60
Ser Ser Ser Asp Ser Asp Asp Leu Glu Glu Asp Glu Glu Glu Glu Asp
 65                  70                  75                  80
Gln Ser Ile Glu Glu Ser Glu Asp Asp Ser Asp Ser Glu Ser Glu
                 85                  90                  95
Ala Gln His Lys Ser Asn Asn Gln Val Leu Leu His Gly Ile Ser Asp
             100                 105                 110
Pro Lys Ala Asp Gly Gln Lys Ala Thr Glu Lys Ala Gln Glu Lys Arg
             115                 120                 125
Ile His Gln Pro Leu Pro Leu Ala Phe Glu Ser Gln Thr His Ser Phe
         130                 135                 140
Gln Ser Gln Gln Lys Gln Pro Gln Val Leu Ser Gln Gln Leu Pro Phe
145                 150                 155                 160
Ile Phe Gln Ser Ser Gln Ala Lys Glu Glu Ser Val Asn Lys His Thr
             165                 170                 175
Ser Val Ile Gln Ser Thr Gly Leu Val Ser Asn Val Lys Pro Leu Ser
         180                 185                 190
Leu Val Asn Gln Ala Lys Lys Glu Thr Tyr Met Lys Leu Ile Val Pro
         195                 200                 205
Ser Pro Asp Val Leu Lys Ala Gly Asn Lys Asn Thr Ser Glu Glu Ser
     210                 215                 220
Ser Leu Leu Thr Ser Glu Leu Arg Ser Lys Arg Glu Gln Tyr Lys Gln
225                 230                 235                 240
Ala Phe Pro Ser Gln Leu Lys Lys Gln Glu Ser Ser Lys Ser Leu Lys
                 245                 250                 255
Lys Val Ile Ala Ala Leu Ser Asn Pro Lys Ala Thr Ser Ser Ser Pro
             260                 265                 270
Ala His Pro Lys Gln Thr Leu Glu Asn Asn His Pro Asn Pro Phe Leu
         275                 280                 285
Thr Asn Ala Leu Leu Gly Asn His Gln Pro Asn Gly Val Ile Gln Ser
     290                 295                 300
Val Ile Gln Glu Ala Pro Leu Ala Leu Thr Thr Lys Thr Lys Met Gln
305                 310                 315                 320
Ser Lys Ile Asn Glu Asn Ile Ala Ala Ser Ser Thr Pro Phe Ser
             325                 330                 335
Ser Pro Val Asn Leu Ser Thr Ser Gly Arg Arg Thr Pro Gly Asn Gln
         340                 345                 350
Thr Pro Val Met Pro Ser Ala Ser Pro Ile Leu His Ser Gln Gly Lys
     355                 360                 365
Glu Lys Ala Val Ser Asn Asn Val Asn Pro Val Lys Thr Gln His His
     370                 375                 380
Ser His Pro Ala Lys Ser Leu Val Glu Gln Phe Arg Gly Thr Asp Ser
385                 390                 395                 400
Asp Ile Pro Ser Ser Lys Asp Ser Glu Asp Ser Asn Glu Asp Glu Glu
                 405                 410                 415
Glu Asp Asp Glu Glu Asp Glu Asp Asp Glu Asp Glu Ser
             420                 425                 430
Asp Asp Ser Gln Ser Glu Ser Asp Ser Asn Ser Glu Ser Asp Thr Glu
         435                 440                 445
```

-continued

```
Gly Ser Glu Glu Asp Asp Asp Lys Asp Gln Asp Glu Ser Asp
    450                 455                 460
Ser Asp Thr Glu Gly Glu Lys Thr Ser Met Lys Leu Asn Lys Thr Thr
465                 470                 475                 480
Ser Ser Val Lys Ser Pro Ser Met Ser Leu Thr Gly His Ser Thr Pro
                485                 490                 495
Arg Asn Leu His Ile Ala Lys Ala Pro Gly Ser Ala Pro Ala Ala Leu
                500                 505                 510
Cys Ser Glu Ser Gln Ser Pro Ala Phe Leu Gly Thr Ser Ser Ser Thr
                515                 520                 525
Leu Thr Ser Ser Pro His Ser Gly Thr Ser Lys Arg Arg Arg Val Thr
                530                 535                 540
Asp Glu Arg Glu Leu Arg Ile Pro Leu Glu Tyr Gly Trp Gln Arg Glu
545                 550                 555                 560
Thr Arg Ile Arg Asn Phe Gly Gly Arg Leu Gln Gly Glu Val Ala Tyr
                565                 570                 575
Tyr Ala Pro Cys Gly Lys Lys Leu Arg Gln Tyr Pro Glu Val Ile Lys
                580                 585                 590
Tyr Leu Ser Arg Asn Gly Ile Met Asp Ile Ser Arg Asp Asn Phe Ser
                595                 600                 605
Phe Ser Ala Lys Ile Arg Val Gly Asp Phe Tyr Glu Ala Arg Asp Gly
                610                 615                 620
Pro Gln Glu Met Gln Trp Cys Leu Leu Lys Glu Glu Asp Val Ile Pro
625                 630                 635                 640
Arg Ile Arg Ala Met Glu Gly Arg Arg Gly Arg Pro Pro Asn Pro Asp
                645                 650                 655
Arg Gln Arg Ala Arg Glu Glu Ser Arg Met Arg Arg Arg Lys Gly Arg
                660                 665                 670
Pro Pro Asn Val Gly Asn Ala Glu Phe Leu Asp Asn Ala Asp Ala Lys
                675                 680                 685
Leu Leu Arg Lys Leu Gln Ala Gln Glu Ile Ala Arg Gln Ala Ala Gln
                690                 695                 700
Ile Lys Leu Leu Arg Lys Leu Gln Lys Gln Glu Gln Ala Arg Val Ala
705                 710                 715                 720
Lys Glu Ala Lys Lys Gln Gln Ala Ile Met Ala Ala Glu Glu Lys Arg
                725                 730                 735
Lys Gln Lys Glu Gln Ile Lys Ile Met Lys Gln Gln Glu Lys Ile Lys
                740                 745                 750
Arg Ile Gln Gln Ile Arg Met Glu Lys Glu Leu Arg Ala Gln Gln Ile
                755                 760                 765
Leu Glu Ala Lys Lys Lys Lys Glu Glu Ala Ala Asn Ala Lys Leu
770                 775                 780
Leu Glu Ala Glu Lys Arg Ile Lys Glu Lys Glu Met Arg Arg Gln Gln
785                 790                 795                 800
Ala Val Leu Leu Lys His Gln Glu Arg Glu Arg Arg Gln His Met
                805                 810                 815
Met Leu Met Lys Ala Met Glu Ala Arg Lys Lys Ala Glu Glu Lys Glu
                820                 825                 830
Arg Leu Lys Gln Glu Lys Arg Asp Glu Lys Arg Leu Asn Lys Glu Arg
                835                 840                 845
Lys Leu Glu Gln Arg Arg Leu Glu Leu Glu Met Ala Lys Glu Leu Lys
                850                 855                 860
```

-continued

```
Lys Pro Asn Glu Asp Met Cys Leu Ala Asp Gln Lys Pro Leu Pro Glu
865                 870                 875                 880

Leu Pro Arg Ile Pro Gly Leu Val Leu Ser Gly Ser Thr Phe Ser Asp
            885                 890                 895

Cys Leu Met Val Val Gln Phe Leu Arg Asn Phe Gly Lys Val Leu Gly
                900                 905                 910

Phe Asp Val Asn Ile Asp Val Pro Asn Leu Ser Val Leu Gln Glu Gly
            915                 920                 925

Leu Leu Asn Ile Gly Asp Ser Met Gly Glu Val Gln Asp Leu Leu Val
        930                 935                 940

Arg Leu Leu Ser Ala Ala Val Cys Asp Pro Gly Leu Ile Thr Gly Tyr
945                 950                 955                 960

Lys Ala Lys Thr Ala Leu Gly Glu His Leu Leu Asn Val Gly Val Asn
                965                 970                 975

Arg Asp Asn Val Ser Glu Ile Leu Gln Ile Phe Met Glu Ala His Cys
            980                 985                 990

Gly Gln Thr Glu Leu Thr Glu Ser Leu Lys Thr Lys Ala Phe Gln Ala
        995                 1000                1005

His Thr Pro Ala Gln Lys Ala Ser Val Leu Ala Phe Leu Ile Asn Glu
    1010                1015                1020

Leu Ala Cys Ser Lys Ser Val Val Ser Glu Ile Asp Lys Asn Ile Asp
1025                1030                1035                1040

Tyr Met Ser Asn Leu Arg Arg Asp Lys Trp Val Val Glu Gly Lys Leu
                1045                1050                1055

Arg Lys Leu Arg Ile Ile His Ala Lys Lys Thr Gly Lys Arg Asp Thr
            1060                1065                1070

Ser Gly Gly Ile Asp Leu Gly Glu Glu Gln His Pro Leu Gly Thr Pro
        1075                1080                1085

Thr Pro Gly Arg Lys Arg Arg Arg Lys Gly Gly Asp Ser Asp Tyr Asp
    1090                1095                1100

Asp Asp Asp Asp Asp Asp Ser Asp Asp Gln Gly Asp Glu Asp Asp Glu
1105                1110                1115                1120

Asp Glu Glu Asp Lys Glu Asp Gln Lys Gly Lys Lys Thr Asp Ile Cys
                1125                1130                1135

Glu Asp Glu Asp Glu Gly Asp Gln Ala Ala Ser Val Glu Glu Leu Glu
            1140                1145                1150

Lys Gln Ile Glu Lys Leu Ser Lys Gln Gln Ser Gln Tyr Arg Arg Lys
        1155                1160                1165

Leu Phe Asp Ala Ser His Ser Leu Arg Ser Val Met Phe Gly Pro Asp
    1170                1175                1180

Arg Tyr Arg Arg Arg Tyr Trp Ile Leu Pro Arg Cys Gly Gly Ile Phe
1185                1190                1195                1200

Val Glu Gly Met Glu Ser Gly Glu Gly Leu Glu Glu Ile Ala Lys Glu
                1205                1210                1215

Arg Glu Lys Leu Lys Lys Ala Glu Ser Val Gln Ile Lys Glu Glu Met
            1220                1225                1230

Phe Glu Thr Ser Gly Asp Ser Leu Asn Cys Ser Asn Thr Asp His Cys
        1235                1240                1245

Glu Gln Lys Glu Asp Leu Lys Lys Asp Asn Thr Asn Leu Phe Leu
    1250                1255                1260

Gln Lys Pro Gly Ser Phe Ser Lys Leu Ser Lys Leu Leu Glu Val Ala
1265                1270                1275                1280

Lys Met Pro Pro Glu Ser Glu Val Met Thr Pro Lys Pro Asn Ala Gly
```

-continued

```
                1285                1290                1295
Ala Asn Gly Cys Thr Leu Ser Tyr Gln Asn Ser Gly Lys His Ser Leu
                1300                1305                1310
Gly Ser Val Gln Ser Thr Ala Thr Gln Ser Asn Val Glu Lys Ala Asp
            1315                1320                1325
Ser Asn Asn Leu Phe Asn Thr Gly Ser Ser Gly Pro Gly Lys Phe Tyr
        1330                1335                1340
Ser Pro Leu Pro Asn Asp Gln Leu Leu Lys Thr Leu Thr Glu Lys Asn
1345                1350                1355                1360
Arg Gln Trp Phe Ser Leu Leu Pro Arg Thr Pro Cys Asp Asp Thr Ser
                1365                1370                1375
Leu Thr His Ala Asp Met Ser Thr Ala Ser Leu Val Thr Pro Gln Ser
            1380                1385                1390
Gln Pro Pro Ser Lys Ser Pro Ser Pro Thr Pro Ala Pro Leu Gly Ser
        1395                1400                1405
Ser Ala Gln Asn Pro Val Gly Leu Asn Pro Phe Ala Leu Ser Pro Leu
    1410                1415                1420
Gln Val Lys Gly Gly Val Ser Met Met Gly Leu Gln Phe Cys Gly Trp
1425                1430                1435                1440
Pro Thr Gly Val Val Thr Ser Asn Ile Pro Phe Thr Leu Ser Val Pro
                1445                1450                1455
Ser Leu Gly Ser Gly Leu Gly Leu Ser Glu Gly Asn Gly Asn Ser Phe
            1460                1465                1470
Leu Thr Ser Asn Val Ala Ser Ser Lys Ser Glu Ser Pro Val Pro Gln
        1475                1480                1485
Asn Glu Lys Ala Thr Ser Ala Gln Pro Ala Ala Val Glu Val Ala Lys
    1490                1495                1500
Pro Val Asp Phe Pro Ser Pro Lys Pro Ile Pro Glu Glu Met Gln Phe
1505                1510                1515                1520
Gly Trp Trp Arg Ile Ile Asp Pro Glu Asp Leu Lys Ala Leu Leu Lys
                1525                1530                1535
Val Leu His Leu Arg Gly Ile Arg Glu Lys Ala Leu Gln Lys Gln Ile
            1540                1545                1550
Gln Lys His Leu Asp Tyr Ile Thr Gln Ala Cys Leu Lys Asn Lys Asp
        1555                1560                1565
Val Ala Ile Ile Glu Leu Asn Glu Asn Glu Asn Gln Val Thr Arg
    1570                1575                1580
Asp Ile Val Glu Asn Trp Ser Val Glu Glu Gln Ala Met Glu Met Asp
1585                1590                1595                1600
Leu Ser Val Leu Gln Gln Val Glu Asp Leu Glu Arg Arg Val Ala Ser
                1605                1610                1615
Ala Ser Leu Gln Val Lys Gly Trp Met Cys Pro Glu Pro Ala Ser Glu
            1620                1625                1630
Arg Glu Asp Leu Val Tyr Phe Glu His Lys Ser Phe Thr Lys Leu Cys
        1635                1640                1645
Lys Glu His Asp Gly Glu Phe Thr Gly Glu Asp Ser Ser Ala His
    1650                1655                1660
Ala Leu Glu Arg Lys Ser Asp Asn Pro Leu Asp Ile Ala Val Thr Arg
1665                1670                1675                1680
Leu Ala Asp Leu Glu Arg Asn Ile Glu Arg Arg Ile Glu Glu Asp Ile
                1685                1690                1695
Ala Pro Gly Leu Arg Val Trp Arg Arg Ala Leu Ser Glu Ala Arg Ser
            1700                1705                1710
```

```
Ala Ala Gln Val Ala Leu Cys Ile Gln Gln Leu Gln Lys Ser Ile Ala
        1715                1720                1725

Trp Glu Lys Ser Ile Met Lys Val Tyr Cys Gln Ile Cys Arg Lys Gly
    1730                1735                1740

Asp Asn Glu Glu Leu Leu Leu Cys Asp Gly Cys Asp Lys Gly Cys
1745                1750                1755                1760

His Thr Tyr Cys His Arg Pro Lys Ile Thr Thr Ile Pro Asp Gly Asp
                1765                1770                1775

Trp Phe Cys Pro Ala Cys Ile Ala Lys Ala Ser Gly Gln Thr Leu Lys
            1780                1785                1790

Ile Lys Lys Leu His Val Lys Gly Lys Lys Thr Asn Glu Ser Lys Lys
        1795                1800                1805

Gly Lys Lys Val Thr Leu Thr Gly Asp Thr Glu Asp Glu Asp Ser Ala
    1810                1815                1820

Ser Thr Ser Ser Ser Leu Lys Arg Gly Asn Lys Asp Leu Gln Lys Arg
1825                1830                1835                1840

Lys Met Glu Glu Asn Thr Ser Ile Asn Leu Ser Lys Gln Glu Ser Phe
                1845                1850                1855

Thr Ser Val Lys Lys Pro Lys Arg Asp Asp Ser Lys Asp Leu Ala Leu
            1860                1865                1870

Cys Ser Met Ile Leu Thr Glu Met Glu Thr His Glu Asp Ala Trp Pro
        1875                1880                1885

Phe Leu Leu Pro Val Asn Leu Lys Leu Val Pro Gly Tyr Lys Lys Val
    1890                1895                1900

Ile Lys Lys Pro Met Asp Phe Ser Thr Ile Arg Glu Lys Leu Ser Ser
1905                1910                1915                1920

Gly Gln Tyr Pro Asn Leu Glu Thr Phe Ala Leu Asp Val Arg Leu Val
                1925                1930                1935

Phe Asp Asn Cys Glu Thr Phe Asn Glu Asp Asp Ser Asp Ile Gly Arg
            1940                1945                1950

Ala Gly His Asn Met Arg Lys Tyr Phe Glu Lys Lys Trp Thr Asp Thr
        1955                1960                1965

Phe Lys Val Ser
    1970

<210> SEQ ID NO 22
<211> LENGTH: 7585
<212> TYPE: DNA
<213> ORGANISM: Homo sapiens
<220> FEATURE:
<221> NAME/KEY: CDS
<222> LOCATION: (367)...(6282)

<400> SEQUENCE: 22
ggtctcgatc tcctgacctt gtgatccacc tcctcggcct cccaaagtgc tgggattaca      60
ggcatgagcc acggcaccca gcctcatttg ctgttaaact catttattga gtcacctttt     120
tcttcctcac acttttttagt cttagaattt ttgtgtgttt ttatttaccc taacctgtca    180
atttcatagt ttccactttc ttgttgaagt ttccaaactt gacctcatgc ctttgaatat     240
actaattcta ttgctttgac acatttttttt cccgaaaaag gtgtaaatgg gtcaataaat    300
ggaagtaata catcatctgt aattggtatc aacacatctg tactatccac tactgcttca    360 agttcc atg gga caa act aaa agt aca agc tca ggt gga gga aat cga        408
       Met Gly Gln Thr Lys Ser Thr Ser Ser Gly Gly Gly Asn Arg
        1               5                   10
```

-continued

| | |
|---|---|
| aaa tgt aat cag gaa caa agc aaa aac cag cct ttg gat gct aga gtt<br>Lys Cys Asn Gln Glu Gln Ser Lys Asn Gln Pro Leu Asp Ala Arg Val<br>15                    20                   25                  30 | 456 |
| gac aaa atc aaa gat aag aaa cca agg aag aaa gca atg gaa agt tct<br>Asp Lys Ile Lys Asp Lys Lys Pro Arg Lys Lys Ala Met Glu Ser Ser<br>                  35                   40                  45 | 504 |
| agc aac agt gat agt gat tca ggc aca tca tca gac acc tca agt gaa<br>Ser Asn Ser Asp Ser Asp Ser Gly Thr Ser Ser Asp Thr Ser Ser Glu<br>        50                   55                   60 | 552 |
| ggc att agt agc agt gat tca gat gat cta gaa gaa gat gaa gaa gaa<br>Gly Ile Ser Ser Ser Asp Ser Asp Asp Leu Glu Glu Asp Glu Glu Glu<br>          65                   70                   75 | 600 |
| gaa gat caa agt att gaa gaa agt gaa gat gat gat tct gat tca gag<br>Glu Asp Gln Ser Ile Glu Glu Ser Glu Asp Asp Asp Ser Asp Ser Glu<br>80                    85                   90 | 648 |
| agt gaa gca caa cat aaa agt aac aac cag gtg cta tta cat ggt att<br>Ser Glu Ala Gln His Lys Ser Asn Asn Gln Val Leu Leu His Gly Ile<br>95                    100                105              110 | 696 |
| tca gac cca aaa gca gat gga cag aaa gca act gaa aaa gcc cag gaa<br>Ser Asp Pro Lys Ala Asp Gly Gln Lys Ala Thr Glu Lys Ala Gln Glu<br>                  115                120              125 | 744 |
| aaa aga ata cac cag cca tta cct ctt gcg ttt gaa tcc cag act cac<br>Lys Arg Ile His Gln Pro Leu Pro Leu Ala Phe Glu Ser Gln Thr His<br>          130                135              140 | 792 |
| tca ttc caa tcc cag cag aag cag cct cag gtt ttg tca cag cag ctt<br>Ser Phe Gln Ser Gln Gln Lys Gln Pro Gln Val Leu Ser Gln Gln Leu<br>145                   150                155 | 840 |
| cca ttt att ttc caa agc tct cag gca aag gag gaa tct gtg aac aaa<br>Pro Phe Ile Phe Gln Ser Ser Gln Ala Lys Glu Glu Ser Val Asn Lys<br>160                   165                170 | 888 |
| cac acc agt gta ata cag tct acg gga ttg gtg tcc aat gtg aaa cct<br>His Thr Ser Val Ile Gln Ser Thr Gly Leu Val Ser Asn Val Lys Pro<br>175                   180                185              190 | 936 |
| tta tct ttg gta aat caa gcc aaa aag gaa act tac atg aaa ctc ata<br>Leu Ser Leu Val Asn Gln Ala Lys Lys Glu Thr Tyr Met Lys Leu Ile<br>                  195                200              205 | 984 |
| gtt cct tct cct gat gtt ctt aaa gca ggg aat aaa aat acc tct gaa<br>Val Pro Ser Pro Asp Val Leu Lys Ala Gly Asn Lys Asn Thr Ser Glu<br>210                 215                220 | 1032 |
| gaa tct agt tta ttg acc agt gaa ttg aga tcc aaa cgg gaa caa tat<br>Glu Ser Ser Leu Leu Thr Ser Glu Leu Arg Ser Lys Arg Glu Gln Tyr<br>          225                230              235 | 1080 |
| aaa cag gca ttc cca tca cag tta aag aaa caa gag tca tcg aag agc<br>Lys Gln Ala Phe Pro Ser Gln Leu Lys Lys Gln Glu Ser Ser Lys Ser<br>240                 245                250 | 1128 |
| ctg aag aag gtt att gca gct ttg tca aat cca aaa gca acc tct agt<br>Leu Lys Lys Val Ile Ala Ala Leu Ser Asn Pro Lys Ala Thr Ser Ser<br>255                 260                265              270 | 1176 |
| tca cca gca cat cca aaa caa aca tta gaa aac aac cac cca aat cca<br>Ser Pro Ala His Pro Lys Gln Thr Leu Glu Asn Asn His Pro Asn Pro<br>                  275                280              285 | 1224 |
| ttc ttg aca aat gca ctt tta ggt aat cac caa cca aat gga gtt att<br>Phe Leu Thr Asn Ala Leu Leu Gly Asn His Gln Pro Asn Gly Val Ile<br>          290                295              300 | 1272 |
| caa agt gtc att caa gaa gct cct cta gca ctt act acc aaa act aaa<br>Gln Ser Val Ile Gln Glu Ala Pro Leu Ala Leu Thr Thr Lys Thr Lys<br>305                    310                315 | 1320 |
| atg cag agc aag att aat gaa aac att gct gct gca agt agc acc cct<br>Met Gln Ser Lys Ile Asn Glu Asn Ile Ala Ala Ala Ser Ser Thr Pro<br>320                    325                330 | 1368 |

```
ttt tcc tca cct gta aat ctg agt aca agt ggg aga aga acc cct ggc      1416
Phe Ser Ser Pro Val Asn Leu Ser Thr Ser Gly Arg Arg Thr Pro Gly
335                 340                 345                 350 aat cag aca cct gta atg cct tct gcc tct ccc atc ctg cat agt caa      1464
Asn Gln Thr Pro Val Met Pro Ser Ala Ser Pro Ile Leu His Ser Gln
                355                 360                 365 ggg aag gaa aaa gca gtt agc aat aat gta aac cca gta aaa aca cag      1512
Gly Lys Glu Lys Ala Val Ser Asn Asn Val Asn Pro Val Lys Thr Gln
            370                 375                 380 cat cac tcc cat cct gca aaa tct tta gtg gaa caa ttc aga gga aca      1560
His His Ser His Pro Ala Lys Ser Leu Val Glu Gln Phe Arg Gly Thr
        385                 390                 395 gat tca gac att ccc agt agt aaa gat tct gaa gat tca aat gag gat      1608
Asp Ser Asp Ile Pro Ser Ser Lys Asp Ser Glu Asp Ser Asn Glu Asp
    400                 405                 410 gaa gag gaa gat gat gaa gaa gaa gat gag gaa gat gat gaa gat gat      1656
Glu Glu Glu Asp Asp Glu Glu Glu Asp Glu Glu Asp Asp Glu Asp Asp
415                 420                 425                 430 gaa tct gat gac agc caa tca gaa tca gat agt aat tca gaa tca gat      1704
Glu Ser Asp Asp Ser Gln Ser Glu Ser Asp Ser Asn Ser Glu Ser Asp
                435                 440                 445 aca gaa gga tca gaa gaa gaa gat gat gat gat aaa gac caa gat gaa      1752
Thr Glu Gly Ser Glu Glu Glu Asp Asp Asp Asp Lys Asp Gln Asp Glu
            450                 455                 460 tca gat agt gat act gaa gga gag aaa act tca atg aaa ctg aat aaa      1800
Ser Asp Ser Asp Thr Glu Gly Glu Lys Thr Ser Met Lys Leu Asn Lys
        465                 470                 475 aca act tcc tct gtc aaa agc cct tcc atg agt ctc aca ggt cac tca      1848
Thr Thr Ser Ser Val Lys Ser Pro Ser Met Ser Leu Thr Gly His Ser
    480                 485                 490 aca cct cgt aac ctc cac ata gca aaa gcc cca ggc tct gct cct gct      1896
Thr Pro Arg Asn Leu His Ile Ala Lys Ala Pro Gly Ser Ala Pro Ala
495                 500                 505                 510 gcc tta tgt tct gaa tcc cag tca cct gct ttt ctt ggt aca tct tct      1944
Ala Leu Cys Ser Glu Ser Gln Ser Pro Ala Phe Leu Gly Thr Ser Ser
                515                 520                 525 tcc aca ctt act tca agc cca cac tct ggc act tcc aaa aga aga aga      1992
Ser Thr Leu Thr Ser Ser Pro His Ser Gly Thr Ser Lys Arg Arg Arg
            530                 535                 540 gta aca gat gaa cgt gaa ctg cgt att cca ttg gaa tat ggc tgg cag      2040
Val Thr Asp Glu Arg Glu Leu Arg Ile Pro Leu Glu Tyr Gly Trp Gln
        545                 550                 555 aga gag aca aga ata aga aac ttt gga ggg cgc ctt caa gga gaa gta      2088
Arg Glu Thr Arg Ile Arg Asn Phe Gly Gly Arg Leu Gln Gly Glu Val
    560                 565                 570 gca tat tat gct cca tgt gga aag aaa ctt agg cag tac cct gaa gta      2136
Ala Tyr Tyr Ala Pro Cys Gly Lys Lys Leu Arg Gln Tyr Pro Glu Val
575                 580                 585                 590 ata aag tat ctc agc aga aat gga ata atg gat atc tca agg gac aat      2184
Ile Lys Tyr Leu Ser Arg Asn Gly Ile Met Asp Ile Ser Arg Asp Asn
                595                 600                 605 ttc agc ttc agt gca aaa ata aga gtg ggt gac ttc tat gaa gcc aga      2232
Phe Ser Phe Ser Ala Lys Ile Arg Val Gly Asp Phe Tyr Glu Ala Arg
            610                 615                 620 gat gga ccg cag gaa atg cag tgg tgt ctt ttg aaa gaa gag gat gtc      2280
Asp Gly Pro Gln Glu Met Gln Trp Cys Leu Leu Lys Glu Glu Asp Val
        625                 630                 635 att cct cgt atc agg gca atg gaa ggt cgt aga gga aga cca cca aat      2328
Ile Pro Arg Ile Arg Ala Met Glu Gly Arg Arg Gly Arg Pro Pro Asn
```

```
                640                 645                 650
cca gat aga caa cga gca aga gag gaa tcc agg atg aga cgt cgg aaa   2376
Pro Asp Arg Gln Arg Ala Arg Glu Glu Ser Arg Met Arg Arg Arg Lys
655                 660                 665                 670 ggt cga cct cca aat gtt ggc aat gct gaa ttc cta gat aac gca gat   2424
Gly Arg Pro Pro Asn Val Gly Asn Ala Glu Phe Leu Asp Asn Ala Asp
                675                 680                 685 gca aag ttg cta aga aaa ctg caa gct caa gaa ata gcc agg caa gca   2472
Ala Lys Leu Leu Arg Lys Leu Gln Ala Gln Glu Ile Ala Arg Gln Ala
            690                 695                 700 gca caa ata aag ctt ttg aga aaa ctt caa aag cag gaa cag gct cgg   2520
Ala Gln Ile Lys Leu Leu Arg Lys Leu Gln Lys Gln Glu Gln Ala Arg
        705                 710                 715 gtt gct aaa gaa gcc aaa aaa caa caa gca ata atg gct gct gag gag   2568
Val Ala Lys Glu Ala Lys Lys Gln Gln Ala Ile Met Ala Ala Glu Glu
    720                 725                 730 aag cgg aag caa aaa gaa cag ata aag att atg aaa cag cag gaa aaa   2616
Lys Arg Lys Gln Lys Glu Gln Ile Lys Ile Met Lys Gln Gln Glu Lys
735                 740                 745                 750 att aag aga ata cag caa atc aga atg gaa aaa gaa ctt cga gct cag   2664
Ile Lys Arg Ile Gln Gln Ile Arg Met Glu Lys Glu Leu Arg Ala Gln
                755                 760                 765 caa att cta gag gct aaa aag aaa aag aag gaa gaa gcg gca aat gcc   2712
Gln Ile Leu Glu Ala Lys Lys Lys Lys Glu Glu Ala Ala Asn Ala
            770                 775                 780 aaa tta ttg gag gcc gag aaa cga ata aag gaa aaa gaa atg aga aga   2760
Lys Leu Leu Glu Ala Glu Lys Arg Ile Lys Glu Lys Glu Met Arg Arg
        785                 790                 795 caa caa gct gtt ctt ctg aaa cat cag gaa cga gag cga agg cga caa   2808
Gln Gln Ala Val Leu Leu Lys His Gln Glu Arg Glu Arg Arg Arg Gln
    800                 805                 810 cac atg atg ctt atg aaa gct atg gaa gct cgt aaa aaa gca gaa gaa   2856
His Met Met Leu Met Lys Ala Met Glu Ala Arg Lys Lys Ala Glu Glu
815                 820                 825                 830 aaa gag cgg ttg aaa caa gaa aaa cgt gat gag aaa aga tta aat aaa   2904
Lys Glu Arg Leu Lys Gln Glu Lys Arg Asp Glu Lys Arg Leu Asn Lys
                835                 840                 845 gag cgt aaa cta gag cag cga aga tta gaa tta gaa atg gca aag gaa   2952
Glu Arg Lys Leu Glu Gln Arg Arg Leu Glu Leu Glu Met Ala Lys Glu
            850                 855                 860 cta aag aag cct aat gaa gac atg tgc tta gca gac caa aag cct ttg   3000
Leu Lys Lys Pro Asn Glu Asp Met Cys Leu Ala Asp Gln Lys Pro Leu
        865                 870                 875 cca gag ttg cct cgt att cca gga ctt gtt ctc tct gga agt aca ttt   3048
Pro Glu Leu Pro Arg Ile Pro Gly Leu Val Leu Ser Gly Ser Thr Phe
    880                 885                 890 tca gac tgt ctc atg gtg gtg cag ttc tta cga aac ttt ggt aaa gtt   3096
Ser Asp Cys Leu Met Val Val Gln Phe Leu Arg Asn Phe Gly Lys Val
895                 900                 905                 910 ttg ggc ttt gat gtg aat att gat gtt cca aac ctg agt gtt ctt caa   3144
Leu Gly Phe Asp Val Asn Ile Asp Val Pro Asn Leu Ser Val Leu Gln
                915                 920                 925 gag gga ttg cta aat ata ggg gac agc atg ggt gaa gta caa gac ttg   3192
Glu Gly Leu Leu Asn Ile Gly Asp Ser Met Gly Glu Val Gln Asp Leu
            930                 935                 940 ctt gtg agg ctc ctc tca gct gct gta tgt gat cca ggt cta ata aca   3240
Leu Val Arg Leu Leu Ser Ala Ala Val Cys Asp Pro Gly Leu Ile Thr
        945                 950                 955 gga tac aag gct aaa aca gct ctt gga gaa cat ttg ctg aat gtt ggt   3288
Gly Tyr Lys Ala Lys Thr Ala Leu Gly Glu His Leu Leu Asn Val Gly
```

```
                                       -continued

Gly Tyr Lys Ala Lys Thr Ala Leu Gly Glu His Leu Leu Asn Val Gly
    960                 965                 970 gtg aat cga gac aat gtt tcc gag att tta cag ata ttt atg gaa gcc    3336
Val Asn Arg Asp Asn Val Ser Glu Ile Leu Gln Ile Phe Met Glu Ala
975                 980                 985                 990 cac tgt gga caa act gag ctt act gaa agt ctg aag acc aaa gct ttt    3384
His Cys Gly Gln Thr Glu Leu Thr Glu Ser Leu Lys Thr Lys Ala Phe
                995                 1000                1005 cag gct cac act cca gca cag aaa gct tca gtc ctg gct ttc ctg atc    3432
Gln Ala His Thr Pro Ala Gln Lys Ala Ser Val Leu Ala Phe Leu Ile
            1010                1015                1020 aat gaa ctg gca tgc agc aag agt gtg gtc agt gaa atc gac aag aac    3480
Asn Glu Leu Ala Cys Ser Lys Ser Val Val Ser Glu Ile Asp Lys Asn
        1025                1030                1035 att gat tat atg tca aac ttg agg aga gat aaa tgg gtg gta gaa ggt    3528
Ile Asp Tyr Met Ser Asn Leu Arg Arg Asp Lys Trp Val Val Glu Gly
    1040                1045                1050 aaa ctc cgc aag ctc aga atc att cat gct aag aaa aca ggc aaa aga    3576
Lys Leu Arg Lys Leu Arg Ile Ile His Ala Lys Lys Thr Gly Lys Arg
1055                1060                1065                1070 gac act tca ggt ggc att gat ctg gga gaa gag cag cat ccc ttg ggc    3624
Asp Thr Ser Gly Gly Ile Asp Leu Gly Glu Glu Gln His Pro Leu Gly
                1075                1080                1085 aca ccc act cca gga cgc aag cga aga agg aag gga gga gac agt gat    3672
Thr Pro Thr Pro Gly Arg Lys Arg Arg Arg Lys Gly Gly Asp Ser Asp
            1090                1095                1100 tat gac gat gat gat gac gat gac agt gat gac caa ggg gat gaa gat    3720
Tyr Asp Asp Asp Asp Asp Asp Asp Ser Asp Asp Gln Gly Asp Glu Asp
        1105                1110                1115 gat gag gat gaa gaa gat aag gaa gac caa aaa gga aaa aag act gat    3768
Asp Glu Asp Glu Glu Asp Lys Glu Asp Gln Lys Gly Lys Lys Thr Asp
    1120                1125                1130 atc tgt gaa gat gag gat gaa ggt gac caa gca gca agt gtt gaa gag    3816
Ile Cys Glu Asp Glu Asp Glu Gly Asp Gln Ala Ala Ser Val Glu Glu
1135                1140                1145                1150 ctg gaa aaa cag att gaa aaa ctg agt aaa caa cag agt cag tac aga    3864
Leu Glu Lys Gln Ile Glu Lys Leu Ser Lys Gln Gln Ser Gln Tyr Arg
                1155                1160                1165 agg aag ctc ttt gat gcg tct cac tca ttg cgt tca gtg atg ttt ggc    3912
Arg Lys Leu Phe Asp Ala Ser His Ser Leu Arg Ser Val Met Phe Gly
            1170                1175                1180 cca gat cgt tac aga cgc cgg tac tgg att ctt ccc cga tgt ggg ggg    3960
Pro Asp Arg Tyr Arg Arg Arg Tyr Trp Ile Leu Pro Arg Cys Gly Gly
        1185                1190                1195 att ttt gta gaa ggc atg gag agt ggt gaa gga cta gaa gaa att gca    4008
Ile Phe Val Glu Gly Met Glu Ser Gly Glu Gly Leu Glu Glu Ile Ala
    1200                1205                1210 aaa gaa aga gaa aaa ctg aaa aag gca gaa agt gtc cag atc aaa gaa    4056
Lys Glu Arg Glu Lys Leu Lys Lys Ala Glu Ser Val Gln Ile Lys Glu
1215                1220                1225                1230 gaa atg ttt gag act tct ggg gac agt tta aat tgt tca aat aca gat    4104
Glu Met Phe Glu Thr Ser Gly Asp Ser Leu Asn Cys Ser Asn Thr Asp
                1235                1240                1245 cac tgt gaa caa aag gaa gat ctt aaa gaa aaa gat aac aca aat cta    4152
His Cys Glu Gln Lys Glu Asp Leu Lys Glu Lys Asp Asn Thr Asn Leu
            1250                1255                1260 ttc ctt cag aaa cct ggc tct ttt tcc aaa tta agc aag ctt ttg gaa    4200
Phe Leu Gln Lys Pro Gly Ser Phe Ser Lys Leu Ser Lys Leu Leu Glu
        1265                1270                1275
```

-continued

| | | |
|---|---|---|
| gta gct aag atg cct cct gag tca gag gtt atg acc ccc aaa cca aat<br>Val Ala Lys Met Pro Pro Glu Ser Glu Val Met Thr Pro Lys Pro Asn<br>    1280                               1285                    1290 | 4248 | |
| gct ggt gca aat ggg tgc acg ttg tct tat cag aac agt gga aaa cat<br>Ala Gly Ala Asn Gly Cys Thr Leu Ser Tyr Gln Asn Ser Gly Lys His<br>1295                    1300                      1305                  1310 | 4296 | |
| tca ctg ggc agc gtt cag tca aca gca acg caa agc aat gtg gaa aag<br>Ser Leu Gly Ser Val Gln Ser Thr Ala Thr Gln Ser Asn Val Glu Lys<br>               1315                      1320                  1325 | 4344 | |
| gca gac tct aat aat ctg ttt aat act ggt tca agt ggt cca ggg aag<br>Ala Asp Ser Asn Asn Leu Phe Asn Thr Gly Ser Ser Gly Pro Gly Lys<br>    1330                               1335                    1340 | 4392 | |
| ttc tac agt cct ctc ccc aat gac cag tta cta aaa acg ctg act gaa<br>Phe Tyr Ser Pro Leu Pro Asn Asp Gln Leu Leu Lys Thr Leu Thr Glu<br>1345                    1350                      1355 | 4440 | |
| aag aat aga caa tgg ttt agt ctt ttg cca cga aca ccc tgt gat gac<br>Lys Asn Arg Gln Trp Phe Ser Leu Leu Pro Arg Thr Pro Cys Asp Asp<br>    1360                               1365                    1370 | 4488 | |
| act tca ctt act cat gcc gat atg tca act gct tct ttg gtg act cct<br>Thr Ser Leu Thr His Ala Asp Met Ser Thr Ala Ser Leu Val Thr Pro<br>1375                    1380                      1385                  1390 | 4536 | |
| cag tct cag cca cca tct aag tca cct tca cct acc cca gct cct ctt<br>Gln Ser Gln Pro Pro Ser Lys Ser Pro Ser Pro Thr Pro Ala Pro Leu<br>               1395                      1400                  1405 | 4584 | |
| gga tct tct gct cag aat cct gtt ggc tta aat cca ttt gct tta tca<br>Gly Ser Ser Ala Gln Asn Pro Val Gly Leu Asn Pro Phe Ala Leu Ser<br>        1410                             1415                    1420 | 4632 | |
| cct ctt cag gtg aaa ggt gga gta tct atg atg gga ctt cag ttt tgt<br>Pro Leu Gln Val Lys Gly Gly Val Ser Met Met Gly Leu Gln Phe Cys<br>               1425                      1430                  1435 | 4680 | |
| gga tgg ccc act ggt gtg gtt act tct aat att cca ttt aca tta tct<br>Gly Trp Pro Thr Gly Val Val Thr Ser Asn Ile Pro Phe Thr Leu Ser<br>    1440                               1445                    1450 | 4728 | |
| gta cct agt cta gga tcg ggg tta ggg tta tca gaa gga aat ggt aat<br>Val Pro Ser Leu Gly Ser Gly Leu Gly Leu Ser Glu Gly Asn Gly Asn<br>1455                    1460                      1465                  1470 | 4776 | |
| tca ttc ttg act tcc aat gtt gct tca agt aaa agt gaa tct cca gta<br>Ser Phe Leu Thr Ser Asn Val Ala Ser Ser Lys Ser Glu Ser Pro Val<br>               1475                      1480                  1485 | 4824 | |
| cca cag aat gaa aag gcc act tca gct caa cct gca gct gtt gaa gta<br>Pro Gln Asn Glu Lys Ala Thr Ser Ala Gln Pro Ala Ala Val Glu Val<br>    1490                               1495                    1500 | 4872 | |
| gca aaa cca gta gat ttt cct agt cca aaa cct att cca gaa gaa atg<br>Ala Lys Pro Val Asp Phe Pro Ser Pro Lys Pro Ile Pro Glu Glu Met<br>1505                    1510                      1515 | 4920 | |
| cag ttt ggt tgg tgg aga att att gac cca gag gac cta aaa gct ttg<br>Gln Phe Gly Trp Trp Arg Ile Ile Asp Pro Glu Asp Leu Lys Ala Leu<br>    1520                               1525                    1530 | 4968 | |
| ctc aaa gtg ctg cat ctc aga gga ata aga gaa aag gca tta caa aaa<br>Leu Lys Val Leu His Leu Arg Gly Ile Arg Glu Lys Ala Leu Gln Lys<br>1535                    1540                      1545                  1550 | 5016 | |
| caa att cag aaa cat ttg gat tat att act caa gcc tgc ctc aag aat<br>Gln Ile Gln Lys His Leu Asp Tyr Ile Thr Gln Ala Cys Leu Lys Asn<br>    1555                               1560                    1565 | 5064 | |
| aag gat gtt gct att att gaa ctg aat gaa aat gaa gaa aac caa gta<br>Lys Asp Val Ala Ile Ile Glu Leu Asn Glu Asn Glu Glu Asn Gln Val<br>        1570                             1575                    1580 | 5112 | |
| act cga gat att gtg gag aac tgg tca gta gaa gaa caa gca atg gaa<br>Thr Arg Asp Ile Val Glu Asn Trp Ser Val Glu Glu Gln Ala Met Glu<br>1585                    1590                      1595 | 5160 | |

-continued

| | |
|---|---|
| atg gat ttg agt gtc ctt caa cag gta gaa gat cta gaa agg aga gtt<br>Met Asp Leu Ser Val Leu Gln Gln Val Glu Asp Leu Glu Arg Arg Val<br>1600                        1605                            1610 | 5208 |
| gca tcc gca agt ttg caa gtg aag ggt tgg atg tgt cca gag cct gca<br>Ala Ser Ala Ser Leu Gln Val Lys Gly Trp Met Cys Pro Glu Pro Ala<br>   1615                       1620                      1625                      1630 | 5256 |
| tca gaa agg gag gac ttg gta tat ttt gaa cat aaa tca ttt act aaa<br>Ser Glu Arg Glu Asp Leu Val Tyr Phe Glu His Lys Ser Phe Thr Lys<br>                         1635                      1640                      1645 | 5304 |
| ttg tgc aag gag cat gat gga gaa ttt act ggc gaa gac gaa agc agt<br>Leu Cys Lys Glu His Asp Gly Glu Phe Thr Gly Glu Asp Glu Ser Ser<br>   1650                       1655                      1660 | 5352 |
| gca cat gca cta gaa cgg aag agt gac aac ccc cta gat ata gct gtt<br>Ala His Ala Leu Glu Arg Lys Ser Asp Asn Pro Leu Asp Ile Ala Val<br>               1665                      1670                      1675 | 5400 |
| acc agg ctg gct gat ttg gag cgg aac att gaa aga aga att gag gaa<br>Thr Arg Leu Ala Asp Leu Glu Arg Asn Ile Glu Arg Arg Ile Glu Glu<br>   1680                       1685                      1690 | 5448 |
| gat att gct cca ggg ctc agg gtg tgg aga agg gca tta tca gaa gct<br>Asp Ile Ala Pro Gly Leu Arg Val Trp Arg Arg Ala Leu Ser Glu Ala<br>1695                        1700                        1705                      1710 | 5496 |
| cgc agt gct gca cag gta gct ctg tgc att cag caa tta cag aaa tca<br>Arg Ser Ala Ala Gln Val Ala Leu Cys Ile Gln Gln Leu Gln Lys Ser<br>               1715                      1720                      1725 | 5544 |
| ata gca tgg gaa aaa tca att atg aaa gtt tac tgc caa atc tgt cga<br>Ile Ala Trp Glu Lys Ser Ile Met Lys Val Tyr Cys Gln Ile Cys Arg<br>   1730                       1735                      1740 | 5592 |
| aag gga gat aat gaa gaa ctg ctt ctt ctt tgt gat ggc tgt gac aaa<br>Lys Gly Asp Asn Glu Glu Leu Leu Leu Leu Cys Asp Gly Cys Asp Lys<br>               1745                      1750                      1755 | 5640 |
| ggc tgt cat acc tac tgc cat aga ccc aag att aca aca atc cca gat<br>Gly Cys His Thr Tyr Cys His Arg Pro Lys Ile Thr Thr Ile Pro Asp<br>   1760                       1765                      1770 | 5688 |
| gga gac tgg ttt tgt cca gct tgc att gct aag gca agt ggt caa act<br>Gly Asp Trp Phe Cys Pro Ala Cys Ile Ala Lys Ala Ser Gly Gln Thr<br>1775                        1780                        1785                      1790 | 5736 |
| cta aaa atc aaa aaa ctt cat gtc aaa gga aaa aag act aat gag tct<br>Leu Lys Ile Lys Lys Leu His Val Lys Gly Lys Lys Thr Asn Glu Ser<br>               1795                      1800                      1805 | 5784 |
| aag aaa ggc aag aag gta act tta aca gga gat act gaa gat gaa gac<br>Lys Lys Gly Lys Lys Val Thr Leu Thr Gly Asp Thr Glu Asp Glu Asp<br>   1810                       1815                      1820 | 5832 |
| tct gca tct aca agt agt tca cta aaa aga gga aac aaa gac ctc cag<br>Ser Ala Ser Thr Ser Ser Ser Leu Lys Arg Gly Asn Lys Asp Leu Gln<br>               1825                      1830                      1835 | 5880 |
| aaa aga aaa atg gag gaa aac act tct att aac ttg tca aaa caa gaa<br>Lys Arg Lys Met Glu Glu Asn Thr Ser Ile Asn Leu Ser Lys Gln Glu<br>   1840                       1845                      1850 | 5928 |
| agt ttt act tca gtt aag aaa cct aaa aga gat gac tcc aag gac cta<br>Ser Phe Thr Ser Val Lys Lys Pro Lys Arg Asp Asp Ser Lys Asp Leu<br>1855                        1860                        1865                      1870 | 5976 |
| gct ctt tgc agt atg att ctg act gaa atg gaa act cat gag gat gca<br>Ala Leu Cys Ser Met Ile Leu Thr Glu Met Glu Thr His Glu Asp Ala<br>               1875                      1880                      1885 | 6024 |
| tgg cct ttt cta ctt cct gta aac ttg aaa ctt gtt cct ggt tat aag<br>Trp Pro Phe Leu Leu Pro Val Asn Leu Lys Leu Val Pro Gly Tyr Lys<br>   1890                       1895                      1900 | 6072 |
| aaa gtt att aag aag cct atg gat ttt tcc aca att aga gag aaa cta<br>Lys Val Ile Lys Lys Pro Met Asp Phe Ser Thr Ile Arg Glu Lys Leu | 6120 |

-continued

```
              1905                1910                1915
agt agt gga cag tat cca aac ctt gaa acc ttt gct cta gat gtc agg        6168
Ser Ser Gly Gln Tyr Pro Asn Leu Glu Thr Phe Ala Leu Asp Val Arg
    1920                1925                1930 ctt gtt ttt gac aac tgt gaa aca ttt aat gaa gat gat tct gat ata        6216
Leu Val Phe Asp Asn Cys Glu Thr Phe Asn Glu Asp Asp Ser Asp Ile
1935                1940                1945                1950 ggc aga gct ggc cac aat atg agg aag tat ttt gaa aaa aag tgg aca        6264
Gly Arg Ala Gly His Asn Met Arg Lys Tyr Phe Glu Lys Lys Trp Thr
                1955                1960                1965 gat act ttc aaa gtg agc tgaagttata ataatctctt tattttttc                6312
Asp Thr Phe Lys Val Ser
            1970 cttctaaaca aggacaaatg agaccagcaa tgtgaactgt atttacataa acgtgcaagg       6372 cacatacata atgactttct ttttccttaa gtataaaaaa aaagtatcag aagaatgata       6432 ccatttttaa aggcttcatt cctacaacaa ccaaggccct cggttattgg tttgtgtgat       6492 ttatcagcta atttaggtag aacagggaag cacacccaaa gaattttcaa aggaaagggt       6552 gttatagtgc aatagcaatt aaaatatatc aaatcgcact gaatactcaa caccagagct       6612 ctaatgtggg aaatggttct cctttccctc tcaataaata tctattttc attttttac        6672 tttgtagttt attttttagt gaatgtattt aatttatga attatttatg attaaaccac       6732 atccagaatc ttcgttttct gtgaaaagga agaactagaa aattgcttta aatcttgaaa       6792 atacaaggaa tgttttaaaa tataaaacaa agccaagtta aactgtttac actgatgtgc       6852 tataaaagca ccaaaaagaa actttactgt agagttacaa gtacatttat atatatatgt      6912 tgctgcatca cttgtgtagt taaattgtat ttcaaaacag tgaaaaatt gacatgtata       6972 tactgttcat tcttgtttat attaagtctt gttttaaata tgtattatgt gtatatattg      7032 tttgcagaca ttattgttca tgccttagag gattgtagca tttatttttc gtctgaaggt      7092 aatgatagct atacagtctg tacagtaatt atcctctacc aacactgtgg cgtctcctta      7152 atcttggtag tgcctgcctt tgaaacaggg tgtaggggat attagttttc cattttttcta     7212 ttttgttata aatttaag ccaccagggc ctaaattaaa gtataatcat ttgtatccat        7272 gtggaataaa attgtgacaa tttcctacgc acacagtatt ttttcataga aacatttccc      7332 tcccatttgc cttgcctcag aaataaattt aaaagacgtt tgtaaccact gtgttttatc      7392 tactgtgtgt tgtggtggcc tgttggaggc aaatagatca gattttttt gtacctacgt       7452 aagagtactt gaagttttat ttaaaataaa atgttgtgga aaaggtagca ttcttttttt      7512 aggagtgtta ttttcacta tgtgtggcac ggatacaata aaagacttt acaaactaaa        7572 aaaaaaaaaa aaa                                                         7585
```

<210> SEQ ID NO 23
<211> LENGTH: 25
<212> TYPE: DNA
<213> ORGANISM: Artificial Sequence
<220> FEATURE:
<223> OTHER INFORMATION: Synthetically generated primer

<400> SEQUENCE: 23
ctgactgaaa tggaaactca tgagg                                            25

<210> SEQ ID NO 24
<211> LENGTH: 25
<212> TYPE: DNA
<213> ORGANISM: Artificial Sequence -continued

```
<220> FEATURE:
<223> OTHER INFORMATION: Synthetically generated primer

<400> SEQUENCE: 24
ctagagcaaa ggtttcaagg tttgg                                              25

<210> SEQ ID NO 25
<211> LENGTH: 24
<212> TYPE: DNA
<213> ORGANISM: Artificial Sequence
<220> FEATURE:
<223> OTHER INFORMATION: Synthetically generated primer

<400> SEQUENCE: 25
tgttgctgca tcacttgtgt agtt                                               24

<210> SEQ ID NO 26
<211> LENGTH: 23
<212> TYPE: DNA
<213> ORGANISM: Artificial Sequence
<220> FEATURE:
<223> OTHER INFORMATION: Synthetically generated primer

<400> SEQUENCE: 26
ggcatgacaa taatgtctgc aaa                                                23

<210> SEQ ID NO 27
<211> LENGTH: 1527
<212> TYPE: PRT
<213> ORGANISM: Homo sapiens

<400> SEQUENCE: 27
```

Met Ala Pro Leu Leu Gly Arg Lys Pro Phe Pro Leu Val Asn Pro Leu
 1               5                  10                  15

Pro Gly Glu Glu Pro Phe Phe Thr Ile Pro His Thr Gln Glu Ala Phe
            20                  25                  30

Arg Thr Arg Glu Glu Tyr Glu Ala Arg Leu Glu Arg Tyr Ser Glu Arg
        35                  40                  45

Ile Trp Thr Cys Lys Ser Thr Gly Ser Ser Gln Leu Thr His Lys Glu
    50                  55                  60

Ala Trp Glu Glu Gln Glu Val Ala Glu Leu Leu Lys Glu Glu Phe
65                  70                  75                  80

Pro Ala Trp Tyr Glu Lys Leu Val Leu Glu Met Val His His Asn Thr
                85                  90                  95

Ala Ser Leu Glu Lys Leu Val Asp Thr Ala Trp Leu Glu Ile Met Thr
            100                 105                 110

Lys Tyr Ala Val Gly Glu Glu Cys Asp Phe Glu Val Gly Lys Glu Lys
        115                 120                 125

Met Leu Lys Val Lys Ile Val Lys Ile His Pro Leu Glu Lys Val Asp
    130                 135                 140

Glu Glu Ala Thr Glu Lys Lys Ser Asp Gly Ala Cys Asp Ser Pro Ser
145                 150                 155                 160

Ser Asp Lys Glu Asn Ser Ser Gln Ile Ala Gln Asp His Gln Lys Lys
                165                 170                 175

Glu Thr Val Val Lys Glu Asp Glu Gly Arg Arg Glu Ser Ile Asn Asp
            180                 185                 190

Arg Ala Arg Arg Ser Pro Arg Lys Leu Pro Thr Ser Leu Lys Lys Gly
        195                 200                 205

Glu Arg Lys Trp Ala Pro Pro Lys Phe Leu Pro His Lys Tyr Asp Val

-continued

```
            210                 215                 220
Lys Leu Gln Asn Glu Asp Lys Ile Ile Ser Asn Val Pro Ala Asp Ser
225                 230                 235                 240

Leu Ile Arg Thr Glu Arg Pro Pro Asn Lys Glu Ile Val Arg Tyr Phe
                245                 250                 255

Ile Arg His Asn Ala Leu Arg Ala Gly Thr Gly Glu Asn Ala Pro Trp
                260                 265                 270

Val Val Glu Asp Glu Leu Val Lys Lys Tyr Ser Leu Pro Ser Lys Phe
                275                 280                 285

Ser Asp Phe Leu Leu Asp Pro Tyr Lys Tyr Met Thr Leu Asn Pro Ser
                290                 295                 300

Thr Lys Arg Lys Asn Thr Gly Ser Pro Asp Arg Lys Pro Ser Lys Lys
305                 310                 315                 320

Ser Lys Thr Asp Asn Ser Ser Leu Ser Ser Pro Leu Asn Pro Lys Leu
                325                 330                 335

Trp Cys His Val His Leu Lys Lys Ser Leu Ser Gly Ser Pro Leu Lys
                340                 345                 350

Val Lys Asn Ser Lys Asn Ser Lys Ser Pro Glu Glu His Leu Glu Glu
                355                 360                 365

Met Met Lys Met Met Ser Pro Asn Lys Leu His Thr Asn Phe His Ile
370                 375                 380

Pro Lys Lys Gly Pro Pro Ala Lys Lys Pro Gly Lys His Ser Asp Lys
385                 390                 395                 400

Pro Leu Lys Ala Lys Gly Arg Ser Lys Gly Ile Leu Asn Gly Gln Lys
                405                 410                 415

Ser Thr Gly Asn Ser Lys Ser Pro Lys Lys Gly Leu Lys Thr Pro Lys
                420                 425                 430

Thr Lys Met Lys Gln Met Thr Leu Leu Asp Met Ala Lys Gly Thr Gln
                435                 440                 445

Lys Met Thr Arg Ala Pro Arg Asn Ser Gly Gly Thr Pro Arg Thr Ser
                450                 455                 460

Ser Lys Pro His Lys His Leu Pro Pro Ala Ala Leu His Leu Ile Ala
465                 470                 475                 480

Tyr Tyr Lys Glu Asn Lys Asp Arg Glu Asp Lys Arg Ser Ala Leu Ser
                485                 490                 495

Cys Val Ile Ser Lys Thr Ala Arg Leu Leu Ser Ser Glu Asp Arg Ala
                500                 505                 510

Arg Leu Pro Glu Glu Leu Arg Ser Leu Val Gln Lys Arg Tyr Glu Leu
                515                 520                 525

Leu Glu His Lys Lys Arg Trp Ala Ser Met Ser Glu Glu Gln Arg Lys
                530                 535                 540

Glu Tyr Leu Lys Lys Arg Glu Glu Leu Lys Lys Lys Leu Lys Glu
545                 550                 555                 560

Lys Ala Lys Glu Arg Arg Glu Lys Glu Met Leu Glu Arg Leu Glu Lys
                565                 570                 575

Gln Lys Arg Tyr Glu Asp Gln Glu Leu Thr Gly Lys Asn Leu Pro Ala
                580                 585                 590

Phe Arg Leu Val Asp Thr Pro Glu Gly Leu Pro Asn Thr Leu Phe Gly
                595                 600                 605

Asp Val Ala Met Val Val Glu Phe Leu Ser Cys Tyr Ser Gly Leu Leu
                610                 615                 620

Leu Pro Asp Ala Gln Tyr Pro Ile Thr Ala Val Ser Leu Met Glu Ala
625                 630                 635                 640
```

-continued

```
Leu Ser Ala Asp Lys Gly Gly Phe Leu Tyr Leu Asn Arg Val Leu Val
                645                 650                 655
Ile Leu Leu Gln Thr Leu Leu Gln Asp Glu Ile Ala Glu Asp Tyr Gly
                660                 665                 670
Glu Leu Gly Met Lys Leu Ser Glu Ile Pro Leu Thr Leu His Ser Val
                675                 680                 685
Ser Glu Leu Val Arg Leu Cys Leu Arg Arg Ser Asp Val Gln Glu Glu
                690                 695                 700
Ser Glu Gly Ser Asp Thr Asp Asp Asn Lys Asp Ser Ala Ala Phe Glu
705                 710                 715                 720
Asp Asn Glu Val Gln Asp Glu Phe Leu Glu Lys Leu Glu Thr Ser Glu
                725                 730                 735
Phe Phe Glu Leu Thr Ser Glu Glu Lys Leu Gln Ile Leu Thr Ala Leu
                740                 745                 750
Cys His Arg Ile Leu Met Thr Tyr Ser Val Gln Asp His Met Glu Thr
                755                 760                 765
Arg Gln Gln Met Ser Ala Glu Leu Trp Lys Glu Arg Leu Ala Val Leu
                770                 775                 780
Lys Glu Glu Asn Asp Lys Lys Arg Ala Glu Lys Gln Lys Arg Lys Glu
785                 790                 795                 800
Met Glu Ala Lys Asn Lys Glu Asn Gly Lys Val Glu Asn Gly Leu Gly
                805                 810                 815
Lys Thr Asp Arg Lys Lys Arg Ile Val Lys Phe Glu Pro Gln Val Asp
                820                 825                 830
Thr Glu Ala Glu Asp Met Ile Ser Ala Val Lys Ser Arg Arg Leu Leu
                835                 840                 845
Ala Ile Gln Ala Lys Lys Glu Arg Glu Ile Gln Glu Arg Glu Met Lys
                850                 855                 860
Val Lys Leu Glu Arg Gln Ala Glu Glu Arg Ile Arg Lys His Lys Lys
865                 870                 875                 880
Ala Ala Ala Glu Lys Ala Phe Gln Glu Gly Ile Ala Lys Ala Lys Leu
                885                 890                 895
Val Met Arg Arg Thr Pro Ile Gly Thr Asp Arg Asn His Asn Arg Tyr
                900                 905                 910
Trp Leu Phe Ser Asp Glu Val Pro Gly Leu Phe Ile Glu Lys Gly Trp
                915                 920                 925
Val His Asp Ser Ile Asp Tyr Arg Phe Asn His His Cys Lys Asp His
                930                 935                 940
Thr Val Ser Gly Asp Glu Asp Tyr Cys Pro Arg Ser Lys Lys Ala Asn
945                 950                 955                 960
Leu Gly Lys Asn Ala Ser Met Asn Thr Gln His Gly Thr Ala Thr Glu
                965                 970                 975
Val Ala Val Glu Thr Thr Thr Pro Lys Gln Gly Gln Asn Leu Trp Phe
                980                 985                 990
Leu Cys Asp Ser Gln Lys Glu Leu Asp Glu Leu Leu Asn Cys Leu His
                995                 1000                1005
Pro Gln Gly Ile Arg Glu Ser Gln Leu Lys Glu Arg Leu Glu Lys Arg
                1010                1015                1020
Tyr Gln Asp Ile Ile His Ser Ile His Leu Ala Arg Lys Pro Asn Leu
1025                1030                1035                1040
Gly Leu Lys Ser Cys Asp Gly Asn Gln Glu Leu Leu Asn Phe Leu Arg
                1045                1050                1055
```

-continued

Ser Asp Leu Ile Glu Val Ala Thr Arg Leu Gln Lys Gly Gly Leu Gly
                1060                1065                1070

Tyr Val Glu Glu Thr Ser Glu Phe Glu Ala Arg Val Ile Ser Leu Glu
            1075                1080                1085

Lys Leu Lys Asp Phe Gly Glu Cys Val Ile Ala Leu Gln Ala Ser Val
        1090                1095                1100

Ile Lys Lys Phe Leu Gln Gly Phe Met Ala Pro Lys Gln Lys Arg Arg
1105                1110                1115                1120

Lys Leu Gln Ser Glu Asp Ser Ala Lys Thr Glu Glu Val Asp Glu Glu
                1125                1130                1135

Lys Lys Met Val Glu Ala Lys Val Ala Ser Ala Leu Glu Lys Trp
            1140                1145                1150

Lys Thr Ala Ile Arg Glu Ala Gln Thr Phe Ser Arg Met His Val Leu
        1155                1160                1165

Leu Gly Met Leu Asp Ala Cys Ile Lys Trp Asp Met Ser Ala Glu Asn
        1170                1175                1180

Ala Arg Cys Lys Val Cys Pro Lys Lys Gly Glu Asp Lys Leu Ile
1185                1190                1195                1200

Leu Cys Asp Glu Cys Asn Lys Ala Phe His Leu Phe Cys Leu Arg Pro
            1205                1210                1215

Ala Leu Tyr Glu Val Pro Asp Gly Glu Trp Gln Cys Pro Ala Cys Gln
        1220                1225                1230

Pro Ala Thr Ala Arg Arg Asn Ser Arg Gly Arg Asn Tyr Thr Glu Glu
        1235                1240                1245

Ser Ala Ser Glu Asp Ser Glu Asp Asp Glu Ser Asp Glu Glu Glu Glu
        1250                1255                1260

Glu Glu Glu Glu Glu Glu Glu Glu Asp Tyr Glu Val Ala Gly Leu
1265                1270                1275                1280

Arg Leu Arg Pro Arg Lys Thr Ile Arg Gly Lys His Ser Val Ile Pro
            1285                1290                1295

Pro Ala Ala Arg Ser Gly Arg Arg Pro Gly Lys Lys Pro His Ser Thr
        1300                1305                1310

Arg Arg Ser Gln Pro Lys Ala Pro Pro Val Asp Asp Ala Glu Val Asp
        1315                1320                1325

Glu Leu Val Leu Gln Thr Lys Arg Ser Ser Arg Arg Gln Ser Leu Glu
        1330                1335                1340

Leu Gln Lys Cys Glu Glu Ile Leu His Lys Ile Val Lys Tyr Arg Phe
1345                1350                1355                1360

Ser Trp Pro Phe Arg Glu Pro Val Thr Arg Asp Glu Ala Glu Asp Tyr
            1365                1370                1375

Tyr Asp Val Ile Thr His Pro Met Asp Phe Gln Thr Val Gln Asn Lys
        1380                1385                1390

Cys Ser Cys Gly Ser Tyr Arg Ser Val Gln Glu Phe Leu Thr Asp Met
        1395                1400                1405

Lys Gln Val Phe Thr Asn Ala Glu Val Tyr Asn Cys Arg Gly Ser His
        1410                1415                1420

Val Leu Ser Cys Met Val Lys Thr Glu Gln Cys Leu Val Val Leu Leu
1425                1430                1435                1440

His Lys His Leu Pro Gly His Pro Tyr Val Arg Lys Arg Lys Lys
            1445                1450                1455

Phe Pro Asp Arg Leu Ala Glu Asp Glu Gly Asp Ser Glu Pro Glu Ala
        1460                1465                1470

Val Gly Gln Ser Arg Asp Glu Asp Arg Arg Ser Arg Glu Ala Glu Ile

```
                  1475                1480                1485
Gln Glu Trp Leu Gln Asp Thr Ser Leu Tyr Ser Ala Lys Ile Asn Ser
    1490                1495                1500
Lys Asp His Asn Cys Phe Met Met Leu Val Asn Thr Gln Phe Cys Met
1505                1510                1515                1520
Ala Leu Thr Asp Thr Val Thr
              1525

<210> SEQ ID NO 28
<211> LENGTH: 5561
<212> TYPE: DNA
<213> ORGANISM: Homo sapiens
<220> FEATURE:
<221> NAME/KEY: CDS
<222> LOCATION: (346)...(4926)

<400> SEQUENCE: 28
cgggcccggg ggaggagggg aatctcccgc cattttttcaa taatttcctc cggtgctgct      60
gaggaggagt cgtgactgcc ggccgccggg acccgaagcg gaggtcggcg ggggggctgct    120 gggaggcgcg gcggtgtgcg cgggagctct gcgccgtggc gttccgctcc atgactgtcg     180
cgcggccgcg ccggcggtga gggagccgga gttcgcgccg ccctctcacc cctcccttcc     240 cccacccac  ccccgggcgc ctggcgctcg ctccgggccg cggggcctag tgctgcgccg     300
cggggccggc cccagcagcc gccagtcccc accgccgccg ccgcg atg gcg ccg ctc     357
                                              Met Ala Pro Leu
                                                  1 ctg ggc cgc aag ccc ttc ccg ctg gtg aat ccg ttg ccc gga gag gag       405
Leu Gly Arg Lys Pro Phe Pro Leu Val Asn Pro Leu Pro Gly Glu Glu
 5                  10                  15                  20 ccg ttc ttc acc atc ccg cac act cag gag gcc ttc cgc acc cgg gaa       453
Pro Phe Phe Thr Ile Pro His Thr Gln Glu Ala Phe Arg Thr Arg Glu
                25                  30                  35 gag tat gaa gcc cgc ttg gaa agg tac agt gag cgc att tgg acg tgc       501
Glu Tyr Glu Ala Arg Leu Glu Arg Tyr Ser Glu Arg Ile Trp Thr Cys
        40                  45                  50 aag agt act gga agc agt cag cta aca cac aag gaa gcc tgg gag gaa       549
Lys Ser Thr Gly Ser Ser Gln Leu Thr His Lys Glu Ala Trp Glu Glu
    55                  60                  65 gaa cag gaa gtt gct gag ctt ttg aag gag gag ttt cct gcc tgg tat       597
Glu Gln Glu Val Ala Glu Leu Leu Lys Glu Glu Phe Pro Ala Trp Tyr
70                  75                  80 gag aag ctt gtt ctg gaa atg gtt cac cat aac aca gcc tcc tta gag       645
Glu Lys Leu Val Leu Glu Met Val His His Asn Thr Ala Ser Leu Glu
 85                  90                  95                 100 aag tta gta gat act gct tgg ttg gag atc atg acc aaa tat gct gtg       693
Lys Leu Val Asp Thr Ala Trp Leu Glu Ile Met Thr Lys Tyr Ala Val
                105                 110                 115 gga gaa gag tgt gac ttc gag gtt ggg aag gag aaa atg ctc aag gtg       741
Gly Glu Glu Cys Asp Phe Glu Val Gly Lys Glu Lys Met Leu Lys Val
        120                 125                 130 aag att gtg aag att cat cct ttg gag aaa gtg gat gaa gag gcc act       789
Lys Ile Val Lys Ile His Pro Leu Glu Lys Val Asp Glu Glu Ala Thr
    135                 140                 145 gag aag aaa tct gat ggt gcc tgt gat tct cca tca agt gac aaa gag       837
Glu Lys Lys Ser Asp Gly Ala Cys Asp Ser Pro Ser Ser Asp Lys Glu
150                 155                 160 aac tcc agt cag att gct cag gac cat cag aag aag gag aca gtt gtg       885
Asn Ser Ser Gln Ile Ala Gln Asp His Gln Lys Lys Glu Thr Val Val
165                 170                 175                 180
```

-continued

| | |
|---|---|
| aaa gag gat gaa gga agg aga gag agt att aat gac aga gca cgt aga<br>Lys Glu Asp Glu Gly Arg Arg Glu Ser Ile Asn Asp Arg Ala Arg Arg<br>                            185                          190                          195 | 933 |
| tcg cca cga aaa ctt cct act tca tta aaa aaa gga gaa agg aaa tgg<br>Ser Pro Arg Lys Leu Pro Thr Ser Leu Lys Lys Gly Glu Arg Lys Trp<br>                  200                          205                          210 | 981 |
| gct cct cca aaa ttt ctg cct cac aaa tat gat gtg aaa cta caa aat<br>Ala Pro Pro Lys Phe Leu Pro His Lys Tyr Asp Val Lys Leu Gln Asn<br>              215                          220                        225 | 1029 |
| gaa gat aag atc atc agt aac gtg cca gca gac agc ttg att cgt aca<br>Glu Asp Lys Ile Ile Ser Asn Val Pro Ala Asp Ser Leu Ile Arg Thr<br>230                        235                        240 | 1077 |
| gag cgc cca cca aat aag gag ata gtt cga tac ttt ata cgg cat aat<br>Glu Arg Pro Pro Asn Lys Glu Ile Val Arg Tyr Phe Ile Arg His Asn<br>245                        250                        255                        260 | 1125 |
| gca tta cga gct ggt act ggt gaa aat gca cct tgg gtc gta gaa gat<br>Ala Leu Arg Ala Gly Thr Gly Glu Asn Ala Pro Trp Val Val Glu Asp<br>                  265                          270                        275 | 1173 |
| gaa ttg gtg aag aaa tac tct ctg ccc agc aag ttc agt gac ttt tta<br>Glu Leu Val Lys Lys Tyr Ser Leu Pro Ser Lys Phe Ser Asp Phe Leu<br>              280                          285                        290 | 1221 |
| ctt gat cca tac aag tat atg act ctc aac cct tct act aag agg aag<br>Leu Asp Pro Tyr Lys Tyr Met Thr Leu Asn Pro Ser Thr Lys Arg Lys<br>          295                        300                        305 | 1269 |
| aat act gga tcc cca gac agg aag ccc tca aag aaa tcc aag aca gac<br>Asn Thr Gly Ser Pro Asp Arg Lys Pro Ser Lys Lys Ser Lys Thr Asp<br>310                        315                        320 | 1317 |
| aac tct tct ctt agt tca cca cta aat cct aag tta tgg tgt cac gta<br>Asn Ser Ser Leu Ser Ser Pro Leu Asn Pro Lys Leu Trp Cys His Val<br>325                        330                        335                        340 | 1365 |
| cac ttg aag aag tca ttg agt ggc tcg cca ctc aaa gtg aag aac tca<br>His Leu Lys Lys Ser Leu Ser Gly Ser Pro Leu Lys Val Lys Asn Ser<br>                  345                          350                        355 | 1413 |
| aag aat tcc aaa tct cct gaa gaa cat cta gaa gaa atg atg aag atg<br>Lys Asn Ser Lys Ser Pro Glu Glu His Leu Glu Glu Met Met Lys Met<br>              360                          365                        370 | 1461 |
| atg tcg ccc aat aag ttg cac act aac ttt cac att cct aaa aaa ggc<br>Met Ser Pro Asn Lys Leu His Thr Asn Phe His Ile Pro Lys Lys Gly<br>          375                        380                        385 | 1509 |
| cca cct gcc aag aaa cca ggg aag cac agt gac aag cct ttg aag gca<br>Pro Pro Ala Lys Lys Pro Gly Lys His Ser Asp Lys Pro Leu Lys Ala<br>390                        395                        400 | 1557 |
| aag ggc aga agc aaa ggc atc ctg aat gga cag aaa tcc aca ggg aat<br>Lys Gly Arg Ser Lys Gly Ile Leu Asn Gly Gln Lys Ser Thr Gly Asn<br>405                        410                        415                        420 | 1605 |
| tcc aaa tct ccc aaa aaa gga ctg aag act cct aaa acc aaa atg aag<br>Ser Lys Ser Pro Lys Lys Gly Leu Lys Thr Pro Lys Thr Lys Met Lys<br>                  425                          430                        435 | 1653 |
| cag atg act ttg ttg gat atg gcc aaa ggc acg cag aag atg aca cga<br>Gln Met Thr Leu Leu Asp Met Ala Lys Gly Thr Gln Lys Met Thr Arg<br>                            440                          445                        450 | 1701 |
| gcc cca cgg aat tct ggg ggt aca cct agg acc tct agt aaa cct cat<br>Ala Pro Arg Asn Ser Gly Gly Thr Pro Arg Thr Ser Ser Lys Pro His<br>          455                        460                        465 | 1749 |
| aaa cat ctg cct cct gca gcc cta cac ctc att gca tac tac aaa gaa<br>Lys His Leu Pro Pro Ala Ala Leu His Leu Ile Ala Tyr Tyr Lys Glu<br>470                        475                        480 | 1797 |
| aac aaa gac agg gag gac aag agg agc gcc ctg tcc tgt gtt atc tcc<br>Asn Lys Asp Arg Glu Asp Lys Arg Ser Ala Leu Ser Cys Val Ile Ser | 1845 |

```
                485                 490                 495                 500
aaa aca gct cgt ctt ctc tct agt gaa gat aga gct cgt ctc cca gaa              1893
Lys Thr Ala Arg Leu Leu Ser Ser Glu Asp Arg Ala Arg Leu Pro Glu
            505                 510                 515 gaa ttg cga agt ctt gtt caa aaa cgc tat gaa ctt cta gag cac aaa              1941
Glu Leu Arg Ser Leu Val Gln Lys Arg Tyr Glu Leu Leu Glu His Lys
        520                 525                 530 aag agg tgg gct tct atg tct gaa gaa caa cgg aaa gaa tat ttg aaa              1989
Lys Arg Trp Ala Ser Met Ser Glu Glu Gln Arg Lys Glu Tyr Leu Lys
    535                 540                 545 aag aaa cgg gag gag ctg aaa aag aag ttg aag gaa aaa gcc aaa gaa              2037
Lys Lys Arg Glu Glu Leu Lys Lys Lys Leu Lys Glu Lys Ala Lys Glu
550                 555                 560 cga aga gag aaa gaa atg ctt gag aga tta gaa aaa cag aag cgg tat              2085
Arg Arg Glu Lys Glu Met Leu Glu Arg Leu Glu Lys Gln Lys Arg Tyr
565                 570                 575                 580 gag gac caa gag tta act ggc aaa aac ctt cca gca ttc aga ttg gtg              2133
Glu Asp Gln Glu Leu Thr Gly Lys Asn Leu Pro Ala Phe Arg Leu Val
            585                 590                 595 gat acc cct gaa ggg ctg ccc aac acg ctg ttt ggg gat gtg gcc atg              2181
Asp Thr Pro Glu Gly Leu Pro Asn Thr Leu Phe Gly Asp Val Ala Met
        600                 605                 610 gtg gtg gaa ttc ttg agc tgt tat tct ggg cta ctt tta cca gat gct              2229
Val Val Glu Phe Leu Ser Cys Tyr Ser Gly Leu Leu Leu Pro Asp Ala
    615                 620                 625 cag tat cct att act gct gtg tcc ctt atg gaa gcc ttg agt gca gat              2277
Gln Tyr Pro Ile Thr Ala Val Ser Leu Met Glu Ala Leu Ser Ala Asp
630                 635                 640 aag ggt ggc ttt tta tac ctt aac agg gtg ttg gtc atc ctc tta cag              2325
Lys Gly Gly Phe Leu Tyr Leu Asn Arg Val Leu Val Ile Leu Leu Gln
645                 650                 655                 660 acc ctc cta caa gat gag ata gcc gaa gac tat ggt gaa ttg gga atg              2373
Thr Leu Leu Gln Asp Glu Ile Ala Glu Asp Tyr Gly Glu Leu Gly Met
            665                 670                 675 aag ctg tca gaa atc ccc ttg act ctg cat tct gtt tca gag ctg gtg              2421
Lys Leu Ser Glu Ile Pro Leu Thr Leu His Ser Val Ser Glu Leu Val
        680                 685                 690 cgg ctc tgc ttg cgc aga tct gat gtt cag gag gaa agc gag ggc tca              2469
Arg Leu Cys Leu Arg Arg Ser Asp Val Gln Glu Glu Ser Glu Gly Ser
    695                 700                 705 gac aca gat gac aat aaa gat tca gct gca ttt gag gat aat gag gta              2517
Asp Thr Asp Asp Asn Lys Asp Ser Ala Ala Phe Glu Asp Asn Glu Val
        710                 715                 720 caa gat gag ttc cta gaa aag ctg gag acc tct gaa ttt ttt gag ctg              2565
Gln Asp Glu Phe Leu Glu Lys Leu Glu Thr Ser Glu Phe Phe Glu Leu
725                 730                 735                 740 acg tca gag gag aag cta cag att ttg aca gca ctg tgc cac cgg atc              2613
Thr Ser Glu Glu Lys Leu Gln Ile Leu Thr Ala Leu Cys His Arg Ile
            745                 750                 755 ctc atg aca tac tca gtg caa gac cac atg gag acc aga cag cag atg              2661
Leu Met Thr Tyr Ser Val Gln Asp His Met Glu Thr Arg Gln Gln Met
        760                 765                 770 tct gca gag ttg tgg aag gaa cgg ctt gct gtg ttg aag gaa gaa aat              2709
Ser Ala Glu Leu Trp Lys Glu Arg Leu Ala Val Leu Lys Glu Glu Asn
    775                 780                 785 gat aag aag aga gca gag aaa cag aaa cgg aaa gaa atg gaa gcc aaa              2757
Asp Lys Lys Arg Ala Glu Lys Gln Lys Arg Lys Glu Met Glu Ala Lys
790                 795                 800 aat aaa gaa aat gga aaa gtt gag aat ggg tta ggc aaa act gat agg              2805
```

```
                                                          -continued

Asn Lys Glu Asn Gly Lys Val Glu Asn Gly Leu Gly Lys Thr Asp Arg
805                 810                 815                 820 aaa aaa aga att gtg aag ttt gag ccc caa gta gat aca gaa gct gaa   2853
Lys Lys Arg Ile Val Lys Phe Glu Pro Gln Val Asp Thr Glu Ala Glu
                825                 830                 835 gac atg att agt gct gtg aag agc aga agg ttg ctt gcc att caa gct   2901
Asp Met Ile Ser Ala Val Lys Ser Arg Arg Leu Leu Ala Ile Gln Ala
            840                 845                 850 aag aag gaa cgg gaa atc cag gaa aga gaa atg aaa gtg aaa ctg gaa   2949
Lys Lys Glu Arg Glu Ile Gln Glu Arg Glu Met Lys Val Lys Leu Glu
        855                 860                 865 cgc caa gct gaa gaa gaa cga ata cgg aag cac aaa gca gct gct gag   2997
Arg Gln Ala Glu Glu Glu Arg Ile Arg Lys His Lys Ala Ala Ala Glu
    870                 875                 880 aaa gct ttc cag gaa ggg att gcc aag gcc aaa cta gtc atg cgc agg   3045
Lys Ala Phe Gln Glu Gly Ile Ala Lys Ala Lys Leu Val Met Arg Arg
885                 890                 895                 900 act cct att ggc aca gat cga aac cat aat aga tac tgg ctc ttc tca   3093
Thr Pro Ile Gly Thr Asp Arg Asn His Asn Arg Tyr Trp Leu Phe Ser
                905                 910                 915 gat gaa gtt cca gga tta ttc att gaa aaa ggc tgg gta cat gac agc   3141
Asp Glu Val Pro Gly Leu Phe Ile Glu Lys Gly Trp Val His Asp Ser
            920                 925                 930 att gac tac cga ttc aac cat cac tgc aaa gac cac aca gtc tct ggt   3189
Ile Asp Tyr Arg Phe Asn His His Cys Lys Asp His Thr Val Ser Gly
        935                 940                 945 gat gag gat tac tgt cct cgc agt aag aaa gca aac tta ggt aaa aat   3237
Asp Glu Asp Tyr Cys Pro Arg Ser Lys Lys Ala Asn Leu Gly Lys Asn
    950                 955                 960 gca agc atg aac aca caa cat gga aca gca aca gaa gtt gct gta gag   3285
Ala Ser Met Asn Thr Gln His Gly Thr Ala Thr Glu Val Ala Val Glu
965                 970                 975                 980 aca acc aca ccc aaa caa gga cag aac cta tgg ttt tta tgt gat agt   3333
Thr Thr Thr Pro Lys Gln Gly Gln Asn Leu Trp Phe Leu Cys Asp Ser
                985                 990                 995 caa aag gag ctg gat gag ttg cta aac tgt ctt cac cct cag gga ata   3381
Gln Lys Glu Leu Asp Glu Leu Leu Asn Cys Leu His Pro Gln Gly Ile
            1000                1005                1010 aga gaa agt caa ctt aaa gag aga cta gag aag agg tac cag gac att   3429
Arg Glu Ser Gln Leu Lys Glu Arg Leu Glu Lys Arg Tyr Gln Asp Ile
        1015                1020                1025 att cac tct att cat cta gca cgg aag cca aat ttg ggt cta aaa tct   3477
Ile His Ser Ile His Leu Ala Arg Lys Pro Asn Leu Gly Leu Lys Ser
    1030                1035                1040 tgt gat ggc aac cag gag ctt tta aac ttc ctt cgt agt gat ctc att   3525
Cys Asp Gly Asn Gln Glu Leu Leu Asn Phe Leu Arg Ser Asp Leu Ile
1045                1050                1055                1060 gaa gtt gca aca agg tta caa aaa gga gga ctt gga tat gtg gaa gaa   3573
Glu Val Ala Thr Arg Leu Gln Lys Gly Gly Leu Gly Tyr Val Glu Glu
                1065                1070                1075 aca tca gaa ttt gaa gcc cgg gtc att tca tta gag aaa ttg aag gat   3621
Thr Ser Glu Phe Glu Ala Arg Val Ile Ser Leu Glu Lys Leu Lys Asp
            1080                1085                1090 ttt ggt gag tgt gtg att gcc ctt cag gcc agt gtc ata aag aaa ttt   3669
Phe Gly Glu Cys Val Ile Ala Leu Gln Ala Ser Val Ile Lys Lys Phe
        1095                1100                1105 ctc caa ggc ttc atg gct ccc aag caa aag aga aga aaa ctc caa agt   3717
Leu Gln Gly Phe Met Ala Pro Lys Gln Lys Arg Arg Lys Leu Gln Ser
    1110                1115                1120
```

-continued

```
gaa gat tca gca aaa act gag gaa gtg gat gaa gag aag aaa atg gta      3765
Glu Asp Ser Ala Lys Thr Glu Glu Val Asp Glu Glu Lys Lys Met Val
1125                1130                1135                1140 gag gaa gca aag gtt gca tct gca ctg gag aaa tgg aag aca gca atc      3813
Glu Glu Ala Lys Val Ala Ser Ala Leu Glu Lys Trp Lys Thr Ala Ile
            1145                1150                1155 cgg gaa gct cag act ttc tcc agg atg cac gtg ctg ctt ggg atg ctt      3861
Arg Glu Ala Gln Thr Phe Ser Arg Met His Val Leu Leu Gly Met Leu
1160                1165                1170 gat gcc tgt atc aag tgg gat atg tcc gca gaa aat gct agg tgc aaa      3909
Asp Ala Cys Ile Lys Trp Asp Met Ser Ala Glu Asn Ala Arg Cys Lys
        1175                1180                1185 gtt tgt cca aag aaa ggt gag gat gac aaa ttg atc ttg tgt gat gag      3957
Val Cys Pro Lys Lys Gly Glu Asp Asp Lys Leu Ile Leu Cys Asp Glu
1190                1195                1200 tgt aat aaa gcc ttc cac ctg ttt tgt ctg agg ccg gcc ctc tat gaa      4005
Cys Asn Lys Ala Phe His Leu Phe Cys Leu Arg Pro Ala Leu Tyr Glu
1205                1210                1215                1220 gta cca gat ggt gag tgg cag tgc cca gct tgc cag ccc gct act gcc      4053
Val Pro Asp Gly Glu Trp Gln Cys Pro Ala Cys Gln Pro Ala Thr Ala
            1225                1230                1235 agg cgc aac tcc cgt ggc agg aac tat act gaa gag tct gct tct gag      4101
Arg Arg Asn Ser Arg Gly Arg Asn Tyr Thr Glu Glu Ser Ala Ser Glu
1240                1245                1250 gac agt gaa gat gat gag agt gat gaa gag gag gag gaa gaa gag          4149
Asp Ser Glu Asp Asp Glu Ser Asp Glu Glu Glu Glu Glu Glu Glu
        1255                1260                1265 gag gag gag gaa gaa gat tat gag gtg gct ggt ttg cga ttg aga cct      4197
Glu Glu Glu Glu Glu Asp Tyr Glu Val Ala Gly Leu Arg Leu Arg Pro
1270                1275                1280 cga aag acc atc cgg ggc aag cac agc gtc atc ccc cct gca gca agg      4245
Arg Lys Thr Ile Arg Gly Lys His Ser Val Ile Pro Pro Ala Ala Arg
1285                1290                1295                1300 tca ggc cgg cgc ccg ggt aag aag cca cac tct acc agg agg tct cag      4293
Ser Gly Arg Arg Pro Gly Lys Lys Pro His Ser Thr Arg Arg Ser Gln
            1305                1310                1315 ccc aag gca cca cct gtg gat gat gct gag gtg gat gag ctg gtg ctt      4341
Pro Lys Ala Pro Pro Val Asp Asp Ala Glu Val Asp Glu Leu Val Leu
1320                1325                1330 cag acc aag cgg agc tcc cgg agg caa agc ctg gag ctg cag aag tgt      4389
Gln Thr Lys Arg Ser Ser Arg Arg Gln Ser Leu Glu Leu Gln Lys Cys
        1335                1340                1345 gaa gag atc ctc cac aag atc gtg aag tac cgc ttc agc tgg ccc ttc      4437
Glu Glu Ile Leu His Lys Ile Val Lys Tyr Arg Phe Ser Trp Pro Phe
1350                1355                1360 agg gag cct gtg acc aga gat gag gcc gag gac tac tat gat gtg atc      4485
Arg Glu Pro Val Thr Arg Asp Glu Ala Glu Asp Tyr Tyr Asp Val Ile
1365                1370                1375                1380 acg cac ccc atg gac ttt cag aca gtg cag aac aaa tgt tcc tgt ggg      4533
Thr His Pro Met Asp Phe Gln Thr Val Gln Asn Lys Cys Ser Cys Gly
            1385                1390                1395 agc tac cgc tct gtg cag gag ttt ctt act gac atg aag caa gtg ttt      4581
Ser Tyr Arg Ser Val Gln Glu Phe Leu Thr Asp Met Lys Gln Val Phe
1400                1405                1410 acc aat gct gag gtt tac aac tgc cgt ggc agc cat gtg cta agc tgc      4629
Thr Asn Ala Glu Val Tyr Asn Cys Arg Gly Ser His Val Leu Ser Cys
        1415                1420                1425 atg gtg aag aca gaa cag tgt cta gtg gtt ctg ttg cat aaa cac ctt      4677
Met Val Lys Thr Glu Gln Cys Leu Val Val Leu Leu His Lys His Leu
1430                1435                1440
```

-continued

```
cct ggc cac cca tat gtc cgc agg aag cgc aag aag ttt cct gat agg    4725
Pro Gly His Pro Tyr Val Arg Arg Lys Arg Lys Lys Phe Pro Asp Arg
1445            1450                1455                1460 ctt gct gaa gat gaa ggg gac agt gag cca gag gcc gtt gga cag tcc    4773
Leu Ala Glu Asp Glu Gly Asp Ser Glu Pro Glu Ala Val Gly Gln Ser
                1465                1470                1475 agg gac gaa gac aga aga agt aga gag gcg gag att cag gaa tgg ctc    4821
Arg Asp Glu Asp Arg Arg Ser Arg Glu Ala Glu Ile Gln Glu Trp Leu
            1480                1485                1490 cag gac acg tcc ctt tac tct gcc aag atc aac tca aaa gac cac aac    4869
Gln Asp Thr Ser Leu Tyr Ser Ala Lys Ile Asn Ser Lys Asp His Asn
        1495                1500                1505 tgt ttc atg atg ctg gtg aat aca caa ttc tgt atg gca ctc act gat    4917
Cys Phe Met Met Leu Val Asn Thr Gln Phe Cys Met Ala Leu Thr Asp
    1510                1515                1520 act gtc acc tgagaggaag acgggggaag agacagagta tgggcttaaa            4966
Thr Val Thr
1525 gaaacaagac tgtataataa atacagatta aaaagaaaa atcgccacca tctcccctgt    5026 tggcctgatt accccgatcc tgctatgtaa cacagcaatc cctcccctgg agaccagagg   5086 ggcttggcac tgtggtggaa ccagaacga gcaggccctt aggaaagaag caggaacag    5146 gaactggctt caccagaaaa gctagaccct cggactcctc ctggaaactc tcagaaggga   5206 gggttatggc cctctttgtc ccttcatatt tctggacaaa gaccaccaac ccaatatcaa   5266 gccccataaa gagcttttag aaaaacagca taagcttggg atgacaggcg tttctggact   5326 ccctgtgatc tcttccaggt tcttggtctt cctcgctcgc ctcccctccca ccctccctag  5386 ctgtcccccc acctcagctc ccttaccacg gccctgcctc tctacttctt ctgtcttcgt   5446 cccctggact gtccaacggc ctctggctca ctgtcccttc atcttcagca acctatcagg   5506 aaacttcttg cgcttcctgc ggacatatgg gtggccagga agtgtttatg caaca        5561
```

<210> SEQ ID NO 29
<211> LENGTH: 1531
<212> TYPE: PRT
<213> ORGANISM: Homo sapiens

<400> SEQUENCE: 29

```
Met Ala Pro Leu Leu Gly Arg Lys Pro Phe Pro Leu Val Asn Pro Leu
 1               5                   10                  15

Pro Gly Glu Glu Pro Phe Phe Thr Ile Pro His Thr Gln Glu Ala Phe
                20                  25                  30

Arg Thr Arg Glu Glu Tyr Glu Ala Arg Leu Glu Arg Tyr Ser Glu Arg
            35                  40                  45

Ile Trp Thr Cys Lys Ser Thr Gly Ser Ser Gln Leu Thr His Lys Glu
        50                  55                  60

Ala Trp Glu Glu Gln Glu Val Ala Glu Leu Leu Lys Glu Glu Phe
65                  70                  75                  80

Pro Ala Trp Tyr Glu Lys Leu Val Leu Glu Met Val His His Asn Thr
                85                  90                  95

Ala Ser Leu Glu Lys Leu Val Asp Thr Ala Trp Leu Glu Ile Met Thr
                100                 105                 110

Lys Tyr Ala Val Gly Glu Glu Cys Asp Phe Glu Val Gly Lys Glu Lys
            115                 120                 125

Met Leu Lys Val Lys Ile Val Lys Ile His Pro Leu Glu Lys Val Asp
        130                 135                 140
```

```
Glu Glu Ala Thr Glu Lys Lys Ser Asp Gly Ala Cys Asp Ser Pro Ser
145                 150                 155                 160

Ser Asp Lys Glu Asn Ser Ser Gln Ile Ala Gln Asp His Gln Lys Lys
            165                 170                 175

Glu Thr Val Val Lys Glu Asp Glu Gly Arg Arg Glu Ser Ile Asn Asp
        180                 185                 190

Arg Ala Arg Arg Ser Pro Arg Lys Leu Pro Thr Ser Leu Lys Lys Gly
    195                 200                 205

Glu Arg Lys Trp Ala Pro Pro Lys Phe Leu Pro His Lys Tyr Asp Val
210                 215                 220

Lys Leu Gln Asn Glu Asp Lys Ile Ile Ser Asn Val Pro Ala Asp Ser
225                 230                 235                 240

Leu Ile Arg Thr Glu Arg Pro Asn Lys Glu Ile Val Arg Tyr Phe
            245                 250                 255

Ile Arg His Asn Ala Leu Arg Ala Gly Thr Gly Glu Asn Ala Pro Trp
            260                 265                 270

Val Val Glu Asp Glu Leu Val Lys Lys Tyr Ser Leu Pro Ser Lys Phe
        275                 280                 285

Ser Asp Phe Leu Leu Asp Pro Tyr Lys Tyr Met Thr Leu Asn Pro Ser
290                 295                 300

Thr Lys Arg Lys Asn Thr Gly Ser Pro Asp Arg Lys Pro Ser Lys Lys
305                 310                 315                 320

Ser Lys Thr Asp Asn Ser Ser Leu Ser Ser Pro Leu Asn Pro Lys Leu
            325                 330                 335

Trp Cys His Val His Leu Lys Lys Ser Leu Ser Gly Ser Pro Leu Lys
            340                 345                 350

Val Lys Asn Ser Lys Asn Ser Lys Ser Pro Glu Glu His Leu Glu Glu
            355                 360                 365

Met Met Lys Met Met Ser Pro Asn Lys Leu His Thr Asn Phe His Ile
            370                 375                 380

Pro Lys Lys Gly Pro Pro Ala Lys Lys Pro Gly Lys His Ser Asp Lys
385                 390                 395                 400

Pro Leu Lys Ala Lys Gly Arg Ser Lys Gly Ile Leu Asn Gly Gln Lys
            405                 410                 415

Ser Thr Gly Asn Ser Lys Ser Pro Lys Lys Gly Leu Lys Thr Pro Lys
            420                 425                 430

Thr Lys Met Lys Gln Met Thr Leu Leu Asp Met Ala Lys Gly Thr Gln
            435                 440                 445

Lys Met Thr Arg Ala Pro Arg Asn Ser Gly Gly Thr Pro Arg Thr Ser
450                 455                 460

Ser Lys Pro His Lys His Leu Pro Pro Ala Ala Leu His Leu Ile Ala
465                 470                 475                 480

Tyr Tyr Lys Glu Asn Lys Asp Arg Glu Asp Lys Arg Ser Ala Leu Ser
            485                 490                 495

Cys Val Ile Ser Lys Thr Ala Arg Leu Leu Ser Ser Glu Asp Arg Ala
            500                 505                 510

Arg Leu Pro Glu Glu Leu Arg Ser Leu Val Gln Lys Arg Tyr Glu Leu
            515                 520                 525

Leu Glu His Lys Lys Arg Trp Ala Ser Met Ser Glu Glu Gln Arg Lys
            530                 535                 540

Glu Tyr Leu Lys Lys Arg Glu Glu Lys Lys Lys Leu Lys Glu
545                 550                 555                 560
```

-continued

```
Lys Ala Lys Glu Arg Arg Glu Lys Glu Met Leu Glu Arg Leu Glu Lys
            565                 570                 575
Gln Lys Arg Tyr Glu Asp Gln Glu Leu Thr Gly Lys Asn Leu Pro Ala
            580                 585                 590
Phe Arg Leu Val Asp Thr Pro Glu Gly Leu Pro Asn Thr Leu Phe Gly
            595                 600                 605
Asp Val Ala Met Val Val Glu Phe Leu Ser Cys Tyr Ser Gly Leu Leu
            610                 615                 620
Leu Pro Asp Ala Gln Tyr Pro Ile Thr Ala Val Ser Leu Met Glu Ala
625                 630                 635                 640
Leu Ser Ala Asp Lys Gly Gly Phe Leu Tyr Leu Asn Arg Val Leu Val
            645                 650                 655
Ile Leu Leu Gln Thr Leu Leu Gln Thr Leu Leu Gln Asp Glu Ile Ala
            660                 665                 670
Glu Asp Tyr Gly Glu Leu Gly Met Lys Leu Ser Glu Ile Pro Leu Thr
            675                 680                 685
Leu His Ser Val Ser Glu Leu Val Arg Leu Cys Leu Arg Arg Ser Asp
            690                 695                 700
Val Gln Glu Glu Ser Glu Gly Ser Asp Thr Asp Asp Asn Lys Asp Ser
705                 710                 715                 720
Ala Ala Phe Glu Asp Asn Glu Val Gln Asp Glu Phe Leu Glu Lys Leu
            725                 730                 735
Glu Thr Ser Glu Phe Phe Glu Leu Thr Ser Glu Glu Lys Leu Gln Ile
            740                 745                 750
Leu Thr Ala Leu Cys His Arg Ile Leu Met Thr Tyr Ser Val Gln Asp
            755                 760                 765
His Met Glu Thr Arg Gln Gln Met Ser Ala Glu Leu Trp Lys Glu Arg
            770                 775                 780
Leu Ala Val Leu Lys Glu Glu Asn Asp Lys Lys Arg Ala Glu Lys Gln
785                 790                 795                 800
Lys Arg Lys Glu Met Glu Ala Lys Asn Lys Glu Asn Gly Lys Val Glu
            805                 810                 815
Asn Gly Leu Gly Lys Thr Asp Arg Lys Lys Arg Ile Val Lys Phe Glu
            820                 825                 830
Pro Gln Val Asp Thr Glu Ala Glu Asp Met Ile Ser Ala Val Lys Ser
            835                 840                 845
Arg Arg Leu Leu Ala Ile Gln Ala Lys Lys Glu Arg Glu Ile Gln Glu
850                 855                 860
Arg Glu Met Lys Val Lys Leu Glu Arg Gln Ala Glu Glu Arg Ile
865                 870                 875                 880
Arg Lys His Lys Ala Ala Glu Lys Ala Phe Gln Glu Gly Ile Ala
            885                 890                 895
Lys Ala Lys Leu Val Met Arg Arg Thr Pro Ile Gly Thr Asp Arg Asn
            900                 905                 910
His Asn Arg Tyr Trp Leu Phe Ser Asp Glu Val Pro Gly Leu Phe Ile
            915                 920                 925
Glu Lys Gly Trp Val His Asp Ser Ile Asp Tyr Arg Phe Asn His His
            930                 935                 940
Cys Lys Asp His Thr Val Ser Gly Asp Glu Asp Tyr Cys Pro Arg Ser
945                 950                 955                 960
Lys Lys Ala Asn Leu Gly Lys Asn Ala Ser Met Asn Thr Gln His Gly
            965                 970                 975
Thr Ala Thr Glu Val Ala Val Glu Thr Thr Thr Pro Lys Gln Gly Gln
```

-continued

```
                980              985              990
Asn Leu Trp Phe Leu Cys Asp Ser Gln Lys Glu Leu Asp Glu Leu Leu
    995             1000            1005

Asn Cys Leu His Pro Gln Gly Ile Arg Glu Ser Gln Leu Lys Glu Arg
    1010            1015            1020

Leu Glu Lys Arg Tyr Gln Asp Ile Ile His Ser Ile His Leu Ala Arg
1025            1030            1035            1040

Lys Pro Asn Leu Gly Leu Lys Ser Cys Asp Gly Asn Gln Glu Leu Leu
            1045            1050            1055

Asn Phe Leu Arg Ser Asp Leu Ile Glu Val Ala Thr Arg Leu Gln Lys
            1060            1065            1070

Gly Gly Leu Gly Tyr Val Glu Glu Thr Ser Glu Phe Glu Ala Arg Val
        1075            1080            1085

Ile Ser Leu Glu Lys Leu Lys Asp Phe Gly Glu Cys Val Ile Ala Leu
    1090            1095            1100

Gln Ala Ser Val Ile Lys Lys Phe Leu Gln Gly Phe Met Ala Pro Lys
1105            1110            1115            1120

Gln Lys Arg Arg Lys Leu Gln Ser Glu Asp Ser Ala Lys Thr Glu Glu
            1125            1130            1135

Val Asp Glu Glu Lys Lys Met Val Glu Glu Ala Lys Val Ala Ser Ala
            1140            1145            1150

Leu Glu Lys Trp Lys Thr Ala Ile Arg Glu Ala Gln Thr Phe Ser Arg
        1155            1160            1165

Met His Val Leu Leu Gly Met Leu Asp Ala Cys Ile Lys Trp Asp Met
        1170            1175            1180

Ser Ala Glu Asn Ala Arg Cys Lys Val Cys Pro Lys Lys Gly Glu Asp
1185            1190            1195            1200

Asp Lys Leu Ile Leu Cys Asp Glu Cys Asn Lys Ala Phe His Leu Phe
            1205            1210            1215

Cys Leu Arg Pro Ala Leu Tyr Glu Val Pro Asp Gly Glu Trp Gln Cys
            1220            1225            1230

Pro Ala Cys Gln Pro Ala Thr Ala Arg Arg Asn Ser Arg Gly Arg Asn
            1235            1240            1245

Tyr Thr Glu Glu Ser Ala Ser Glu Asp Ser Glu Asp Asp Glu Ser Asp
1250            1255            1260

Glu Glu Glu Glu Glu Glu Glu Glu Glu Glu Glu Glu Asp Tyr Glu
1265            1270            1275            1280

Val Ala Gly Leu Arg Leu Arg Pro Arg Lys Thr Ile Arg Gly Lys His
            1285            1290            1295

Ser Val Ile Pro Pro Ala Ala Arg Ser Gly Arg Arg Pro Gly Lys Lys
        1300            1305            1310

Pro His Ser Thr Arg Arg Ser Gln Pro Lys Ala Pro Pro Val Asp Asp
        1315            1320            1325

Ala Glu Val Asp Glu Leu Val Leu Gln Thr Lys Arg Ser Ser Arg Arg
1330            1335            1340

Gln Ser Leu Glu Leu Gln Lys Cys Glu Glu Ile Leu His Lys Ile Val
1345            1350            1355            1360

Lys Tyr Arg Phe Ser Trp Pro Phe Arg Glu Pro Val Thr Arg Asp Glu
            1365            1370            1375

Ala Glu Asp Tyr Tyr Asp Val Ile Thr His Pro Met Asp Phe Gln Thr
            1380            1385            1390

Val Gln Asn Lys Cys Ser Cys Gly Ser Tyr Arg Ser Val Gln Glu Phe
            1395            1400            1405
```

```
Leu Thr Asp Met Lys Gln Val Phe Thr Asn Ala Glu Val Tyr Asn Cys
    1410                1415                1420
Arg Gly Ser His Val Leu Ser Cys Met Val Lys Thr Glu Gln Cys Leu
1425                1430                1435                1440
Val Val Leu Leu His Lys His Leu Pro Gly His Pro Tyr Val Arg Arg
                1445                1450                1455
Lys Arg Lys Lys Phe Pro Asp Arg Leu Ala Glu Asp Glu Gly Asp Ser
                1460                1465                1470
Glu Pro Glu Ala Val Gly Gln Ser Arg Asp Asp Arg Arg Ser Arg
            1475                1480                1485
Glu Ala Glu Ile Gln Glu Trp Leu Gln Asp Thr Ser Leu Tyr Ser Ala
            1490                1495                1500
Lys Ile Asn Ser Lys Asp His Asn Cys Phe Met Met Leu Val Asn Thr
1505                1510                1515                1520
Gln Phe Cys Met Ala Leu Thr Asp Thr Val Thr
                1525                1530

<210> SEQ ID NO 30
<211> LENGTH: 5573
<212> TYPE: DNA
<213> ORGANISM: Homo sapiens
<220> FEATURE:
<221> NAME/KEY: CDS
<222> LOCATION: (346)...(4938)

<400> SEQUENCE: 30
cgggcccggg ggaggagggg aatctcccgc cattttttcaa taatttcctc cggtgctgct      60
gaggaggagt cgtgactgcc ggccgccggg acccgaagcg gaggtcggcg ggggggctgct    120 gggaggcgcg gcggtgtgcg cgggagctct gcgccgtggc gttccgctcc atgactgtcg    180
cgcggccgcg ccggcggtga gggagccgga gttcgcgccg ccctctcacc cctcccttcc    240
cccaccccac ccccgggcgc ctggcgctcg ctccgggccg cggggcctag tgctgcgccg    300
cggggccggc cccagcagcc gccagtcccc accgccgccg ccgcg atg gcg ccg ctc    357
                                                    Met Ala Pro Leu
                                                        1 ctg ggc cgc aag ccc ttc ccg ctg gtg aat ccg ttg ccc gga gag gag      405
Leu Gly Arg Lys Pro Phe Pro Leu Val Asn Pro Leu Pro Gly Glu Glu
    5                   10                  15                  20 ccg ttc ttc acc atc ccg cac act cag gag gcc ttc cgc acc cgg gaa      453
Pro Phe Phe Thr Ile Pro His Thr Gln Glu Ala Phe Arg Thr Arg Glu
                25                  30                  35 gag tat gaa gcc cgc ttg gaa agg tac agt gag cgc att tgg acg tgc      501
Glu Tyr Glu Ala Arg Leu Glu Arg Tyr Ser Glu Arg Ile Trp Thr Cys
            40                  45                  50 aag agt act gga agc agt cag cta aca cac aag gaa gcc tgg gag gaa      549
Lys Ser Thr Gly Ser Ser Gln Leu Thr His Lys Glu Ala Trp Glu Glu
        55                  60                  65 gaa cag gaa gtt gct gag ctt ttg aag gag gag ttt cct gcc tgg tat      597
Glu Gln Glu Val Ala Glu Leu Leu Lys Glu Glu Phe Pro Ala Trp Tyr
    70                  75                  80 gag aag ctt gtt ctg gaa atg gtt cac cat aac aca gcc tcc tta gag      645
Glu Lys Leu Val Leu Glu Met Val His His Asn Thr Ala Ser Leu Glu
85                  90                  95                 100 aag tta gta gat act gct tgg ttg gag atc atg acc aaa tat gct gtg      693
Lys Leu Val Asp Thr Ala Trp Leu Glu Ile Met Thr Lys Tyr Ala Val
                105                 110                 115 gga gaa gag tgt gac ttc gag gtt ggg aag gag aaa atg ctc aag gtg      741
```

```
Gly Glu Glu Cys Asp Phe Glu Val Gly Lys Glu Lys Met Leu Lys Val
            120                 125                 130 aag att gtg aag att cat cct ttg gag aaa gtg gat gaa gag gcc act      789
Lys Ile Val Lys Ile His Pro Leu Glu Lys Val Asp Glu Glu Ala Thr
                135                 140                 145 gag aag aaa tct gat ggt gcc tgt gat tct cca tca agt gac aaa gag      837
Glu Lys Lys Ser Asp Gly Ala Cys Asp Ser Pro Ser Ser Asp Lys Glu
            150                 155                 160 aac tcc agt cag att gct cag gac cat cag aag aag gag aca gtt gtg      885
Asn Ser Ser Gln Ile Ala Gln Asp His Gln Lys Lys Glu Thr Val Val
165                 170                 175                 180 aaa gag gat gaa gga agg aga gag agt att aat gac aga gca cgt aga      933
Lys Glu Asp Glu Gly Arg Arg Glu Ser Ile Asn Asp Arg Ala Arg Arg
                185                 190                 195 tcg cca cga aaa ctt cct act tca tta aaa aaa gga gaa agg aaa tgg      981
Ser Pro Arg Lys Leu Pro Thr Ser Leu Lys Lys Gly Glu Arg Lys Trp
            200                 205                 210 gct cct cca aaa ttt ctg cct cac aaa tat gat gtg aaa cta caa aat     1029
Ala Pro Pro Lys Phe Leu Pro His Lys Tyr Asp Val Lys Leu Gln Asn
            215                 220                 225 gaa gat aag atc atc agt aac gtg cca gca gac agc ttg att cgt aca     1077
Glu Asp Lys Ile Ile Ser Asn Val Pro Ala Asp Ser Leu Ile Arg Thr
            230                 235                 240 gag cgc cca cca aat aag gag ata gtt cga tac ttt ata cgg cat aat     1125
Glu Arg Pro Pro Asn Lys Glu Ile Val Arg Tyr Phe Ile Arg His Asn
245                 250                 255                 260 gca tta cga gct ggt act ggt gaa aat gca cct tgg gtc gta gaa gat     1173
Ala Leu Arg Ala Gly Thr Gly Glu Asn Ala Pro Trp Val Val Glu Asp
                265                 270                 275 gaa ttg gtg aag aaa tac tct ctg ccc agc aag ttc agt gac ttt tta     1221
Glu Leu Val Lys Lys Tyr Ser Leu Pro Ser Lys Phe Ser Asp Phe Leu
            280                 285                 290 ctt gat cca tac aag tat atg act ctc aac cct tct act aag agg aag     1269
Leu Asp Pro Tyr Lys Tyr Met Thr Leu Asn Pro Ser Thr Lys Arg Lys
            295                 300                 305 aat act gga tcc cca gac agg aag ccc tca aag aaa tcc aag aca gac     1317
Asn Thr Gly Ser Pro Asp Arg Lys Pro Ser Lys Lys Ser Lys Thr Asp
            310                 315                 320 aac tct tct ctt agt tca cca cta aat cct aag tta tgg tgt cac gta     1365
Asn Ser Ser Leu Ser Ser Pro Leu Asn Pro Lys Leu Trp Cys His Val
325                 330                 335                 340 cac ttg aag aag tca ttg agt ggc tcg cca ctc aaa gtg aag aac tca     1413
His Leu Lys Lys Ser Leu Ser Gly Ser Pro Leu Lys Val Lys Asn Ser
                345                 350                 355 aag aat tcc aaa tct cct gaa gaa cat cta gaa gaa atg atg aag atg     1461
Lys Asn Ser Lys Ser Pro Glu Glu His Leu Glu Glu Met Met Lys Met
            360                 365                 370 atg tcg ccc aat aag ttg cac act aac ttt cac att cct aaa aaa ggc     1509
Met Ser Pro Asn Lys Leu His Thr Asn Phe His Ile Pro Lys Lys Gly
            375                 380                 385 cca cct gcc aag aaa cca ggg aag cac agt gac aag cct ttg aag gca     1557
Pro Pro Ala Lys Lys Pro Gly Lys His Ser Asp Lys Pro Leu Lys Ala
            390                 395                 400 aag ggc aga agc aaa ggc atc ctg aat gga cag aaa tcc aca ggg aat     1605
Lys Gly Arg Ser Lys Gly Ile Leu Asn Gly Gln Lys Ser Thr Gly Asn
405                 410                 415                 420 tcc aaa tct ccc aaa aaa gga ctg aag act cct aaa acc aaa atg aag     1653
Ser Lys Ser Pro Lys Lys Gly Leu Lys Thr Pro Lys Thr Lys Met Lys
            425                 430                 435
```

-continued

```
cag atg act ttg ttg gat atg gcc aaa ggc acg cag aag atg aca cga    1701
Gln Met Thr Leu Leu Asp Met Ala Lys Gly Thr Gln Lys Met Thr Arg
            440                 445                 450 gcc cca cgg aat tct ggg ggt aca cct agg acc tct agt aaa cct cat    1749
Ala Pro Arg Asn Ser Gly Gly Thr Pro Arg Thr Ser Ser Lys Pro His
        455                 460                 465 aaa cat ctg cct cct gca gcc cta cac ctc att gca tac tac aaa gaa    1797
Lys His Leu Pro Pro Ala Ala Leu His Leu Ile Ala Tyr Tyr Lys Glu
    470                 475                 480 aac aaa gac agg gag gac aag agg agc gcc ctg tcc tgt gtt atc tcc    1845
Asn Lys Asp Arg Glu Asp Lys Arg Ser Ala Leu Ser Cys Val Ile Ser
485                 490                 495                 500 aaa aca gct cgt ctt ctc tct agt gaa gat aga gct cgt ctc cca gaa    1893
Lys Thr Ala Arg Leu Leu Ser Ser Glu Asp Arg Ala Arg Leu Pro Glu
                505                 510                 515 gaa ttg cga agt ctt gtt caa aaa cgc tat gaa ctt cta gag cac aaa    1941
Glu Leu Arg Ser Leu Val Gln Lys Arg Tyr Glu Leu Leu Glu His Lys
            520                 525                 530 aag agg tgg gct tct atg tct gaa gaa caa cgg aaa gaa tat ttg aaa    1989
Lys Arg Trp Ala Ser Met Ser Glu Glu Gln Arg Lys Glu Tyr Leu Lys
        535                 540                 545 aag aaa cgg gag gag ctg aaa aag aag ttg aag gaa aaa gcc aaa gaa    2037
Lys Lys Arg Glu Glu Leu Lys Lys Lys Leu Lys Glu Lys Ala Lys Glu
    550                 555                 560 cga aga gag aaa gaa atg ctt gag aga tta gaa aaa cag aag cgg tat    2085
Arg Arg Glu Lys Glu Met Leu Glu Arg Leu Glu Lys Gln Lys Arg Tyr
565                 570                 575                 580 gag gac caa gag tta act ggc aaa aac ctt cca gca ttc aga ttg gtg    2133
Glu Asp Gln Glu Leu Thr Gly Lys Asn Leu Pro Ala Phe Arg Leu Val
                585                 590                 595 gat acc cct gaa ggg ctg ccc aac acg ctg ttt ggg gat gtg gcc atg    2181
Asp Thr Pro Glu Gly Leu Pro Asn Thr Leu Phe Gly Asp Val Ala Met
            600                 605                 610 gtg gtg gaa ttc ttg agc tgt tat tct ggg cta ctt tta cca gat gct    2229
Val Val Glu Phe Leu Ser Cys Tyr Ser Gly Leu Leu Leu Pro Asp Ala
        615                 620                 625 cag tat cct att act gct gtg tcc ctt atg gaa gcc ttg agt gca gat    2277
Gln Tyr Pro Ile Thr Ala Val Ser Leu Met Glu Ala Leu Ser Ala Asp
    630                 635                 640 aag ggt ggc ttt tta tac ctt aac agg gtg ttg gtc atc ctc tta cag    2325
Lys Gly Gly Phe Leu Tyr Leu Asn Arg Val Leu Val Ile Leu Leu Gln
645                 650                 655                 660 acc ctc cta cag acc ctc cta caa gat gag ata gcc gaa gac tat ggt    2373
Thr Leu Leu Gln Thr Leu Leu Gln Asp Glu Ile Ala Glu Asp Tyr Gly
                665                 670                 675 gaa ttg gga atg aag ctg tca gaa atc ccc ttg act ctg cat tct gtt    2421
Glu Leu Gly Met Lys Leu Ser Glu Ile Pro Leu Thr Leu His Ser Val
            680                 685                 690 tca gag ctg gtg cgg ctc tgc ttg cgc aga tct gat gtt cag gag gaa    2469
Ser Glu Leu Val Arg Leu Cys Leu Arg Arg Ser Asp Val Gln Glu Glu
        695                 700                 705 agc gag ggc tca gac aca gat gac aat aaa gat tca gct gca ttt gag    2517
Ser Glu Gly Ser Asp Thr Asp Asp Asn Lys Asp Ser Ala Ala Phe Glu
    710                 715                 720 gat aat gag gta caa gat gag ttc cta gaa aag ctg gag acc tct gaa    2565
Asp Asn Glu Val Gln Asp Glu Phe Leu Glu Lys Leu Glu Thr Ser Glu
725                 730                 735                 740 ttt ttt gag ctg acg tca gag gag aag cta cag att ttg aca gca ctg    2613
Phe Phe Glu Leu Thr Ser Glu Glu Lys Leu Gln Ile Leu Thr Ala Leu
                745                 750                 755
```

```
tgc cac cgg atc ctc atg aca tac tca gtg caa gac cac atg gag acc    2661
Cys His Arg Ile Leu Met Thr Tyr Ser Val Gln Asp His Met Glu Thr
            760                 765                 770 aga cag cag atg tct gca gag ttg tgg aag gaa cgg ctt gct gtg ttg    2709
Arg Gln Gln Met Ser Ala Glu Leu Trp Lys Glu Arg Leu Ala Val Leu
        775                 780                 785 aag gaa gaa aat gat aag aag aga gca gag aaa cag aaa cgg aaa gaa    2757
Lys Glu Glu Asn Asp Lys Lys Arg Ala Glu Lys Gln Lys Arg Lys Glu
    790                 795                 800 atg gaa gcc aaa aat aaa gaa aat gga aaa gtt gag aat ggg tta ggc    2805
Met Glu Ala Lys Asn Lys Glu Asn Gly Lys Val Glu Asn Gly Leu Gly
805                 810                 815                 820 aaa act gat agg aaa aaa aga att gtg aag ttt gag ccc caa gta gat    2853
Lys Thr Asp Arg Lys Lys Arg Ile Val Lys Phe Glu Pro Gln Val Asp
            825                 830                 835 aca gaa gct gaa gac atg att agt gct gtg aag agc aga agg ttg ctt    2901
Thr Glu Ala Glu Asp Met Ile Ser Ala Val Lys Ser Arg Arg Leu Leu
        840                 845                 850 gcc att caa gct aag aag gaa cgg gaa atc cag gaa aga gaa atg aaa    2949
Ala Ile Gln Ala Lys Lys Glu Arg Glu Ile Gln Glu Arg Glu Met Lys
    855                 860                 865 gtg aaa ctg gaa cgc caa gct gaa gaa gaa cga ata cgg aag cac aaa    2997
Val Lys Leu Glu Arg Gln Ala Glu Glu Glu Arg Ile Arg Lys His Lys
870                 875                 880 gca gct gct gag aaa gct ttc cag gaa ggg att gcc aag gcc aaa cta    3045
Ala Ala Ala Glu Lys Ala Phe Gln Glu Gly Ile Ala Lys Ala Lys Leu
885                 890                 895                 900 gtc atg cgc agg act cct att ggc aca gat cga aac cat aat aga tac    3093
Val Met Arg Arg Thr Pro Ile Gly Thr Asp Arg Asn His Asn Arg Tyr
            905                 910                 915 tgg ctc ttc tca gat gaa gtt cca gga tta ttc att gaa aaa ggc tgg    3141
Trp Leu Phe Ser Asp Glu Val Pro Gly Leu Phe Ile Glu Lys Gly Trp
        920                 925                 930 gta cat gac agc att gac tac cga ttc aac cat cac tgc aaa gac cac    3189
Val His Asp Ser Ile Asp Tyr Arg Phe Asn His His Cys Lys Asp His
    935                 940                 945 aca gtc tct ggt gat gag gat tac tgt cct cgc agt aag aaa gca aac    3237
Thr Val Ser Gly Asp Glu Asp Tyr Cys Pro Arg Ser Lys Lys Ala Asn
950                 955                 960 tta ggt aaa aat gca agc atg aac aca caa cat gga aca gca aca gaa    3285
Leu Gly Lys Asn Ala Ser Met Asn Thr Gln His Gly Thr Ala Thr Glu
965                 970                 975                 980 gtt gct gta gag aca acc aca ccc aaa caa gga cag aac cta tgg ttt    3333
Val Ala Val Glu Thr Thr Thr Pro Lys Gln Gly Gln Asn Leu Trp Phe
            985                 990                 995 tta tgt gat agt caa aag gag ctg gat gag ttg cta aac tgt ctt cac    3381
Leu Cys Asp Ser Gln Lys Glu Leu Asp Glu Leu Leu Asn Cys Leu His
        1000                1005                1010 cct cag gga ata aga gaa agt caa ctt aaa gag aga cta gag aag agg    3429
Pro Gln Gly Ile Arg Glu Ser Gln Leu Lys Glu Arg Leu Glu Lys Arg
    1015                1020                1025 tac cag gac att att cac tct att cat cta gca cgg aag cca aat ttg    3477
Tyr Gln Asp Ile Ile His Ser Ile His Leu Ala Arg Lys Pro Asn Leu
    1030                1035                1040 ggt cta aaa tct tgt gat ggc aac cag gag ctt tta aac ttc ctt cgt    3525
Gly Leu Lys Ser Cys Asp Gly Asn Gln Glu Leu Leu Asn Phe Leu Arg
1045                1050                1055                1060 agt gat ctc att gaa gtt gca aca agg tta caa aaa gga gga ctt gga    3573
Ser Asp Leu Ile Glu Val Ala Thr Arg Leu Gln Lys Gly Gly Leu Gly
```

```
                    1065              1070             1075
tat gtg gaa gaa aca tca gaa ttt gaa gcc cgg gtc att tca tta gag    3621
Tyr Val Glu Glu Thr Ser Glu Phe Glu Ala Arg Val Ile Ser Leu Glu
            1080             1085             1090 aaa ttg aag gat ttt ggt gag tgt gtg att gcc ctt cag gcc agt gtc    3669
Lys Leu Lys Asp Phe Gly Glu Cys Val Ile Ala Leu Gln Ala Ser Val
            1095             1100             1105 ata aag aaa ttt ctc caa ggc ttc atg gct ccc aag caa aag aga aga    3717
Ile Lys Lys Phe Leu Gln Gly Phe Met Ala Pro Lys Gln Lys Arg Arg
            1110             1115             1120 aaa ctc caa agt gaa gat tca gca aaa act gag gaa gtg gat gaa gag    3765
Lys Leu Gln Ser Glu Asp Ser Ala Lys Thr Glu Glu Val Asp Glu Glu
1125             1130             1135             1140 aag aaa atg gta gag gaa gca aag gtt gca tct gca ctg gag aaa tgg    3813
Lys Lys Met Val Glu Glu Ala Lys Val Ala Ser Ala Leu Glu Lys Trp
            1145             1150             1155 aag aca gca atc cgg gaa gct cag act ttc tcc agg atg cac gtg ctg    3861
Lys Thr Ala Ile Arg Glu Ala Gln Thr Phe Ser Arg Met His Val Leu
            1160             1165             1170 ctt ggg atg ctt gat gcc tgt atc aag tgg gat atg tcc gca gaa aat    3909
Leu Gly Met Leu Asp Ala Cys Ile Lys Trp Asp Met Ser Ala Glu Asn
            1175             1180             1185 gct agg tgc aaa gtt tgt cca aag aaa ggt gag gat gac aaa ttg atc    3957
Ala Arg Cys Lys Val Cys Pro Lys Lys Gly Glu Asp Asp Lys Leu Ile
1190             1195             1200 ttg tgt gat gag tgt aat aaa gcc ttc cac ctg ttt tgt ctg agg ccg    4005
Leu Cys Asp Glu Cys Asn Lys Ala Phe His Leu Phe Cys Leu Arg Pro
1205             1210             1215             1220 gcc ctc tat gaa gta cca gat ggt gag tgg cag tgc cca gct tgc cag    4053
Ala Leu Tyr Glu Val Pro Asp Gly Glu Trp Gln Cys Pro Ala Cys Gln
            1225             1230             1235 ccc gct act gcc agg cgc aac tcc cgt ggc agg aac tat act gaa gag    4101
Pro Ala Thr Ala Arg Arg Asn Ser Arg Gly Arg Asn Tyr Thr Glu Glu
            1240             1245             1250 tct gct tct gag gac agt gaa gat gat gag agt gat gaa gag gag gag    4149
Ser Ala Ser Glu Asp Ser Glu Asp Asp Glu Ser Asp Glu Glu Glu Glu
            1255             1260             1265 gag gaa gaa gag gag gag gag gaa gaa gat tat gag gtg gct ggt ttg    4197
Glu Glu Glu Glu Glu Glu Glu Glu Asp Tyr Glu Val Ala Gly Leu
            1270             1275             1280 cga ttg aga cct cga aag acc atc cgg ggc aag cac agc gtc atc ccc    4245
Arg Leu Arg Pro Arg Lys Thr Ile Arg Gly Lys His Ser Val Ile Pro
1285             1290             1295             1300 cct gca gca agg tca ggc cgg cgc ccg ggt aag aag cca cac tct acc    4293
Pro Ala Ala Arg Ser Gly Arg Arg Pro Gly Lys Lys Pro His Ser Thr
            1305             1310             1315 agg agg tct cag ccc aag gca cca cct gtg gat gat gct gag gtg gat    4341
Arg Arg Ser Gln Pro Lys Ala Pro Pro Val Asp Asp Ala Glu Val Asp
            1320             1325             1330 gag ctg gtg ctt cag acc aag cgg agc tcc cgg agg caa agc ctg gag    4389
Glu Leu Val Leu Gln Thr Lys Arg Ser Ser Arg Arg Gln Ser Leu Glu
            1335             1340             1345 ctg cag aag tgt gaa gag atc ctc cac aag atc gtg aag tac cgc ttc    4437
Leu Gln Lys Cys Glu Glu Ile Leu His Lys Ile Val Lys Tyr Arg Phe
            1350             1355             1360 agc tgg ccc ttc agg gag cct gtg acc aga gat gag gcc gag gac tac    4485
Ser Trp Pro Phe Arg Glu Pro Val Thr Arg Asp Glu Ala Glu Asp Tyr
1365             1370             1375             1380 tat gat gtg atc acg cac ccc atg gac ttt cag aca gtg cag aac aaa    4533
```

```

Tyr Asp Val Ile Thr His Pro Met Asp Phe Gln Thr Val Gln Asn Lys
            1385                1390                1395 tgt tcc tgt ggg agc tac cgc tct gtg cag gag ttt ctt act gac atg    4581
Cys Ser Cys Gly Ser Tyr Arg Ser Val Gln Glu Phe Leu Thr Asp Met
        1400                1405                1410 aag caa gtg ttt acc aat gct gag gtt tac aac tgc cgt ggc agc cat    4629
Lys Gln Val Phe Thr Asn Ala Glu Val Tyr Asn Cys Arg Gly Ser His
    1415                1420                1425 gtg cta agc tgc atg gtg aag aca gaa cag tgt cta gtg gtt ctg ttg    4677
Val Leu Ser Cys Met Val Lys Thr Glu Gln Cys Leu Val Val Leu Leu
1430                1435                1440 cat aaa cac ctt cct ggc cac cca tat gtc cgc agg aag cgc aag aag    4725
His Lys His Leu Pro Gly His Pro Tyr Val Arg Arg Lys Arg Lys Lys
1445                1450                1455                1460 ttt cct gat agg ctt gct gaa gat gaa ggg gac agt gag cca gag gcc    4773
Phe Pro Asp Arg Leu Ala Glu Asp Glu Gly Asp Ser Glu Pro Glu Ala
                1465                1470                1475 gtt gga cag tcc agg gac gaa gac aga aga agt aga gag gcg gag att    4821
Val Gly Gln Ser Arg Asp Glu Asp Arg Arg Ser Arg Glu Ala Glu Ile
            1480                1485                1490 cag gaa tgg ctc cag gac acg tcc ctt tac tct gcc aag atc aac tca    4869
Gln Glu Trp Leu Gln Asp Thr Ser Leu Tyr Ser Ala Lys Ile Asn Ser
        1495                1500                1505 aaa gac cac aac tgt ttc atg atg ctg gtg aat aca caa ttc tgt atg    4917
Lys Asp His Asn Cys Phe Met Met Leu Val Asn Thr Gln Phe Cys Met
    1510                1515                1520 gca ctc act gat act gtc acc tgagaggaag acgggggaag agacagagta       4968
Ala Leu Thr Asp Thr Val Thr
1525            1530 tgggcttaaa gaaacaagac tgtataataa atacagatta aaaagaaaaa atcgccacca    5028
tctcccctgt tggcctgatt accccgatcc tgctatgtaa cacagcaatc cctcccctgg    5088
agaccagagg ggcttggcac tgtggtggaa gccagaacga gcaggcccctt aggaaagaag   5148 gcaggaacag gaactggctt caccagaaaa gctagaccct cggactcctc ctggaaactc    5208
tcagaaggga gggttatggc cctctttgtc ccttcatatt tctggacaaa gaccaccaac    5268
ccaatatcaa gccccataaa gagcttttag aaaaacagca taagcttggg atgacaggcg    5328
tttctggact ccctgtgatc tcttccaggt tcttggtctt cctcgctcgc ctccctccca    5388
ccctccctag ctgtcccccc acctcagctc ccttaccacg gccctgcctc tctacttctt    5448
ctgtcttcgt cccctggact gtccaacggc ctctggctca ctgtcccttc atcttcagca    5508
acctatcagg aaacttcttg cgcttcctgc ggacatatgg gtggccagga agtgtttatg    5568
caaca                                                              5573

<210> SEQ ID NO 31
<211> LENGTH: 22
<212> TYPE: DNA
<213> ORGANISM: Artificial Sequence
<220> FEATURE:
<223> OTHER INFORMATION: Synthetically generated primer

<400> SEQUENCE: 31
tggatgatgc tgaggtggat ga                                              22

<210> SEQ ID NO 32
<211> LENGTH: 22
<212> TYPE: DNA
<213> ORGANISM: Artificial Sequence
<220> FEATURE:
```

<223> OTHER INFORMATION: Synthetically generated primer

<400> SEQUENCE: 32
ggggtgcgtg atgacatcat ag                                    22

<210> SEQ ID NO 33
<211> LENGTH: 24
<212> TYPE: DNA
<213> ORGANISM: Artificial Sequence
<220> FEATURE:
<223> OTHER INFORMATION: Synthetically generated primer

<400> SEQUENCE: 33
gagtgcagat aagggtggct tttt                                  24

<210> SEQ ID NO 34
<211> LENGTH: 24
<212> TYPE: DNA
<213> ORGANISM: Artificial Sequence
<220> FEATURE:
<223> OTHER INFORMATION: Synthetically generated primer

<400> SEQUENCE: 34
ccaattcacc atagtcttcg gcta                                  24

<210> SEQ ID NO 35
<211> LENGTH: 22
<212> TYPE: DNA
<213> ORGANISM: Artificial Sequence
<220> FEATURE:
<223> OTHER INFORMATION: Synthetically generated primer

<400> SEQUENCE: 35
gaaacgggag gagctgaaaa ag                                    22

<210> SEQ ID NO 36
<211> LENGTH: 22
<212> TYPE: DNA
<213> ORGANISM: Artificial Sequence
<220> FEATURE:
<223> OTHER INFORMATION: Synthetically generated primer

<400> SEQUENCE: 36
ccttcagggg tatccaccaa tc                                    22

<210> SEQ ID NO 37
<211> LENGTH: 5
<212> TYPE: PRT
<213> ORGANISM: Homo sapiens
<220> FEATURE:
<221> NAME/KEY: VARIANT
<222> LOCATION: (1)...(5)
<223> OTHER INFORMATION: Xaa = Any Amino Acid

<400> SEQUENCE: 37

Leu Xaa Xaa Leu Leu
 1               5

<210> SEQ ID NO 38
<211> LENGTH: 59
<212> TYPE: PRT
<213> ORGANISM: Homo sapiens

<400> SEQUENCE: 38

Ser Trp Pro Phe Leu Lys Leu Val Ser Lys Ile Gln Val Pro Asp Tyr
 1               5                  10                  15

Tyr Asp Ile Ile Lys Lys Pro Ile Ala Leu Asn Ile Ile Arg Glu Lys
              20                  25                  30

Val Asn Lys Cys Glu Tyr Lys Leu Ala Ser Glu Phe Ile Asp Asp Ile
          35                  40                  45

Glu Leu Met Phe Ser Asn Cys Phe Glu Tyr Asn
      50                  55

<210> SEQ ID NO 39
<211> LENGTH: 59
<212> TYPE: PRT
<213> ORGANISM: Saccharomyces cerevisiae

<400> SEQUENCE: 39

Ser Trp Pro Phe Leu Lys Pro Val Asn Lys Gln Val Lys Asp Tyr
 1               5                  10                  15

Tyr Thr Val Ile Lys Arg Pro Met Asp Ile Glu Ile Ile Gly Lys Asn
              20                  25                  30

Ile Glu Ala His Arg Tyr His Ser Arg Ala Glu Tyr Leu Ala Asp Ile
          35                  40                  45

Glu Leu Ile Ala Thr Asn Cys Glu Gln Tyr Asn
      50                  55

<210> SEQ ID NO 40
<211> LENGTH: 59
<212> TYPE: PRT
<213> ORGANISM: Homo sapiens

<400> SEQUENCE: 40

Thr Tyr Pro Phe His Thr Pro Val Asn Ala Lys Val Val Lys Asp Tyr
 1               5                  10                  15

Tyr Lys Ile Ile Thr Arg Pro Met Asp Leu Gln Ile Leu Arg Glu Asn
              20                  25                  30

Val Arg Lys Arg Leu Tyr Pro Ser Arg Glu Glu Phe Arg Glu His Leu
          35                  40                  45

Glu Leu Ile Val Lys Asn Ser Ala Thr Tyr Asn
      50                  55

<210> SEQ ID NO 41
<211> LENGTH: 59
<212> TYPE: PRT
<213> ORGANISM: Homo sapiens

<400> SEQUENCE: 41

Ala Trp Pro Phe Met Glu Pro Val Lys Arg Thr Glu Ala Pro Gly Tyr
 1               5                  10                  15

Tyr Glu Val Ile Arg Ser Pro Met Asp Leu Lys Ile Met Ser Glu Arg
              20                  25                  30

Leu Lys Asn Arg Tyr Tyr Val Ser Lys Lys Leu Phe Met Ala Asp Leu
          35                  40                  45

Gln Arg Val Phe Thr Asn Cys Lys Glu Tyr Asn
      50                  55

<210> SEQ ID NO 42
<211> LENGTH: 61
<212> TYPE: PRT
<213> ORGANISM: Homo sapiens

<400> SEQUENCE: 42

Ser Leu Pro Phe Arg Gln Pro Val Asp Pro Gln Leu Leu Gly Ile Pro

```
              1               5                  10                 15
Asp Tyr Glu Asp Ile Val Lys Asn Pro Met Asp Leu Ser Ile Ile Lys
                            20                 25                 30

Arg Lys Leu Asp Thr Gly Gln Tyr Gln Glu Pro Trp Gln Tyr Val Asp
            35                 40                 45

Asp Val Trp Leu Met Phe Asn Asn Ala Trp Leu Tyr Asn
        50                 55                 60

<210> SEQ ID NO 43
<211> LENGTH: 45
<212> TYPE: PRT
<213> ORGANISM: Homo sapiens

<400> SEQUENCE: 43

Cys Lys Ile Cys Arg Lys Lys Gly Asp Ala Glu Asn Met Val Leu Cys
  1               5                  10                 15

Asp Gly Cys Asp Arg Gly His His Thr Tyr Cys Val Arg Pro Lys Leu
            20                 25                 30

Lys Thr Val Pro Glu Gly Asp Trp Phe Cys Pro Glu Cys
        35                 40                 45

<210> SEQ ID NO 44
<211> LENGTH: 44
<212> TYPE: PRT
<213> ORGANISM: Caenorhabditis elegans

<400> SEQUENCE: 44

Cys Gln Ile Cys Lys Ser Met Asp Gly Asp Glu Met Leu Val Cys Asp
  1               5                  10                 15

Gly Cys Glu Ser Gly Cys His Met Glu Cys Phe Arg Pro Arg Met Thr
            20                 25                 30

Lys Val Pro Glu Gly Asp Trp Phe Cys Gln Arg Cys
        35                 40

<210> SEQ ID NO 45
<211> LENGTH: 45
<212> TYPE: PRT
<213> ORGANISM: Homo sapiens

<400> SEQUENCE: 45

Cys Met Phe Cys Gly Arg Gly Asn Asn Glu Asp Lys Leu Leu Leu Cys
  1               5                  10                 15

Asp Gly Cys Asp Asp Ser Tyr His Thr Phe Cys Glu Ile Pro Pro Leu
            20                 25                 30

Pro Asp Val Pro Lys Gly Asp Trp Arg Cys Pro Lys Cys
        35                 40                 45

<210> SEQ ID NO 46
<211> LENGTH: 54
<212> TYPE: PRT
<213> ORGANISM: Homo sapiens

<400> SEQUENCE: 46

Cys Met Phe Cys Leu Gly Thr Lys Glu Gln Asn Arg Glu Lys Lys Pro
  1               5                  10                 15

Glu Glu Leu Ile Ser Cys Ala Asp Cys Gly Asn Ser Gly His Pro Ser
            20                 25                 30

Cys Leu Lys Phe Ser Pro Glu Leu Thr Val Arg Val Lys Ala Leu Arg
        35                 40                 45
```

-continued

```
Trp Gln Cys Ile Glu Cys
    50

<210> SEQ ID NO 47
<211> LENGTH: 46
<212> TYPE: PRT
<213> ORGANISM: Homo sapiens

<400> SEQUENCE: 47

Cys Ser Ser Cys Arg Asp Gln Gly Lys Asn Ala Asp Asn Met Leu Phe
  1               5                  10                  15

Cys Asp Ser Cys Asp Arg Gly Phe His Met Glu Cys Cys Asp Pro Pro
                 20                  25                  30

Leu Thr Arg Met Pro Lys Gly Met Trp Ile Cys Gln Ile Cys
             35                  40                  45

<210> SEQ ID NO 48
<211> LENGTH: 75
<212> TYPE: PRT
<213> ORGANISM: Homo sapiens

<400> SEQUENCE: 48

Cys Glu Lys Cys Phe Asn Glu Ile Gln Gly Glu Ser Val Ser Leu Gly
  1               5                  10                  15

Asp Asp Pro Ser Gln Pro Gln Thr Thr Ile Asn Asn Glu Gln Phe Ser
                 20                  25                  30

Lys Arg Lys Asn Asp Thr Leu Asp Pro Glu Leu Phe Val Glu Cys Thr
             35                  40                  45

Glu Cys Gly Arg Lys Met His Gln Ile Cys Val Leu His His Glu Ile
         50                  55                  60

Ile Trp Pro Ala Gly Phe Val Cys Asp Gly Cys
     65                  70                  75

<210> SEQ ID NO 49
<211> LENGTH: 75
<212> TYPE: PRT
<213> ORGANISM: Homo sapiens

<400> SEQUENCE: 49

Cys Glu Lys Cys Phe Thr Glu Ile Gln Gly Glu Asn Val Thr Leu Gly
  1               5                  10                  15

Asp Asp Pro Ser Gln Pro Gln Thr Thr Ile Ser Lys Asp Gln Phe Glu
                 20                  25                  30

Lys Lys Lys Asn Asp Thr Leu Asp Pro Glu Pro Phe Val Asp Cys Lys
             35                  40                  45

Glu Cys Gly Arg Lys Met His Gln Ile Cys Val Leu His Tyr Asp Ile
         50                  55                  60

Ile Trp Pro Ser Gly Phe Val Cys Asp Asn Cys
     65                  70                  75

<210> SEQ ID NO 50
<211> LENGTH: 59
<212> TYPE: PRT
<213> ORGANISM: Homo sapiens

<400> SEQUENCE: 50

Ser Trp Pro Phe Leu Lys Leu Val Ser Lys Ile Gln Val Pro Asp Tyr
  1               5                  10                  15

Tyr Asp Ile Ile Lys Lys Pro Ile Ala Leu Asn Ile Ile Arg Glu Lys
                 20                  25                  30
```

-continued

Val Asn Lys Cys Glu Tyr Lys Leu Ala Ser Glu Phe Ile Asp Asp Ile
        35                  40                  45

Glu Leu Met Phe Ser Asn Cys Phe Glu Tyr Asn
    50                  55

<210> SEQ ID NO 51
<211> LENGTH: 59
<212> TYPE: PRT
<213> ORGANISM: Homo sapiens

<400> SEQUENCE: 51

Ser Trp Pro Phe His His Pro Val Asn Lys Lys Phe Val Pro Asp Tyr
 1               5                  10                  15

Tyr Lys Val Ile Val Asn Pro Met Asp Ile Glu Thr Ile Arg Lys Asn
            20                  25                  30

Ile Ser Lys His Lys Tyr Gln Ser Arg Glu Ser Phe Leu Asp Asp Val
        35                  40                  45

Asn Leu Ile Leu Ala Asn Ser Val Lys Tyr Asn
    50                  55

<210> SEQ ID NO 52
<211> LENGTH: 59
<212> TYPE: PRT
<213> ORGANISM: Homo sapiens

<400> SEQUENCE: 52

Ala Trp Pro Phe Leu Glu Pro Val Asn Pro Arg Leu Val Ser Gly Tyr
 1               5                  10                  15

Arg Arg Ile Ile Lys Asn Pro Met Asp Phe Ser Thr Met Arg Glu Arg
            20                  25                  30

Leu Leu Arg Gly Gly Tyr Thr Ser Ser Glu Glu Phe Ala Ala Asp Ala
        35                  40                  45

Leu Leu Val Phe Asp Asn Cys Gln Thr Phe Asn
    50                  55

<210> SEQ ID NO 53
<211> LENGTH: 59
<212> TYPE: PRT
<213> ORGANISM: Homo sapiens

<400> SEQUENCE: 53

Ala Trp Pro Phe Met Glu Pro Val Lys Arg Thr Glu Ala Pro Gly Tyr
 1               5                  10                  15

Tyr Glu Val Ile Arg Ser Pro Met Asp Leu Lys Thr Met Ser Glu Arg
            20                  25                  30

Leu Lys Asn Arg Tyr Tyr Val Ser Lys Lys Leu Phe Met Ala Asp Leu
        35                  40                  45

Gln Arg Val Phe Thr Asn Cys Lys Glu Tyr Asn
    50                  55

<210> SEQ ID NO 54
<211> LENGTH: 82
<212> TYPE: PRT
<213> ORGANISM: Caenorhabditis elegans

<400> SEQUENCE: 54

Ala Leu Pro Phe Leu Glu Pro Val Asn Pro Lys Leu Val Pro Gly Tyr
 1               5                  10                  15

Lys Met Ile Ile Ser Lys Pro Met Asp Leu Lys Thr Ile Arg Gln Lys

-continued

```
                  20                  25                  30

Asn Glu Lys Leu Ile Val Ser Glu Thr Tyr Gln Phe Cys Phe Phe Ala
             35                  40                  45

Ile Phe Asp Leu Lys Leu Lys Met Lys Ile Thr Gln Tyr Glu Thr Pro
     50                  55                  60

Glu Asp Phe Ala Glu Asp Ile Glu Leu Met Phe Ala Asn Cys Arg Gln
 65                  70                  75                  80

Phe Asn
```

<210> SEQ ID NO 55
<211> LENGTH: 61
<212> TYPE: PRT
<213> ORGANISM: Homo sapiens

<400> SEQUENCE: 55

```
Ser Leu Pro Phe Arg Gln Pro Val Asp Pro Gln Leu Leu Gly Ile Pro
  1               5                  10                  15

Asp Tyr Phe Asp Ile Val Lys Met Pro Met Asp Leu Ser Thr Ile Lys
             20                  25                  30

Arg Lys Leu Asp Thr Gly Gln Tyr Gln Glu Pro Trp Gln Tyr Val Asp
         35                  40                  45

Asp Val Trp Leu Met Phe Asn Asn Ala Trp Leu Tyr Asn
     50                  55                  60
```

<210> SEQ ID NO 56
<211> LENGTH: 45
<212> TYPE: PRT
<213> ORGANISM: Homo sapiens

<400> SEQUENCE: 56

```
Cys Lys Ile Cys Arg Lys Lys Gly Asp Ala Glu Asn Met Val Leu Cys
  1               5                  10                  15

Asp Gly Cys Asp Arg Gly His His Thr Tyr Cys Val Arg Pro Lys Leu
             20                  25                  30

Lys Thr Val Pro Glu Gly Asp Trp Phe Cys Pro Glu Cys
         35                  40                  45
```

<210> SEQ ID NO 57
<211> LENGTH: 44
<212> TYPE: PRT
<213> ORGANISM: Caenorhabditis elegans

<400> SEQUENCE: 57

```
Cys Gln Ile Cys Lys Ser Met Asp Gly Asp Glu Met Leu Val Cys Asp
  1               5                  10                  15

Gly Cys Glu Ser Gly Cys His Met Glu Cys Phe Arg Pro Arg Met Thr
             20                  25                  30

Lys Val Pro Glu Gly Asp Trp Phe Cys Gln Arg Cys
         35                  40
```

<210> SEQ ID NO 58
<211> LENGTH: 44
<212> TYPE: PRT
<213> ORGANISM: Homo sapiens

<400> SEQUENCE: 58

```
Cys Met Phe Cys Gly Arg Gly Asn Asn Glu Asp Lys Leu Leu Leu Cys
  1               5                  10                  15

Asp Gly Cys Asp Ser Tyr His Thr Phe Cys Leu Ile Pro Pro Leu Pro
```

```
                  20                  25                  30

Asp Val Pro Lys Gly Asp Trp Arg Cys Pro Lys Cys
            35                  40

<210> SEQ ID NO 59
<211> LENGTH: 54
<212> TYPE: PRT
<213> ORGANISM: Homo sapiens

<400> SEQUENCE: 59

Cys Ser Phe Cys Leu Gly Thr Lys Glu Gln Asn Arg Glu Lys Lys Pro
1               5                   10                  15

Glu Glu Leu Ile Ser Cys Ala Asp Cys Gly Asn Ser Gly His Pro Ser
            20                  25                  30

Cys Leu Lys Phe Ser Pro Glu Leu Thr Val Arg Val Lys Ala Leu Arg
            35                  40                  45

Trp Gln Cys Ile Glu Cys
            50

<210> SEQ ID NO 60
<211> LENGTH: 46
<212> TYPE: PRT
<213> ORGANISM: Homo sapiens

<400> SEQUENCE: 60

Cys Ser Ser Cys Arg Asp Gln Gly Lys Asn Ala Asp Asn Met Leu Phe
1               5                   10                  15

Cys Asp Ser Cys Asp Arg Gly Phe His Met Glu Cys Cys Asp Pro Pro
            20                  25                  30

Leu Thr Arg Met Pro Lys Gly Met Trp Ile Cys Gln Ile Cys
            35                  40                  45

<210> SEQ ID NO 61
<211> LENGTH: 75
<212> TYPE: PRT
<213> ORGANISM: Homo sapiens

<400> SEQUENCE: 61

Cys Glu Lys Cys Phe Asn Glu Ile Gln Gly Glu Ser Val Ser Leu Gly
1               5                   10                  15

Asp Asp Pro Ser Gln Pro Gln Thr Thr Ile Asn Lys Glu Gln Phe Ser
            20                  25                  30

Lys Arg Lys Asn Asp Thr Leu Asp Pro Glu Leu Phe Val Glu Cys Thr
            35                  40                  45

Glu Cys Gly Arg Lys Met His Gln Ile Cys Val Leu His His Glu Ile
      50                  55                  60

Ile Trp Pro Ala Gly Phe Val Cys Asp Gly Cys
65                  70                  75

<210> SEQ ID NO 62
<211> LENGTH: 45
<212> TYPE: PRT
<213> ORGANISM: Homo sapiens

<400> SEQUENCE: 62

Cys Leu Val Cys Arg Lys Gly Asp Asn Asp Arg Phe Leu Leu Leu Cys
1               5                   10                  15

Asp Gly Cys Asp Arg Gly Cys His Ile Tyr Cys His Arg Pro Lys Met
            20                  25                  30
```

Glu Ala Val Pro Glu Gly Asp Trp Phe Cys Thr Val Cys
         35                  40                  45

<210> SEQ ID NO 63
<211> LENGTH: 211
<212> TYPE: PRT
<213> ORGANISM: Homo sapiens

<400> SEQUENCE: 63

Arg Glu Glu Lys Arg Lys Tyr Val Glu Tyr Leu Lys Gln Trp Ser Lys
  1               5                  10                  15

Pro Arg Glu Asp Met Glu Cys Asp Asp Leu Lys Glu Leu Pro Glu Pro
                 20                  25                  30

Thr Pro Val Lys Thr Arg Leu Pro Pro Glu Ile Phe Gly Asp Ala Leu
             35                  40                  45

Met Val Leu Glu Phe Leu Asn Ala Phe Gly Glu Leu Phe Asp Leu Gln
         50                  55                  60

Asp Glu Phe Pro Asp Gly Val Thr Leu Glu Val Leu Glu Ala Leu
 65                  70                  75                  80

Val Gly Asn Asp Ser Glu Gly Pro Leu Cys Glu Leu Leu Phe Phe Phe
                 85                  90                  95

Leu Thr Ala Ile Phe Gln Ala Ile Ala Glu Glu Glu Glu Val Ala
                100                 105                 110

Lys Glu Gln Leu Thr Asp Ala Asp Thr Lys Gly Cys Ser Leu Lys Ser
            115                 120                 125

Leu Asp Leu Asp Ser Cys Thr Leu Ser Glu Ile Leu Arg Leu His Ile
130                 135                 140

Leu Ala Ser Gly Ala Asp Val Thr Ser Ala Asn Ala Lys Tyr Arg Tyr
145                 150                 155                 160

Gln Lys Arg Gly Gly Phe Asp Ala Thr Asp Ala Cys Met Glu Leu
                165                 170                 175

Arg Leu Ser Asn Pro Ser Leu Val Lys Lys Leu Ser Ser Thr Ser Val
                180                 185                 190

Tyr Asp Leu Thr Pro Gly Glu Lys Met Lys Ile Leu His Ala Leu Cys
            195                 200                 205

Gly Lys Leu
        210

<210> SEQ ID NO 64
<211> LENGTH: 185
<212> TYPE: PRT
<213> ORGANISM: Caenorhabditis elegans

<400> SEQUENCE: 64

Leu Asn Asp Glu Phe Thr Glu Glu Leu Val His Ser Gln Ile Met Ser
  1               5                  10                  15

Asn Gly Val Asp Glu Cys Lys Ile Arg Glu Arg Glu Ala Asp Asp Leu
                 20                  25                  30

Leu Val Asn Ile Asn Asp Val Arg His Leu Pro Asp Phe Ser Arg Ile
             35                  40                  45

Gly Asn Gln Cys Leu Ser Ser Gln Gly Phe Ala Asp Ala Leu Met Val
         50                  55                  60

His Glu Phe Val Gln Asn Phe Gly His Val Leu Gly Ile Asp Leu Glu
 65                  70                  75                  80

Ile Ala Pro Lys Leu Glu Ser Leu Cys Ala Gly Leu Asp Gly Asp Ala
                 85                  90                  95

```
Asn His Ala Glu Gln Thr Leu Gln Leu Thr Arg Gln Leu Leu Arg Leu
                100                 105                 110

Ala Leu Glu Phe Pro Gly Met Gly Asn Glu Lys Arg Phe Gly Gln Gly
            115                 120                 125

Gly Gly Glu Met Gly Leu Asp Arg Glu Asn Phe Ser Glu Val Met Arg
        130                 135                 140

Leu Phe Leu Ile Asp Lys Gly Lys Arg Gly Glu Glu Leu Ser Gln Pro
145                 150                 155                 160

Leu Leu Thr Cys Asn Phe Leu Ser Ile Ser Pro Glu Gln Lys Ala Ser
                165                 170                 175

Ile Leu Ala Phe Leu Cys Asp Glu Leu
                180                 185

<210> SEQ ID NO 65
<211> LENGTH: 175
<212> TYPE: PRT
<213> ORGANISM: Homo sapiens

<400> SEQUENCE: 65

Leu Glu Glu Arg Gln Lys Gln Gln Met Ile Leu Glu Glu Met Lys Lys
1               5                   10                  15

Pro Thr Glu Asp Met Cys Leu Thr Asp His Gln Pro Leu Pro Asp Phe
            20                  25                  30

Ser Arg Val Pro Gly Leu Thr Leu Pro Ser Gly Ala Phe Ser Asp Cys
        35                  40                  45

Leu Thr Ile Val Glu Phe Leu His Ser Phe Gly Lys Val Leu Gly Phe
    50                  55                  60

Asp Pro Ala Lys Asp Val Pro Ser Leu Gly Val Leu Gln Glu Gly Leu
65                  70                  75                  80

Leu Cys Gln Gly Asp Ser Leu Gly Glu Val Gln Asp Leu Leu Val Arg
                85                  90                  95

Leu Leu Lys Ala Ala Leu His Asp Pro Gly Phe Pro Ser Tyr Cys Gln
            100                 105                 110

Ser Leu Lys Ile Leu Gly Glu Lys Val Ser Glu Ile Pro Leu Thr Arg
        115                 120                 125

Asp Asn Val Ser Glu Ile Leu Arg Cys Pro Leu Met Ala Tyr Gly Val
    130                 135                 140

Glu Pro Ala Leu Cys Asp Arg Leu Arg Thr Gln Pro Pro Gln Ala Gln
145                 150                 155                 160

Pro Pro Gln Lys Ala Ala Val Leu Ala Phe Pro Val His Glu Leu
                165                 170                 175

<210> SEQ ID NO 66
<211> LENGTH: 176
<212> TYPE: PRT
<213> ORGANISM: Homo sapiens

<400> SEQUENCE: 66

Leu Glu Gln Arg Arg Leu Glu Leu Glu Met Ala Lys Glu Leu Lys Lys
1               5                   10                  15

Pro Asn Glu Asp Met Cys Leu Ala Asp Gln Lys Pro Leu Pro Glu Leu
            20                  25                  30

Pro Arg Ile Pro Gly Leu Val Leu Ser Gly Ser Thr Phe Ser Asp Cys
        35                  40                  45

Leu Met Val Val Gln Phe Leu Arg Asn Phe Gly Lys Val Leu Gly Phe
    50                  55                  60
```

-continued

Asp Val Asn Ile Asp Val Pro Asn Leu Ser Val Leu Gln Glu Gly Leu
 65                  70                  75                  80

Leu Asn Ile Gly Asp Ser Met Gly Glu Val Gln Asp Leu Leu Val Arg
                 85                  90                  95

Leu Leu Ser Ala Ala Val Cys Asp Pro Gly Leu Ile Thr Gly Tyr Lys
                100                 105                 110

Ala Lys Thr Ala Leu Gly Glu His Leu Leu Asn Val Gly Val Asn Arg
            115                 120                 125

Asp Asn Val Ser Glu Ile Leu Gln Ile Phe Met Glu Ala His Cys Gly
130                 135                 140

Gln Thr Glu Leu Thr Glu Ser Leu Lys Thr Lys Ala Phe Gln Ala His
145                 150                 155                 160

Thr Pro Ala Gln Lys Ala Ser Val Leu Ala Phe Leu Ile Asn Glu Leu
                165                 170                 175

<210> SEQ ID NO 67
<211> LENGTH: 59
<212> TYPE: PRT
<213> ORGANISM: Homo sapiens

<400> SEQUENCE: 67

Tyr Pro Ile Thr Ala Val Ser Leu Met Glu Ala Leu Ser Ala Asp Lys
  1               5                  10                  15

Gly Gly Phe Leu Tyr Leu Asn Arg Val Leu Val Ile Leu Leu Gln Thr
                 20                  25                  30

Leu Leu Gln Asp Glu Ile Ala Glu Asp Tyr Gly Glu Leu Gly Met Lys
             35                  40                  45

Leu Ser Glu Ile Pro Leu His Ser Val Ser Glu
         50                  55

<210> SEQ ID NO 68
<211> LENGTH: 65
<212> TYPE: PRT
<213> ORGANISM: Homo sapiens

<400> SEQUENCE: 68

Tyr Pro Ile Thr Ala Val Ser Leu Met Glu Ala Leu Ser Ala Asp Lys
  1               5                  10                  15

Gly Gly Phe Leu Tyr Leu Asn Arg Val Leu Val Ile Leu Leu Gln Thr
                 20                  25                  30

Leu Leu Gln Thr Leu Leu Gln Asp Glu Ile Ala Glu Asp Tyr Gly Glu
             35                  40                  45

Leu Gly Met Lys Leu Ser Lys Ile Pro Leu Thr Leu His Ser Val Ser
 50                  55                  60

Glu
 65

<210> SEQ ID NO 69
<211> LENGTH: 1525
<212> TYPE: PRT
<213> ORGANISM: Homo sapiens

<400> SEQUENCE: 69

Met Ala Pro Leu Leu Gly Arg Lys Pro Phe Pro Leu Val Asn Pro Leu
  1               5                  10                  15

Pro Gly Glu Glu Pro Phe Phe Thr Ile Pro His Thr Gln Glu Ala Phe
                 20                  25                  30

Arg Thr Arg Glu Glu Tyr Glu Ala Arg Leu Glu Arg Tyr Ser Glu Arg

-continued

```
                35                  40                  45
Ile Trp Thr Cys Lys Ser Thr Gly Ser Ser Gln Leu Thr His Lys Glu
     50                  55                  60

Ala Trp Glu Glu Gln Glu Val Ala Glu Leu Leu Lys Glu Glu Phe
 65                  70                  75                  80

Pro Ala Trp Tyr Glu Lys Leu Val Leu Glu Met Val His His Asn Thr
                 85                  90                  95

Ala Ser Leu Glu Lys Leu Val Asp Thr Ala Trp Leu Glu Ile Met Thr
                100                 105                 110

Lys Tyr Ala Val Gly Glu Glu Cys Asp Phe Glu Val Gly Lys Glu Lys
                115                 120                 125

Met Leu Lys Val Lys Ile Val Lys Ile His Pro Leu Glu Lys Val Asp
                130                 135                 140

Glu Glu Ala Thr Glu Lys Lys Ser Asp Gly Ala Cys Asp Ser Pro Ser
145                 150                 155                 160

Ser Asp Lys Glu Asn Ser Ser Gln Ile Ala Gln Asp His Gln Lys Lys
                165                 170                 175

Glu Thr Val Val Lys Glu Asp Glu Gly Arg Arg Glu Ser Ile Asn Asp
                180                 185                 190

Arg Ala Arg Arg Ser Pro Arg Lys Leu Pro Thr Ser Leu Lys Lys Gly
                195                 200                 205

Glu Arg Lys Trp Ala Pro Pro Lys Phe Leu Pro His Lys Tyr Asp Val
210                 215                 220

Lys Leu Gln Asn Glu Asp Lys Ile Ile Ser Asn Val Pro Ala Asp Ser
225                 230                 235                 240

Leu Ile Arg Thr Glu Arg Pro Pro Asn Lys Glu Ile Val Arg Tyr Phe
                245                 250                 255

Ile Arg His Asn Ala Leu Arg Ala Gly Thr Gly Glu Asn Ala Pro Trp
                260                 265                 270

Val Val Glu Asp Glu Leu Val Lys Lys Tyr Ser Leu Pro Ser Lys Phe
                275                 280                 285

Ser Asp Phe Leu Leu Asp Pro Tyr Lys Tyr Met Thr Leu Asn Pro Ser
290                 295                 300

Thr Lys Arg Lys Asn Thr Gly Ser Pro Asp Arg Lys Pro Ser Lys Lys
305                 310                 315                 320

Ser Lys Thr Asp Asn Ser Ser Leu Ser Ser Pro Leu Asn Pro Lys Leu
                325                 330                 335

Trp Cys His Val His Leu Lys Lys Ser Leu Ser Gly Ser Pro Leu Lys
                340                 345                 350

Val Lys Asn Ser Lys Asn Ser Lys Ser Pro Glu Glu His Leu Glu Glu
                355                 360                 365

Met Met Lys Met Met Ser Pro Asn Lys Leu His Thr Asn Pro His Ile
370                 375                 380

Pro Lys Lys Gly Pro Pro Ala Lys Lys Pro Gly Lys His Ser Asp Lys
385                 390                 395                 400

Pro Leu Lys Ala Lys Gly Arg Ser Lys Gly Ile Leu Asn Gly Gln Lys
                405                 410                 415

Ser Thr Gly Asn Ser Lys Ser Pro Lys Lys Gly Leu Lys Thr Pro Lys
                420                 425                 430

Thr Lys Met Lys Gln Met Thr Leu Leu Asp Met Ala Lys Gly Thr Gln
                435                 440                 445

Lys Met Thr Arg Ala Pro Arg Asn Ser Gly Gly Thr Pro Arg Thr Ser
450                 455                 460
```

-continued

```
Ser Lys Pro His Lys His Leu Pro Pro Ala Ala Leu His Leu Ile Ala
465                 470                 475                 480

Tyr Tyr Lys Glu Asn Lys Asp Arg Glu Asp Lys Arg Ser Ala Leu Ser
                485                 490                 495

Cys Val Ile Ser Lys Thr Ala Arg Leu Leu Ser Ser Glu Asp Arg Ala
            500                 505                 510

Arg Leu Pro Glu Glu Leu Arg Ser Leu Val Gln Lys Arg Tyr Glu Leu
        515                 520                 525

Leu Glu His Lys Lys Arg Trp Ala Ser Met Ser Glu Glu Gln Arg Lys
    530                 535                 540

Glu Tyr Leu Lys Lys Arg Glu Glu Leu Lys Lys Lys Leu Lys Glu
545                 550                 555                 560

Lys Ala Lys Glu Arg Arg Glu Lys Glu Met Leu Glu Arg Leu Glu Lys
                565                 570                 575

Gln Lys Arg Tyr Glu Asp Gln Glu Leu Thr Gly Lys Asn Leu Pro Ala
            580                 585                 590

Phe Arg Leu Val Asp Thr Pro Glu Gly Leu Pro Asn Thr Leu Phe Gly
        595                 600                 605

Asp Val Ala Met Val Val Glu Phe Leu Ser Cys Tyr Ser Gly Leu Leu
    610                 615                 620

Leu Pro Asp Ala Gln Tyr Pro Ile Thr Ala Val Ser Leu Met Glu Ala
625                 630                 635                 640

Leu Ala Asp Lys Gly Gly Phe Leu Tyr Leu Asn Arg Val Leu Val Ile
                645                 650                 655

Leu Leu Gln Thr Leu Leu Gln Asp Glu Ile Ala Glu Asp Tyr Gly Glu
            660                 665                 670

Leu Gly Met Lys Leu Ser Glu Ile Pro Leu Thr Leu His Ser Val Ser
        675                 680                 685

Glu Leu Val Arg Leu Cys Leu Arg Arg Ser Asp Val Gln Glu Glu Ser
    690                 695                 700

Glu Gly Ser Asp Thr Asp Asp Asn Lys Asp Ser Ala Ala Phe Glu Asp
705                 710                 715                 720

Asn Glu Val Gln Asp Glu Phe Leu Glu Lys Leu Glu Thr Ser Glu Phe
                725                 730                 735

Phe Glu Leu Thr Ser Glu Glu Lys Leu Gln Ile Leu Thr Ala Leu Cys
            740                 745                 750

His Arg Ile Leu Met Thr Tyr Ser Val Gln Asp His Met Glu Thr Arg
        755                 760                 765

Gln Gln Met Ser Ala Glu Leu Trp Lys Glu Arg Leu Ala Val Leu Lys
    770                 775                 780

Glu Glu Asn Asp Lys Lys Arg Ala Glu Lys Gln Lys Arg Lys Glu Met
785                 790                 795                 800

Glu Ala Lys Asn Lys Glu Asn Gly Lys Val Glu Asn Gly Leu Gly Lys
                805                 810                 815

Thr Asp Arg Lys Lys Arg Ile Val Lys Phe Glu Pro Gln Val Asp Thr
            820                 825                 830

Glu Ala Glu Asp Met Ile Ser Ala Val Lys Ser Arg Arg Leu Leu Ala
        835                 840                 845

Ile Gln Ala Lys Lys Glu Arg Glu Ile Gln Glu Arg Glu Met Lys Val
    850                 855                 860

Lys Leu Glu Arg Gln Ala Glu Glu Glu Arg Ile Arg Lys His Lys Ala
865                 870                 875                 880
```

-continued

```
Ala Ala Glu Lys Ala Phe Gln Glu Gly Ile Ala Lys Ala Lys Leu Val
            885                 890                 895

Met Arg Arg Thr Pro Ile Gly Thr Asp Arg Asn His Asn Arg Tyr Trp
            900                 905                 910

Leu Phe Ser Asp Glu Val Pro Gly Leu Phe Ile Glu Lys Gly Trp Val
            915                 920                 925

His Asp Ser Ile Asp Tyr Arg Phe Asn His His Cys Lys Asp His Thr
            930                 935                 940

Val Ser Gly Cys Glu Asp Tyr Cys Pro Arg Ser Lys Lys Ala Asn Leu
945                 950                 955                 960

Gly Lys Asn Ala Ser Met Asn Thr Gln His Gly Thr Ala Thr Glu Val
            965                 970                 975

Ala Val Glu Thr Thr Pro Lys Gln Gly Gln Asn Leu Trp Phe Leu
            980                 985                 990

Cys Asp Ser Gln Lys Glu Leu Asp Glu Leu Leu Asn Cys Leu His Pro
            995                 1000                1005

Gln Gly Ile Arg Glu Ser Gln Leu Lys Glu Arg Leu Glu Lys Arg Tyr
            1010                1015                1020

Gln Asp Ile Ile His Ser Leu His Leu Ala Arg Lys Pro Asn Leu Gly
1025                1030                1035                1040

Leu Lys Ser Cys Asp Gly Asn Gln Glu Leu Leu Asn Phe Leu Arg Ser
            1045                1050                1055

Asp Leu Ile Glu Val Ala Thr Arg Leu Gln Lys Gly Gly Leu Gly Tyr
            1060                1065                1070

Val Glu Glu Thr Ser Glu Phe Glu Ala Arg Val Ile Ser Leu Glu Lys
            1075                1080                1085

Leu Lys Asp Phe Gly Glu Cys Val Ile Ala Leu Gln Ala Ser Val Ile
            1090                1095                1100

Lys Lys Phe Leu Gln Gly Phe Met Ala Pro Lys Gln Lys Arg Arg Lys
1105                1110                1115                1120

Leu Gln Ser Glu Asp Ser Ala Lys Thr Glu Glu Val Asp Glu Glu Lys
            1125                1130                1135

Lys Met Val Glu Glu Ala Lys Val Ala Ser Ala Leu Glu Lys Trp Lys
            1140                1145                1150

Thr Ala Ile Arg Glu Ala Gln Thr Phe Ser Arg Met His Val Leu Leu
            1155                1160                1165

Gly Met Leu Asp Ala Cys Ile Lys Trp Asp Met Ser Ala Glu Asn Ala
            1170                1175                1180

Arg Cys Lys Val Cys Pro Lys Lys Gly Glu Asp Asp Lys Leu Ile Leu
1185                1190                1195                1200

Cys Asp Glu Cys Asn Lys Ala Phe His Leu Phe Cys Leu Arg Pro Ala
            1205                1210                1215

Leu Tyr Glu Val Pro Asp Gly Trp Gln Cys Pro Ala Cys Gln Pro
            1220                1225                1230

Ala Thr Ala Arg Arg Asn Ser Arg Gly Arg Asn Tyr Thr Glu Glu Ser
            1235                1240                1245

Ala Ser Glu Asp Ser Glu Asp Glu Ser Asp Glu Glu Glu Glu Glu
            1250                1255                1260

Glu Glu Glu Glu Glu Glu Asp Tyr Glu Val Ala Gly Leu Arg Leu
1265                1270                1275                1280

Arg Pro Arg Lys Thr Ile Arg Gly Lys His Ser Val Ile Pro Ala
            1285                1290                1295

Ala Arg Ser Gly Arg Arg Pro Gly Lys Lys Pro His Ser Thr Arg Arg
```

-continued

```
                    1300                1305                1310
Ser Gln Pro Lys Ala Pro Val Asp Ala Glu Val Asp Glu Leu Val
            1315                1320                1325

Leu Gln Thr Lys Arg Ser Arg Arg Gln Ser Leu Glu Leu Gln Lys
    1330                1335                1340

Cys Glu Glu Ile Leu His Lys Ile Val Lys Tyr Arg Phe Ser Trp Pro
1345                1350                1355                1360

Phe Arg Glu Pro Val Thr Arg Asp Glu Ala Glu Asp Tyr Tyr Asp Val
            1365                1370                1375

Ile Thr His Pro Met Asp Phe Gln Thr Val Gln Asn Lys Cys Ser Cys
            1380                1385                1390

Gly Ser Tyr Arg Ser Val Gln Glu Phe Leu Thr Asp Met Lys Gln Val
            1395                1400                1405

Phe Thr Asn Ala Glu Val Tyr Asn Cys Arg Gly Ser His Val Leu Ser
    1410                1415                1420

Cys Met Val Lys Thr Glu Gln Cys Leu Val Val Leu Leu His Lys His
1425                1430                1435                1440

Leu Pro Gly His Pro Tyr Val Arg Lys Arg Lys Lys Phe Pro Asp
            1445                1450                1455

Arg Leu Ala Glu Asp Glu Gly Asp Ser Glu Pro Glu Ala Val Gly Gln
            1460                1465                1470

Ser Arg Asp Glu Asp Arg Arg Ser Arg Glu Ala Glu Ile Gln Glu Trp
            1475                1480                1485

Leu Gln Asp Thr Ser Leu Tyr Ala Ser Ala Lys Ile Asn Ser Lys Asp
            1490                1495                1500

His Asn Cys Phe Met Met Leu Val Asn Thr Gln Phe Cys Met Ala Leu
1505                1510                1515                1520

Thr Asp Thr Val Thr
                1525

<210> SEQ ID NO 70
<211> LENGTH: 1673
<212> TYPE: PRT
<213> ORGANISM: Homo sapiens

<400> SEQUENCE: 70

Met Glu Asp Ala Ser Glu Ser Arg Gly Val Ala Pro Leu Ile Asn
1               5                   10                  15

Asn Val Leu Pro Gly Ser Pro Leu Ser Leu Pro Val Ser Val Thr
                20                  25                  30

Gly Cys Lys Ser His Arg Val Ala Asn Lys Lys Val Glu Ala Arg Ser
            35                  40                  45

Glu Lys Leu Leu Pro Thr Ala Leu Pro Pro Ser Glu Pro Lys Val Asp
    50                  55                  60

Gln Lys Leu Pro Arg Ser Ser Glu Arg Arg Gly Ser Gly Gly Gly Thr
65                  70                  75                  80

Gln Phe Pro Ala Arg Ser Arg Ala Val Ala Ala Gly Glu Ala Ala Ala
            85                  90                  95

Arg Gly Ala Ala Gly Pro Glu Arg Gly Ser Pro Leu Gly Arg Arg Val
            100                 105                 110

Ser Pro Arg Cys Leu Cys Ser Gly Glu Gly Gln Val Ala Val Gly
        115                 120                 125

Val Ile Ala Gly Lys Arg Gly Arg Gly Arg Asp Gly Ser Arg Arg
    130                 135                 140
```

-continued

```
Ala Pro Gly Gly Arg Glu Met Pro Leu Leu His Arg Lys Pro Phe Val
145                 150                 155                 160

Arg Gln Lys Pro Pro Ala Asp Leu Arg Pro Asp Glu Val Phe Tyr
                165                 170                 175

Cys Lys Val Thr Asn Glu Ile Phe Arg His Tyr Asp Asp Phe Phe Glu
                180                 185                 190

Arg Thr Ile Leu Cys Asn Ser Leu Val Trp Ser Cys Ala Val Thr Gly
            195                 200                 205

Arg Pro Gly Leu Thr Tyr Gln Glu Ala Leu Glu Ser Glu Lys Lys Ala
        210                 215                 220

Arg Gln Asn Leu Gln Ser Phe Pro Glu Pro Leu Ile Ile Pro Val Leu
225                 230                 235                 240

Tyr Leu Thr Ser Leu Thr His Arg Ser Arg Leu His Glu Ile Cys Asp
                245                 250                 255

Asp Ile Phe Ala Tyr Val Lys Asp Arg Tyr Phe Val Glu Glu Thr Val
                260                 265                 270

Glu Val Ile Arg Asn Asn Gly Ala Arg Leu Gln Cys Thr Ile Leu Glu
            275                 280                 285

Val Leu Pro Pro Ser His Gln Asn Gly Phe Ala Asn Gly His Val Asn
        290                 295                 300

Ser Val Asp Gly Glu Thr Ile Ile Ser Asp Ser Asp Ser Glu
305                 310                 315                 320

Thr Gln Ser Cys Ser Phe Gln Asn Gly Lys Lys Lys Asp Ala Ile Asp
                325                 330                 335

Pro Leu Leu Phe Lys Tyr Lys Val Gln Pro Thr Lys Lys Glu Leu His
                340                 345                 350

Glu Ser Ala Ile Val Lys Ala Thr Gln Ile Ser Arg Arg Lys His Leu
            355                 360                 365

Phe Ser Arg Asp Lys Leu Lys Leu Phe Leu Lys Gln His Cys Glu Pro
        370                 375                 380

Gln Glu Gly Val Ile Lys Ile Lys Ala Ser Ser Leu Ser Thr Tyr Lys
385                 390                 395                 400

Ile Ala Glu Gln Asp Phe Ser Tyr Phe Phe Pro Asp Asp Pro Pro Thr
                405                 410                 415

Phe Ile Phe Ser Pro Ala Asn Arg Arg Arg Gly Arg Pro Pro Lys Arg
            420                 425                 430

Ile His Ile Ser Gln Glu Asp Asn Val Ala Asn Lys Gln Thr Leu Ala
        435                 440                 445

Ser Tyr Arg Ser Lys Ala Thr Lys Glu Arg Asp Lys Leu Leu Lys Gln
    450                 455                 460

Glu Glu Met Lys Ser Leu Ala Phe Glu Lys Ala Lys Leu Lys Arg Glu
465                 470                 475                 480

Lys Ala Asp Ala Leu Glu Ala Lys Lys Glu Lys Glu Asp Lys Glu
                485                 490                 495

Lys Lys Arg Glu Glu Leu Lys Lys Ile Val Glu Glu Arg Leu Lys
            500                 505                 510

Lys Lys Glu Glu Lys Glu Arg Leu Lys Val Glu Arg Glu Lys Glu Arg
        515                 520                 525

Glu Lys Leu Arg Glu Lys Arg Lys Tyr Val Glu Tyr Lys Gln Trp
        530                 535                 540

Ser Lys Pro Arg Glu Asp Met Glu Cys Asp Asp Leu Lys Glu Leu Pro
545                 550                 555                 560

Glu Pro Thr Pro Val Lys Thr Arg Leu Pro Pro Glu Ile Phe Gly Asp
```

```
                    565                 570                 575
Ala Leu Met Val Leu Glu Phe Leu Asn Ala Phe Gly Glu Leu Phe Asp
                580                 585                 590
Leu Gln Asp Glu Phe Pro Asp Gly Val Thr Leu Glu Val Leu Glu Glu
                595                 600                 605
Ala Leu Val Gly Asn Asp Ser Glu Gly Pro Leu Cys Glu Leu Leu Phe
                610                 615                 620
Phe Phe Leu Thr Ala Ile Phe Gln Ala Ile Ala Glu Glu Glu Glu Glu
625                 630                 635                 640
Val Ala Lys Glu Gln Leu Thr Asp Ala Asp Thr Lys Gly Cys Ser Leu
                645                 650                 655
Lys Ser Leu Asp Leu Asp Ser Cys Thr Leu Ser Glu Ile Leu Arg Leu
                660                 665                 670
His Ile Leu Ala Ser Gly Ala Asp Val Thr Ser Ala Asn Ala Lys Tyr
                675                 680                 685
Arg Tyr Gln Lys Arg Gly Gly Phe Asp Ala Thr Asp Asp Ala Cys Met
                690                 695                 700
Glu Leu Arg Leu Ser Asn Pro Ser Leu Val Lys Lys Leu Ser Ser Thr
705                 710                 715                 720
Ser Val Tyr Asp Leu Thr Pro Gly Glu Lys Met Lys Ile Leu His Ala
                725                 730                 735
Leu Cys Gly Lys Leu Leu Thr Leu Val Ser Thr Arg Asp Phe Ile Glu
                740                 745                 750
Asp Tyr Val Asp Ile Leu Arg Gln Ala Lys Gln Glu Phe Arg Glu Leu
                755                 760                 765
Lys Ala Glu Gln His Arg Lys Glu Arg Glu Glu Ala Ala Ala Arg Ile
                770                 775                 780
Arg Lys Arg Lys Glu Glu Lys Leu Lys Glu Gln Glu Gln Lys Met Lys
785                 790                 795                 800
Glu Lys Gln Glu Lys Leu Lys Glu Asp Glu Gln Arg Asn Ser Thr Ala
                805                 810                 815
Asp Ile Ser Ile Gly Glu Glu Glu Arg Glu Asp Phe Asp Thr Ser Ile
                820                 825                 830
Glu Ser Lys Asp Thr Glu Gln Lys Glu Leu Asp Gln Asp Met Phe Thr
                835                 840                 845
Glu Asp Glu Asp Asp Pro Gly Ser His Lys Arg Gly Arg Arg Gly Lys
850                 855                 860
Arg Gly Gln Asn Gly Phe Lys Glu Phe Thr Arg Gln Glu Gln Ile Asn
865                 870                 875                 880
Cys Val Thr Arg Glu Leu Leu Thr Ala Asp Glu Glu Ala Leu Lys
                885                 890                 895
Gln Glu His Gln Arg Lys Glu Lys Glu Leu Leu Glu Lys Leu Gln Ser
                900                 905                 910
Ala Ile Ala Cys Thr Asn Ile Phe Pro Leu Gly Arg Asp Arg Met Tyr
                915                 920                 925
Arg Arg Tyr Trp Ile Phe Pro Ser Leu Pro Gly Leu Phe Ile Glu Glu
                930                 935                 940
Asp Tyr Ser Gly Leu Thr Glu Asp His Leu Leu Pro Arg Pro Ser Ser
945                 950                 955                 960
Phe Gln Asn Asn Val Gln Ser Gln Asp Pro Gln Val Ser Thr Lys Thr
                965                 970                 975
Gly Glu Pro Leu Met Ser Glu Ser Thr Ser Asn Ile Asp Gln Gly Pro
                980                 985                 990
```

-continued

```
Arg Asp His Ser Val Gln Leu Pro Lys Pro Val His Lys Pro Asn Arg
        995                 1000                1005
Trp Cys Phe Tyr Ser Ser Cys Glu Gln Leu Asp Gln Leu Ile Glu Ala
    1010                1015                1020
Leu Asn Ser Arg Gly His Arg Glu Ser Ala Leu Lys Glu Thr Leu Leu
1025                1030                1035                1040
Gln Glu Lys Ser Arg Ile Cys Ala Gln Leu Ala Arg Phe Ser Glu Glu
            1045                1050                1055
Lys Phe His Phe Ser Asp Lys Arg Gln Pro Asp Ser Lys Pro Thr Tyr
            1060                1065                1070
Ser Arg Gly Arg Ser Ser Asn Ala Tyr Asp Pro Ser Gln Met Cys Ala
            1075                1080                1085
Glu Lys Gln Leu Glu Leu Arg Leu Arg Asp Phe Leu Leu Asp Ile Glu
            1090                1095                1100
Asp Arg Ile Tyr Gln Gly Thr Leu Gly Ala Ile Lys Val Thr Asp Arg
1105                1110                1115                1120
His Ile Trp Arg Ser Ala Leu Glu Ser Gly Arg Tyr Glu Leu Leu Ser
            1125                1130                1135
Glu Glu Asn Lys Glu Asn Gly Ile Ile Lys Thr Val Asn Glu Asp Val
            1140                1145                1150
Glu Glu Met Glu Ile Asp Glu Gln Thr Lys Val Ile Val Lys Asp Arg
            1155                1160                1165
Leu Leu Gly Ile Lys Thr Glu Thr Pro Ser Thr Val Ser Thr Asn Ala
            1170                1175                1180
Ser Thr Pro Gln Ser Val Ser Ser Val Val His Tyr Leu Ala Met Ala
1185                1190                1195                1200
Leu Phe Gln Ile Glu Gln Gly Leu Glu Arg Arg Phe Leu Lys Ala Pro
            1205                1210                1215
Leu Asp Ala Ser Asp Ser Gly Arg Ser Tyr Lys Thr Val Leu Asp Arg
            1220                1225                1230
Trp Arg Glu Ser Leu Leu Ser Ser Ala Ser Leu Ser Gln Val Phe Leu
            1235                1240                1245
His Leu Ser Thr Leu Asp Arg Ser Val Ile Trp Ser Lys Ser Ile Leu
            1250                1255                1260
Asn Ala Arg Cys Lys Ile Cys Arg Lys Lys Gly Asp Ala Glu Asn Met
1265                1270                1275                1280
Val Leu Cys Asp Gly Cys Asp Arg Gly His His Thr Tyr Cys Val Arg
            1285                1290                1295
Pro Lys Leu Lys Ile Val Pro Glu Gly Asp Trp Phe Cys Pro Glu Cys
            1300                1305                1310
Arg Pro Lys Gln Arg Cys Arg Arg Leu Ser Phe Arg Gln Arg Pro Ser
            1315                1320                1325
Leu Glu Ser Asp Glu Asp Val Glu Asp Ser Met Gly Gly Glu Asp Asp
            1330                1335                1340
Glu Val Asp Gly Asp Glu Glu Gly Gln Ser Glu Glu Glu Tyr
1345                1350                1355                1360
Glu Val Glu Gln Asp Glu Asp Ser Gln Glu Glu Glu Val Ser
            1365                1370                1375
Leu Pro Lys Arg Gly Arg Pro Gln Val Arg Leu Pro Val Lys Thr Arg
            1380                1385                1390
Gly Lys Leu Ser Ser Ser Phe Ser Arg Gly Gln Gln Gln Glu Pro
            1395                1400                1405
```

-continued

```
Gly Arg Tyr Pro Ser Arg Ser Gln Gln Ser Thr Pro Lys Thr Thr Val
    1410                1415                1420
Ser Ser Lys Thr Gly Arg Ser Leu Arg Lys Ile Asn Ser Ala Pro Pro
1425                1430                1435                1440
Thr Glu Thr Lys Ser Leu Arg Ile Ala Ser Arg Ser Thr Arg His Ser
            1445                1450                1455
His Gly Pro Leu Gln Ala Asp Val Phe Val Glu Leu Leu Ser Pro Arg
        1460                1465                1470
Arg Lys Arg Arg Gly Arg Lys Ser Ala Asn Asn Thr Pro Glu Asn Ser
    1475                1480                1485
Pro Asn Phe Pro Asn Phe Arg Val Ile Ala Thr Lys Ser Ser Glu Gln
    1490                1495                1500
Ser Arg Ser Val Asn Ile Ala Ser Lys Leu Ser Leu Gln Glu Ser Glu
1505                1510                1515                1520
Ser Lys Arg Arg Cys Arg Lys Arg Gln Ser Pro Glu Pro Ser Pro Val
            1525                1530                1535
Thr Leu Gly Arg Arg Ser Ser Gly Arg Gln Gly Gly Val His Glu Leu
        1540                1545                1550
Ser Ala Phe Glu Gln Leu Val Val Glu Leu Val Arg His Asp Asp Ser
    1555                1560                1565
Trp Pro Phe Leu Lys Leu Val Ser Lys Ile Gln Val Pro Asp Tyr Tyr
    1570                1575                1580
Asp Ile Ile Lys Lys Pro Ile Ala Leu Asn Ile Ile Arg Glu Lys Val
1585                1590                1595                1600
Asn Lys Cys Glu Tyr Lys Leu Ala Ser Glu Phe Ile Asp Asp Ile Glu
            1605                1610                1615
Leu Met Phe Ser Asn Cys Phe Glu Tyr Asn Pro Arg Asn Thr Ser Glu
        1620                1625                1630
Ala Lys Ala Gly Thr Arg Leu Gln Ala Phe Phe His Ile Gln Ala Gln
    1635                1640                1645
Lys Leu Gly Leu His Val Thr Pro Ser Asn Val Asp Gln Val Ser Thr
1650                1655                1660
Pro Pro Ala Ala Lys Lys Ser Arg Ile
1665                1670

<210> SEQ ID NO 71
<211> LENGTH: 1876
<212> TYPE: PRT
<213> ORGANISM: Homo sapiens

<400> SEQUENCE: 71

Met Glu Met Glu Ala Asn Glu Ala Asn Asp His Phe Asn Phe Thr Gly
 1               5                  10                  15
Leu Pro Pro Ala Pro Ala Ala Ser Gly Leu Lys Pro Ser Pro Ser Ser
                20                  25                  30
Gly Glu Gly Leu Tyr Thr Asn Gly Ser Pro His Asn Phe Pro Gln Gln
            35                  40                  45
Gly Lys Ser Leu Asn Gly Asp Val Asn Val Asn Gly Leu Ser Thr Val
        50                  55                  60
Ser His Thr Thr Thr Ser Gly Ile Leu Asn Ser Ala Pro His Ser Ser
65                  70                  75                  80
Ser Thr Ser His Leu His His Pro Ser Val Ala Tyr Asp Cys Leu Trp
                85                  90                  95
Asn Tyr Ser Gln Tyr Pro Ser Ala Asn Pro Gly Ser Asn Leu Lys Asp
                100                 105                 110
```

-continued

```
Pro Pro Leu Leu Ser Gln Phe Ser Gly Gly Gln Tyr Pro Leu Asn Gly
        115                 120                 125

Ile Leu Gly Gly Ser Arg Gln Pro Ser Pro Ser His Asn Thr Asn
        130                 135             140

Leu Arg Ala Gly Ser Gln Lys Phe Trp Ala Asn Gly Thr His Ser Pro
145                 150                 155                 160

Met Gly Leu Asn Phe Asp Ser Gln Glu Leu Tyr Asp Ser Phe Pro Asp
                165                 170                 175

Gln Asn Phe Glu Glu Val Cys Ser Gly Ile His Pro Asp Glu Ala Ala
                180                 185                 190

Glu Lys Glu Met Thr Ser Val Val Ala Glu Asn Gly Thr Gly Leu Val
            195                 200                 205

Cys Ser Leu Glu Leu Glu Glu Gln Pro Glu Leu Lys Met Cys Gly
        210                 215                 220

Tyr Asn Gly Ser Val Pro Ser Val Glu Ser Leu His Gln Glu Val Ser
225                 230                 235                 240

Val Leu Val Pro Asp Pro Thr Val Ser Cys Leu Asp Asp Pro Ser His
                245                 250                 255

Leu Pro Asp Gln Leu Glu Asp Thr Pro Ile Leu Ser Glu Asp Ser Leu
        260                 265                 270

Glu Pro Phe Asn Ser Leu Ala Pro Glu Pro Val Ser Gly Gly Leu Tyr
    275                 280                 285

Gly Ile Asp Asp Thr Glu Leu Met Gly Ala Glu Asp Lys Leu Pro Leu
        290                 295                 300

Glu Asp Ser Pro Val Ile Ser Ala Leu Asp Cys Pro Ser Leu Asn Asn
305                 310                 315                 320

Ala Thr Ala Phe Ser Leu Leu Ala Asp Asp Ser Gln Thr Ser Thr Ser
                325                 330                 335

Ile Phe Ala Ser Pro Thr Ser Pro Pro Val Leu Gly Glu Ser Val Leu
            340                 345                 350

Gln Asp Asn Ser Phe Asp Leu Asn Asn Gly Ser Asp Ala Glu Gln Glu
        355                 360                 365

Glu Met Glu Thr Gln Ser Ser Asp Phe Pro Pro Ser Leu Thr Gln Pro
    370                 375                 380

Ala Pro Asp Gln Ser Ser Thr Ile Gln Leu His Pro Ala Thr Ser Pro
385                 390                 395                 400

Ala Val Ser Pro Thr Thr Ser Pro Ala Val Ser Leu Val Val Ser Pro
                405                 410                 415

Ala Ala Ser Pro Glu Ile Ser Pro Glu Val Cys Pro Ala Ala Ser Thr
            420                 425                 430

Val Val Ser Pro Ala Val Phe Ser Val Val Ser Pro Ala Ser Ser Ala
        435                 440                 445

Val Leu Pro Ala Val Ser Leu Glu Val Pro Leu Thr Ala Ser Val Thr
    450                 455                 460

Ser Pro Lys Ala Ser Pro Val Thr Ser Pro Ala Ala Ala Phe Pro Thr
465                 470                 475                 480

Ala Ser Pro Ala Asn Lys Asp Val Ser Ser Phe Leu Glu Thr Thr Ala
                485                 490                 495

Asp Val Glu Glu Ile Thr Gly Glu Gly Leu Thr Ala Ser Gly Ser Gly
            500                 505                 510

Asp Val Met Arg Arg Ile Ala Thr Pro Glu Glu Val Arg Leu Pro
        515                 520                 525
```

-continued

```
Leu Gln His Gly Trp Arg Arg Glu Val Arg Ile Lys Lys Gly Ser His
    530                 535                 540
Arg Trp Gln Gly Glu Thr Trp Tyr Tyr Gly Pro Cys Gly Lys Arg Met
545                 550                 555                 560
Lys Gln Phe Pro Glu Val Ile Lys Tyr Leu Ser Arg Asn Leu Val His
                565                 570                 575
Ser Val Arg Arg Glu His Phe Ser Phe Ser Pro Arg Met Pro Val Gly
            580                 585                 590
Asp Phe Phe Glu Glu Arg Asp Thr Pro Glu Gly Leu Gln Trp Val Gln
        595                 600                 605
Leu Ser Ala Glu Glu Ile Pro Ser Arg Ile Gln Ala Ile Thr Gly Lys
    610                 615                 620
Arg Gly Arg Pro Arg Asn Thr Glu Lys Ala Lys Thr Lys Glu Val Pro
625                 630                 635                 640
Lys Val Lys Arg Gly Arg Gly Arg Pro Pro Lys Val Lys Ile Thr Glu
                645                 650                 655
Leu Leu Asn Lys Thr Asp Asn Arg Pro Leu Lys Lys Leu Glu Ala Gln
            660                 665                 670
Glu Thr Leu Asn Glu Glu Asp Lys Ala Lys Ile Ala Lys Ser Lys Lys
        675                 680                 685
Lys Met Arg Gln Lys Val Gln Arg Gly Glu Cys Leu Thr Thr Ile Gln
    690                 695                 700
Gly Gln Ala Arg Asn Lys Phe Lys Gln Glu Thr Lys Ser Leu Lys His
705                 710                 715                 720
Lys Glu Ala Lys Lys Lys Ser Lys Ala Glu Lys Glu Arg Gly Lys Thr
                725                 730                 735
Lys Gln Glu Lys Leu Lys Glu Lys Val Lys Arg Glu Lys Lys Glu Lys
            740                 745                 750
Val Lys Lys Glu Lys Glu Val Thr Lys Ala Lys Pro Ala Cys Lys
    755                 760                 765
Ala Asp Lys Thr Leu Ala Thr Gln Arg Arg Leu Glu Glu Arg Gln Lys
770                 775                 780
Gln Gln Met Ile Leu Glu Glu Met Lys Lys Pro Thr Glu Asp Met Cys
785                 790                 795                 800
Leu Thr Asp His Gln Pro Leu Pro Asp Phe Ser Arg Val Pro Gly Leu
                805                 810                 815
Thr Leu Pro Ser Gly Ala Phe Ser Asp Cys Leu Thr Ile Val Glu Phe
            820                 825                 830
Leu His Ser Pro Gly Lys Val Leu Gly Phe Asp Pro Ala Lys Asp Val
        835                 840                 845
Pro Ser Leu Gly Val Leu Gln Glu Gly Leu Leu Cys Gln Gly Asp Ser
    850                 855                 860
Leu Gly Glu Val Gln Asp Leu Leu Val Arg Leu Leu Lys Ala Ala Leu
865                 870                 875                 880
His Asp Pro Gly Phe Pro Ser Tyr Cys Gln Ser Lys Lys Ile Leu Gly
                885                 890                 895
Glu Lys Val Ser Glu Ile Pro Leu Thr Arg Asp Asn Val Ser Glu Ile
            900                 905                 910
Leu Arg Cys Phe Leu Met Ala Tyr Gly Val Glu Pro Ala Leu Cys Asp
        915                 920                 925
Arg Leu Arg Thr Gln Pro Phe Gln Ala Gln Pro Gln Gln Lys Ala
    930                 935                 940
Ala Val Leu Ala Phe Pro Val His Glu Leu Asn Gly Ser Thr Leu Ile
```

-continued

```
945              950              955              960
Ile Asn Glu Ile Asp Lys Thr Leu Glu Ser Met Ser Tyr Arg Lys
                965              970              975

Asn Lys Trp Ile Val Glu Gly Arg Leu Arg Leu Lys Thr Val Leu
            980              985              990

Ala Lys Arg Thr Gly Arg Ser Glu Val Glu Met Gly Arg Pro Glu Glu
        995             1000             1005

Cys Leu Gly Arg Arg Arg Ser Ser Arg Ile Met Glu Glu Thr Ser Gly
       1010             1015             1020

Met Glu Glu Glu Glu Glu Glu Ser Ile Ala Ala Val Pro Gly Arg
1025            1030             1035             1040

Arg Gly Arg Arg Asp Gly Glu Val Asp Ala Thr Ala Ser Ser Ile Pro
           1045             1050             1055

Glu Leu Glu Arg Gln Ile Glu Lys Leu Ser Lys Arg Gln Leu Phe Phe
           1060             1065             1070

Arg Lys Lys Leu Leu His Ser Ser Gln Met Leu Arg Ala Val Ser Leu
           1075             1080             1085

Gly Gln Asp Arg Tyr Arg Arg Tyr Trp Val Leu Pro Tyr Leu Ala
           1090             1095             1100

Gly Ile Phe Val Glu Gly Thr Glu Gly Asn Leu Val Pro Glu Val
1105            1110             1115             1120

Ile Lys Lys Glu Thr Asp Ser Leu Lys Val Ala Ala His Ala Ser Leu
           1125             1130             1135

Asn Pro Ala Leu Phe Ser Met Lys Met Glu Leu Ala Gly Ser Asn Thr
           1140             1145             1150

Thr Ala Ser Ser Pro Ala Arg Ala Arg Ser Arg Pro Leu Lys Thr Lys
           1155             1160             1165

Pro Gly Phe Met Gln Pro Arg Glu Phe Lys Ser Pro Val Arg Gly Gln
           1170             1175             1180

Asp Ser Glu Gln Pro Gln Ala Gln Leu Gln Pro Glu Ala Gln Leu His
1185            1190             1195             1200

Val Pro Ala Gln Pro Gln Pro Gln Leu Gln Leu Gln Leu Gln Ser His
           1205             1210             1215

Lys Gly Phe Leu Glu Gln Glu Gly Ser Pro Leu Ser Leu Gly Gln Ser
           1220             1225             1230

Gln His Asp Leu Ser Gln Ser Ala Phe Leu Ser Trp Leu Ser Gln Thr
           1235             1240             1245

Gln His Ser Ser Leu Leu Ser Ser Val Leu Thr Pro Asp Ser Ser
           1250             1255             1260

Pro Gly Lys Leu Asp Pro Ala Pro Ser Gln Pro Pro Glu Glu Pro Glu
1265            1270             1275             1280

Pro Asp Glu Ala Glu Ser Ser Pro Asp Leu Gln Ala Phe Trp Phe Asn
           1285             1290             1295

Ile Ser Ala Gln Met Pro Cys Asn Ala Ala Pro Thr Pro Pro Leu Ala
           1300             1305             1310

Val Ser Glu Asp Gln Pro Thr Pro Ser Pro Gln Gln Leu Ala Ser Ser
           1315             1320             1325

Lys Pro Met Asn Arg Pro Ser Ala Ala Asn Pro Cys Ser Pro Val Gln
           1330             1335             1340

Phe Ser Ser Thr Pro Leu Ala Gly Leu Ala Pro Lys Arg Arg Ala Gly
1345            1350             1355             1360

Asp Pro Gly Glu Met Pro Gln Ser Pro Thr Gly Leu Gly Gln Pro Lys
           1365             1370             1375
```

-continued

```
Arg Arg Gly Arg Pro Pro Ser Lys Phe Phe Lys Gln Met Glu Gln Arg
            1380                1385                1390
Val Leu Thr Gln Leu Thr Ala Gln Pro Val Pro Pro Glu Met Cys Ser
        1395                1400                1405
Gly Trp Trp Trp Ile Pro Asp Pro Glu Met Leu Asp Ala Met Leu Lys
        1410                1415                1420
Ala Leu His Pro Arg Gly Ile Arg Glu Lys Ala Leu His Lys His Leu
1425                1430                1435                1440
Asn Lys His Arg Asp Phe Leu Gln Glu Val Cys Leu Arg Pro Ser Ala
            1445                1450                1455
Asp Pro Ile Pro Glu Pro Arg Gln Leu Pro Ala Phe Gln Glu Gly Ile
            1460                1465                1470
Met Ser Trp Ser Pro Lys Glu Lys Thr Tyr Glu Thr Asp Leu Ala Val
        1475                1480                1485
Leu Gln Trp Val Glu Glu Leu Glu Gln Arg Val Ile Met Ser Asp Leu
    1490                1495                1500
Gln Ile Arg Gly Trp Thr Cys Pro Ser Pro Asp Ser Thr Arg Glu Asp
1505                1510                1515                1520
Leu Ala Tyr Cys Glu His Leu Ser Asp Ser Gln Glu Asp Ile Thr Trp
            1525                1530                1535
Arg Gly Pro Gly Arg Glu Gly Leu Ala Pro Gln Arg Lys Thr Thr Asn
            1540                1545                1550
Pro Leu Asp Leu Ala Val Met Arg Leu Ala Ala Leu Glu Gln Asn Val
        1555                1560                1565
Lys Arg Arg Tyr Leu Arg Glu Pro Leu Trp Pro Thr His Glu Trp Val
    1570                1575                1580
Leu Glu Lys Ala Leu Leu Ser Thr Pro Asn Gly Ala Pro Glu Gly Thr
1585                1590                1595                1600
Thr Thr Glu Ile Ser Tyr Glu Ile Thr Pro Arg Ile Arg Ile Trp Arg
            1605                1610                1615
Gln Thr Leu Gln Arg Cys Arg Ser Ala Ala His Val Cys Leu Cys Leu
            1620                1625                1630
Gly His Leu Glu Arg Ser Ile Ala Trp Glu Lys Ser Val Asn Lys Val
        1635                1640                1645
Thr Cys Leu Val Cys Arg Lys Gly Asp Asn Asp Glu Phe Leu Leu Leu
    1650                1655                1660
Cys Asp Gly Cys Asp Arg Gly Cys His Ile Tyr Cys His Arg Pro Lys
1665                1670                1675                1680
Met Glu Ala Val Pro Glu Gly Asp Trp Phe Cys Thr Val Cys Leu Ala
            1685                1690                1695
Gln Gln Val Glu Gly Glu Phe Thr Gln Lys Pro Gly Phe Pro Lys Arg
            1700                1705                1710
Gly Gln Lys Arg Lys Ser Gly Tyr Ser Leu Asn Phe Ser Glu Gly Asp
        1715                1720                1725
Gly Arg Arg Arg Val Leu Leu Lys Gly Arg Glu Ser Pro Ala Ala
    1730                1735                1740
Gly Pro Arg Tyr Ser Glu Glu Arg Leu Ser Pro Ser Lys Arg Arg Pro
1745                1750                1755                1760
Leu Ser Met Arg Asn His His Ser Asp Leu Thr Phe Cys Glu Ile Ile
            1765                1770                1775
Leu Met Glu Met Glu Ser His Asp Ala Ala Trp Pro Phe Leu Glu Pro
        1780                1785                1790
```

-continued

```
Val Asn Pro Arg Leu Val Ser Gly Tyr Arg Arg Ile Ile Lys Asn Pro
            1795                1800                1805

Met Asp Phe Ser Thr Met Arg Glu Arg Leu Leu Arg Gly Gly Tyr Thr
    1810                1815                1820

Ser Ser Glu Glu Phe Ala Ala Asp Ala Leu Leu Val Phe Asp Asn Cys
1825                1830                1835                1840

Gln Thr Phe Asn Glu Asp Asp Ser Glu Val Gly Lys Ala Gly His Ile
                1845                1850                1855

Met Arg Arg Phe Phe Glu Ser Arg Trp Glu Gly Phe Tyr Gln Gly Lys
                1860                1865                1870

Gln Ala Asn Leu
        1875

<210> SEQ ID NO 72
<211> LENGTH: 1969
<212> TYPE: PRT
<213> ORGANISM: Homo sapiens

<400> SEQUENCE: 72

Met Gly Gln Thr Lys Ser Thr Ser Ser Gly Gly Asn Arg Lys Cys
1               5                   10                  15

Asn Gln Glu Gln Ser Lys Asn Gln Pro Leu Asp Ala Arg Val Asp Lys
                20                  25                  30

Ile Lys Asp Lys Lys Pro Arg Lys Lys Ala Met Glu Ser Ser Ser Asn
            35                  40                  45

Ser Asp Ser Asp Ser Gly Thr Ser Ser Asp Thr Ser Ser Glu Gly Ile
        50                  55                  60

Ser Ser Ser Asp Ser Asp Asp Leu Glu Glu Asp Glu Glu Glu Glu Asp
65                  70                  75                  80

Gln Ser Ile Glu Glu Ser Glu Asp Asp Ser Asp Ser Glu Ser Glu
                85                  90                  95

Ala Gln His Lys Ser Asn Asn Gln Val Leu Leu His Gly Ile Ser Asp
                100                 105                 110

Pro Lys Ala Asp Gly Gln Lys Ala Thr Glu Lys Ala Gln Glu Lys Arg
            115                 120                 125

Ile His Gln Pro Leu Pro Leu Ala Phe Glu Ser Gln Thr His Ser Phe
        130                 135                 140

Gln Ser Gln Gln Lys Gln Pro Gln Val Leu Ser Gln Leu Pro Phe
145                 150                 155                 160

Ile Phe Gln Ser Ser Gln Ala Lys Glu Glu Ser Val Asn Lys His Thr
                165                 170                 175

Ser Val Ile Gln Ser Thr Gly Leu Val Ser Asn Val Lys Pro Leu Ser
                180                 185                 190

Leu Val Asn Gln Ala Lys Lys Glu Thr Tyr Met Lys Leu Ile Val Pro
            195                 200                 205

Ser Pro Asp Val Leu Lys Ala Gly Asn Lys Asn Thr Ser Glu Glu Ser
        210                 215                 220

Ser Leu Leu Thr Ser Glu Leu Arg Ser Lys Arg Glu Gly Tyr Lys Gln
225                 230                 235                 240

Ala Phe Pro Ser Gln Leu Lys Lys Gln Glu Ser Ser Lys Ser Leu Lys
                245                 250                 255

Lys Val Ile Ala Ala Leu Ser Asn Pro Lys Ala Thr Ser Ser Ser Pro
            260                 265                 270

Ala His Pro Lys Gln Thr Leu Glu Asn Asn His Pro Asn Pro Phe Leu
        275                 280                 285
```

```
Thr Asn Ala Leu Leu Gly Asn His Gln Pro Asn Gly Val Ile Gln Ser
    290                 295                 300
Val Ile Gln Glu Ala Pro Leu Ala Leu Thr Thr Lys Thr Lys Met Gln
305                 310                 315                 320
Ser Lys Ile Asn Glu Asn Ile Ala Ala Ser Ser Thr Pro Phe Ser
                325                 330                 335
Ser Pro Val Asn Leu Ser Thr Ser Gly Arg Arg Thr Pro Gly Asn Gln
                340                 345                 350
Thr Pro Val Met Pro Ser Ala Ser Pro Ile Leu His Ser Gln Gly Lys
                355                 360                 365
Glu Lys Ala Val Ser Asn Asn Val Asn Pro Val Lys Thr Gln His His
    370                 375                 380
Ser His Pro Ala Lys Ser Leu Val Glu Gln Phe Arg Gly Thr Asp Ser
385                 390                 395                 400
Asp Ile Pro Ser Ser Lys Asp Ser Glu Asp Ser Asn Glu Asp Glu Glu
                405                 410                 415
Glu Asp Asp Glu Glu Asp Glu Glu Asp Glu Asp Asp Glu Ser Asp
            420                 425                 430
Asp Ser Gln Ser Glu Ser Asp Ser Asn Ser Glu Ser Asp Thr Glu Gly
        435                 440                 445
Ser Glu Glu Asp Asp Asp Lys Asp Gln Asp Glu Ser Asp Ser
    450                 455                 460
Asp Thr Glu Gly Glu Lys Thr Ser Met Lys Leu Asn Lys Thr Thr Ser
465                 470                 475                 480
Ser Lys Ser Pro Ser Met Ser Leu Thr Gly His Ser Thr Pro Arg Asn
                485                 490                 495
Leu His Ile Ala Lys Ala Pro Gly Ser Ala Pro Ala Ala Leu Cys Ser
                500                 505                 510
Glu Ser Gln Ser Pro Ala Phe Leu Gly Thr Ser Ser Ser Thr Leu Thr
    515                 520                 525
Ser Ser Pro His Ser Gly Thr Ser Lys Arg Arg Val Thr Asp Glu
    530                 535                 540
Arg Glu Leu Arg Leu Pro Leu Glu Tyr Gly Trp Gln Arg Glu Thr Arg
545                 550                 555                 560
Ile Arg Asn Phe Gly Gly Arg Leu Gln Gly Glu Val Ala Tyr Tyr Ala
                565                 570                 575
Pro Cys Gly Lys Lys Leu Arg Gln Tyr Pro Glu Val Ile Lys Tyr Leu
                580                 585                 590
Ser Arg Asn Gly Ile Met Asp Ile Ser Arg Asp Asn Phe Ser Phe Ser
                595                 600                 605
Ala Lys Ile Arg Val Gly Asp Phe Tyr Glu Ala Arg Asp Gly Pro Gln
    610                 615                 620
Glu Met Gln Trp Cys Leu Leu Lys Glu Glu Asp Val Ile Pro Arg Ile
625                 630                 635                 640
Arg Ala Met Glu Gly Arg Arg Gly Arg Pro Pro Asn Pro Asp Arg Gln
                645                 650                 655
Arg Ala Arg Glu Glu Ser Arg Met Arg Arg Lys Gly Arg Pro Pro
            660                 665                 670
Asn Val Gly Asn Ala Glu Phe Leu Asp Asn Ala Asp Ala Lys Leu Leu
        675                 680                 685
Arg Lys Leu Gln Ala Gln Glu Ala Arg Gln Ala Ala Gln Ile Lys Leu
    690                 695                 700
```

-continued

```
Leu Arg Lys Leu Gln Lys Gln Glu Gln Ala Arg Val Ala Lys Glu Ala
705                 710                 715                 720

Lys Lys Gln Gln Ala Ile Met Ala Ala Glu Glu Lys Arg Lys Gln Lys
                725                 730                 735

Glu Gln Ile Lys Ile His Lys Gln Gln Glu Lys Ile Lys Arg Ile Gln
            740                 745                 750

Gln Ile Arg Met Glu Lys Glu Leu Arg Ala Gln Ile Leu Glu Ala
        755                 760                 765

Lys Lys Lys Lys Glu Glu Ala Ala Asn Ala Lys Leu Leu Glu Ala
770                 775                 780

Glu Lys Arg Ile Lys Glu Arg Glu Met Arg Arg Gln Gln Ala Val Leu
785                 790                 795                 800

Leu Lys Arg Gln Glu Arg Glu Arg Arg Gln His Met Met Leu Met
                805                 810                 815

Lys Ala Met Glu Ala Arg Lys Lys Ala Glu Glu Lys Glu Arg Leu Lys
                820                 825                 830

Gln Glu Lys Arg Asp Glu Lys Arg Leu Asn Lys Glu Arg Lys Leu Glu
                835                 840                 845

Gln Arg Arg Leu Glu Leu Glu Met Ala Lys Glu Leu Lys Lys Pro Asn
850                 855                 860

Glu Asp Met Cys Leu Ala Asp Gln Lys Pro Leu Pro Glu Leu Pro Arg
865                 870                 875                 880

Ile Pro Gly Leu Val Leu Ser Gly Ser Thr Phe Ser Asp Cys Leu Met
                885                 890                 895

Val Val Gln Phe Leu Arg Asn Phe Gly Lys Val Leu Gly Phe Asp Val
                900                 905                 910

Asn Ile Asp Val Pro Asn Leu Ser Val Leu Gln Glu Gly Ile Leu Leu
            915                 920                 925

Asn Ile Gly Asp Ser Met Gly Glu Val Gln Asp Leu Leu Val Arg Leu
            930                 935                 940

Leu Ser Ala Ala Val Cys Asp Pro Gly Leu Ile Thr Gly Tyr Lys Ala
945                 950                 955                 960

Lys Thr Ala Leu Gly Glu His Leu Leu Asn Val Gly Val Asn Arg Asp
                965                 970                 975

Asn Val Ser Glu Ile Leu Gln Ile Phe Met Glu Ala His Cys Gly Gln
            980                 985                 990

Thr Glu Leu Thr Glu Ser Leu Lys Thr Lys Ala Phe Gln Ala His Thr
        995                 1000                1005

Pro Ala Gln Lys Ala Val Leu Ala Phe Leu Ile Asn Glu Leu Ala Cys
        1010                1015                1020

Ser Lys Ser Val Val Ser Glu Ile Asp Lys Asn Ile Asp Tyr Met Ser
1025                1030                1035                1040

Asn Leu Arg Arg Asp Lys Asn Val Val Glu Gly Lys Leu Arg Lys Leu
                1045                1050                1055

Arg Ile Ile His Ala Lys Lys Thr Gly Lys Arg Asp Thr Ser Gly Gly
            1060                1065                1070

Ile Asp Leu Gly Glu Glu Gln His Pro Leu Gly Thr Pro Thr Pro Gly
        1075                1080                1085

Arg Lys Arg Arg Arg Lys Gly Gly Asp Ser Asp Tyr Asp Asp Asp Asp
            1090                1095                1100

Asp Asp Asp Ser Asp Asp Gln Gly Asp Glu Asp Asp Glu Asp Glu Glu
1105                1110                1115                1120

Asp Lys Glu Asp Gln Lys Gly Lys Lys Thr Asp Ile Cys Glu Asp Glu
```

-continued

```
                1125                1130                1135
Asp Glu Gly Asp Gln Ala Ala Ser Val Glu Glu Leu Glu Lys Gln Ile
            1140                1145                1150

Glu Lys Leu Ser Lys Gln Ser Gln Tyr Arg Arg Lys Leu Phe Asp
        1155                1160                1165

Ala Ser His Ser Leu Arg Ser Val Met Phe Gly Pro Asp Arg Tyr Arg
        1170                1175                1180

Arg Arg Tyr Trp Ile Leu Pro Arg Cys Gly Ile Phe Val Glu Gly
1185                1190                1195                1200

Met Glu Ser Gly Glu Gly Leu Glu Glu Ile Ala Lys Glu Arg Glu Lys
            1205                1210                1215

Leu Lys Lys Ala Glu Ser Val Gln Ile Lys Glu Glu Met Phe Glu Thr
            1220                1225                1230

Ser Gly Asp Ser Leu Asn Cys Ser Asn Thr Asp His Cys Glu Gln Lys
            1235                1240                1245

Glu Asp Leu Lys Glu Lys Asp Asn Thr Asn Leu Phe Leu Gln Lys Pro
        1250                1255                1260

Gly Ser Phe Ser Lys Leu Ser Lys Leu Leu Glu Val Ala Lys Met Pro
1265                1270                1275                1280

Pro Glu Ser Glu Val Met Thr Pro Lys Pro Asn Ala Gly Ala Asn Gly
            1285                1290                1295

Cys Thr Leu Ser Tyr Gln Asn Ser Gly Lys His Ser Leu Gly Ser Val
            1300                1305                1310

Gln Ser Thr Ala Thr Gln Ser Asn Val Glu Lys Ala Asp Ser Asn Asn
            1315                1320                1325

Leu Phe Asn Thr Gly Ser Ser Gly Pro Gly Lys Phe Tyr Ser Pro Leu
            1330                1335                1340

Pro Asn Asp Gln Leu Leu Lys Thr Leu Thr Glu Lys Asn Arg Gln Trp
1345                1350                1355                1360

Phe Ser Leu Leu Pro Arg Thr Pro Cys Asp Asp Thr Ser Leu Thr His
                1365                1370                1375

Ala Asp Met Ser Thr Ala Ser Leu Val Thr Pro Gln Ser Gln Pro Pro
            1380                1385                1390

Ser Lys Ser Pro Ser Pro Thr Pro Ala Pro Leu Gly Ser Ser Ala Gln
        1395                1400                1405

Asn Pro Val Gly Leu Asn Pro Phe Ala Leu Ser Pro Leu Gln Val Lys
        1410                1415                1420

Gly Gly Val Ser Met Met Gly Leu Gln Phe Cys Gly Trp Pro Thr Gly
1425                1430                1435                1440

Val Val Thr Ser Asn Ile Pro Phe Thr Leu Ser Val Pro Ser Leu Gly
                1445                1450                1455

Ser Gly Leu Gly Leu Ser Glu Gly Asn Gly Asn Ser Phe Leu Thr Ser
            1460                1465                1470

Asn Val Ala Ser Ser Lys Ser Glu Ser Pro Val Pro Gln Asn Glu Lys
        1475                1480                1485

Ala Thr Ser Ala Gln Pro Ala Val Glu Val Ala Lys Pro Val Asp
        1490                1495                1500

Phe Pro Ser Pro Lys Pro Ile Pro Glu Glu Met Gln Phe Gly Trp Trp
1505                1510                1515                1520

Arg Ile Ile Asp Pro Glu Asp Leu Lys Ala Leu Leu Lys Val Leu His
                1525                1530                1535

Leu Arg Gly Ile Arg Glu Lys Ala Leu Gln Lys Gln Ile Gln Lys His
            1540                1545                1550
```

-continued

```
Leu Asp Tyr Ile Thr Gln Ala Cys Leu Lys Asn Lys Asp Val Ala Ile
        1555                1560                1565
Ile Glu Leu Asn Glu Asn Glu Glu Asn Gln Val Thr Arg Asp Ile Val
    1570                1575                1580
Glu Asn Trp Ser Val Glu Glu Gln Ala Met Glu Met Asp Leu Ser Val
1585                1590                1595                1600
Leu Gln Gln Val Glu Asp Leu Glu Arg Arg Val Ala Ser Ala Ser Leu
                1605                1610                1615
Gln Val Lys Gly Trp Met Cys Pro Glu Pro Ala Ser Glu Arg Glu Asp
            1620                1625                1630
Leu Val Tyr Phe Glu His Lys Ser Phe Thr Lys Leu Cys Lys Glu His
        1635                1640                1645
Asp Gly Glu Phe Thr Gly Glu Asp Ser Ser Ala His Ala Leu Glu
    1650                1655                1660
Arg Lys Ser Asp Asn Pro Leu Asp Ile Ala Val Thr Arg Leu Ala Asp
1665                1670                1675                1680
Leu Glu Arg Asn Ile Glu Arg Arg Ile Glu Glu Asp Ile Ala Pro Gly
                1685                1690                1695
Leu Arg Val Trp Arg Arg Ala Leu Ser Glu Ala Arg Ser Ala Ala Gln
            1700                1705                1710
Val Ala Leu Cys Ile Gln Gln Leu Gln Lys Ser Ile Ala Trp Glu Lys
        1715                1720                1725
Ser Ile Met Lys Val Tyr Cys Gln Ile Cys Arg Lys Gly Asp Asn Glu
    1730                1735                1740
Glu Leu Leu Leu Cys Asp Gly Cys Asp Lys Gly Cys His Thr Tyr
1745                1750                1755                1760
Cys His Arg Pro Lys Ile Thr Thr Ile Pro Asp Gly Asp Trp Phe Cys
                1765                1770                1775
Pro Ala Cys Ile Ala Lys Ala Ser Gly Gln Thr Leu Lys Ile Lys Lys
            1780                1785                1790
Leu His Val Lys Gly Lys Lys Thr Asn Glu Ser Lys Lys Gly Lys Lys
        1795                1800                1805
Val Thr Leu Thr Gly Asp Thr Glu Asp Glu Asp Ser Ala Ser Thr Ser
    1810                1815                1820
Ser Ser Leu Lys Arg Gly Asn Lys Asp Leu Gln Lys Arg Lys Met Glu
1825                1830                1835                1840
Glu Asn Thr Ser Ile Asn Leu Ser Lys Gln Glu Ser Phe Thr Ser Val
                1845                1850                1855
Lys Lys Pro Lys Arg Asp Asp Ser Lys Asp Leu Ala Leu Cys Ser Met
            1860                1865                1870
Ile Leu Thr Glu Met Glu Thr His Glu Asp Ala Trp Pro Phe Leu Leu
        1875                1880                1885
Pro Val Asn Leu Lys Leu Val Pro Gly Tyr Lys Lys Val Ile Lys Lys
    1890                1895                1900
Pro Met Asp Phe Ser Thr Ile Arg Glu Lys Leu Ser Ser Gly Gln Tyr
1905                1910                1915                1920
Pro Asn Leu Glu Thr Phe Ala Leu Asp Val Arg Leu Val Phe Asp Asn
                1925                1930                1935
Cys Glu Thr Phe Trp Glu Asp Asp Ser Asp Ile Gly Arg Ala Gly His
            1940                1945                1950
Asn Met Arg Lys Tyr Phe Glu Lys Lys Trp Thr Asp Thr Phe Lys Val
        1955                1960                1965
```

-continued

Ser

```
<210> SEQ ID NO 73
<211> LENGTH: 12
<212> TYPE: DNA
<213> ORGANISM: Homo sapiens

<400> SEQUENCE: 73
tacagaccct cc                                                          12
```